United States Patent
Baumhof et al.

(10) Patent No.: US 11,478,552 B2
(45) Date of Patent: Oct. 25, 2022

(54) HYBRID CARRIERS FOR NUCLEIC ACID CARGO

(71) Applicant: CureVac AG, Tübingen (DE)

(72) Inventors: Patrick Baumhof, Dusslingen (DE); Carolin Thiele, Tübingen (DE); Joanna Rejman, Tübingen (DE)

(73) Assignee: CureVac AG, Tübingen (DE)

( * ) Notice: Subject to any disclaimer, the term of this patent is extended or adjusted under 35 U.S.C. 154(b) by 773 days.

(21) Appl. No.: 16/308,632

(22) PCT Filed: Jun. 9, 2017

(86) PCT No.: PCT/EP2017/064059
§ 371 (c)(1),
(2) Date: Dec. 10, 2018

(87) PCT Pub. No.: WO2017/212009
PCT Pub. Date: Dec. 14, 2017

(65) Prior Publication Data
US 2020/0179526 A1  Jun. 11, 2020

(30) Foreign Application Priority Data
Jun. 9, 2016  (WO) .................. PCT/EP2016/063226

(51) Int. Cl.
| | | |
|---|---|---|
| A61K 47/64 | (2017.01) | |
| A61K 47/69 | (2017.01) | |
| A61K 48/00 | (2006.01) | |
| C07C 215/14 | (2006.01) | |
| C07C 233/56 | (2006.01) | |
| C07C 237/12 | (2006.01) | |
| A61K 9/00 | (2006.01) | |

(52) U.S. Cl.
CPC ........ *A61K 47/645* (2017.08); *A61K 47/6929* (2017.08); *A61K 48/0041* (2013.01); *C07C 215/14* (2013.01); *C07C 233/56* (2013.01); *C07C 237/12* (2013.01); *A61K 9/0048* (2013.01)

(58) Field of Classification Search
CPC .............. A61K 47/645; A61K 47/6929; A61K 48/0041; A61K 9/0048; C07C 215/14; C07C 233/56; C07C 237/12
See application file for complete search history.

(56) References Cited

U.S. PATENT DOCUMENTS

| | | | |
|---|---|---|---|
| 7,973,019 | B1 * | 7/2011 | Chatterton |
| 8,969,353 | B2 | 3/2015 | Mahon et al. |
| 2005/0032730 | A1 | 2/2005 | von der Mülbe et al. |
| 2005/0059624 | A1 | 3/2005 | Hoerr et al. |
| 2005/0250723 | A1 | 11/2005 | Hoerr et al. |
| 2006/0188490 | A1 | 8/2006 | Hoerr et al. |
| 2008/0025944 | A1 | 1/2008 | Hoerr et al. |
| 2008/0153166 | A1 | 6/2008 | Huang et al. |
| 2008/0267873 | A1 | 10/2008 | Hoerr et al. |
| 2009/0209037 | A1 | 8/2009 | Tagawa et al. |
| 2009/0324584 | A1 | 12/2009 | Hoerr et al. |
| 2010/0048883 | A1 | 2/2010 | Ketterer et al. |
| 2010/0189729 | A1 | 7/2010 | Hoerr et al. |
| 2010/0203076 | A1 | 8/2010 | Fotin-Mleczek et al. |
| 2010/0291156 | A1 | 11/2010 | Barner et al. |
| 2010/0305196 | A1 | 12/2010 | Probst et al. |
| 2011/0053829 | A1 | 3/2011 | Baumhof et al. |
| 2011/0200624 | A1 | 8/2011 | Jessee |
| 2011/0250225 | A1 | 10/2011 | Fotin-Mleczek et al. |
| 2012/0009222 | A1 | 1/2012 | Nguyen et al. |
| 2012/0021043 | A1 | 1/2012 | Kramps et al. |
| 2012/0258046 | A1 | 10/2012 | Mutzke |
| 2013/0129754 | A1 | 5/2013 | Thess et al. |
| 2013/0142818 | A1 | 6/2013 | Baumhof et al. |
| 2013/0190689 | A1 * | 7/2013 | Slager |
| 2013/0259879 | A1 | 10/2013 | Baumhof et al. |
| 2013/0280283 | A1 | 10/2013 | Lorenz et al. |
| 2013/0295043 | A1 | 11/2013 | Kallen et al. |
| 2013/0336998 | A1 | 12/2013 | Kallen et al. |
| 2015/0037326 | A1 | 2/2015 | Butler-Ransohoff et al. |
| 2015/0050302 | A1 | 2/2015 | Thess |
| 2015/0057340 | A1 | 2/2015 | Thess et al. |
| 2015/0093413 | A1 | 4/2015 | Thess et al. |
| 2015/0118183 | A1 | 4/2015 | Baumhof |
| 2015/0118264 | A1 | 4/2015 | Baumhof et al. |
| 2015/0165006 | A1 | 6/2015 | Thess et al. |
| 2015/0184195 | A1 | 7/2015 | Thess et al. |
| 2015/0218554 | A1 | 8/2015 | Thess |
| 2015/0306249 | A1 | 10/2015 | Baumhof et al. |

(Continued)

FOREIGN PATENT DOCUMENTS

| | | |
|---|---|---|
| EP | 1083232 | 3/2001 |
| WO | WO 1999/015206 | 4/1999 |

(Continued)

OTHER PUBLICATIONS

Li et al. (Bioconjugate Chemistry, Published Aug. 5, 2013, pp. 1543-1551) (Year: 2013).*
International Preliminary Report on Patentability issued in corresponding PCT Application No. PCT/EP2017/064059, dated Dec. 11, 2018.
International Search Report and Written Opinion issued in corresponding PCT Application No. PCT/EP2017/064059, dated Sep. 21, 2017.
Kim et al., "Homodimeric SV40 NLS peptide formed by disulfide bond as enhancer for gene delivery", *Bioorg. Med. Chem. Lett.*, 22(17):5415-5418, 2012.
Wang et al., "Lipid nanoparticles for ocular gene delivery", *J. Funct. Biomater.*, 6(2):379-394, 2015.

(Continued)

*Primary Examiner* — Alma Pipic
(74) *Attorney, Agent, or Firm* — Parker Highlander PLLC

(57) ABSTRACT

A composition for the delivery of a nucleic acid compound is provided which comprises a cationic peptide or polymer and a lipidoid compound. The nucleic acid compound may be any chemically modified or unmodified DNA or RNA. The amount of the lipidoid in the composition is preferably low, relative to the cationic peptide or polymer.

19 Claims, 13 Drawing Sheets

Specification includes a Sequence Listing.

(56) References Cited

U.S. PATENT DOCUMENTS

| | | |
|---|---|---|
| 2015/0320847 A1 | 11/2015 | Thess et al. |
| 2016/0130345 A1 | 5/2016 | Fotin-Mleczek et al. |
| 2016/0166668 A1 | 6/2016 | Kallen et al. |
| 2016/0166678 A1 | 6/2016 | Kallen et al. |
| 2016/0166710 A1 | 6/2016 | Baumhof |
| 2016/0166711 A1 | 6/2016 | Schnee et al. |
| 2016/0168207 A1 | 6/2016 | Kramps et al. |
| 2016/0168227 A1 | 6/2016 | Kallen et al. |
| 2016/0235864 A1 | 8/2016 | Schlake et al. |
| 2016/0304883 A1 | 10/2016 | Grund et al. |
| 2016/0304938 A1 | 10/2016 | Wochner |
| 2016/0326575 A1 | 11/2016 | von der Mülbe et al. |
| 2016/0331844 A1 | 11/2016 | Fotin-Mleczek et al. |
| 2017/0014496 A1 | 1/2017 | Fotin-Mleczek et al. |
| 2017/0029847 A1 | 2/2017 | Thess |
| 2017/0114378 A1 | 4/2017 | Wochner et al. |
| 2017/0252430 A1 | 9/2017 | Fotin-Mleczek et al. |
| 2017/0326225 A1 | 11/2017 | Rauch et al. |
| 2018/0044687 A1 | 2/2018 | Thess et al. |
| 2018/0125952 A1 | 5/2018 | Fotin-Mleczek et al. |
| 2018/0126003 A1 | 5/2018 | Hoerr |
| 2018/0142275 A1 | 5/2018 | Roos et al. |
| 2018/0147146 A1 | 5/2018 | Eber et al. |
| 2018/0148727 A1 | 5/2018 | Grund et al. |
| 2018/0201967 A1 | 7/2018 | Eber et al. |
| 2018/0208957 A1 | 7/2018 | Roos et al. |
| 2018/0214537 A1 | 8/2018 | Mutzke et al. |
| 2018/0237786 A1 | 8/2018 | Schlake et al. |
| 2018/0237817 A1 | 8/2018 | Roos et al. |
| 2018/0243219 A1 | 8/2018 | Ketterer et al. |
| 2018/0296663 A1 | 10/2018 | Hipp et al. |
| 2018/0298372 A1 | 10/2018 | Funkner et al. |
| 2018/0312545 A1 | 11/2018 | Baumhof et al. |
| 2018/0371392 A1 | 12/2018 | Mayer et al. |
| 2019/0010485 A1 | 1/2019 | Yazdan Panah et al. |
| 2019/0017100 A1 | 1/2019 | Wochner et al. |
| 2019/0024096 A1 | 1/2019 | Schmid et al. |
| 2019/0040378 A1 | 2/2019 | Fotin-Mleczek et al. |
| 2019/0049414 A1 | 2/2019 | Wochner et al. |
| 2019/0083602 A1 | 3/2019 | Roos et al. |
| 2019/0100784 A1 | 4/2019 | Eber et al. |
| 2019/0125857 A1 | 5/2019 | Rauch et al. |
| 2019/0133950 A1 | 5/2019 | Eber et al. |

FOREIGN PATENT DOCUMENTS

| | | | |
|---|---|---|---|
| WO | WO 2001/092542 | | 12/2001 |
| WO | 2010/053572 | * | 5/2010 |
| WO | WO 2010/088927 | | 8/2010 |
| WO | WO 2011/026641 | | 3/2011 |
| WO | WO 2012/113513 | | 8/2012 |
| WO | WO 2014/207231 | | 12/2014 |
| WO | WO 2015/149944 | | 10/2015 |
| WO | WO 2016/170176 | | 10/2016 |
| WO | WO 2016/184576 | | 11/2016 |
| WO | WO 2017/021546 | | 2/2017 |
| WO | WO 2017/025447 | | 2/2017 |
| WO | WO 2017/064146 | | 4/2017 |
| WO | WO 2017/081110 | | 5/2017 |
| WO | WO 2017/109134 | | 6/2017 |
| WO | WO 2017/137095 | | 8/2017 |
| WO | WO 2017/140905 | | 8/2017 |
| WO | WO 2017/149139 | | 9/2017 |
| WO | WO 2017/162297 | | 9/2017 |
| WO | WO 2017/182634 | | 10/2017 |
| WO | WO 2017/186928 | | 11/2017 |
| WO | WO 2017/191258 | | 11/2017 |
| WO | WO 2017/191264 | | 11/2017 |
| WO | WO 2017/191274 | | 11/2017 |
| WO | WO 2017/203008 | | 11/2017 |
| WO | WO 2017/212006 | | 12/2017 |
| WO | WO 2017/212007 | | 12/2017 |
| WO | WO 2017/212008 | | 12/2017 |
| WO | WO 2017/212009 | | 12/2017 |
| WO | WO 2018/033254 | | 2/2018 |
| WO | WO 2018/078053 | | 5/2018 |
| WO | WO 2019/008001 | | 1/2019 |

OTHER PUBLICATIONS

Anwer et al., "Peptide-mediated gene transfer of cationic lipid/plasmid DNA complexes to endothelial cells", *J. Drug Target.*, 12(4):215-221, 2004.

Bald et al., "Immune Cell-Poor Melanomas Benefit from PD-1 Blockade after Targeted Type I IFN Activation", *Cancer Discov.*, 4(6):674-687, 2014.

Garcia et al., "Serum-resistant lipopolyplexes for gene delivery to liver tumour cells", *Eur. J. Pharm. Biopharm.*, 67(1):58-66, 2007.

Hardy et al., "Synergistic effects on gene delivery—co-formulation of small disulfide-linked dendritic polycations with Lipofectamine 2000", *Org. Biomol. Chem.*, 7(4):789-793, 2009.

Heidenreich et al., "A novel RNA-based adjuvant combines strong immunostimulatory capacities with a favorable safety profile", *Int. J. Cancer*, 137(2):372-384, 2015.

Perche et al., "Enhancement of dendritic cells transfection in vivo and of vaccination against B16F10 melanoma with mannosylated histidylated lipopolyplexes loaded with tumor antigen messenger RNA", *Nanomed. Nanotech. Biol. Med.*, 7(4):445-453, 2011.

Pruitt et al., "Enhancement of anti-tumor immunity through local modulation of CLTA-4 and GITR by dendritic cells", *Eur. J. Immunol.*, 41(12):3553-3563, 2011.

Wong et al., "Cationic lipid binding to DNA: characterization of complex formation", *Biochemistry*, 35(18):5756-5763, 1996.

Yamano et al., "Modified Tat peptide with cationic lipids enhances gene transfection efficiency via temperature-dependent and caveolae-mediated endocytosis", *J. Control. Release*, 152(2):278-285, 2011.

\* cited by examiner

HYBRID CARRIERS FOR NUCLEIC ACID CARGO

This application is a national phase application under 35 U.S.C. § 371 of International Application No. PCT/EP2017/064059, filed Jun. 9, 2017, which claims benefit of International Application No. PCT/EP2016/063226, filed Jun. 9, 2016, the entire contents of each of which are hereby incorporated by reference.

BACKGROUND OF THE INVENTION

The present invention is in the fields of medical therapy, disease prevention and drug delivery. It relates in particular to carriers that are useful for delivering certain types of active ingredients to subjects in need thereof. More specifically, the invention relates to the delivery of such active ingredients which represent bioactive compounds that are challenging to deliver across biological barriers to their targets within a living organism, such as to target organs, tissues, or cells. Examples of such bioactive compounds that are of great therapeutic value and at the same time difficult to deliver to their biological targets include nucleic acid-based vaccines and therapeutics.

Various diseases today require a treatment which involves administration of peptide-, protein-, and nucleic acid-based drugs, particularly the transfection of nucleic acids into cells or tissues. The full therapeutic potential of peptide-, protein-, and nucleic acid-based drugs is frequently compromised by their limited ability to cross the plasma membrane of mammalian cells due to their size and electric charge, resulting in poor cellular access and inadequate therapeutic efficacy. Today this hurdle represents a major challenge for the biomedical development and commercial success of many biopharmaceuticals (see e.g. Foerg and Merkle, Journal of Pharmaceutical Sciences, published online at www.interscience.wiley.com, 2008, 97(1): 144-62).

For some diseases or disorders, gene therapeutic approaches have been developed as a specific form of such treatments which require the transfection of cells or tissues with genes and their insertion into the DNA of the cells, e.g. in the case of hereditary diseases in which a defective mutant allele is replaced with a functional one. Transfer or insertion of nucleic acids or genes into an individual's cells, however, still represents a major challenge today, even though it is absolutely necessary for achieving a significant therapeutic effect of the gene therapy.

To achieve successful transfer of nucleic acids or genes into an individual's cells, a number of different hurdles have to be passed. The transport of nucleic acids typically occurs via association of the nucleic acid with the cell membrane and subsequent uptake by the endosomes. In the endosomes, the introduced nucleic acids are separated from the cytosol. As expression occurs in the cytosol, these nucleic acids have to depart the endosome. If the nucleic acids do not leave the endosome before the endosome fuses with a lysosome, they will suffer the usual fate of the content of the endosome and become degraded. Alternatively, the endosome may fuse with the cell membrane, leading to the return of its content into the extracellular medium. For efficient transfer of nucleic acids, the endosomal escape thus appears to be one of the most important steps additionally to the efficiency of transfection itself. Until now, there are different approaches addressing these issues. However, no approach has been entirely successful in all aspects so far.

Transfection agents used in the art today typically include various types of peptides, polymers, lipids, as well as other carrier compounds, which may be assembled into nano- or microparticles (see e.g. Gao, X., K. S. Kim, et al. (2007), AAPS J 9(1): E92-104). Most of these transfection agents have been successfully used only in in vitro reactions. When transfecting cells of a living animal with nucleic acids, further requirements have to be fulfilled. As an example, the complex of the nucleic acid and the carrier has to be stable in physiological salt solutions with respect to agglomeration. Furthermore, it must not interact with parts of the complement system of the host. Additionally, the complex must protect the nucleic acid from early extracellular degradation by ubiquitously occurring nucleases. For gene therapeutic applications, it is furthermore of great importance that the carrier is not recognized by the adaptive immune system (immunogenicity) and does not stimulate an unspecific cytokine storm (acute immune response) (see Gao, Kim et al., (2007, supra); Martin, M. E. and K. G. Rice (2007), AAPS J 9(1): E18-29; and Foerg and Merkle, (2008, supra)).

Foerg and Merkle (2008, supra) discuss the therapeutic potential of peptide-, protein and nucleic acid-based drugs. According to their analysis, the full therapeutic potential of these drugs is frequently compromised by their limited ability to cross the plasma membrane of mammalian cells, resulting in poor cellular access and inadequate therapeutic efficacy. Today this hurdle represents a major challenge for the biomedical development and commercial success of many biopharmaceuticals.

In this context, Gao et al. (Gao et al. The AAPS Journal 2007; 9(1) Article 9) see the primary challenge for gene therapy in the development of a method that delivers a therapeutic gene to selected cells where proper gene expression can be achieved. Gene delivery and particularly successful introduction of nucleic acids into cells or tissue is, however, not simple and typically dependent on many factors. For successful delivery, e.g., delivery of nucleic acids or genes into cells or tissue, many barriers must be overcome. According to Gao et al. (2007) an ideal gene delivery method needs to meet 3 major criteria: (1) it should protect the transgene against degradation by nucleases in intercellular matrices, (2) it should bring the transgene across the plasma membrane and (3) it should have no detrimental effects.

Typically, the transfection of cells with nucleic acids is carried out using viral or non-viral vectors or carriers. For successful delivery, these viral or non-viral vectors must be able to overcome the above mentioned barriers. The most successful gene therapy strategies available today rely on the use of viral vectors, such as adenoviruses, adeno-associated viruses, retroviruses, and herpes viruses. Viral vectors are able to mediate gene transfer with high efficiency and the possibility of long-term gene expression, and satisfy 2 out of 3 criteria. However, the acute immune response, immunogenicity, and insertion mutagenesis uncovered in gene therapy clinical trials have raised serious safety concerns about some commonly used viral vectors.

A solution to this problem may be found in the use of non-viral vectors. Although non-viral vectors are not as efficient as viral vectors, many non-viral vectors have been developed to provide safer alternatives in gene therapy. Methods of non-viral gene delivery have been explored using physical (carrier-free gene delivery) and chemical approaches (synthetic vector-based gene delivery). Physical approaches usually include simple injection using injection needles, electroporation, gene gun, ultrasound, and hydrodynamic delivery. Some of these approaches employ a physical force that permeates the cell membrane and facilitates intracellular gene transfer. The chemical approaches typically use synthetic or naturally occurring compounds, e.g. cationic lipids or cationic polymers, as carriers to deliver the transgene into cells. Although significant progress has been made in the basic science and applications of various non-viral gene delivery systems, the majority of non-viral approaches is still less efficient than viral vectors, especially for in vivo gene delivery (see e.g. Gao et al. The AAPS Journal 2007; 9(1) Article 9).

Over the past decade, attractive prospects for a substantial improvement in the cellular delivery of nucleic acids have been announced that were supposed to result from their physical assembly or chemical ligation to so-called cell penetrating peptides (CPPs), also denoted as protein-transduction domains (PTDs) (see Foerg and Merkle, (2008, supra)). CPPs represent short peptide sequences of 10 to about 30 amino acids which can cross the plasma membrane of mammalian cells and may thus offer unprecedented opportunities for cellular drug delivery. Nearly all of these peptides comprise a series of cationic amino acids in combination with a sequence, which forms an α-helix at low pH. As the pH is continuously lowered in vivo by proton pumps, a conformational change of the peptide is usually initiated rapidly. This helix motif mediates an insertion into the membrane of the endosome leading to a release of its content into the cytoplasm (see Foerg and Merkle, (2008, supra); and Vives, E., P. Brodin, et al. (1997); A truncated HIV-1 Tat protein basic domain rapidly translocates through the plasma membrane and accumulates in the cell nucleus. J Biol Chem 272(25): 16010-7). Despite these advantages, a major obstacle to CPP mediated drug delivery is thought to consist in the often rapid metabolic clearance of the peptides when in contact or passing the enzymatic barriers of epithelia and endothelia. Consequently, the metabolic stability of CPPs represents an important biopharmaceutical factor for their cellular bioavailability. However, there are no CPPs available in the art which are on the one hand side stable enough to carry their cargo to the target before they are metabolically cleaved, and which on the other hand side can be cleared from the tissue before they can accumulate and reach toxic levels.

One further approach in the art for delivering cargo molecules into cells, e.g. for gene therapy, comprises the use of other types of peptide ligands (see Martin and Rice (see Martin and Rice, The AAPS Journal 2007; 9 (1) Article 3)). Such peptide ligands can be short sequences taken from larger proteins that represent the essential amino acids needed for receptor recognition, such as EGF peptide used to target cancer cells. Other peptide ligands have been identified including the ligands used to target the lectin-like oxidized LDL receptor (LOX-1). Up-regulation of LOX-1 in endothelial cells is associated with dysfunctional states such as hypertension and atherosclerosis. Such peptide ligands, however, are not suitable for many gene therapeutic approaches, as they cannot be linked to their cargo molecules by complexation or adhesion but require covalent bonds, e.g. crosslinkers, which typically exhibit cytotoxic effects in the cell.

Synthetic vectors may also be used for delivering cargo molecules into cells, e.g., for the purpose of gene therapy. However, one main disadvantage of many synthetic vectors is their poor transfection efficiency compared to viral vectors and significant improvements are required to enable further clinical development. Several barriers that limit nucleic acid transfer both in vitro and in vivo have been identified, and include poor intracellular delivery, toxicity and instability of vectors in physiological conditions (see. e.g. Read, M. L., K. H. Bremner, et al. (2003): Vectors based on reducible polycations facilitate intracellular release of nucleic acids. J Gene Med 5(3): 232-45).

One specific approach in gene therapy uses cationic or cationisable lipids. However, although many cationic or cationisable lipids show excellent transfection activity in cell culture, most do not perform well in the presence of serum, and only a few are active in vivo. A dramatic change in size, surface charge, and lipid composition occurs when lipoplexes are exposed to the overwhelming amount of negatively charged and often amphipathic proteins and polysaccharides that are present in blood, mucus epithelial lining fluid, or tissue matrix. Once administered in vivo, lipoplexes tend to interact with negatively charged blood components and form large aggregates that could be absorbed onto the surface of circulating red blood cells, trapped in a thick mucus layer or embolized in microvasculatures, preventing them from reaching the intended target cells in the distal location. Furthermore, toxicity related to lipoplexes has been observed. Symptoms include inter alia induction of inflammatory cyokines. In humans, various degrees of adverse inflammatory reactions, including flu-like symptoms were noted among subjects who received lipoplexes. Accordingly, it appears questionable as to whether lipoplexes can be safely used in humans, in particular when repeated administration is required.

One further approach in gene therapy utilizes cationic or cationisable polymers. Such polymers turned out to be efficient in the delivery of nucleic acids, as they can tightly complex and condense a negatively charged nucleic acid. Thus, a number of cationic or cationisable polymers have been explored as carriers for in vitro and in vivo gene delivery. These include polyethylenimine (PEI), polyamidoamine and polypropylamine dendrimers, polyallylamine, cationic dextran, chitosan, various proteins and peptides. Although most cationic or cationisable polymers share the function of condensing DNA into small particles and facilitating cellular uptake via endocytosis through charge-charge interaction with anionic sites on cell surfaces, their transfection activity and toxicity differ dramatically. Interestingly, cationic or cationisable polymers exhibit better transfection efficiency with rising molecular weight due to stronger complexation of the negatively charged nucleic acid cargo. However, a rising molecular weight also leads to a rising toxicity of the polymer. PEI is perhaps the most active and most studied polymer for gene delivery, but its main drawback as a transfection reagent relates to its non-biodegradable nature and toxicity. Furthermore, even though polyplexes formed by high molecular weight polymers exhibit improved stability under physiological conditions, data have indicated that such polymers can hinder vector unpacking. For example, poly(L-lysine) (PLL) of 19 and 36 amino acid residues was shown to dissociate from DNA more rapidly than PLL of 180 residues resulting in significantly enhanced short-term gene expression. A minimum length of six to eight cationic amino acids is required to compact DNA into structures active in receptor-mediated gene delivery. However, polyplexes formed with short polycations are unstable under physiological conditions and typically aggregate rapidly in physiological salt solutions. To overcome this negative impact, Read et al. (see Read, M. L., K. H. Bremner, et al. (2003): Vectors based on reducible polycations facilitate intracellular release of nucleic acids. J Gene Med 5(3): 232-45; and Read, M. L., S. Singh, et al. (2005): A versatile reducible polycation-based system for efficient delivery of a broad range of nucleic acids. Nucleic Acids Res 33(9): e86) developed a new type of synthetic vector based on a linear reducible polycation (RPC) prepared by oxidative polycondensation of the peptide Cys-Lys$_{10}$-Cys that can be cleaved by the intracellular environment to facilitate release of nucleic acids. They could show that polyplexes formed by RPC are destabilised by reducing conditions enabling efficient release of DNA and mRNA. Cleavage of the RPC also reduced toxicity of the polycation to levels comparable with low molecular weight peptides. The disadvantage of this approach of Read et al. (2003, supra) was that the endosomolytic agent chloroquine or the cationic lipids DOTAP was additionally necessary to enhance transfection efficiency to adequate levels. As a consequence Read et al. (2005, supra) included histidine residues in the RPCs which have a known endosomal buffering capacity. They could show that histidine-rich RPCs can be cleaved by the intracellular reducing environment enabling efficient cytoplasmic delivery of a broad range of nucleic acids, including plasmid DNA, mRNA and siRNA molecules without the requirement for the endosomolytic agent chloroquine.

Read et al. (2005, supra) did not assess whether histidine-rich RPCs can be directly used for in vivo applications. In their study, transfections were performed in the absence of serum to avoid masking the ability of histidine residues to enhance gene transfer that may have arisen from binding of serum proteins to polyplexes restricting cellular uptake. Preliminary experiments indicate that the transfection properties of histidine-rich RPC polyplexes can be affected by the presence of serum proteins with a 50% decrease in GFP-positive cells observed in 10% FCS (fetal calf serum). For in vivo application they propose modifications with the hydrophilic polymer poly-[N-(2hydroxy-propyl)methacrylamide]. Thus, Read et al. (2005, supra) did not achieve the prevention of aggregation of polyplexes and binding of polycationic proteins to serum proteins. Furthermore, due to the large excess of polymer, which is characterized by the high N/P ratio, strong complexes are formed when complexing the nucleic acid, which are only of limited use in vivo due to their strong tendency of salt induced agglomeration and interactions with serum contents (opsonization). Additionally, these complexes may excite an acute immune response, when used for purposes of gene therapy. Neither did Read et al. (2003, supra) provide in vivo data for the RPC based complexes shown in the publication. It has turned out that these strong RPC based complexes are completely inactive subsequent to local administration into the dermis. Furthermore Read et al. (2005, supra) used stringent oxidation conditions (30% DMSO) to induce the generation of high molecular polymers with as long as possible chain lengths ("step-growth polymerization") to ensure complete complexation of the nucleic acid cargo.

In an approach similar to Read et al., McKenzie et al. (McKenzie, D. L., K. Y. Kwok, et al. (2000), J Biol Chem 275(14): 9970-7., McKenzie, D. L., E. Smiley, et al. (2000), Bioconjug Chem 11(6): 901-9, and U.S. Pat. No. 6,770,740 B1) developed self-crosslinking peptides as gene delivery agents by inserting multiple cysteines into short synthetic peptides for the purpose of decreasing toxicity as observed with high-molecular polycations. For complexation of DNA they mixed the self-crosslinking peptides with DNA to induce interpeptide disulfide bonds concurrently to complexation of the DNA cargo. For in vivo gene delivery approaches they propose the derivatization of the self-crosslinking peptides with a stealthing (e.g. polyethylene glycol) or targeting agent operatively attached to the peptide at a site distal from each terminus. In a further approach the same authors developed for the purpose of masking DNA peptide condensates and thereby reducing interaction with blood components, the derivatization of the non crosslinking peptide CWK$_{18}$ with polyethylene glycol by reducible or non-reducible linkages (Kwok, K. Y., D. L. McKenzie, et al. (1999). "Formulation of highly soluble poly(ethylene glycol)-peptide DNA condensates." J Pharm Sci 88(10): 996-1003.).

Summarizing the above, the present prior art as exemplified above suffers from various disadvantages. One particular disadvantage of the self-crosslinking peptides as described by Read et al. (2003, supra) or McKenzie et al. (2000 I and II, supra and U.S. Pat. No. 6,770,740 B1) concerns the high positive charge on the surface of the particles formed. Due to this charge, the particles exhibit a high instability towards agglomeration when subjecting these particles in vivo to raised salt concentrations. Such salt concentrations, however, typically occur in vivo in cells or extracellular media. Furthermore, complexes with a high positive charge show a strong tendency of opsonization. This leads to an enhanced uptake by macrophages and to a fast inactivation of the complex due to degradation. Particularly the uptake of these complexes by cells of the immune system in general leads to a downstream stimulation of different cytokines. This unspecific activation of the innate immune system, however, represents a severe disadvantage of these systems and should be avoided, particularly for the purpose of several aspects of gene therapy, where an acute immune response (cytokine storm) is strictly to be avoided. Additionally, in biological systems positively charged complexes can easily be bound or immobilized by negatively charged components of the extracellular matrix or the serum. Also, the nucleic acids in the complex may be released too early, leading to reduced efficiency of the transfer and half life of the complexes in vivo. Furthermore, a reversible derivatization of carriers with a stealthing agent being advantageous for in vivo gene delivery, such as polyethylene glycol (PEG), was only possible for peptide monomers but not for self-crosslinking peptides or rather for a polymeric carrier with a defined polymer chain length. In particular, such a reversible derivatization was not possible at the terminal ends of the crosslinked cationic peptide carrier. Additionally, in the prior art only high-molecular polymers with long polymer chains or with an undefined polymer chain length consisting of self-crosslinking peptides were described, which unfortunately compact their cargo to such an extent that cargo release in the cell is limited. The extremely undefined polymer chain length is further problematic regarding regulatory approvement of a medicament based on RPC. One precondition for such approvement is that every preparation of the medicament has the same composition, the same structure and the same properties. This cannot be ensured for complexes based on RPC's from the prior art. Furthermore, the RPC-based polymers or complexes provided in the prior art are difficult to characterize due to their undefined structure or polymer chain length.

In consequence, no generally applicable method or carrier have been presented until today which allows both compacting and stabilizing a nucleic acid for the purposes of gene therapy and other therapeutic applications, and which show a good transfection activity in combination with a good release of the nucleic acid cargo, particularly in vivo and low or even no toxicity, e.g. due to the combination of a reversible stealthing and a reversible complexation of the nucleic acid by self-crosslinking polymers. Accordingly, there is still a need in the art to provide improved carriers for the purpose of gene transfer which are both stable enough to carry their cargo to the target before they being metabolically cleaved and which are nevertheless cleared from the tissue before they can accumulate and reach toxic levels.

The object underlying the present invention is therefore to provide a carrier, particularly for the delivery of nucleic acids for therapeutic or prophylactic applications, which is capable of compacting the nucleic acids and which allows their efficient introduction into different cell lines in vitro but also enables transfection in vivo. As uptake by cells occurs via the endosomal route, such a carrier or a complexing agent should also allow or provide for efficient release of the nucleic acid from endosomes. A further object is to provide a carrier that upon complexation with a nucleic acid exhibits resistance to agglomeration. A yet further object is to provide enhanced stability to the nucleic acid cargo with respect to serum containing media. Another object is to enable efficient in vivo activity without a strong acute immune reaction. A further object is to overcome any of the disadvantages or limitations of the known carriers for nucleic acid delivery as described e.g. herein-above. Further objects that are addressed by the present invention will become clear on the basis of the following description, the examples and the patent claims.

The objects are solved by the subject matter of the present invention as set forth in the patent claims.

SUMMARY OF THE INVENTION

In a first aspect, the invention provides a composition comprising a cationic peptide or polymer, a cationic lipidoid compound, and a nucleic acid compound. The lipidoid compound is preferably a compound which comprises two or more cationic nitrogen atoms and at least two lipophilic tails. In contrast to many conventional cationic lipids, the lipidoid compound may be free of a hydrolysable linking group, in particular linking groups comprising hydrolysable ester, amide or carbamate groups. The cationic nitrogen atoms of the lipidoid may be cationisable or permanently cationic, or both types of cationic nitrogens may be present in the compound.

In one embodiment, the lipidoid compound is a compound according to formula I

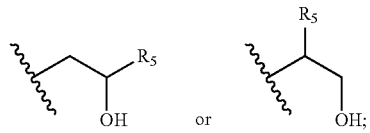
(formula I)

wherein each occurrence of $R_A$ is independently unsubstituted, cyclic or acyclic, branched or unbranched $C_{1-20}$ aliphatic; substituted or unsubstituted, cyclic or acyclic, branched or unbranched $C_{1-20}$ heteroaliphatic; substituted or unsubstituted aryl; substituted or unsubstituted heteroaryl;

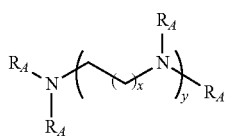

and wherein at least one $R_A$ is

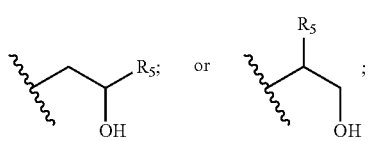

Moreover, each occurrence of $R_5$ is independently unsubstituted, cyclic or acyclic, branched or unbranched $C_{8-16}$ aliphatic; substituted or unsubstituted aryl; or substituted or unsubstituted heteroaryl. Each occurrence of x is an integer between 1 and 10, inclusive; and each occurrence of y is an integer between 1 and 10, inclusive. In addition, any pharmaceutically acceptable salt of the compound of formula I is included within the scope of the lipidoid compound. In some embodiments the lipidoid compound according to formula I comprises a PEG moiety.

In another embodiment, the lipidoid is a compound that comprises two or three moieties of formula IIa and/or formula IIb:

$$—N(R_1)—CH_2—CH(R_5)—R_2$$ (formula IIa)

$$—N^+(R_3)(R_4)—CH_2—CH(R_5)—R_2$$ (formula IIb)

wherein, independently for each individual moiety of formula IIa or formula IIb, $R_1$ is selected from hydrogen or $C_1$-$C_4$-alkyl; $R_2$ is selected from linear or branched, saturated or unsaturated $C_6$-$C_{16}$ hydrocarbyl chain, $R_3$ and $R_4$ are at each occurrence independently selected from $C_1$-$C_4$-alkyl, and $R_5$ is hydrogen or hydroxyl, preferably hydroxyl. In some embodiments the lipidoid compound according to formula IIa and/or IIb comprises a PEG moiety.

In a further embodiment, the lipidoid is a compound according to formula III

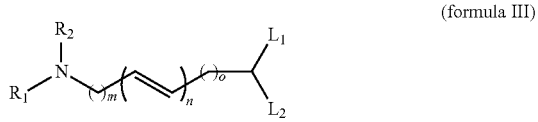
(formula III)

wherein $R_1$ and $R_2$ are each independently selected from the group consisting of hydrogen, an optionally substituted, saturated or unsaturated $C_1$-$C_{20}$ hydrocarbyl, and an optionally substituted, saturated or unsaturated $C_6$-$C_{20}$ acyl; $L_1$ and $L_2$ are each independently selected from optionally substituted, saturated or unsaturated $C_1$-$C_{30}$ hydrocarbyls; m and o are each independently selected from the group consisting of zero and any positive integer; and n is any positive integer. In some embodiments of the invention $R_1$, $R_2$, $L_1$ and/or $L_2$ are each independently a PEG moiety or substituted with a PEG moiety.

The cationic peptide or polymer may, for example, be an oligo- or polypeptide comprising, or based on, basic amino acids selected from Arg, Lys, His and/or Orn. Alternatively, it may be a polymer based on monomeric units which do not represent amino acids, such as a cationic polysaccharide, polyimine or polyacrylate.

The nucleic acid compound may, for example, selected from chemically modified or unmodified DNA, single stranded or double stranded DNA, coding or non-coding DNA, optionally selected from plasmid, (short) oligodesoxynucleotide (i.e. a (short) DNA oligonucleotide), genomic DNA, DNA primers, DNA probes, immunostimulatory DNA, aptamer, or any combination thereof. Alternatively, or in addition, such a nucleic acid molecule may be selected e.g. from any PNA (peptide nucleic acid). Further alternatively, or in addition, and also according to a particularly preferred embodiment, the nucleic acid is selected from chemically modified or unmodified RNA, single-stranded or double-stranded RNA, coding or non-coding RNA, optionally selected from messenger RNA (mRNA), (short) oligoribonucleotide (i.e. a (short) RNA oligonucleotide), viral RNA, replicon RNA, transfer RNA (tRNA), ribosomal RNA (rRNA), immunostimulatory RNA (isRNA), microRNA, small interfering RNA (siRNA), small nuclear RNA (snRNA), small-hairpin RNA (shRNA), or a riboswitch, an RNA aptamer, an RNA decoy, an antisense RNA, a ribozyme, or any combination thereof. Preferably, the nucleic acid molecule of the complex is an RNA. More preferably, the nucleic acid molecule of the complex is a (linear) single-stranded RNA, even more preferably an mRNA or an immunostimulatory RNA.

The composition may further be characterised in that its content of lipidoid is relatively low, relative to the amount of cationic peptide or polymer, or to the amount of nucleic acid. In one embodiment, the weight ratio of the cationic peptide or polymer to the nucleic acid compound is at least about 1, and the ratio of the lipidoid to the nucleic acid compound is not higher than about 15 nmol/µg. In another embodiment, the weight ratio of the lipidoid to the cationic peptide or polymer is not higher than about 1:50, and/or the ratio of the lipidoid to the cationic peptide or polymer is not higher than about 2 nmol/µg.

In a further aspect, the invention provides a nanoparticle comprising the cationic peptide or polymer, the lipidoid and the nucleic acid compound, for example in the form of a complex.

In a further aspect, the invention provides a composition comprising such nanoparticle, or a plurality of such nanoparticles. The composition may be formulated, for example, as a sterile liquid dispersion or as a sterile solid composition, such as a powder or lyophilised form for reconstitution with an aqueous liquid carrier.

In a yet further aspect, the invention provides a kit for preparing a composition as defined above. For example, the kit may comprise a first kit component comprising the cationic peptide or polymer, and/or the lipidoid; and a second kit component comprising the nucleic acid compound.

In a yet further aspect, the invention relates to the medical use of the composition, the nanoparticle, or the kit according to any of the aspects above. The medical use may, for example, comprise the prophylaxis, treatment and/or amelioration of diseases selected from cancer or tumour diseases, infectious diseases, preferably (viral, bacterial or protozoological) infectious diseases, autoimmune diseases, allergies or allergic diseases, monogenetic diseases, i.e. (hereditary) diseases, or genetic diseases in general, diseases which have a genetic inherited background and which are typically caused by a defined gene defect and are inherited according to Mendel's laws, cardiovascular diseases, neuronal diseases, diseases of the respiratory system, diseases of the digestive system, diseases of the skin, musculoskeletal disorders, disorders of the connective tissue, neoplasms, immune deficiencies, endocrine, nutritional and metabolic diseases, eye diseases, ear diseases and diseases associated with a peptide or protein deficiency.

The invention is based on the discovery that the delivery of biologically active cargo materials such as nucleic acids to certain tissues or target cells may be substantially improved by using a vehicle which combines a cationic peptide or polymer and a lipidoid, in that the cargo material is effectively taken up by cells whereas the toxicity that is usually associated with the lipidoid is substantially reduced.

Further objects, aspects, useful embodiments, applications, beneficial effects and advantages of the invention will become apparent on the basis of the detailed description, the examples and claims below.

BRIEF DESCRIPTION OF THE FIGURES

Similarly.

DETAILED DESCRIPTION OF THE INVENTION

Figure 1A:
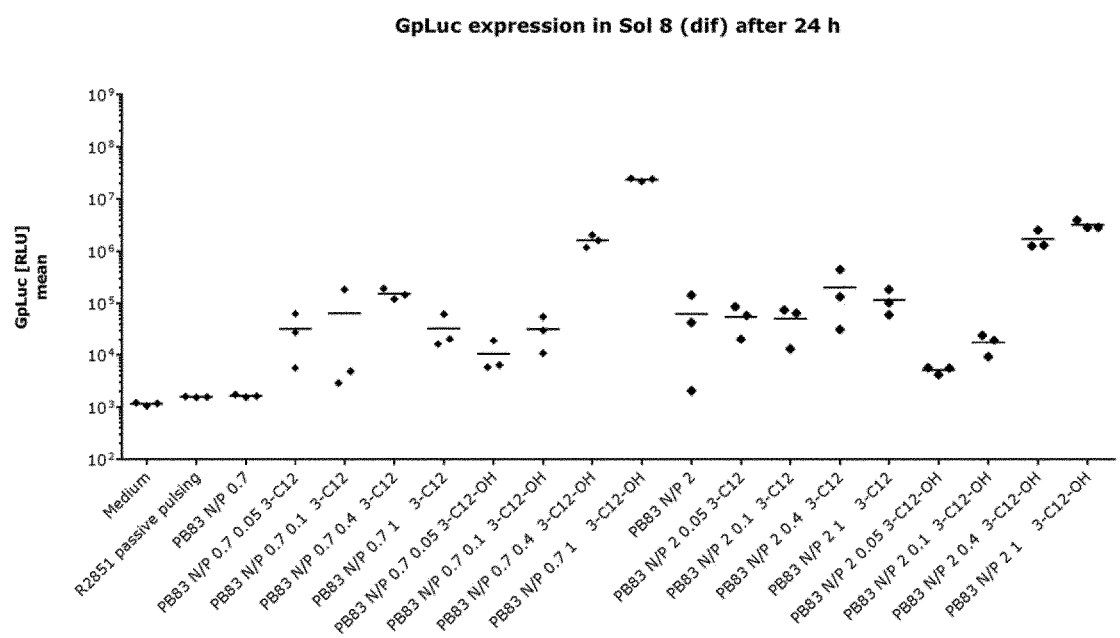
FIGS. 1A to 1C show the effect of the inventive polymer-lipid or polymer-lipidoid formulations on transfection efficiency on Sol8 muscle cells in vitro. All transfection experiments were performed in triplicates, using GpLuc mRNA (SEQ ID NO: 12) as a cargo. Moreover, negative controls (buffer, passive pulsing) have been included. In addition to the inventive polymer-lipid or polymer-lipidoid transfection reagents, polymer only has been used for comparison as well as the pure GpLuc mRNA without the use of transfection reagents (also labelled as R2851 herein).

Unless defined otherwise, or unless the specific context requires otherwise, all technical terms used herein have the same meaning as is commonly understood by a person skilled in the relevant technical field.

Unless the context indicates or requires otherwise, the words "comprise", "comprises" and "comprising" and similar expressions are to be construed in an open and inclusive sense, as "including, but not limited to" in this description and in the claims.

The expressions, "one embodiment", "an embodiment", "a specific embodiment" and the like mean that a particular feature, property or characteristic, or a particular group or combination of features, properties or characteristics, as referred to in combination with the respective expression, is present in at least one of the embodiments of the invention. The occurrence of these expressions in various places throughout this description do not necessarily refer to the same embodiment. Moreover, the particular features, properties or characteristics may be combined in any suitable manner in one or more embodiments.

The singular forms "a", "an" and "the" should be understood as to include plural references unless the context clearly dictates otherwise.

Percentages in the context of numbers should be understood as relative to the total number of the respective items. In other cases, and unless the context dictates otherwise, percentages should be understood as percentages by weight (wt.-%).

In a first aspect, the invention provides a composition comprising a cationic peptide or polymer, a cationic lipidoid compound, and a nucleic acid compound.

In the context of the invention, a "composition" refers to any type of composition in which the specified ingredients may be incorporated, optionally along with any further constituents. Thus, the composition may be a dry composition such as a powder or granules, or a solid unit such as a lyophilised form or a tablet. Alternatively, the composition may be in liquid form, and each constituent may be independently incorporated in dissolved or dispersed (e.g. suspended or emulsified) form. In one of the preferred embodiments, the composition is formulated as a sterile solid composition, such as a powder or lyophilised form for reconstitution with an aqueous liquid carrier. Such formulation is also preferred for those versions of the composition which comprise a nucleic acid cargo as described in further detail below.

As used herein, a "compound" means a chemical substance, which is a material consisting of molecules having essentially the same chemical structure and properties. For a small molecular compound, the molecules are typically identical with respect to their atomic composition and structural configuration. For a macromolecular or polymeric compound, the molecules of a compound are highly similar but not all of them are necessarily identical. For example, a segment of a polymer that is designated to consist of 50 monomeric units may also contain individual molecules with e.g. 48 or 53 monomeric units.

As used herein, a peptide is a compound comprising a plurality of amino acid monomers linked by peptide, or amide, bonds. Depending on the size of the peptide, it may also be referred to as an oligopeptide or a polypeptide. In principle, a protein is also a polypeptide.

A polymer, in the context of the invention, is a compound whose molecules are composed of a plurality repeating subunits. A polymer may be based on different subunits, such as a copolymer.

A lipidoid compound, also simply referred to as lipidoid, is a lipid-like compound, i.e. an amphiphilic compound with lipid-like physical properties. The lipidoid compound is preferably a compound which comprises two or more cationic nitrogen atoms and at least two lipophilic tails. In contrast to many conventional cationic lipids, the lipidoid compound may be free of a hydrolysable linking group, in particular linking groups comprising hydrolysable ester, amide or carbamate groups. The cationic nitrogen atoms of the lipidoid may be cationisable or permanently cationic, or both types of cationic nitrogens may be present in the compound.

Unless a different meaning is clear from the specific context, the term "cationic" means that the respective structure bears a positive charge, either permanently, or not permanently but in response to certain conditions such as pH. Thus, the term "cationic" covers both "permanently cationic" and "cationisable".

As used herein, "permanently cationic" means that the respective compound, or group or atom, is positively charged at any pH value or hydrogen ion activity of its environment. Typically, the positive charge is results from the presence of a quaternary nitrogen atom. Where a compound carries a plurality of such positive charges, it may be referred to as permanently polycationic, which is a subcategory of permanently cationic.

In this context, the prefix "poly-" refers to a plurality of atoms or groups having the respective property in a compound. If put in parenthesis, the presence of a plurality is optional. For example, (poly)cationic means cationic and/or polycationic. However, the absence of the prefix should not be interpreted such as to exclude a plurality. For example, a polycationic compound is also a cationic compound and may be referred to as such.

"Cationisable" means that a compound, or group or atom, is positively charged at a lower pH and uncharged at a higher pH of its environment. Also in non-aqueous environments where no pH value can be determined, a cationisable compound, group or atom is positively charged at a high hydrogen ion concentration and uncharged at a low concentration or activity of hydrogen ions. It depends on the individual properties of the cationisable or polycationisable compound, in particular the $pK_a$ of the respective cationisable group or atom, at which pH or hydrogen ion concentration it is charged or uncharged. In diluted aqueous environments, the fraction of cationisable compounds, groups or atoms bearing a positive charge may be estimated using the so-called Henderson-Hasselbalch equation which is well-known to a person skilled in the art.

For example, if a compound or moiety is cationisable, it is preferred that it is positively charged at a pH value of about 1 to 9, preferably 4 to 9, 5 to 8 or even 6 to 8, more preferably of a pH value of or below 9, of or below 8, of or below 7, most preferably at physiological pH values, e.g. about 7.3 to 7.4, i.e. under physiological conditions, particularly under physiological salt conditions of the cell in vivo.

Unless a different meaning is clear from the specific context, "cationised" typically means that a cationisable structure is in a state where it actually bears a positively charge, as for example in the case of a basic amino acid such as arginine in a neutral physiological environment.

A "multimer" of a compound, as in the case of the disulfide-linked multimer of the cationic compound comprising at least one cationic moiety P, should be understood as a compound comprising at least two units of the first compound of which it is the multimer. This is independent of whether or not the first compound already contains a plurality of repeating units.

An —SH group means a sulfhydryl group.

The invention is based on the discovery that the combination of a lipidoid with a cationic peptide or polymer is highly effective in complexing and delivering nucleic acids into cells, at an unexpected degree of tolerability. More specifically, the inventors have found that such combination shows an additive effect of the carrier components (i.e. the lipidoid and the polymer or peptide) in terms of their effectiveness to deliver a cargo into cells, whereas there is no or surprisingly little additive effect in terms of toxicity.

Advantageously, the cationic peptide or polymer allows to considerably vary its peptide or polymeric content and thus to modulate its biophysical/biochemical properties quite easily, e.g. allowing to incorporate various types of cationic or cationisable peptides, proteins or polymers and optionally adding other components, e.g. other amino acid components.

Also very surprising is the observation that even small amounts of the lipidoid—relative to the amount of the cationic peptide or polymer, and/or relative to the nucleic acid compound, are able to enhance the cellular delivery of nucleic acid cargo without substantially increasing the undesirable effects or the toxicity of the composition. The invention may be practised with as little as about 0.1 to about 10% of the typical amount of lipids used in lipoplexes or lipid nanoparticles that have been proposed for the delivery of e.g. RNA and the transfection of cells. Without wishing to be bound by theory, the inventors assume that such low amount of lipidoid has been pivotal in achieving the high tolerability of the composition of the invention.

The cationic peptide or polymer may be any permanently cationic or cationisable compound based on monomeric units which may or may not represent amino acids. The cationic peptide or polymer may, for example, be selected from those cationic peptides or polymers that are commonly known to have the ability to form complexes with nucleic acid compounds.

In one embodiment, the cationic peptide or polymer is selected from protamine, nucleoline, oligo- or polylysine, oligo- or polyarginine, cell-penetrating peptides, chimeric CPPs, transportan, MPG peptides, HIV-binding peptides, Tat, HIV-1 Tat, Tat-derived peptides, members of the penetratin family, penetratin, Antennapedia-derived peptides, pAntp, pIsl, antimicrobial-derived CPPs, buforin-2, Bac715-24, SynB, SynB(1), pVEC, hCT-derived peptides, SAP, MAP, KALA, PpTG20, FGF, lactoferrin, histones, VP22, VP22-derived peptides, HSV, protein transduction domains, PpT620, proline-rich peptides, arginine-rich peptides, lysine-rich peptides, Pep-1, calcitonin peptides, β-amino acids, reversed polyamides, poly(N-ethyl-4-vinylpyridinium bromide), poly(dimethylaminoethyl methylacrylate), poly (amidoamine), polybetaaminoester, diamine-modified 1,4-butanediol diacrylate-co-5-amino-1-pentanol polymers, polypropylamine dendrimers, pAMAM-based dendrimers, polyimines, poly(ethyleneimine), poly(propyleneimine), polyallylamine, 1,5-dimethyl-1,5-diazaundecamethylene polymethobromide, hexadimethrine bromide, cationic polysaccharides, cationic cyclodextrin-based polymers, cationic dextran-based polymers, chitosans, silane backbone-based polymers, PMOXA-PDMS copolymers, block copolymers of one or more cationic blocks and one or more neutral blocks.

In one embodiment, the cationic peptide or polymer is selected from native peptides. Native means that the peptide is produced by nature, i.e. by a living organism. Of course, a native peptide may also be chemically synthesised, nevertheless it is a peptide occurring in nature. Optionally, a native peptide may be chemically modified.

The native cationic peptide selected for the composition of the invention may, for example, be a member of the group of cell-penetrating peptides (CPPs). Many CPPs have an amino acid composition that is rich in basic amino acids such as lysine or arginine.

In one embodiment, the cell-penetrating peptide is from the group of cysteine-free versions of TAT-derived peptides (TAT meaning "trans-activator of transcription"), such as TAT or $HIV_1$-TAT, Tat-AIE dots, $TAT_{(47-57)}$, $TAT_{(49-57)}$, $TAT_{(48-60)}$, R9-TAT, Tat-GFP-Tat, Tat-GFP, 6His-TAT-Ainp1, 6His-TAT-GFP, 6×His-TAT-SOD, TAT-gelonin, pTat, EGFP-TAT, Tat-Dex, Tat-PCP, P42-TAT.

In another embodiment, the cell-penetrating peptide is from the group of antennapedia-derived peptides, also known as the penetratin family or pAntp, such as $pAntp_{43-58}$.

In a further embodiment, the cell-penetrating peptide is selected from hCT-derived peptides, such as hCT9-32, hCT12-32, hCT15-32, hCT18-32, hCT21-32. A further group of cell-penetrating peptides potentially of interest is the group of histones, such as H2A or H4.

According to a further embodiment, the cell-penetrating peptide is an antimicrobial-derived cationic CPP, such as buforin-2, magainin II, cecropin, andropin, moricin, ceratotoxin, melittin, bombinin, brevinin-1, esculentins, CAP18, LL37, Bac715-24/BAC715-24, Bac1-7, Bac1-15, Bac1-17, Bac1-24, Bac5-24, Bac7-24, Bac9-24, Bac11-24, Bac13-24, Bac15-24, SynB1, SynB3, SynB5, dermaseptin S4, abaecin, apidaecin, prophenin, or indolicidin.

Optionally, the CPP is a cysteine-free member of the transportan family.

Optionally, the CPP is a chimeric or synthetically modified peptide, such as a member of the MPG peptide family, such as MPG-NLS, EGFP-MPG, MPGα, MPGβ; or biotinyl-penetratin, PAF26, PAF95, PAF96, CRGDK, P28, RALA peptide, RTAT-ELPBC, GST-(HE)12EFG5-TAT, FabRev1-Tat, G3R6TAT, MAP, Pep-1, ppTG, ppTG1, ppTG20, EGFP-ppTG20; or MPG, $KLA-TAT_{(47-57)}$, or TatLK15.

According to another embodiment, the cationic peptide or polymer is from the group consisting of synthetic peptides, or oligo- or poly(amino acids), which are not known to occur in nature. Preferred synthetic peptides are compounds composed of 2 to about 50 amino acid residues, or more preferably from about 5 to about 30 amino acid residues, which are rich in basic amino acids such as arginine, lysine, histidine, and/or ornithine. Preferably, at least about 50% of the amino acid residues of the cationic peptide are represented by the basic amino acids.

Optionally, the cationic peptide is entirely or predominantly composed of one specific basic amino acid, such as a segment of about 5 to about 30 Arg, Lys, His or Orn, for example $Arg_5$, $Arg_6$, $Arg_7$, $Arg_8$, $Arg_9$, $Arg_{10}$, $Arg_{11}$, $Arg_{12}$, $Arg_{13}$, $Arg_{14}$, $Arg_{15-30}$; $Lys_5$, $Lys_6$, $Lys_7$, $Lys_8$, $Lys_9$, $Lys_{10}$, $Lys_{11}$, $Lys_{12}$, $Lys_{13}$, $Lys_{14}$, $Lys_{15-30}$; $His_5$, $His_6$, $His_7$, $His_8$, $His_9$, $His_{10}$, $His_{11}$, $His_{12}$, $His_{13}$, $His_{14}$, $His_{15-30}$; or $Orn_5$, $Orn_6$, $Orn_7$, $Orn_8$, $Orn_9$, $Orn_{10}$, $Orn_{11}$, $Orn_{12}$, $Orn_{13}$, $Orn_{14}$, $Orn_{15-30}$.

Other useful peptides are composed of two or more different basic amino acids, as in the following examples which are meant to refer to the composition of sequence without specifying a particular order in which the amino acid residues occur:

$Arg_{(4-29)}Lys_1$, $Arg_{(4-29)}His_1$, $Arg_{(4-29)}Orn_1$, $Lys_{(4-29)}His_1$, $Lys_{(4-29)}Orn_1$, $His_{(4-29)}Orn_1$, $Arg_{(3-28)}Lys_2$, $Arg_{(3-28)}His_2$, $Arg_{(3-28)}Orn_2$, $Lys_{(3-28)}His_2$, $Lys_{(3-28)}Orn_2$, $His_{(3-28)}Orn_2$, $Arg_{(2-27)}Lys_3$, $Arg_{(2-27)}His_3$, $Arg_{(2-27)}Orn_3$, $Lys_{(2-27)}His_3$, $Lys_{(2-27)}Orn_3$, $His_{(2-27)}Orn_3$, $Arg_{(1-26)}Lys_4$, $Arg_{(1-26)}His_4$, $Arg_{(1-26)}Orn_4$, $Lys_{(1-26)}His_4$, $Lys_{(1-26)}Orn_4$, $His_{(1-26)}Orn_4$, $Arg_{(3-28)}Lys_1His_1$, $Arg_{(3-28)}Lys_1Orn_1$, $Arg_{(3-28)}His_1Orn_1$, $Arg_1Lys_{(3-28)}His_1$, $Arg_1Lys_{(3-28)}Orn_1$, $Lys_{(3-28)}His_1Orn_1$, $Arg_1Lys_1His_{(3-28)}$, $Arg_1His_{(3-28)}Orn_1$, $Lys_1His_{(3-28)}Orn_1$;

$Arg_{(2-27)}Lys_2His_1$, $Arg_{(2-27)}Lys_1His_2$, $Arg_{(2-27)}Lys_2Orn_1$, $Arg_{(2-27)}Lys_1Orn_2$, $Arg_{(2-27)}His_2Orn_1$, $Arg_{(2-27)}His_1Orn_2$, $Arg_2Lys_{(2-27)}His_1$, $Arg_1Lys_{(2-27)}His_2$, $Arg_2Lys_{(2-27)}Orn_1$, $Arg_1Lys_{(2-27)}Orn_2$, $Lys_{(2-27)}His_1Orn_1$, $Lys_{(2-27)}His_1Orn_2$, $Arg_2Lys_1His_{(2-27)}$, $Arg_1Lys_2His_{(2-27)}$, $Arg_2His_{(2-27)}Orn_1$, $Arg_1His_{(2-27)}Orn_2$, $Lys_2His_{(2-27)}Orn_1$, $Lys_1His_{(2-27)}Orn_2$;

$Arg_{(1-26)}Lys_3His_1$, $Arg_{(1-26)}Lys_2His_2$, $Arg_{(1-26)}Lys_1His_3$, $Arg_{(1-26)}Lys_3Orn_1$, $Arg_{(1-26)}Lys_2Orn_2$, $Arg_{(1-26)}Lys_1Orn_3$, $Arg_{(1-26)}His_3Orn_1$, $Arg_{(1-26)}His_2Orn_2$, $Arg_{(1-26)}His_1Orn_3$, $Arg_3Lys_{(1-26)}His_1$, $Arg_2Lys_{(1-26)}His_2$, $Arg_1Lys_{(1-26)}His_3$, $Arg_3Lys_{(1-26)}Orn_1$, $Arg_2Lys_{(1-26)}Orn_2$, $Arg_1Lys_{(1-26)}Orn_3$, $Lys_{(1-26)}His_3Orn_1$, $Lys_{(1-26)}His_2Orn_2$, $Lys_{(1-26)}His_1Orn_3$, $Arg_3Lys_1His_{(1-26)}$, $Arg_2Lys_2His_{(1-26)}$, $Arg_1Lys_3His_{(1-26)}$, $Arg_3His_{(1-26)}Orn_1$, $Arg_2His_{(1-26)}Orn_2$, $Arg_1His_{(1-26)}Orn_3$, $Lys_3His_{(1-26)}Orn_1$, $Lys_2His_{(1-26)}Orn_2$, $Lys_1His_{(1-26)}Orn_3$;

$Arg_{(2-27)}Lys_1His_1Orn_1$, $Arg_1Lys_{(2-27)}His_1Orn_1$, $Arg_1Lys_1His_{(2-27)}Orn_1$, $Arg_1Lys_1His_1Orn_{(2-27)}$;

$Arg_{(1-26)}Lys_2His_1Orn_1$, $Arg_{(1-26)}Lys_1His_2Orn_1$, $Arg_{(1-26)}Lys_1His_1Orn_2$, $Arg_2Lys_{(1-26)}His_1Orn_1$, $Arg_1Lys_{(1-26)}His_2Orn_1$, $Arg_1Lys_{(1-26)}His_1Orn_2$, $Arg_2Lys_1His_{(1-26)}Orn_1$, $Arg_1Lys_2His_{(1-26)}Orn_1$, $Arg_1Lys_1His_{(1-26)}Orn_2$, $Arg_2Lys_1His_1Orn_{(1-26)}$, $Arg_1Lys_2His_1Orn_{(1-26)}$, $Arg_1Lys_1His_2Orn_{(1-26)}$.

It may further be useful to incorporate within the cationic peptide one or more hydrophilic amino acid residues along with the basic amino acids. Among the hydrophilic amino acids useful for this purpose, those with an uncharged polar side chain are preferred, in particular Thr, Ser, Asn and/or Gln. The incorporation of such amino acids or of sequences rich in these amino acids enables a more flexible binding to the nucleic acid cargo. This may lead to a more effective compaction of the nucleic acid cargo and hence to a better protection against nucleases and unwanted decompaction. It also allows provision of a carrier which exhibits a reduced cationic charge over the entire carrier and in this context to better adjusted binding properties, if desired or necessary.

Examples for useful partial sequences to be incorporated in the cationic include the following: Ser-Thr, Thr-Ser, Ser-Ser, Thr-Thr, Ser-Thr-Ser, Thr-Ser-Thr, Ser-Ser-Ser, Thr-Thr-Thr, Ser-Thr-Ser-Thr, Thr-Ser-Thr-Ser, Ser-Ser-Ser-Ser, Thr-Thr-Thr-Thr, Gln-Asn, Asn-Gln, Gln-Gln, Asn-Asn, Gln-Asn-Gln, Asn-Gln-Asn, Gln-Gln-Gln, Asn-Asn-Asn, Gln-Asn-Gln-Asn, Asn-Gln-Asn-Gln, Gln-Gln-Gln-Gln, Asn-Asn-Asn-Asn, Ser-Asn, Asn-Ser, Ser-Ser, Asn-Asn, Ser-Asn-Ser, Asn-Ser-Asn, Ser-Ser-Ser, Asn-Asn-Asn, Ser-Asn-Ser-Asn, Asn-Ser-Asn-Ser, Ser-Ser-Ser-Ser, or Asn-Asn-Asn-Asn, etc. Such sequences may be repeated e.g. 1, 2, 3, 4, 5, 6, 7, 8, 9, 10, 12, 13, 14, 15 or even more times, or combined with each other as suitable.

Optionally, the sequence rich in hydrophilic amino acids may contain at least one proline, which may serve as a structure breaker of longer sequences of Ser, Thr and Asn. Two, three or more prolines may also be incorporated, in particular in longer sequences.

It may further be useful to incorporate within the cationic peptide one or more lipophilic amino acids, in particular Leu, Val, Ile, Ala, and/or Met. Such lipophilic amino acids may be able to participate in the complex formed upon combination of the cationic peptide with a nucleic acid cargo.

The use of lipophilic amino acids enables a stronger compaction of the nucleic acid. This may be due to specific interactions of the lipophilic amino acids and the nucleic acid cargo which provide for additional stability of the complex formed between the carrier(s) and the cargo. The stabilisation may be similar to noncovalent association or crosslinking between polymer strands. Especially in an aqueous environment, this type of interaction is typically strong and provides a significant effect.

Examples for useful subsequences include Leu-Val, Val-Leu, Leu-Leu, Val-Val, Leu-Val-Leu, Val-Leu-Val, Leu-Leu-Leu, Val-Val-Val, Leu-Val-Leu-Val, Val-Leu-Val-Leu, Leu-Leu-Leu-Leu, Val-Val-Val-Val, Ile-Ala, Ala-Ile, Ile-Ile, Ala-Ala, Ile-Ala-Ile, Ala-Ile-Ala, Ile-Ile-Ile, Ala-Ala-Ala, Ile-Ala-Ile-Ala, Ala-Ile-Ala-Ile, Ile-Ile-Ile-Ile, Ala-Ala-Ala-Ala, Met-Ala, Ala-Met, Met-Met, Ala-Ala, Met-Ala-Met, Ala-Met-Ala, Met-Met-Met, Ala-Ala-Ala, Met-Ala-Met-Ala, Ala-Met-Ala-Met, or Met-Met-Met-Met etc. Such sequences may be repeated e.g. 1, 2, 3, 4, 5, 6, 7, 8, 9, 10, 12, 13, 14, 15 or more times, or combined with each other.

Optionally, the sequence rich in lipophilic amino acids may contain at least one proline, which may serve as a structure breaker of longer sequences of Leu, Val, Ile, Ala and/or Met. Two, three or more prolines may also be incorporated, in particular in longer sequences.

The properties of the cationic peptide may be further modulated by including in its sequence a non-native amino acid, or by chemical modification of the peptide. For example, specific chemical groups may be introduced. Such groups may be selected such as to allow the attachment of further components or ligands, e.g. by amide formation (e.g. by reaction with carboxylic acids, sulphonic acids, amines, etc.), by Michael addition (e.g using maleinimide moieties, α,β unsaturated carbonyls, etc.), by click chemistry (e.g. using azides or alkines), by alkene/alkine methatesis (e.g. using alkenes or alkines), imine or hydrozone formation (using aldehydes or ketons, hydrazins, hydroxylamins, amines), complexation reactions (using avidin, biotin, protein G or the like) or components which allow $S_n$-type substitution reactions (e.g with halogenalkans, thiols, alcohols, amines, hydrazines, hydrazides, sulphonic acid esters, oxyphosphonium salts) or other chemical moieties which can be utilised in the attachment of further components.

In another embodiment, the cationic peptide or polymer is selected from natural, synthetic or semisynthetic polymers. Preferably, the polymer exhibits a molecular weight of about 0.5 kDa to about 20 kDa, such as from about 0.5 kDa to about 11.5 kDa, or from about 1 kDa to about 10 kDa, or from about 0.1 kDa to about 8 kDa, or from about 0.1 kDa to about 6 kDa, or from about 0.1 kDa to about 5 kDa, or from about 0.5 kDa to about 5 kDa, or from about 0.3 kDa to about 20 kDa, or from about 0.3 kDa to about 10 kDa, or from about 0.4 kDa to about 10 kDa, or from about 0.5 kDa to about 10 kDa, or from about 0.5 kDa to about 7.5 kDa, or from about 0.5 kDa to about 4 kDa, or from about 0.5 kDa to about 3 kDa, or from about 0.67 kDa to about 2.7 kDa, respectively.

In one embodiment, the cationic polymer is an optionally modified polyacrylate, chitosan, polyethylenimine, polyamine, polyaminoesters, or polyamidoamine, or any copolymer thereof.

Specific preferred cationic polymers include e.g. modified polyaminoacids, such as β-aminoacid-polymers or reversed polyamides; modified polyethylenes, such as (poly(N-ethyl-4-vinylpyridinium bromide)) (PEVP), etc.; modified acrylates, such as (poly(dimethylaminoethyl methylacrylate)) (pDMAEMA), etc.; modified amidoamines such as (poly(amidoamine)) (pAMAM), etc.; modified polybetaaminoester (PBAE), such as diamine end modified 1,4 butanediol diacrylate-co-5-amino-1-pentanol polymers, etc.; dendrimers, such as polypropylamine dendrimers or pAMAM based dendrimers, etc.; polyimine(s), such as poly(ethyleneimine) (PEI or pEI), poly(propyleneimine), etc.; polyallylamine, (1,5-dimethyl-1,5-diazaundecamethylene polymethobromide, or hexadimethrine bromide.

Also preferred are cationic polysaccharides, i.e. sugar backbone-based polymers, such as cyclodextrin based polymers, dextran based polymers, chitosan, etc.; silane backbone-based polymers, such as PMOXA-PDMS copolymers, etc.; as well as blockpolymers consisting of a combination of one or more cationic blocks (e.g. selected of a cationic polymer as mentioned above) and of one or more hydrophilic- or hydrophobic blocks (e.g. polyethylene glycol).

In one of the preferred embodiments, the cationic peptide or polymer is cationic compound comprising at least one cationic moiety P having at least one —SH group capable of forming a disulfide linkage, or a disulfide-linked multimer thereof, wherein moiety P is either a polymer moiety having a molecular weight from about 0.5 kDa to about 30 kDa, or a peptide moiety composed of about 3 to about 100 amino acids wherein at least 10% of the total number of amino acids of the peptide moiety represent basic amino acids selected from arginine (Arg), lysine (Lys), histidine (His) and/or ornithine (Orn).

In one embodiments, the cationic moiety P of the cationic compound is a peptide moiety composed of 3 to 100 amino acids, wherein at least 10% of the total number of amino acids of the peptide moiety represent basic amino acids selected from Arg, Lys, His and/or Orn. Examples of such peptides are disclosed e.g. in WO2012/013326, the disclosure of which is incorporated herein in its entirety.

In this context, a "basic amino acid" is an amino acid which is cationised in a physiological environment, or—more precisely—the majority of whose molecules have a net positive charge at a relatively neutral pH, such as at the physiological pH of extracellular body fluids. This is the case for Arg, Lys, His and Orn.

In the case that P is a peptide moiety, a "disulfide-linked multimer" of P means a peptide or protein resulting from the formation of at least one disulfide linkage between at least two molecules of peptide P. For example, two molecules of peptide P may be connected via one disulfide linkage e.g. to form a longer peptide chain; or they may be connected via two disulfide linkages, e.g. to form a cyclic peptide, a longer peptide chain, or still another structure, depending on the positions of the —SH groups that participate in the formation of the disulfide linkage. A disulfide-linked multimer from more than two peptides P may also have various different shapes, dependent on the nature of P and the disulfide linkage that have formed. If the composition comprises two or more different peptides P, the multimers may result from disulfide linkages between identical or different molecules.

Preferably, a peptide moiety selected as moiety P has a length of about 3 to about 50 amino acids, and more preferably of about 7 to about 30 amino acids, or of about 3 to about 25 amino acids. Also preferred are lengths in the ranges from about 3 to about 20 amino acids, or from about 5 to about 20 amino acids, or from about 7 to about 30 amino acids, or from about 6 to about 18 amino acids, or from about 7 to about 17 amino acids, such as about 5 to about 15 amino acids.

Typically, a peptide moiety selected as moiety P has a molecular weight in the range from about 0.3 kDa to about 50 kDa, in particular from about 0.5 kDa to about 30 kDa, or from about 0.6 kDa to about 10 kDa, or from about 0.8 kDa to about 5 kDa, such as from about 1 kDa to about 3 kDa.

The —SH group(s) in such peptide moiety may be provided by a chemical modification of any of the amino acid residues in the peptide sequence representing P, by the incorporation of a structural unit which is not an amino acid but which comprises a sulfhydryl group, and/or by one or more amino acids comprising such —SH group, such as cysteine (Cys). In one of the preferred embodiments, at least one of the —SH groups of the peptide moiety representing P is provided by Cys. In another embodiment, substantially all —SH groups of P are provided by Cys residues. For example, P may comprise one —SH group which is provided by Cys, or it may provide two —SH groups both of which are provided by Cys.

In a further preferred embodiment, moiety P is a peptide moiety composed of 7 to 30 amino acids, and wherein the at least one —SH group is provided by a Cys residue. Also preferred within this embodiment are peptide moieties comprising one or two —SH groups, each of which —SH group is provided by Cys. Moreover, such peptide moiety may have two terminal ends, as for example in the case of a linear peptide sequence, and the Cys residue may be located at, or in proximity to, one of the terminal ends. Also preferred is such peptide moiety having two terminal ends and at least two Cys residues, wherein at least one of the Cys residues is located at, or in proximity to, each of the terminal ends.

The content of basic amino acids in the peptide moiety selected as P is at least 10% of the total number of amino acids of the peptide sequence, and preferably higher, such as at least about 20%, or at least about 30%, or at least about 40%, or at least about 50%, or at least about 60%, or at least about 70%, respectively. The content of basic amino acids may also be selected in view of the length of the peptide, taking into consideration that the peptide typically also requires the incorporation of at least one, and more preferably at least two, residues having an —SH group that is capable of forming a disulfide linkage, such as cysteine residues or other amino acids modified such as to have an —SH group. In one of the preferred embodiments, the number of basic amino acids in the peptide is between 2 and 5 less than the total number of amino acids in the peptide, in particular between 2 and 4 less than the total number of amino acids, such as 2 or 3 less than the total number of amino acids in P. In a particular embodiment, the peptide is composed of 2 Cys and otherwise only basic amino acids.

The peptide moiety selected as P may comprise a core sequence which is derived from known peptides or proteins that are rich in basic amino acids. In this context, "derived" means that P may comprise further amino acids which are not present in the known peptide from which it has been derived, such as those which are required for its ability to form disulfide linkages, e.g. Cys. Examples of such known peptides rich in basic amino acids include protamine, nucleoline, spermine or spermidine, oligo- or poly-L-lysine (PLL), basic polypeptides, oligo- or polyarginine, cell penetrating peptides (CPPs), chimeric CPPs, such as Transportan, or MPG peptides, HIV-binding peptides, Tat, HIV-1 Tat (HIV), Tat-derived peptides, members of the penetratin family, e.g. penetratin, Antennapedia-derived peptides (particularly from *Drosophila* antennapedia), pAntp, pIsl, etc., antimicrobial-derived CPPs e.g. Buforin-2, Bac715-24, SynB, SynB(1), pVEC, hCT-derived peptides, SAP, PpTG20, FGF, lactoferrin, histones, VP22 derived or analog peptides, HSV, VP22 (Herpes simplex), MAP, KALA or protein transduction domains (PTDs, PpT620, proline-rich peptides, arginine-rich peptides, lysine-rich peptides, Pep-1, L-oligomers, calcitonin peptide(s).

In some of the preferred embodiments, the peptide moiety selected as P comprises a core sequence which is entirely or predominantly composed of one specific basic amino acid, such as a segment of about 5 to about 30 Arg, Lys, His or Orn, for example $Arg_5$, $Arg_6$, $Arg_7$, $Arg_8$, $Arg_9$, $Arg_{10}$, $Arg_{11}$, $Arg_{12}$, $Arg_{13}$, $Arg_{14}$, $Arg_{15-30}$; $Lys_5$, $Lys_6$, $Lys_7$, $Lys_8$, $Lys_9$, $Lys_{10}$, $Lys_{11}$, $Lys_{12}$, $Lys_{13}$, $Lys_{14}$, $Lys_{15-30}$; $His_5$, $His_6$, $His_7$, $His_8$, $His_9$, $His_{10}$, $His_{11}$, $His_{12}$, $His_{13}$, $His_{14}$, $His_{15-30}$; or $Orn_5$, $Orn_6$, $Orn_7$, $Orn_8$, $Orn_9$, $Orn_{10}$, $Orn_{11}$, $Orn_{12}$, $Orn_{13}$, $Orn_{14}$, $Orn_{15-30}$.

The expression "core sequence" means that one or more additional amino acids may be present in the peptide outside of the respective core sequence, in particular amino acids exhibiting a —SH group, such as cysteines. Other useful core sequences are composed of two or more different basic amino acids, as in the following examples which are meant to refer to the composition of sequence without specifying a particular order in which the amino acids occur:

$Arg_{(4-29)}Lys_1$, $Arg_{(4-29)}His_1$, $Arg_{(4-29)}Orn_1$, $Lys_{(4-29)}His_1$, $Lys_{(4-29)}Orn_1$, $His_{(4-29)}Orn_1$, $Arg_{(3-28)}Lys_2$, $Arg_{(3-28)}His_2$, $Arg_{(3-28)}Orn_2$, $Lys_{(3-28)}His_2$, $Lys_{(3-28)}Orn_2$, $His_{(3-28)}Orn_2$, $Arg_{(2-27)}Lys_3$, $Arg_{(2-27)}His_3$, $Arg_{(2-27)}Orn_3$, $Lys_{(2-27)}His_3$, $Lys_{(2-27)}Orn_3$, $His_{(2-27)}Orn_3$, $Arg_{(1-26)}Lys_4$, $Arg_{(1-26)}His_4$, $Arg_{(1-26)}Orn_4$, $Lys_{(1-26)}His_4$, $Lys_{(1-26)}Orn_4$, $His_{(1-26)}Orn_4$, $Arg_{(3-28)}Lys_1His_1$, $Arg_{(3-28)}Lys_1Orn_1$, $Arg_{(3-28)}His_1Orn_1$, $Arg_1Lys_{(3-28)}His_1$, $Arg_1Lys_{(3-28)}Orn_1$, $Lys_{(3-28)}His_1Orn_1$, $Arg_1Lys_1His_{(3-28)}$, $Arg_1His_{(3-28)}Orn_1$, $Lys_1His_{(3-28)}Orn_1$;

$Arg_{(2-27)}Lys_2His_1$, $Arg_{(2-27)}Lys_1His_2$, $Arg_{(2-27)}Lys_2Orn_1$, $Arg_{(2-27)}Lys_1Orn_2$, $Arg_{(2-27)}His_2Orn_1$, $Arg_{(2-27)}His_1Orn_2$, $Arg_2Lys_{(2-27)}His_1$, $Arg_1Lys_{(2-27)}His_2$, $Arg_2Lys_{(2-27)}Orn_1$, $Arg_1Lys_{(2-27)}Orn_2$, $Lys_{(2-27)}His_2Orn_1$, $Lys_{(2-27)}His_1Orn_2$, $Arg_2Lys_1His_{(2-27)}$, $Arg_1Lys_2His_{(2-27)}$, $Arg_2His_{(2-27)}Orn_1$, $Arg_1His_{(2-27)}Orn_2$, $Lys_2His_{(2-27)}Orn_1$, $Lys_1His_{(2-27)}Orn_2$;

$Arg_{(1-26)}Lys_3His_1$, $Arg_{(1-26)}Lys_2His_2$, $Arg_{(1-26)}Lys_1His_3$, $Arg_{(1-26)}Lys_3Orn_1$, $Arg_{(1-26)}Lys_2Orn_2$, $Arg_{(1-26)}Lys_1Orn_3$, $Arg_{(1-26)}His_3Orn_1$, $Arg_{(1-26)}His_2Orn_2$, $Arg_{(1-26)}His_1Orn_3$, $Arg_3Lys_{(1-26)}His_1$, $Arg_2Lys_{(1-26)}His_2$, $Arg_1Lys_{(1-26)}His_3$, $Arg_3Lys_{(1-26)}Orn_1$, $Arg_2Lys_{(1-26)}Orn_2$, $Arg_1Lys_{(1-26)}Orn_3$, $Lys_{(1-26)}His_3Orn_1$, $Lys_{(1-26)}His_2Orn_2$, $Lys_{(1-26)}His_1Orn_3$, $Arg_3Lys_1His_{(1-26)}$, $Arg_2Lys_2His_{(1-26)}$, $Arg_1Lys_3His_{(1-26)}$, $Arg_3His_{(1-26)}Orn_1$, $Arg_2His_{(1-26)}Orn_2$, $Arg_1His_{(1-26)}Orn_3$, $Lys_3His_{(1-26)}Orn_1$, $Lys_2His_{(1-26)}Orn_2$, $Lys_1His_{(1-26)}Orn_3$;

$Arg_{(2-27)}Lys_1His_1Orn_1$, $Arg_1Lys_{(2-27)}His_1Orn_1$, $Arg_1Lys_1His_{(2-27)}Orn_1$, $Arg_1Lys_1His_1Orn_{(2-27)}$;

$Arg_{(1-26)}Lys_2His_1Orn_1$, $Arg_{(1-26)}Lys_1His_2Orn_1$, $Arg_{(1-26)}Lys_1His_1Orn_2$, $Arg_2Lys_{(1-26)}His_1Orn_1$, $Arg_1Lys_{(1-26)}His_2Orn_1$, $Arg_1Lys_{(1-26)}His_1Orn_2$, $Arg_2Lys_1His_{(1-26)}Orn_1$, $Arg_1Lys_2His_{(1-26)}Orn_1$, $Arg_1Lys_1His_{(1-26)}Orn_2$, $Arg_2Lys_1His_1Orn_{(1-26)}$, $Arg_1Lys_2His_1Orn_{(1-26)}$, $Arg_1Lys_1His_2Orn_{(1-26)}$.

As mentioned, these are core sequences, and the complete peptide sequence of such peptidic moiety P further comprises at least one —SH group capable of forming a disulfide linkage. Cys is one of the preferred moieties in the peptide which carries such —SH group. Therefore, the core sequences shown above are preferably part of a peptide moiety which further comprises at least one Cys, such as one or two Cys, wherein the one or two Cys residues are located at one of the terminal ends or at each terminal end of the peptide, respectively. Such particularly preferred sequences selected as moiety P include the following:

Sequences with one terminal Cys residue:
$CysArg_5$, $CysArg_6$, $CysArg_7$, $CysArg_8$, $CysArg_9$, $CysArg_{10}$, $CysArg_{11}$, $CysArg_{12}$, $CysArg_{13}$, $CysArg_{14}$, $CysArg_{15}$, $CysArg_{16}$, $CysArg_{17}$, $CysArg_{18}$, $CysArg_{19}$, -continued CysArg$_{20}$, CysArg$_{21-30}$; CysLys$_5$, CysLys$_6$, CysLys$_7$, CysLys$_8$, CysLys$_9$, CysLys$_{10}$, CysLys$_{11}$, CysLys$_{12}$, CysLys$_{13}$, CysLys$_{14}$, CysLys$_{15}$, CysLys$_{16}$, CysLys$_{17}$, CysLys$_{18}$, CysLys$_{19}$, CysLys$_{20}$, CysLys$_{21-30}$; CysHis$_5$, CysHis$_6$, CysHis$_7$, CysHis$_8$, CysHis$_9$, CysHis$_{10}$, CysHis$_{11}$, CysHis$_{12}$, CysHis$_{13}$, CysHis$_{14}$, CysHis$_{15}$, CysHis$_{16}$, CysHis$_{17}$, CysHis$_{18}$, CysHis$_{19}$, CysHis$_{20}$, CysHis$_{21-30}$; CysOrn$_5$, CysOrn$_6$, CysOrn$_7$, CysOrn$_8$, CysOrn$_9$, CysOrn$_{10}$, CysOrn$_{11}$, CysOrn$_{12}$, CysOrn$_{13}$, CysOrn$_{14}$, CysOrn$_{15}$, CysOrn$_{16}$, CysOrn$_{17}$, CysOrn$_{18}$, CysOrn$_{19}$, CysOrn$_{20}$, CysOrn$_{21-30}$.

Sequences with two terminal Cys residues:
CysArg$_5$Cys, CysArg$_6$Cys, CysArg$_7$Cys, CysArg$_8$Cys, CysArg$_9$Cys, CysArg$_{10}$Cys, CysArg$_{11}$Cys, CysArg$_{12}$Cys, CysArg$_{13}$Cys, CysArg$_{14}$Cys, CysArg$_{15}$Cys, CysArg$_{16}$Cys, CysArg$_{17}$Cys, CysArg$_{18}$Cys, CysArg$_{19}$Cys, CysArg$_{20}$Cys, CysArg$_{21-30}$Cys; CysLys5Cys, CysLys$_6$Cys, CysLys$_7$Cys, CysLys$_8$Cys, CysLys$_9$Cys, CysLys$_{10}$Cys, CysLys$_{11}$Cys, CysLys$_{12}$Cys, CysLys$_{13}$Cys, CysLys$_{14}$Cys, CysLys$_{15}$Cys, CysLys$_{16}$Cys, CysLys$_{17}$Cys, CysLys$_{18}$Cys, CysLys$_{19}$Cys, CysLys$_{20}$Cys, CysLys$_{21-30}$Cys; CysHis$_5$Cys, CysHis$_6$Cys, CysHis$_7$Cys, CysHis$_8$Cys, CysHis$_9$Cys, CysHis$_{10}$Cys, CysHis$_{11}$Cys, CysHis$_{12}$Cys, CysHis$_{13}$Cys, CysHis$_{14}$Cys, CysHis$_{15}$Cys, CysHis$_{16}$Cys, CysHis$_{17}$Cys, CysHis$_{18}$Cys, CysHis$_{19}$Cys, CysHis$_{20}$Cys, CysHis$_{21-30}$Cys; CysOrn$_5$Cys, CysOrn$_6$Cys, CysOrn$_7$Cys, CysOrn$_8$Cys, CysOrn$_9$Cys, CysOrn$_{10}$Cys, CysOrn$_{11}$Cys, CysOrn$_{12}$Cys, CysOrn$_{13}$Cys, CysOrn$_{14}$Cys, CysOrn$_{15}$Cys, CysOrn$_{16}$Cys, CysOrn$_{17}$Cys, CysOrn$_{18}$Cys, CysOrn$_{19}$Cys, CysOrn$_{20}$Cys, CysOrn$_{21-30}$Cys.

Of course it is also within the scope of the invention to include two or more different cationic compounds with different peptide moieties as described above selected as P within the composition, or to combine a peptide moiety P with a compound of formula I as described below.

Moreover, the composition may comprise a cationic peptide moiety P in combination with one or more other peptides that do not fall within the definition of P, but which may be useful to modulate the physical, chemical or biological properties of the carrier system or of the complex which is formed when the composition of the invention is combined with a cargo material, such as a nucleic acid. Such other peptide sequences which do not follow the definition of P may either be part of the cationic compound comprising moiety P or of the disulfide-linked multimer thereof, or they may be incorporated as separate compounds within the composition of the invention. It is preferred that such separate compounds also comprise one or more —SH group such as to be capable of forming a disulfide linkage with the cationic compound comprising the cationic moiety P.

For example, it may be useful to incorporate peptides comprising one or more aromatic amino acids such as Trp, Tyr, or Phe. Of course, aromatic amino acids may also be incorporated within moiety P itself. Alternatively, such aromatic amino acids may be incorporated within the composition in the form of other peptides which however comprise one or more —SH groups such as to be able to form a disulfide linkage with another component, such as with the cationic compound comprising the cationic moiety P. In this manner, the aromatic amino acids will also participate in the complex formed upon combination of the carrier composition with a nucleic acid cargo.

The incorporation of aromatic amino acids enables an additional binding of the carrier to the nucleic acid cargo due to interactions of the aromatic structures of the amino acid(s) with the bases of the nucleic acid, which may contribute to a more stable complex. This binding is different from the interaction of cationic or cationised groups with the phosphate backbone of the nucleic acid. The interaction between aromatic amino acids and the bases of the nucleic acid may occur e.g. by intercalations or by minor or major groove binding. It is not prone to decompaction by anionic complexing partners (e.g. heparin, hyaluronic acid) which are found mainly in the extracellular matrix in vivo, and it is also less susceptible to salt effects.

In some specific embodiments, the composition comprises one or more peptides comprising a core sequence which is rich in, or substantially composed of, aromatic amino acids. The aromatic amino acids within such peptide may be identical or different from each other. The core sequence is preferably flanked with one or—more preferably—two moieties comprising a —SH group, such as Cys, which impart the capability to form disulfide linkages.

Examples of useful core sequences include Trp-Tyr, Tyr-Trp, Trp-Trp, Tyr-Tyr, Trp-Tyr-Trp, Tyr-Trp-Tyr, Trp-Trp-Trp, Tyr-Tyr-Tyr, Trp-Tyr-Trp-Tyr, Tyr-Trp-Tyr-Trp, Trp-Trp-Trp-Trp, Phe-Tyr, Tyr-Phe, Phe-Phe, Phe-Tyr-Phe, Tyr-Phe-Tyr, Phe-Phe-Phe, Phe-Tyr-Phe-Tyr, Tyr-Phe-Tyr-Phe, Phe-Phe-Phe-Phe, Phe-Trp, Trp-Phe, Phe-Phe, Phe-Trp-Phe, Trp-Phe-Trp, Phe-Trp-Phe-Trp, Trp-Phe-Trp-Phe, and Tyr-Tyr-Tyr-Tyr, etc. Such sequences may be repeated 1, 2, 3, 4, 5, 6, 7, 8, 9, 10, 12, 13, 14, 15 or even more times. They may also be combined with each other as suitable.

Examples of complete peptide sequences which also include the terminal Cys residues are, for example:
Cys-Tyr, Cys-Trp, Cys-Trp-Tyr, Cys-Tyr-Trp, Cys-Trp-Trp, Cys-Tyr-Tyr, Cys-Trp-Tyr-Trp, Cys-Tyr-Trp-Tyr, Cys-Trp-Trp-Trp, Cys-Tyr-Tyr-Tyr, Cys-Trp-Tyr-Trp-Tyr, Cys-Tyr-Trp-Tyr-Trp, Cys-Trp-Trp-Trp-Trp, Cys-Tyr-Tyr-Tyr-Tyr, Cys-Phe, Cys-Phe-Tyr, Cys-Tyr-Phe, Cys-Phe-Phe, Cys-Tyr-Tyr, Cys-Phe-Tyr-Phe, Cys-Tyr-Phe-Tyr, Cys-Phe-Phe-Phe, Cys-Tyr-Tyr-Tyr, Cys-Phe-Tyr-Phe-Tyr, Cys-Tyr-Phe-Tyr-Phe, or Cys-Phe-Phe-Phe-Phe, Cys-Phe-Trp, Cys-Trp-Phe, Cys-Phe-Phe, Cys-Phe-Trp-Phe, Cys-Trp-Phe-Trp, Cys-Phe-Trp-Phe-Trp, Cys-Trp-Phe-Trp-Phe;

Cys-Tyr-Cys, Cys-Trp-Cys, Cys-Trp-Tyr-Cys, Cys-Tyr-Trp-Cys, Cys-Trp-Trp-Cys, Cys-Tyr-Tyr-Cys, Cys-Trp-Tyr-Trp-Cys, Cys-Tyr-Trp-Tyr-Cys, Cys-Trp-Trp-Trp-Cys, Cys-Tyr-Tyr-Tyr-Cys, Cys-Trp-Tyr-Trp-Tyr-Cys, Cys-Tyr-Trp-Tyr-Trp-Cys, Cys-Trp-Trp-Trp-Trp-Cys, Cys-Tyr-Tyr-Tyr-Tyr-Cys, Cys-Phe-Cys, Cys-Phe-Tyr-Cys, Cys-Tyr-Phe-Cys, Cys-Phe-Phe-Cys, Cys-Tyr-Tyr-Cys, Cys-Phe-Tyr-Phe-Cys, Cys-Tyr-Phe-Tyr-Cys, Cys-Phe-Phe-Phe-Cys, Cys-Tyr-Tyr-Tyr-Cys, Cys-Phe-Tyr-Phe-Tyr-Cys, Cys-Tyr-Phe-Tyr-Phe-Cys, or Cys-Phe-Phe-Phe-Phe-Cys, Cys-Phe-Trp-Cys, Cys-Trp-Phe-Cys, Cys-Phe-Phe-Cys, Cys-Phe-Trp-Phe-Cys, Cys-Trp-Phe-Trp-Cys, Cys-Phe-Trp-Phe-Trp-

Cys, Cys-Trp-Phe-Trp-Phe-Cys, etc. Each Cys may also be replaced by a modified amino acid or chemical compound carrying a free —SH-moiety. A peptide may also be used which represents combinations or repetitions of the sequences, in particular those with two terminal Cys residues, e.g. 1, 2, 3, 4, 5, 6, 7, 8, 9, 10, 12, 13, 14, 15 or even more times.

Additionally, such peptide rich in aromatic amino acids may contain at least one proline, which may serve as a structure breaker of longer sequences of Trp, Tyr and Phe. Depending on the length of the aromatic amino acid sequence, it may be preferred to incorporate two, three or more prolines.

It may further be useful to incorporate within the composition of the invention a peptide comprising one or more hydrophilic amino acids along with the cationic compound comprising the peptide moiety P. Of course, hydrophilic amino acids may also be incorporated within the peptide moiety P itself. Alternatively, such amino acids may be incorporated within the composition in the form of other peptides which again also comprise one or more —SH groups, or disulfide linkages, and may be able to participate in the complex formed upon combination of the carrier composition with a nucleic acid cargo such as to modify the properties of the complex.

Among the hydrophilic amino acids useful for this purpose, those with an uncharged polar side chain are preferred, in particular Thr, Ser, Asn and/or Gln. The incorporation of such amino acids or of sequences rich in these amino acids enables a more flexible binding to the nucleic acid cargo. This may lead to a more effective compaction of the nucleic acid cargo and hence to a better protection against nucleases and unwanted decompaction. It also allows provision of a carrier which exhibits a reduced cationic charge over the entire carrier and in this context to better adjusted binding properties, if desired or necessary.

Examples for useful core sequences include sequences based on identical or different hydrophilic amino acids, such as the following: Ser-Thr, Thr-Ser, Ser-Ser, Thr-Thr, Ser-Thr-Ser, Thr-Ser-Thr, Ser-Ser-Ser, Thr-Thr-Thr, Ser-Thr-Ser-Thr, Thr-Ser-Thr-Ser, Ser-Ser-Ser-Ser, Thr-Thr-Thr-Thr, Gln-Asn, Asn-Gln, Gln-Gln, Asn-Asn, Gln-Asn-Gln, Asn-Gln-Asn, Gln-Gln-Gln, Asn-Asn-Asn, Gln-Asn-Gln-Asn, Asn-Gln-Asn-Gln, Gln-Gln-Gln-Gln, Asn-Asn-Asn-Asn, Ser-Asn, Asn-Ser, Ser-Ser, Asn-Asn, Ser-Asn-Ser, Asn-Ser-Asn, Ser-Ser-Ser, Asn-Asn-Asn, Ser-Asn-Ser-Asn, Asn-Ser-Asn-Ser, Ser-Ser-Ser-Ser, or Asn-Asn-Asn-Asn, etc. Again, such sequences may be repeated e.g. 1, 2, 3, 4, 5, 6, 7, 8, 9, 10, 12, 13, 14, 15 or even more times, or combined with each other as suitable. Moreover, the core sequence is preferably flanked with one or two residues comprising a —SH group or forming a disulfide linkage, such as Cys, which impart the capability to form disulfide linkages.

Examples of complete peptide sequences which also include such terminal Cys residues are Cys-Thr-Cys, Cys-Ser-Cys, Cys-Ser-Thr-Cys, Cys-Thr-Ser-Cys, Cys-Ser-Ser-Cys, Cys-Thr-Thr-Cys, Cys-Ser-Thr-Ser-Cys, Cys-Thr-Ser-Thr-Cys, Cys-Ser-Ser-Ser-Cys, Cys-Thr-Thr-Thr-Cys, Cys-Ser-Thr-Ser-Thr-Cys, Cys-Thr-Ser-Thr-Ser-Cys, Cys-Ser-Ser-Ser-Ser-Cys, Cys-Thr-Thr-Thr-Thr-Cys, Cys-Asn-Cys, Cys-Gln-Cys, Cys-Gln-Asn-Cys, Cys-Asn-Gln-Cys, Cys-Gln-Gln-Cys, Cys-Asn-Asn-Cys, Cys-Gln-Asn-Gln-Cys, Cys-Asn-Gln-Asn-Cys, Cys-Gln-Gln-Gln-Cys, Cys-Asn-Asn-Asn-Cys, Cys-Gln-Asn-Gln-Asn-Cys, Cys-Asn-Gln-Asn-Gln-Cys, Cys-Gln-Gln-Gln-Gln-Cys, Cys-Asn-Asn-Asn-Asn-Cys, Cys-Asn-Ser-Cys, Cys-Ser-Cys, Cys-Ser-Asn-Cys, Cys-Asn-Ser-Cys, Cys-Ser-Ser-Cys, Cys-Asn-Asn-Cys, Cys-Ser-Asn-Ser-Cys, Cys-Asn-Ser-Asn-Cys, Cys-Ser-Ser-Ser-Cys, Cys-Asn-Asn-Asn-Cys, Cys-Ser-Asn-Ser-Asn-Cys, Cys-Asn-Ser-Asn-Ser-Cys, Cys-Ser-Ser-Ser-Ser-Cys, or Cys-Asn-Asn-Asn-Asn-Cys, etc. Each Cys may also be replaced by a modified amino acid or chemical compound carrying a free —SH-moiety or a sulfur atom participating in a disulfide linkage. The sequences may be repeated e.g. 1, 2, 3, 4, 5, 6, 7, 8, 9, 10, 12, 13, 14, 15 or even more times, or combined with each other.

Optionally, the sequence rich in hydrophilic amino acids may contain at least one proline, which may serve as a structure breaker of longer sequences of Ser, Thr and Asn. Two, three or more prolines may also be incorporated, in particular in longer sequences.

It may further be useful to incorporate within the composition of the invention a peptide comprising one or more lipophilic amino acids along with the cationic compound comprising the peptide moiety P, in particular Leu, Val, Ile, Ala, and/or Met. Such lipophilic amino acids may also be incorporated within the peptide moiety P itself. Alternatively, they may be incorporated within the composition in the form of other peptides which again also comprise one or more —SH groups, or disulfide linkages, and which may be able to participate in the complex formed upon combination of the carrier composition with a nucleic acid cargo.

The use of lipophilic amino acids enables a stronger compaction of the nucleic acid. This may be due to specific interactions of the lipophilic amino acids and the nucleic acid cargo which provide for additional stability of the complex formed between the carrier(s) and the cargo. The stabilisation may be similar to noncovalent association or crosslinking between polymer strands. Especially in an aqueous environment, this type of interaction is typically strong and provides a significant effect.

Examples for useful core sequences include sequences based on identical or different lipophilic amino acids, such as Leu-Val, Val-Leu, Leu-Leu, Val-Val, Leu-Val-Leu, Val-Leu-Val, Leu-Leu-Leu, Val-Val-Val, Leu-Val-Leu-Val, Val-Leu-Val-Leu, Leu-Leu-Leu-Leu, Val-Val-Val-Val, Ile-Ala, Ala-Ile, Ile-Ile, Ala-Ala, Ile-Ala-Ile, Ala-Ile-Ala, Ile-Ile-Ile, Ala-Ala-Ala, Ile-Ala-Ile-Ala, Ala-Ile-Ala-Ile, Ile-Ile-Ile-Ile, Ala-Ala-Ala-Ala, Met-Ala, Ala-Met, Met-Met, Ala-Ala, Met-Ala-Met, Ala-Met-Ala, Met-Met-Met, Ala-Ala-Ala, Met-Ala-Met-Ala, Ala-Met-Ala-Met, or Met-Met-Met-Met etc. Such sequences may be repeated e.g. 1, 2, 3, 4, 5, 6, 7, 8, 9, 10, 12, 13, 14, 15 or more times, or combined with each other. Moreover, the core sequence is preferably flanked with one or two residues comprising a —SH group, or a sulfur atom participating in a disulfide linkage, such as Cys.

Examples of complete peptide sequences which also include such terminal Cys residues are Cys-Val-Cys, Cys-Leu-Cys, Cys-Leu-Val-Cys, Cys-Val-Leu-Cys, Cys-Leu-Leu-Cys, Cys-Val-Val-Cys, Cys-Leu-Val-Leu-Cys, Cys-Val-Leu-Val-Cys, Cys-Leu-Leu-Leu-Cys, Cys-Val-Val-Val-Cys, Cys-Leu-Val-Leu-Val-Cys, Cys-Val-Leu-Val-Leu-Cys, Cys-Leu-Leu-Leu-Leu-Cys, Cys-Val-Val-Val-Val-Cys, Cys-Ala-Cys, Cys-Ile-Cys, Cys-Ile-Ala-Cys, Cys-Ala-Ile-Cys, Cys-Ile-Ile-Cys, Cys-Ala-Ala-Cys, Cys-Ile-Ala-Ile-Cys, Cys-Ala-Ile-Ala-Cys, Cys-Ile-Ile-Ile-Cys, Cys-Ala-Ala-Ala-Cys, Cys-Ile-Ala-Ile-Ala-Cys, Cys-Ala-Ile-Ala-Ile-Cys, Cys-Ile-Ile-Ile-Ile-Cys, or Cys-Ala-Ala-Ala-Ala-Cys, Cys-Met-Cys, Cys-Met-Ala-Cys, Cys-Ala-Met-Cys, Cys-Met-Met-Cys, Cys-Ala-Ala-Cys, Cys-Met-Ala-Met-Cys, Cys-Ala-Met-Ala-Cys, Cys-Met-Met-Met-Cys, Cys-Ala-Ala-Ala-Cys, Cys-Met-Ala-Met-Ala-Cys, Cys-Ala-Met-Ala-Met-Cys, Cys-Met-Met-Met-Met-Cys, or Cys-Ala-Ala-Ala-Ala-Cys, etc. Each Cys may also be replaced by a modified amino acid or chemical compound carrying a free —SH-group or participating in a disulfide linkage derived from such —SH group. Such sequences may be repeated e.g. 1, 2, 3, 4, 5, 6, 7, 8, 9, 10, 12, 13, 14, 15 or more times, or combined with each other.

Optionally, the sequence rich in lipophilic amino acids may contain at least one proline, which may serve as a structure breaker of longer sequences of Leu, Val, Ile, Ala and/or Met. Two, three or more prolines may also be incorporated, in particular in longer sequences.

Optionally, the peptide moiety P may contain a functional peptide sequence. Alternatively or in addition, a functional peptide may be incorporated within the composition of the invention along with the cationic compound comprising the peptide moiety P, optionally after being modified such as to exhibit one or more —SH groups or sulfur atoms participating in a disulfide linkage. Alternatively, such functional peptide sequence may also be attached to another carrier component such as peptide P through an acid-labile bond, preferably via a side chain of a carrier component, which allows to detach or release the functional peptide sequence at lower pH-values, e.g. at physiological pH-values.

The functional peptide or peptide sequence may represent, or be derived from, a signal peptide or signal sequence, a localisation signal or sequence, a nuclear localisation signal or sequence (NLS), an antibody, a cell penetrating peptide, (e.g. TAT), etc.

In this context, a signal peptide, a localization signal or sequence or a nuclear localization signal or sequence (NLS), may be used to direct the carrier-cargo complex to specific target cells (e.g. hepatocytes or antigen-presenting cells) or subcellular structures and may allow the translocalisation to a specific target, e.g. into the cell, into the nucleus, into the endosomal compartment, the mitochondrial matrix, the plasma membrane, the Golgi apparatus, the nucleus, the cytoplasm and the cytosceleton, the endoplasmic reticulum etc. A signal sequence or nuclear localisation signal may be used for the transport of any of the nucleic acids defined herein, in particular an RNA or a DNA, more preferably an shRNA or a pDNA, e.g. into the nucleus. The nuclear localisation sequence may include e.g. KDEL, DDEL, DEEL, QEDL, RDEL, GQNLSTSN, PKKKRKV, PQKKIKS, QPKKP, RKKR, RKKRRQRRRAHQ, RQARRNRRRRWRERQR, MPLTRRRPAASQALAPPTP, GAALTILV, or GAALTLLG. An example for a localisation sequence for the endosomal compartment is MDDQRDLIS-NNEQLP. An exemplary localisation sequence for the mitochondrial matrix is MLFNLRXXLNNAAF-RHGHNFMVRNFRCGQPLX. Localisation sequences for the plasma membrane include e.g. GCVCSSNP, GQTVTTPL, GQELSQHE, GNSPSYNP, GVSGSKGQ, GQTITTPL, GQTLTTPL, GQIFSRSA, GQIHGLSP, GARASVLS, and GCTLSAEE. Localisation sequences for the endoplasmic reticulum and the nucleus include GAQVSSQK and GAQLSRNT. Localisation sequences for the Golgi apparatus, the nucleus, the cytoplasm and the cytosceleton include GNAAAAKK. Localisation sequences for the cytoplasm and cytosceleton include GNEASYPL. Localisation sequences for the plasma membrane and cytosceleton include GSSKSKPK. Examples of secretory signal peptide sequences include classical or non-classical MHC-sequences (e.g. signal sequences of MHC I and II molecules, e.g. of the MHC class I molecule HLA-A*0201). Useful peptides may also incorporate signal sequences of cytokines or immunoglobulins, such as signal sequences of the invariant chain of immunoglobulins or antibodies; signal sequences of Lamp1, tapasin, Erp57, calreticulin, calnexin, other membrane-associated proteins, or proteins associated with the endoplasmic reticulum (ER) or the endosomal-lysosomal compartment. Particularly preferred are signal sequences of MHC class I molecule HLA-A*0201.

The properties of the peptide moiety P may be further modulated by including in its sequence a non-native amino acid, or by chemical modification of the peptide. For example, specific chemical groups may be introduced. Such groups may be selected such as to allow the attachment of further components or ligands, e.g. by amide formation (e.g. by reaction with carboxylic acids, sulphonic acids, amines, etc.), by Michael addition (e.g using maleinimide moieties, α,β unsatured carbonyls, etc.), by click chemistry (e.g. using azides or alkines), by alkene/alkine methatesis (e.g. using alkenes or alkines), imine or hydrozone formation (using aldehydes or ketons, hydrazins, hydroxylamins, amines), complexation reactions (using avidin, biotin, protein G or the like) or components which allow $S_n$-type substitution reactions (e.g with halogenalkans, thiols, alcohols, amines, hydrazines, hydrazides, sulphonic acid esters, oxyphosphonium salts) or other chemical moieties which can be utilised in the attachment of further components.

One of the particular advantages of the composition of the invention comprising the cationic compound with a peptide moiety P is that such peptide moiety may be easily designed and adapted to the specific needs associated with a specific therapeutic purpose or application. For example, the amount of positive charge which is required to form a complex with a particular cargo such as a nucleic acid construct may be optimised by varying the content of basic amino acids in the peptide sequence. At the same time, the length of the peptide may be varied in order to optimise its biodegradability and tolerability.

It has been found by the inventors that the peptide molecules readily form disulfide linkages with each other under conditions which also allow for the formation of a complex with a nucleic acid cargo. Under certain in vivo conditions, such as in the typical cytosol environment where e.g. cytosolic GSH is present, the disulfide linkages are reduced, leading to smaller peptide units which are easily metabolised by most cells, first into small oligopeptides, eventually into amino acids. No significant toxicities have been found even for larger oligopeptides as described above.

In another preferred embodiment, the cationic compound comprising moiety P is a compound according to formula IV $$L^1\text{-}P^1\text{-}[P\text{-}]_n\text{-}P^3\text{-}L^2 \qquad \text{(formula IV)}$$

wherein P is as defined above, i.e. P is either a polymer moiety having a molecular weight from about 0.5 kDa to about 30 kDa, or a peptide moiety composed of 3 to 100 amino acids, wherein at least 10% of the total number of amino acids of the peptide moiety represent basic amino acids selected from Arg, Lys, His and/or Orn. $P^3$ is optional. $P^1$ and $P^3$ (if present) are independently selected, each representing a linear or branched hydrophilic polymer chain selected from polyethylene glycol (PEG), poly-N-(2-hydroxypropyl)methacrylamide, poly-2-(methacryloyloxy) ethyl phosphorylcholines, poly(hydroxyalkyl L-asparagine), poly(2-(methacryloyloxy)ethyl phosphorylcholine), hydroxyethylstarch or poly(hydroxyalkyl L-glutamine), wherein the polymer chain exhibits a molecular weight from about 1 kDa to about 100 kDa, and wherein each of $P^1$ and $P^3$ is linked with a moiety P through a disulfide linkage. $L^1$ and $L^2$ are optional ligands and independently selected from RGD, an RGD peptide, transferrin, folate, a signal peptide or signal sequence, a localization signal or sequence, a nuclear localization signal or sequence (NLS), an antibody, a cell penetrating peptide such as WEAKLAKALAKA-LAKHLAKALAKALKACEA, TAT, a ligand of a receptor, cytokine, hormone, growth factor, small molecule, carbohydrate, mannose, galactose, n-acetylgalactosamine, synthetic ligand, small molecule agonist, inhibitor or antagonist of a receptor, or a RGD peptidomimetic analogue.

Moreover, n in formula IV is an integer selected from 1 to about 50, and preferably in the range from 2, 3, 4, or 5 to about 10, or from 2, 3, or 4 to about 9, such as 6, or 7; provided that if n is greater than 1, each moiety P is linked with another moiety P through a disulfide linkage. Also preferred is the selection of n from the range of 2 to about 20, or from about 4 to about 10, such as about 4, 5, 6, 7, 8, 9 or 10.

Any references to an optional segment $L_1$, $L_2$, or $P_3$ should be interpreted as applicable to optional embodiments in which the respective segment is present.

As apparent from formula IV, the respective cationic compounds comprise disulfide bonds at least between components or moieties P, $P^1$ and $P^3$, respectively, and optionally further disulfide linkages within moiety P, and/or between $P^1$ and $L^1$ and/or $P^3$ and $L^3$. The disulfide linkages are derived from —SH groups which may originate from residues such as Cys, or from chemically modified amino acids, or from other residues which, in their reduced form, carry an —SH group.

Optionally, one or more additional —SH groups or disulfide linkages may also be present in the compound in order to attach further components, such as an amino acid component, e.g. antigen epitopes, antigens, antibodies, cell penetrating peptides (e.g. TAT), ligands, etc.

Further examples of compounds according to formula II and methods for their preparation are disclosed e.g. in WO 2011/026641, the disclosure of which is incorporated herein in its entirety.

The use of a compound according to formula IV for carrying out the invention is associated with the advantage of high versatility. Moreover, the embodiment based on formula II allows to define the length of the polymer chain and to combine desired properties of different short polymers in one polymer, e.g. to efficiently compact nucleic acids for the purpose of efficient transfection of nucleic acids for the purposes of gene therapy or other therapeutic applications without loss of activity, particularly efficient transfection of a nucleic acid into different cell lines in vitro but also transfection in vivo. The carrier molecule is furthermore not toxic to cells and provides for efficient release of its nucleic acid cargo. Finally, it shows improved resistance to agglomeration due to the reversible addition of hydrophilic polymer chains (e.g. PEG) particularly towards the terminal ends of the molecule, which additionally confers enhanced stability of the nucleic acid cargo with respect to serum containing media and prevents recognition of the polymeric carrier cargo complex by the immune system or other undesired interactions with serum contents. In the cytosol, the "coating" achieved by the segments $P^1$ and $P^3$ is easily removed under the reducing conditions of the cell. Also this effect promotes the release of the nucleic acid cargo in the cytosol.

As defined above, ligands $L^1$ and $L^2$ may be optionally comprised in the compound according to formula IV. They may be used e.g. for directing a cargo such as a complexed nucleic acid into specific cells. They may be selected independently from one another. Examples of potentially suitable ligands include RGD, transferrin, folate, a signal peptide or signal sequence, a localization signal or sequence, a nuclear localization signal or sequence (NLS), an antibody, a cell penetrating peptide, (e.g. TAT), a ligand of a receptor (e.g. cytokines, hormones, growth factors etc.), small molecules (e.g. carbohydrates like mannose or galactose or synthetic ligands), small molecule agonists, inhibitors or antagonists of receptors (e.g. RGD peptidomimetic analogues) etc.

Some of the preferred ligands include WEAKLAKA-LAKALAKHLAKALAKALKACEA (also referred to as KALA) and N-acetylgalactosamine (GalNac). Also preferred in this context is mannose as ligand to target antigen presenting cells which carry mannose receptors on their cell membranes. In a further preferred embodiment, galactose as optional ligand can be used to target hepatocytes.

Such ligands $L^1$ and $L^2$ may be attached to component $P^1$ and/or $P^3$ by reversible disulfide bonds or by any other possible chemical attachment, e.g. by binding of a 3-thio propionic acid or 2-iminothiolane (Traut's reagent), by amide formation (e.g. carboxylic acids, sulphonic acids, amines, etc.), by Michael addition (e.g. maleinimide moieties, unsaturated carbonyls, etc.), by click chemistry (e.g. azides or alkynes), by alkene/alkyne methatesis (e.g. alkenes or alkynes), imine or hydrozone formation (aldehydes or ketones, hydrazines, hydroxylamines, amines), complexation reactions (avidin, biotin, protein G) or components which allow $S_n$-type substitution reactions (e.g. halogenalkanes, thiols, alcohols, amines, hydrazines, hydrazides, sulphonic acid esters, oxyphosphonium salts) or other chemical moieties which can be utilized in the attachment of further components.

As defined above, components $P^1$ and $P^3$ are independently selected, and each represents a linear or branched hydrophilic polymer chain containing at least one sulfur atom which participates in a disulfide linkage with component P. The polymer chain of each of $P^1$ and $P^3$ is independently selected from polyethylene glycol (PEG), poly-N-(2-hydroxypropyl) methacrylamide, poly-2-(methacryloyloxy) ethyl phosphorylcholines, poly(hydroxyalkyl L-asparagine), poly(2-(methacryloyloxy)ethyl phosphorylcholine), hydroxyethylstarch or poly(hydroxyalkyl L-glutamine). Each of $P^1$ and $P^3$ exhibits a molecular weight from about 1 kDa to about 100 kDa.

The molecular weight of the polymer chain of $P^1$ and/or $P^3$ is preferably about 1 kDa to about 75 kDa, or from about 5 kDa to about 50 kDa, even more preferably of about 5 kDa to about 25 kDa. According to another preference, $P^1$ and/or $P^3$ is an optionally modified polyethylene glycol chain of about 5 kDa to about 25 kDa.

The sulfur atoms enabling the disulfide linkages may be provided for each of the hydrophilic polymer chains $P^1$ and $P^3$ by an internal cysteine or any further (modified) amino acid or moiety which in its reduced form and before incorporation into the compound of formula IV carries a —SH moiety.

Alternatively, the hydrophilic polymer chains $P^1$ and/or $P^3$ may be derived from polymers modified with a —SH moiety, preferably via a chemical reaction with a compound carrying a —SH moiety, such that each of the hydrophilic polymers $P^1$ and $P^3$ carries at least one such —SH moiety before being incorporated into the compound of formula IV. Such a compound carrying a —SH moiety may be e.g. an (additional) cysteine or any further (modified) amino acid which carries a —SH moiety.

Such a compound may also be any non-amino compound or moiety, which contains or allows to introduce a —SH moiety into hydrophilic polymer chains $P^1$ and $P^3$. Such non-amino compounds may be attached to $P^1$ and/or $P^3$ via chemical reactions or binding of compounds, e.g. by binding of a 3-thio propionic acid or thioimolane (Traut's reagent), by amide formation (e.g. carboxylic acids, sulphonic acids, amines, etc.), by Michael addition (e.g. maleinimide moieties, unsaturated carbonyls, etc.), by click chemistry (e.g. azides or alkynes), by alkene/alkyne methatesis (e.g. alkenes or alkynes), imine or hydrozone formation (aldehydes or ketones, hydrazines, hydroxylamines, amines), complexation reactions (avidin, biotin, protein G) or components which allow $S_n$-type substitution reactions (e.g. halogenalkanes, thiols, alcohols, amines, hydrazines, hydrazides, sulphonic acid esters, oxyphosphonium salts) or other chemical moieties which can be utilized in the attachment of further components. A particularly preferred PEG derivate in this context is alpha-methoxy-omega-mercapto poly(ethylene glycol). In each case, the sulfur atom which participates in the disulfide linkage, e.g. of a cysteine or of any further (modified) amino acid or compound, may be present at the terminal ends or internally at any position of $P^1$ and $P^3$. In one embodiment, each of $P^1$ and $P^3$ exhibits at least one disulfide linkage at one terminal end and at least one further-SH group or disulfide linkage, which may be used to additionally attach further components as defined herein, e.g. a ligand, an amino acid component $(AA)_x$, antibodies, cell penetrating peptides (e.g. TAT), etc.

According to a further preferred embodiment, each of hydrophilic polymer chains $P^1$ and $P^3$ may also contain at least one further functional group which allows attaching further components as defined herein, e.g. a ligand, an amino acid component $(AA)_x$, etc., e.g. by amide formation (e.g. carboxylic acids, sulphonic acids, amines, etc.), by Michael addition (e.g. maleinimide moieties, unsaturated carbonyls, etc.), by click chemistry (e.g. azides or alkynes), by alkene/alkyne methatesis (e.g. alkenes or alkynes), imine or hydrozone formation (aldehydes or ketones, hydrazines, hydroxylamines, amines), complexation reactions (avidin, biotin, protein G) or components which allow $S_n$-type substitution reactions (e.g. halogenalkanes, thiols, alcohols, amines, hydrazines, hydrazides, sulphonic acid esters, oxyphosphonium salts) or via other chemical groups which can be used for the attachment of further components.

As defined above, P in the compound of formula IV is a polymer moiety having a molecular weight from about 0.5 kDa to about 30 kDa, or a peptide moiety composed of 3 to 100 amino acids, wherein at least 10% of the total number of amino acids of the peptide moiety represent basic amino acids selected from Arg, Lys, His and/or Orn. If P is a peptide moiety, the same preferences apply by analogy which have been described above in the context of P in general; preferences relating to —SH groups should also be applied to the disulfide linkages in the compound of formula II which are derived from such —SH groups.

For example, a peptide moiety selected as P in the compound of formula IV preferably has a length of about 3 to about 50 amino acids, and more preferably of about 7 to about 30 amino acid, or of about 3 to about 25 amino acids. Also preferred are lengths in the ranges from about 3 to about 20 amino acids, or from about 5 to about 20 amino acids, or from about 7 to about 30 amino acids, or from about 6 to about 18 amino acids, or from about 7 to about 17 amino acids, such as about 5 to about 15 amino acids. It is further preferred that a peptide moiety P in formula II has a molecular weight in the range from about 0.3 kDa to about 50 kDa, in particular from about 0.5 kDa to about 30 kDa, or from about 0.6 kDa to about 10 kDa, or from about 0.8 kDa to about 5 kDa, such as from about 1 kDa to about 3 kDa.

Moreover, the content of basic amino acids in the peptide moiety selected as P in formula IV is at least 10% of the total number of amino acids of the peptide sequence, and preferably higher, such as at least about 20%, or at least about 30%, or at least about 40%, or at least about 50%, or at least about 60%, or at least about 70%, respectively.

In some of the preferred embodiments, the peptide moiety selected as P in the compound of formula IV comprises a core sequence which is entirely or predominantly composed of one specific basic amino acid, such as a segment of about 5 to about 30 Arg, Lys, His or Orn, and may be flanked by one or two terminal Cys residues. Examples for such preferred versions of peptide moieties P in formula IV include:

```
Sequences of P with one terminal Cys residue:
CysArg₅, CysArg₆, CysArg₇, CysArg₈, CysArg₉, CysArg₁₀, CysArg₁₁, CysArg₁₂, CysArg₁₃, CysArg₁₄, CysArg₁₅, CysArg₁₆, CysArg₁₇, CysArg₁₈, CysArg₁₉, CysArg₂₀, CysArg₂₁₋₃₀; CysLys₅, CysLys₆, CysLys₇, CysLys₈, CysLys₉, CysLys₁₀, CysLys₁₁, CysLys₁₂, CysLys₁₃, CysLys₁₄, CysLys₁₅, CysLys₁₆, CysLys₁₇, CysLys₁₈, CysLys₁₉, CysLys₂₀, CysLys₂₁₋₃₀; CysHis₅, CysHis₆, CysHis₇, CysHis₈, CysHis₉, CysHis₁₀, CysHis₁₁, CysHis₁₂, CysHis₁₃, CysHis₁₄, CysHis₁₅, CysHis₁₆, CysHis₁₇, CysHis₁₈, CysHis₁₉, CysHis₂₀, CysHis₂₁₋₃₀; CysOrn₅, CysOrn₆, CysOrn₇, CysOrn₈, CysOrn₉, CysOrn₁₀, CysOrn₁₁, CysOrn₁₂, CysOrn₁₃, CysOrn₁₄, CysOrn₁₅, CysOrn₁₆, CysOrn₁₇, CysOrn₁₈, CysOrn₁₉, CysOrn₂₀, CysOrn₂₁₋₃₀.

Sequences of P with two terminal Cys residues:
CysArg₅Cys, CysArg₆Cys, CysArg₇Cys, CysArg₈Cys, CysArg₉Cys, CysArg₁₀Cys, CysArg₁₁Cys, CysArg₁₂Cys, CysArg₁₃Cys, CysArg₁₄Cys, CysArg₁₅Cys, CysArg₁₆Cys, CysArg₁₇Cys, CysArg₁₈Cys, CysArg₁₉Cys, CysArg₂₀Cys, CysArg₂₁₋₃₀Cys; CysLys₅Cys, CysLys₆Cys, CysLys₇Cys, CysLys₈Cys, CysLys₉Cys, CysLys₁₀Cys, CysLys₁₁Cys, CysLys₁₂Cys, CysLys₁₃Cys, CysLys₁₄Cys, CysLys₁₅Cys, CysLys₁₆Cys, CysLys₁₇Cys, CysLys₁₈Cys, CysLys₁₉Cys, CysLys₂₀Cys, CysLys₂₁₋₃₀Cys; CysHis₅Cys, CysHis₆Cys, CysHis₇Cys, CysHis₈Cys, CysHis₉Cys, CysHis₁₀Cys, CysHis₁₁Cys, CysHis₁₂Cys, CysHis₁₃Cys, CysHis₁₄Cys, CysHis₁₅Cys, CysHis₁₆Cys, CysHis₁₇Cys, CysHis₁₈Cys, CysHis₁₉Cys, CysHis₂₀Cys, CysHis₂₁₋₃₀Cys; CysOrn₅Cys, CysOrn₆Cys, CysOrn₇Cys, CysOrn₈Cys, CysOrn₉Cys, CysOrn₁₀Cys, CysOrn₁₁Cys, CysOrn₁₂Cys, CysOrn₁₃Cys, CysOrn₁₄Cys, CysOrn₁₅Cys, CysOrn₁₆Cys, CysOrn₁₇Cys, CysOrn₁₈Cys, CysOrn₁₉Cys, CysOrn₂₀Cys, CysOrn₂₁₋₃₀Cys.
```

Alternatively, peptide sequences useful for moiety P in formula IV are composed of two or more different basic amino acids, as in the following examples which are meant to refer to the composition of sequence without specifying a particular order in which the basic amino acids occur, while the Cys residues are in a terminal position:

CysArg$_{(4-29)}$Lys$_1$, CysArg$_{(4-29)}$His$_1$, CysArg$_{(4-29)}$Orn$_1$,

CysLys$_{(4-29)}$His$_1$, CysLys$_{(4-29)}$Orn$_1$, CysHis$_{(4-29)}$Orn$_1$,

CysArg$_{(3-28)}$Lys$_2$, CysArg$_{(3-28)}$His$_2$, CysArg$_{(3-28)}$Orn$_2$,

CysLys$_{(3-28)}$His$_2$, CysLys$_{(3-28)}$Orn$_2$, CysHis$_{(3-28)}$Orn$_2$,

CysArg$_{(2-27)}$Lys$_3$, CysArg$_{(2-27)}$His$_3$, CysArg$_{(2-27)}$Orn$_3$,

CysLys$_{(2-27)}$His$_3$, CysLys$_{(2-27)}$Orn$_3$, CysHis$_{(2-27)}$Orn$_3$,

CysArg$_{(1-26)}$Lys$_4$, CysArg$_{(1-26)}$His$_4$, CysArg$_{(1-26)}$Orn$_4$,

CysLys$_{(1-26)}$His$_4$, CysLys$_{(1-26)}$Orn$_4$, CysHis$_{(1-26)}$Orn$_4$,

CysArg$_{(3-28)}$Lys$_1$His$_1$, CysArg$_{(3-28)}$Lys$_1$Orn$_1$,

CysArg$_{(3-28)}$His$_1$Orn$_1$, CysArg$_1$Lys$_{(3-28)}$His$_1$,

CysArg$_1$Lys$_{(3-28)}$Orn$_1$, CysLys$_{(3-28)}$His$_1$Orn$_1$,

CysArg$_1$Lys$_1$His$_{(3-28)}$, CysArg$_1$His$_{(3-28)}$Orn$_1$,

CysLys$_1$His$_{(3-28)}$Orn$_1$; CysArg$_{(2-27)}$Lys$_2$His$_1$,

CysArg$_{(2-27)}$Lys$_1$His$_2$, CysArg$_{(2-27)}$Lys$_2$Orn$_1$,

CysArg$_{(2-27)}$Lys$_1$Orn$_2$, CysArg$_{(2-27)}$His$_2$Orn$_1$,

CysArg$_{(2-27)}$His$_1$Orn$_2$, CysArg$_2$Lys$_{(2-27)}$His$_1$,

CysArg$_1$Lys$_{(2-27)}$His$_2$, CysArg$_2$Lys$_{(2-27)}$Orn$_1$,

CysArg$_1$Lys$_{(2-27)}$Orn$_2$, CysLys$_{(2-27)}$His$_2$Orn$_1$,

CysLys$_{(2-27)}$His$_1$Orn$_2$, CysArg$_2$Lys$_1$His$_{(2-27)}$,

CysArg$_1$Lys$_2$His$_{(2-27)}$, CysArg$_2$His$_{(2-27)}$Orn$_1$,

CysArg$_1$His$_{(2-27)}$Orn$_2$, CysLys$_2$His$_{(2-27)}$Orn$_1$,

CysLys$_1$His$_{(2-27)}$Orn$_2$; CysArg$_{(1-26)}$Lys$_3$His$_1$,

CysArg$_{(1-26)}$Lys$_2$His$_2$, CysArg$_{(1-26)}$Lys$_1$His$_3$,

CysArg$_{(1-26)}$Lys$_3$Orn$_1$, CysArg$_{(1-26)}$Lys$_2$Orn$_2$,

CysArg$_{(1-26)}$Lys$_1$Orn$_3$, CysArg$_{(1-26)}$His$_3$Orn$_1$,

CysArg$_{(1-26)}$His$_2$Orn$_2$, CysArg$_{(1-26)}$His$_1$Orn$_3$,

CysArg$_3$Lys$_{(1-26)}$His$_1$, CysArg$_2$Lys$_{(1-26)}$His$_2$,

CysArg$_1$Lys$_{(1-26)}$His$_3$, CysArg$_3$Lys$_{(1-26)}$Orn$_1$,

CysArg$_2$Lys$_{(1-26)}$Orn$_2$, CysArg$_1$Lys$_{(1-26)}$Orn$_3$,

CysLys$_{(1-26)}$His$_3$Orn$_1$, CysLys$_{(1-26)}$His$_2$Orn$_2$,

CysLys$_{(1-26)}$His$_1$Orn$_3$, CysArg$_3$Lys1His$_{(1-26)}$,

CysArg$_2$Lys$_2$His$_{(1-26)}$, CysArg$_1$Lys$_3$His$_{(1-26)}$,

CysArg$_3$His$_{(1-26)}$Orn$_1$, CysArg$_2$His$_{(1-26)}$Orn$_2$,

CysArg$_1$His$_{(1-26)}$Orn$_3$, CysLys$_3$His$_{(1-26)}$Orn$_1$,

CysLys$_2$His$_{(1-26)}$Orn$_2$, CysLys$_1$His$_{(1-26)}$Orn$_3$;

CysArg$_{(2-27)}$Lys$_1$His$_1$Orn$_1$, CysArg$_1$Lys$_{(2-27)}$His$_1$Orn$_1$,

CysArg$_1$Lys$_1$His$_{(2-27)}$Orn$_1$, CysArg$_1$Lys$_1$His$_1$Orn$_{(2-27)}$,

CysArg$_{(1-26)}$Lys$_2$His$_1$Orn$_1$, CysArg$_{(1-26)}$Lys$_1$His$_2$Orn$_1$,

CysArg$_{(1-26)}$Lys$_1$His$_1$Orn$_2$, CysArg$_2$Lys$_{(1-26)}$His$_1$Orn$_1$,

CysArg$_1$Lys$_{(1-26)}$His$_2$Orn$_1$, CysArg$_1$Lys$_{(1-26)}$His$_1$Orn$_2$,

CysArg$_2$Lys$_1$His$_{(1-26)}$Orn$_1$, CysArg$_1$Lys$_2$His$_{(1-26)}$Orn$_1$,

CysArg$_1$Lys$_1$His$_{(1-26)}$Orn$_2$, CysArg$_2$Lys$_1$His$_1$Orn$_{(1-26)}$,

CysArg$_1$Lys$_2$His$_1$Orn$_{(1-26)}$, CysArg$_1$Lys$_1$His$_2$Orn$_{(1-26)}$;

CysArg$_{(4-29)}$Lys$_1$Cys, CysArg$_{(4-29)}$His$_1$Cys,

CysArg$_{(4-29)}$Orn$_1$Cys, CysLys$_{(4-29)}$His$_1$Cys,

CysLys$_{(4-29)}$Orn$_1$Cys, CysHis$_{(4-29)}$Orn$_1$Cys,

CysArg$_{(3-28)}$Lys$_2$Cys, CysArg$_{(3-28)}$His$_2$Cys,

CysArg$_{(3-28)}$Orn$_2$Cys, CysLys$_{(3-28)}$His$_2$Cys,

CysLys$_{(3-28)}$Orn$_2$Cys, CysHis$_{(3-28)}$Orn$_2$Cys,

CysArg$_{(2-27)}$Lys$_3$Cys, CysArg$_{(2-27)}$His$_3$Cys,

CysArg$_{(2-27)}$Orn$_3$Cys, CysLys$_{(2-27)}$His$_3$Cys,

CysLys$_{(2-27)}$Orn$_3$Cys, CysHis$_{(2-27)}$Orn$_3$Cys,

CysArg$_{(1-26)}$Lys$_4$Cys, CysArg$_{(1-26)}$His$_4$Cys,

CysArg$_{(1-26)}$Orn$_4$Cys, CysLys$_{(1-26)}$His$_4$Cys,

CysLys$_{(1-26)}$Orn$_4$Cys, CysHis$_{(1-26)}$Orn$_4$Cys,

CysArg$_{(3-28)}$Lys$_1$His$_1$Cys, CysArg$_{(3-28)}$Lys$_1$Orn$_1$Cys,

CysArg$_{(3-28)}$His$_1$Orn$_1$Cys, CysArg$_1$Lys$_{(3-28)}$His$_1$Cys,

CysArg$_1$Lys$_{(3-28)}$Orn$_1$Cys, CysLys$_{(3-28)}$His$_1$Orn$_1$Cys,

CysArg$_1$Lys$_1$His$_{(3-28)}$Cys, CysArg$_1$His$_{(3-28)}$Orn$_1$Cys,

CysLys$_1$His$_{(3-28)}$Orn$_1$Cys; CysArg$_{(2-27)}$Lys$_2$His$_1$Cys,

CysArg$_{(2-27)}$Lys$_1$His$_2$Cys, CysArg$_{(2-27)}$Lys$_2$Orn$_1$Cys,

CysArg$_{(2-27)}$Lys$_1$Orn$_2$Cys, CysArg$_{(2-27)}$His$_2$Orn$_1$Cys,

CysArg$_{(2-27)}$His$_1$Orn$_2$Cys, CysArg$_2$Lys$_{(2-27)}$His$_1$Cys,

CysArg$_1$Lys$_{(2-27)}$His$_2$Cys, CysArg$_2$Lys$_{(2-27)}$Orn$_1$Cys,

CysArg$_1$Lys$_{(2-27)}$Orn$_2$Cys, CysLys$_{(2-27)}$His$_2$Orn$_1$Cys,

CysLys$_{(2-27)}$His$_1$Orn$_2$Cys, CysArg$_2$Lys$_1$His$_{(2-27)}$Cys,

CysArg$_1$Lys$_2$His$_{(2-27)}$Cys, CysArg$_2$His$_{(2-27)}$Orn$_1$Cys,

CysArg$_1$His$_{(2-27)}$Orn$_2$Cys, CysLys$_2$His$_{(2-27)}$Orn$_1$Cys,

CysLys$_1$His$_{(2-27)}$Orn$_2$Cys; CysArg$_{(1-26)}$Lys$_3$His$_1$Cys,

CysArg$_{(1-26)}$Lys$_2$His$_2$Cys, CysArg$_{(1-26)}$Lys$_1$His$_3$Cys,

CysArg$_{(1-26)}$Lys$_3$Orn$_1$Cys, CysArg$_{(1-26)}$Lys$_2$Orn$_2$Cys,

CysArg$_{(1-26)}$Lys$_1$Orn$_3$Cys, CysArg$_{(1-26)}$His$_3$Orn$_1$Cys,

CysArg$_{(1-26)}$His$_2$Orn$_2$Cys, CysArg$_{(1-26)}$His$_1$Orn$_3$Cys,

CysArg$_3$Lys$_{(1-26)}$His$_1$Cys, CysArg$_2$Lys$_{(1-26)}$His$_2$Cys,

CysArg$_1$Lys$_{(1-26)}$His$_3$Cys, CysArg$_3$Lys$_{(1-26)}$Orn$_1$Cys,

CysArg$_2$Lys$_{(1-26)}$Orn$_2$Cys, CysArg$_1$Lys$_{(1-26)}$Orn$_3$Cys,

CysLys$_{(1-26)}$His$_3$Orn$_1$Cys, CysLys$_{(1-26)}$His$_2$Orn$_2$Cys,

CysLys$_{(1-26)}$His$_1$Orn$_3$Cys, CysArg$_3$Lys$_1$His$_{(1-26)}$Cys,

CysArg$_2$Lys$_2$His$_{(1-26)}$Cys, CysArg$_1$Lys$_3$His$_{(1-26)}$Cys,

CysArg$_3$His$_{(1-26)}$Orn$_1$Cys, CysArg$_2$His$_{(1-26)}$Orn$_2$Cys,

CysArg$_1$His$_{(1-26)}$Orn$_3$Cys, CysLys$_3$His$_{(1-26)}$Orn$_1$Cys,

CysLys$_2$His$_{(1-26)}$Orn$_2$Cys, CysLys$_1$His$_{(1-26)}$Orn$_3$Cys;

CysArg$_{(2-27)}$Lys$_1$His$_1$Orn$_1$Cys,

CysArg$_1$Lys$_{(2-27)}$His$_1$Orn$_1$Cys,

CysArg$_1$Lys$_1$His$_{(2-27)}$Orn$_1$Cys,

CysArg$_1$Lys$_1$His$_1$Orn$_{(2-27)}$Cys,

CysArg$_{(1-26)}$Lys$_2$His$_1$Orn$_1$Cys,

CysArg$_{(1-26)}$Lys$_1$His$_2$Orn$_1$Cys,

CysArg$_{(1-26)}$Lys$_1$His$_1$Orn$_2$Cys,

CysArg$_2$Lys$_{(1-26)}$His$_1$Orn$_1$Cys,

CysArg$_1$Lys$_{(1-26)}$His$_2$Orn$_1$Cys,

CysArg$_1$Lys$_{(1-26)}$His$_1$Orn$_2$Cys,

CysArg$_2$Lys$_1$His$_{(1-26)}$Orn$_1$Cys,

CysArg$_1$Lys$_2$His$_{(1-26)}$Orn$_1$Cys,

CysArg$_1$Lys$_1$His$_{(1-26)}$Orn$_2$Cys,

CysArg$_2$Lys$_1$His$_1$Orn$_{(1-26)}$Cys,

CysArg$_1$Lys$_2$His$_1$Orn$_{(1-26)}$Cys,

CysArg$_1$Lys$_1$His$_2$Orn$_{(1-26)}$Cys.

Moreover, the peptide moiety P in formula IV may comprise one or more aromatic amino acids, in particular Trp, Tyr, or Phe, as described above in more detail. Optionally, a peptide sequence rich in aromatic amino acids may further contain at least one proline, which may serve as a structure breaker of longer sequences of Trp, Tyr and Phe. Depending on the length of the aromatic amino acid sequence, it may be preferred to incorporate two, three or more prolines.

Optionally, moiety P in formula IV, if a peptide sequence is selected, such sequence may further contain one or more hydrophilic amino acids, in particular selected from those with an uncharged polar side chain such as Thr, Ser, Asn and/or Gln. Reference is made to the more detailed description above relating to the incorporation of such amino acids into P in general. The same applies to the incorporation of lipophilic amino acids in moiety P, in particular Leu, Val, Ile, Ala, and/or Met, and to any other modifications of P.

Alternatively, the cationic compound according to formula IV may comprise a moiety P represented by a polymer moiety having a molecular weight from about 0.5 kDa to about 30 kDa. Also in this case, the options and preferences generally described for polymer moiety P above should be applied this specific case in which P is a part of a compound of formula IV.

Again, as P occurs in this case in multimeric form, comprising several units of a P and/or linked with P$^1$ and P$^3$ and connected by disulfide linkages derived from —SH groups, P may in this case comprise no —SH groups as such any more in its oxidised form as represented by formula IV.

As mentioned, P may be an optionally modified polyacrylate, chitosan, polyethylenimine, polyamine, polyaminoesters, or polyamidoamine, or any copolymer thereof.

Preferably, the polymer moiety selected for P exhibits a molecular weight of about 0.5 kDa to about 20 kDa, such as from about 0.5 kDa to about 11.5 kDa, or from about 1 kDa to about 10 kDa, or from about 0.1 kDa to about 8 kDa, or from about 0.1 kDa to about 6 kDa, or from about 0.1 kDa to about 5 kDa, or from about 0.5 kDa to about 5 kDa, or from about 0.3 kDa to about 20 kDa, or from about 0.3 kDa to about 10 kDa, or from about 0.4 kDa to about 10 kDa, or from about 0.5 kDa to about 10 kDa, or from about 0.5 kDa to about 7.5 kDa, or from about 0.5 kDa to about 4 kDa, or from about 0.5 kDa to about 3 kDa, or from about 0.67 kDa to about 2.7 kDa, respectively.

Preferred polymer moieties selected for P include e.g. modified polyaminoacids, such as β-aminoacid-polymers or reversed polyamides; modified polyethylenes, such as (poly(N-ethyl-4-vinylpyridinium bromide)) (PEVP), etc.; modified acrylates, such as (poly(dimethylaminoethyl methylacrylate)) (pDMAEMA), etc.; modified amidoamines such as (poly(amidoamine)) (pAMAM), etc.; modified polybetaaminoester (PBAE), such as diamine end modified 1,4 butanediol diacrylate-co-5-amino-1-pentanol polymers, etc.; dendrimers, such as polypropylamine dendrimers or pAMAM based dendrimers, etc.; polyimine(s), such as poly(ethyleneimine) (PEI or pEI), poly(propyleneimine), etc.; polyallylamine, (1,5-dimethyl-1,5-diazaundecamethylene polymethobromide, or hexadimethrine bromide (Polybrene®).

Also preferred are cationic polysaccharides, i.e. sugar backbone-based polymers, such as cyclodextrin based polymers, dextran based polymers, chitosan, etc.; silane backbone-based polymers, such as PMOXA-PDMS copolymers, etc.; as well as blockpolymers consisting of a combination of one or more cationic blocks (e.g. selected of a cationic polymer as mentioned above) and of one or more hydrophilic- or hydrophobic blocks (e.g. polyethylene glycol).

In one embodiment, the cationic compound comprising at least one cationic moiety P is a compound according to formula IVa

   (formula IVa)

wherein

P, P$^1$, P$^3$, L$^1$, and L$^2$ are defined as above;

(AA)$_x$ is an amino acid (AA) component wherein x is an integer selected from 1 to about 100;

a and b are integers independently selected from 1 to about 49 such that the sum of a+b is in the range from 2 to about 50;

the moieties [P-] and [(AA)$_x$-] may be arranged in any order within the subformula $\{[P-]_a[(AA)_x-]_b\}$; and wherein each of P, P$^1$, P$^3$ and (AA)$_x$ is linked to each neighboring P, P$^1$, P$^3$ and (AA)$_x$ through a disulfide linkage.

Again, the options and preferences previously described for P, P$^1$, P$^3$, L$^1$, and L$^2$ in the context of formula IV are also applicable to this embodiment by analogy. Formula IVa differs from formula IV in that it further comprises one or more peptide sequences (AA)$_x$ in combination with the one or more moieties P in the core region of the compound.

Each individual unit of (AA)$_x$ may be independently selected, as well as each amino acid within a unit. One or more (AA)$_x$ units may be used to introduce specific non-basic amino acids, such as one or more aromatic amino acids, in particular Trp, Tyr, and/or Phe; or one or more hydrophilic amino acids, in particular Thr, Ser, Asn and/or Gln; or lipophilic amino acids, in particular Leu, Val, Ile, Ala, and/or Met. As such, and as described above, the incorporation via (AA)$_x$ units is an alternative to the introduction of the respective amino acids within the peptide sequence P itself. When separately incorporated as $(AA)_x$ units according to formula IVa, each of these $(AA)_x$ units is linked to each neighboring P, $P^1$, $P^3$ and $(AA)_x$ moiety through a disulfide linkage, which in one of the preferred embodiments involves a terminal Cys residue, as described above.

Preferably, the number of amino acids per $(AA)_x$ moiety is from about 2 to about 50, or from about 3 to about 50, and more preferably of about 7 to about 30, or of about 3 to about 25. Also preferred are lengths in the ranges from about 3 to about 20 amino acids, or from about 5 to about 20 amino acids, or from about 7 to about 30 amino acids, or from about 6 to about 18 amino acids, or from about 7 to about 17 amino acids, such as about 5 to about 15 amino acids.

In the case that P in formula IVa is a peptide moiety, it is preferred that the content of cationic amino acids in component $\{[P-]_a[(AA)_x-]_b\}$ is at least 10%, 20%, or 30%, preferably at least 40%, more preferably at least 50% or 60%. Optionally, it is about 50±10%, 60±10%, 70±10%, or 80±10%. In this context, the content (i.e. number) of all amino acids in the entire component $\{[P-]_a[(AA)_x-]b\}$ is defined as 100%.

In the case that moiety P in formula IVa is a polymer chain, the content of cationic charges in component $\{[P-]_a[(AA)_x-]_b\}$ at a (physiological) pH as defined herein is preferably more than 50%, such as at least 60%, 70%, 80%, 90%, or even 95%, 96%, 97%, 98%, 99% or 100%, or may be in the range of higher than about 50% to 100%, or from about 60% to about 100%, or in a range formed by any two of the afore mentioned values, provided, that the content of all charges, e.g. positive and negative charges at a (physiological) pH as defined herein, in the entire component $\{[P-]_a[(AA)_x-]_b\}$ is 100%.

In a further embodiment, the cationic compound comprising at least one cationic moiety P is a compound according to one of the following formulae IVb or IVc:

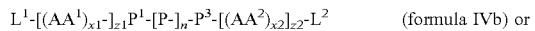

(formula IVb) or

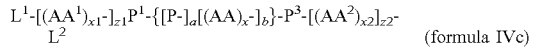

(formula IVc)

wherein P, $P^1$, $P^3$, $(AA)_x$, $L^1$, and $L^2$ are defined as above;
$(AA^1)_{x1}$ and $(AA^2)_{x2}$ are amino acid (AA) components, wherein the amino acids $AA^1$ and $AA^2$ may be the same or different from AA and/or each other, and wherein x1 and x2 are integers independently selected from 1 to about 100;

z1 and z2 are integers independently selected from 1 to about 30;

the moieties [P-] and $[(AA)_x-]$ may be arranged in any order within the subformula $\{[P-]_a[(AA)_x-]_b\}$; and wherein any of P, $P^1$, $P^3$, $(AA)_x$, $(AA^1)_{x1}$ or $(AA^2)_{x2}$ may be linked to a neighboring P, $P^1$, $P^3$, $(AA)_x$, $(AA^1)_{x1}$, $(AA^2)_{x2}$, $L^1$ and/or $L^2$ through a disulfide linkage.

Again, the options and preferences previously described for P, $P^1$, $P^3$, $L^1$, $L^2$ and $(AA)_x$ as well as a and b in the context of formula IV and formula IVa are also applicable to these embodiments with cationic compounds according to formulas IVb and IVc by analogy. The preferences previously described for x also apply to x1 and x2. Formula IVb differs from formula VIa in that the amino acid component $(AA)_x$ has been replaced by the amino acid components $(AA^1)_{x1}$ and $(AA^2)_{x2}$ which are also defined as independently selected repeating units of amino acids with 1 to about 100 amino acids per unit and from 1 to about 30 units per molecule; instead of being located at or near the core portion of the molecule, $(AA^1)_{x1}$ and $(AA^2)_{x2}$ are positioned outside the core and between $P^1$ and the optional component $L^1$ and between $P^3$ and the optional component $L^2$, respectively, providing for a modulation of the physical and biological properties of the molecular construct. In the compound according to formula IVc, amino acid components are present both in the core region of the molecule as in formula IVa and also towards the two terminal ends as in formula IVb.

The integers z1 and z2 are selected from the range of 1 to about 30, and more preferably from about 1 to about 20, or from 1 to about 15, or from 1 to about 10, respectively.

In one embodiment, the composition comprises two or more different species of cationic peptides and/or polymers. In this embodiment, each of the cationic peptides and/or polymers may be individually selected, wherein all options and preferences mentioned above apply to each selection.

As mentioned, the cationic lipidoid compound, also simply referred to as lipidoid, is a lipid-like compound, i.e. an amphiphilic compound with lipid-like physical properties.

In one embodiment, the lipidoid is a compound comprising at least two cationic nitrogen atoms and at least two lipophilic tails. As used herein, a "tail" is a substructure of a molecule representing a chain or chain-like structure, such as an optionally substituted hydrocarbyl, acyl or acyloxyalkyl chain of at least four, and more preferably at least six, carbon atoms. The optionally substituted hydrocarbyl, acyl or acyloxyalkyl chain representing the lipophilic tail may be directly connected with a cationic nitrogen atom.

In one specific embodiment, the lipidoid is a compound comprising two identical lipophilic tails, each of which is directly connected with a cationic nitrogen atom. In another specific embodiment, the lipidoid is a compound comprising three identical lipophilic tails, each tail being directly connected with a cationic nitrogen atom. In a further specific embodiment, the lipidoid is a compound comprising four or more identical lipophilic tails, each tail being directly connected with a cationic nitrogen atom. In each of these embodiments, the lipidoid may optionally comprise a further nitrogen atom to which no lipophilic tail is connected. Such lipidoid may also be understood as a compound having a cationic backbone derived from an oligoamine with the lipophilic tails being attached to the, or some of the, cationic nitrogens of the oligoamine.

If the lipophilic tails are substituted hydrocarbyl (e.g. alkyl) chains, the substituent may, for example, be a methyl or a hydroxyl.

The optionally substituted hydrocarbyl chain may be saturated, such as to resemble an alkyl, or it may be unsaturated, i.e. an alkenyl or alkynyl, each optionally having one, two, three or more carbon-carbon double bonds and/or triple bonds. In the case of tail structures representing or including an acyl or acyloxyalkyl group, these may also comprise one, two or more carbon-carbon double bonds and/or triple bonds in the hydrocarbon segment of the tail.

In one embodiment, the lipidoid compound is free of hydrolysable linking groups, such as ester, amide or carbamate groups. As used herein, a linking group is a group which links the lipophilic tails of the lipidoid molecule to the hydrophilic region comprising the cationic nitrogen atoms. Conventional cationic lipids that have been proposed as carriers or agents to deliver nucleic acids to cells and enhance transfection often—if not typically—exhibit such linkers or linking groups, which are most often hydrolysable and/or enzymatically cleavable. In particular, linkers with ester groups have been proposed, but also linkers with amide groups or carbamate groups, all of which are susceptible to hydrolytic and/or enzymatic cleavage in vivo.

As used herein, hydrolysable means that an appreciable degree of hydrolysis occurs in a physiological fluid (such as interstitial fluid) under in vivo conditions within seconds, minutes, hours, or days; preferably, the respective compound or group is hydrolysed to at least 50% after not more than 7 days, or even after not more than 2 days.

In some embodiments of the inventions, the lipidoid compound comprises a PEG moiety.

As said, the lipidoid compound is cationic, which means that it is cationisable or permanently cationic. In one embodiment, the lipidoid is cationisable, i.e. it comprises one or more cationisable nitrogen atoms, but no permanently cationic nitrogen atoms. In another embodiment, at least one of the cationic nitrogen atoms of the lipidoid is permanently cationic. Optionally, the lipidoid comprises two permanently cationic nitrogen atoms, three permanently cationic nitrogen atoms, or even four or more permanently cationic nitrogen atoms.

In a further embodiment, the lipidoid compound is a compound according to formula I

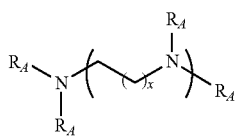

(formula I)

or a pharmaceutically acceptable salt thereof.

In formula I, each occurrence of $R_A$ is independently unsubstituted, cyclic or acyclic, branched or unbranched $C_{1-20}$ aliphatic; substituted or unsubstituted, cyclic or acyclic, branched or unbranched $C_{1-20}$ heteroaliphatic; substituted or unsubstituted aryl; substituted or unsubstituted heteroaryl;

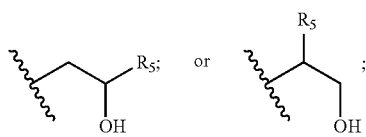

wherein at least one $R_A$ is

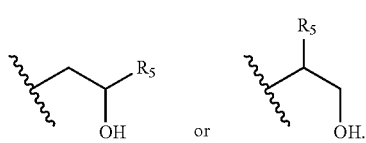

Moreover, each occurrence of $R_5$ is independently unsubstituted, cyclic or acyclic, branched or unbranched $C_{8-16}$ aliphatic; substituted or unsubstituted aryl; or substituted or unsubstituted heteroaryl. Furthermore, each occurrence of x is an integer from 1 to 10, and each occurrence of y is an integer from 1 to 10. In some embodiments of the invention $R_A$ or $R_5$ is or is substituted with a PEG-moiety.

Optionally, $R_5$ is $C_8$-$C_{16}$ alkyl for at least one occurrence, or even at each occurrence. According to one of the preferred embodiments, at least one x is selected from 1 or 2, and optionally all occurrences of x are 1 or 2. Moreover, at least one y is selected from 1 or 2, and optionally all occurrences of y are 1 or 2. In a further embodiment, all occurrences of $R_5$ are $C_8$-$C_{16}$ alkyl, all occurrences of x are 1 or 2, and all occurrences of y are 1 or 2.

In some embodiments, such lipidoids may be prepared by reacting an oligoamine and an epoxide-terminated aliphatic compound at elevated temperatures, such as at 80 to 95° C., in the absence of a solvent. Such lipidoid compound includes a hydrophilic portion resulting from the opening of the epoxide by the amine and a hydrophobic aliphatic tail. Preferably, the oligoamine comprises from 2 to 5 nitrogen atoms. Among the preferred oligoamines are, without limitation:

$H_2N$—$CH_2$—$CH_2$—$NH_2$ $H_2N$—$CH_2$—$CH_2$—$CH_2$—$NH_2$ $H_3C$—$NH$—$CH_2$—$CH_2$—$CH_2$—$NH_2$ $H_3C$—$NH$—$CH_2$—$CH_2$—$CH_2$—$NH$—$CH_3$ $H_2N$—$CH_2$—$CH_2$—$NH$—$CH_2$—$CH_2$—$OH$ $H_2N$—$CH_2$—$CH_2$—$NH$—$CH_2$—$CH_2$—$NH_2$ $H_2N$—$CH_2$—$CH_2$—$CH_2$—$NH$—$CH_2$—$CH_2$—$NH_2$ $H_2N$—$CH_2$—$CH_2$—$NH(CH_3)$—$CH_2$—$CH_2$—$NH_2$ $HO$—$CH_2$—$CH_2$—$NH$—$CH_2$—$CH_2$—$NH$—$CH_2$—$CH_2$—$OH$ $H_2N$—$CH_2$—$CH_2$—$NH$—$CH_2$—$CH_2$—$NH$—$CH_2$—$CH_2$—$NH_2$ $H_2N$—$CH_2$—$CH_2$—$N(CH_2$—$CH_2$—$NH_2)$—$CH_2$—$CH_2$—$NH_2$ $H_2N$—$CH_2$—$CH_2$—$NH$—$CH_2$—$CH_2$—$NH$—$CH_2$—$CH_2$—$NH$—$CH_2$—$CH_2$—$NH_2$

In some embodiments of the invention, the oligoamine based lipidoids are optionally substituted with a PEG moiety.

Among the preferred epoxide-terminated aliphatic compound are, without limitation, 2-alkyloxiranes wherein alkyl is butyl, hexyl, octyl, decyl, dodecyl, tetradecyl or octadecyl. Optionally, the alkyl group may further exhibit an alkyl side chain, such as a methyl, ethyl, propyl, or isopropyl side chain. Moreover, the alkyl group of the 2-alkyloxirane may also comprise one or more heteroatoms such as oxygen. Furthermore, the epoxide-terminated aliphatic compound may comprise one or more carbon-carbon double or triple bonds.

For further guidance regarding the preparation of such lipidoid compounds, reference is made to U.S. Pat. No. 8,969,353, the disclosure of which is incorporated herein in its entirety.

According to a further embodiment, wherein the lipidoid compound comprises two or three moieties of formula IIa and/or formula IIb:

—N($R_1$)—$CH_2$—CH($R_5$)—$R_2$ (formula IIa)

—$N^+$($R_3$)($R_4$)—$CH_2$—CH($R_5$)—$R_2$ (formula IIb)

wherein independently for each individual moiety of formula IIa or formula IIb, $R_1$ is selected from hydrogen or $C_1$-$C_4$-alkyl; $R_2$ is selected from linear or branched, saturated or unsaturated $C_6$-$C_{16}$ hydrocarbyl chain; $R_3$ and $R_4$ are selected from $C_1$-$C_4$-alkyl, and $R_5$ is hydrogen or hydroxyl. Optionally, in some embodiments, each moiety of formula IIa and/or IIb individually may or may not be substituted with a PEG moiety.

$R_1$ may be the same or different for each occurrence. In one embodiment, it is the same for each occurrence, in particular when $R_1$ is hydrogen or methyl. $R_3$ and $R_4$ may also be the same for each occurrence; for example, all instances of $R_3$ and $R_4$ may be methyl.

In yet a further embodiment, the lipidoid compound is a compound comprising three identical moieties of formula IIa and/or formula IIb, wherein $R_1$ is hydrogen, $R_2$ is a linear or branched $C_6$-$C_{16}$ alkyl chain, $R_3$ and $R_4$ are methyl, and $R_5$ is hydroxyl. For example, a compound according to formula IIa may be based on the oligoamine backbone

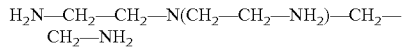

wherein for each of the three primary amino groups, one of the hydrogen atoms is substituted with

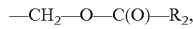

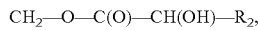

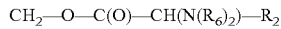

and/or

wherein $R_2$ is a linear or branched $C_6$-$C_{16}$ alkyl, in particular a linear $C_6$, $C_8$, $C_{10}$ or $C_{12}$ alkyl and each $R_6$ may be independently H or $CH_3$. A compound according to formula IIb may be based on the same oligoamine backbone and the same substituent —$CH_2$—$CH(OH)$—$R_2$, but in addition have two methyl groups at each of the nitrogen atoms to which also the substituent —$CH_2$—$CH(OH)$—$R_2$ is attached. Again, $R_2$ is a linear or branched $C_6$-$C_{16}$ alkyl, in particular a linear $C_6$, $C_8$, $C_{10}$ or $C_{12}$ alkyl.

Optionally, wherein for each of the three primary amino groups, one of the hydrogen atoms is substituted with a PEG moiety or is PEGylated.

In one specific embodiment, the permanently cationic lipidoid is a compound comprising the cation depicted in formula IX:

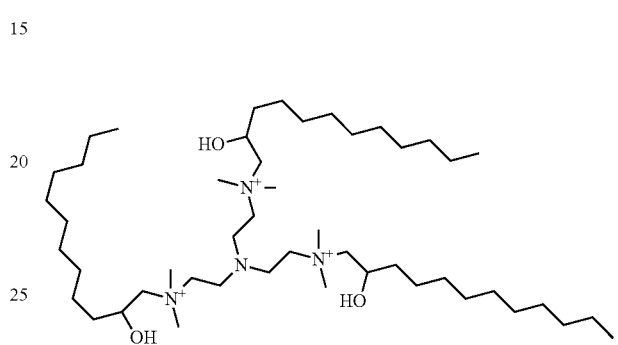

and further optionally an anion, preferably an anion as described above. The compound may be prepared by first reacting the oligoamine of the formula:

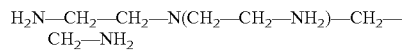

with an unbranched, saturated terminal $C_{12}$ alkyl expoxide followed by quaternisation with activated methyl such as methyl iodide. One aspect of the invention is directed to this compound as such, including any salts thereof.

In a further specific embodiment of the invention, the lipidoid is a compound according to formula X:

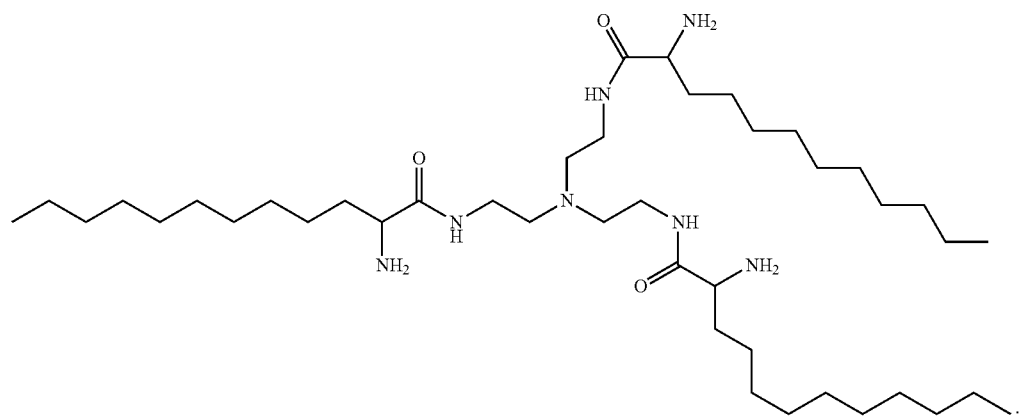 [SMILES: CCCCCCCCCCC(N)C(=O)NCCN(CCNC(=O)C(N)CCCCCCCCCC)CCNC(=O)C(N)CCCCCCCCCC]

Optionally, the lipidoid compound is a lipidoid compound according to formula X, wherein the primary amines are each independently substituted once or twice with methyl. In a particular preferred embodiment, the lipidoid compound is a compound according to formula Xa:

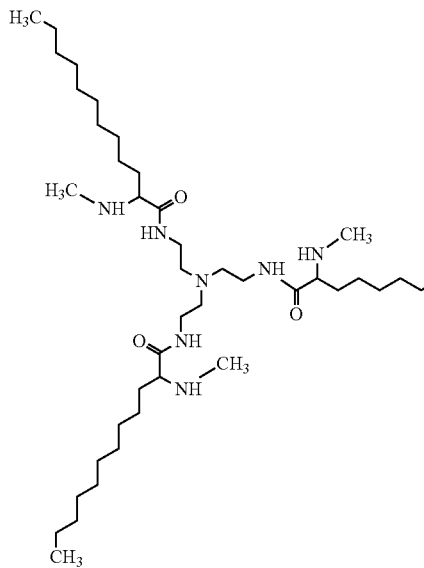

In a further particular preferred embodiment of the invention the lipidoid compound is a compound according to formula Xb:

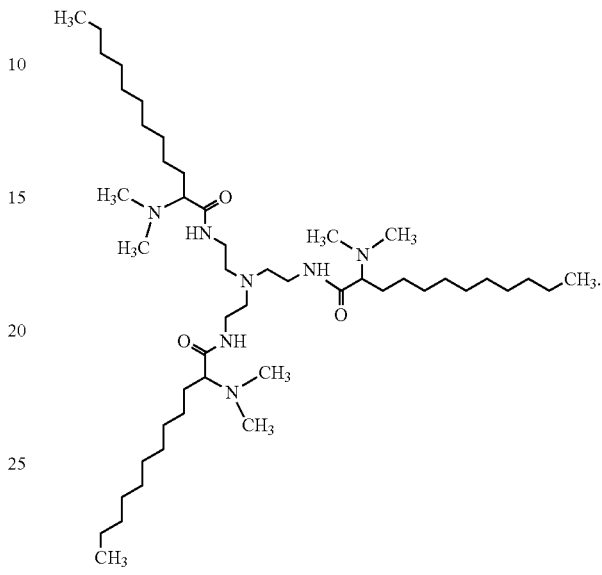

In a particular preferred embodiment, the lipidoid compound is a compound comprising the structure:

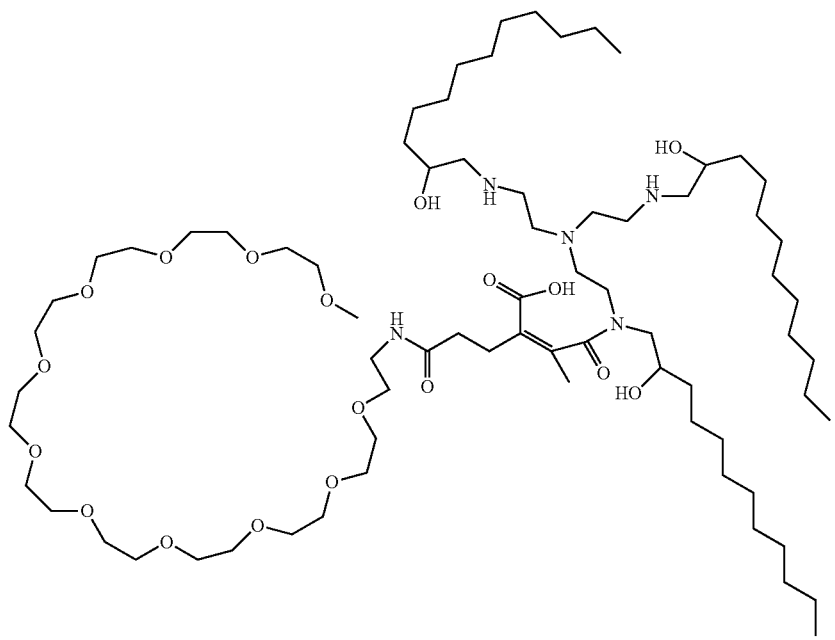 [SMILES: CCCCCCCCCCC(O)CNCCN(CCNCC(O)CCCCCCCCCC)CCN(CC(O)CCCCCCCCCC)C(=O)/C(C)=C(/CCC(=O)NCCOCCOCCOCCOCCOCCOCCOCCOCCOCCOCCOC)C(=O)O]

In a further preferred embodiment of the invention, the lipidoid compound is a compound comprising the structure:

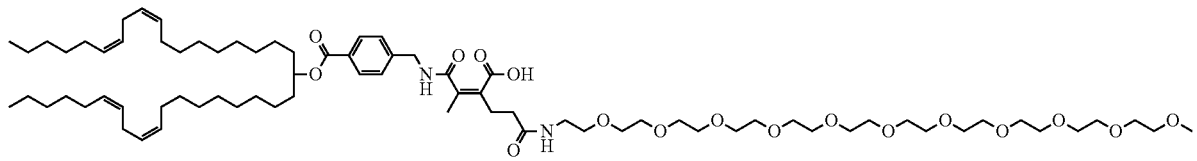 [SMILES: CCCCC/C=C\C/C=C\CCCCCCCCC(CCCCCCCC/C=C\C/C=C\CCCCC)OC(=O)c1ccc(CNC(=O)/C(C)=C(/CCC(=O)NCCOCCOCCOCCOCCOCCOCCOCCOCCOCCOCCOC)C(=O)O)cc1]

In a further embodiment, the lipidoid compound is a compound according to formula III

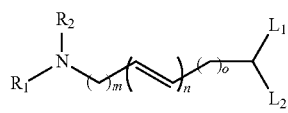

(formula III)

wherein $R_1$ and $R_2$ are each independently selected from the group consisting of hydrogen, an optionally substituted, saturated or unsaturated $C_1$-$C_{20}$ hydrocarbyl, and an optionally substituted, saturated or unsaturated $C_6$-$C_{20}$ acyl. Moreover, $L_1$ and $L_2$ are each independently selected from optionally substituted, saturated or unsaturated $C_1$-$C_{30}$ hydrocarbyls; m and o are each independently selected from the group consisting of zero and any positive integer; and n is any positive integer. In some embodiments, the lipidoids according to formulas I or II are PEGylated. In other embodiments, the lipidoids according to formula III are PEGylated. In other embodiments, the general cationic or ionizable lipid is PEGylated. In some embodiments, the number of ethylene glycol moieties in PEG is from 5 to 9, 10 to 20, 21-30, 31-40, 41 to 50 or more or the PEG moiety is selected from PEG200 to PEG10000. Preferably the PEG moiety is selected from PEG500 to PEG2000. In other embodiments, PEG polymers which are branched, Y shaped or comb shaped are used.

In one of the preferred embodiments, $R_1$ and $R_2$ of the lipidoid of formula III are both $C_1$-$C_{20}$ alkyl, more preferably $C_1$-$C_6$alkyl, in particular methyl, ethyl, propyl or isopropyl. For example, both of $R_1$ and $R_2$ may be methyl. Moreover, n is preferably not higher than about 5, in particular not higher than about 2, such as 1. Furthermore, o is preferably selected from 0 or 1, and m is preferably selected from the range from 1 to 6, such as 1, 2, 3, 4, 5 or 6.

In a further embodiment, $L_1$ and $L_2$ are each independently selected from unsaturated $C_6$-$C_{22}$ hydrocarbyls, in particular from $C_{10}$-$C_{22}$ hydrocarbyls. Among the preferred hydrocarbyls are linear omega-6 and omega-9 unsaturated hydrocarbon chains with 14, 16, 18, 20, or 22 carbon atoms.

Also preferred are lipidoids of formula III wherein $R_1$ and $R_2$ are both methyl, m is 3 or 4, n is 1, o is 0 or 1, and $L_1$ and $L_2$ are identical linear omega-6 and omega-9 unsaturated hydrocarbon chains with 16 or 18 carbon atoms. In some embodiments at least one of $R_1$, $R_2$, $L_1$ or $L_2$ may be a PEG moiety or substituted with a PEG moiety.

In a further embodiment, the lipidoid is a compound according to formula III as defined above except that n is 0.

Optionally, the composition comprises two or more lipidoids, each being independently selected as described above; or it may comprise a combination of a lipidoid with another cationic lipid.

In one embodiment, the composition is substantially free of lipids other than the lipidoid defined above; or is substantially free of lipids other than those defined in one of the claims. In fact, it is one of the particular advantages of the present invention that it does benefit from the properties and advantageous effects of the lipidoid in terms of effective delivery of the nucleic acid but without requiring the presence of those other lipids which are not cationic as defined above and which are often used to prepare lipoplexes or lipid nanoparticles, such as zwitterionic phospholipids or steroids such as cholesterol, which are sometimes referred to as helper lipids. Accordingly, it is one of the preferred embodiments of the invention that the composition is free of neutral or zwitterionic lipids; or that it is free of steroids such as cholesterol.

Without being restricted thereto, the following lipidoid structures have been used in the present invention:

3-C12—OH

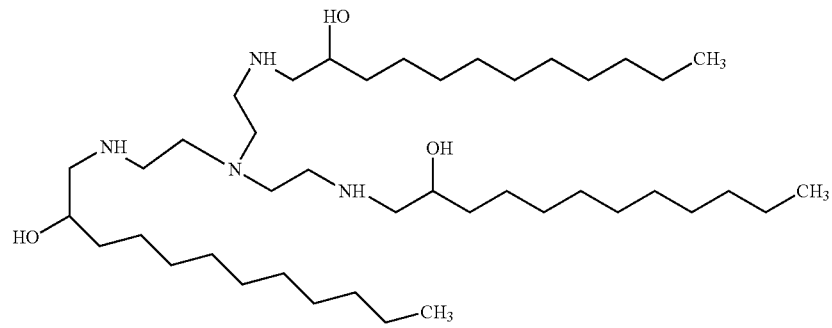 [SMILES: CCCCCCCCCCC(O)CNCCN(CCNCC(O)CCCCCCCCCC)CCNCC(O)CCCCCCCCCC]

-continued
3-C12—
OH-cat
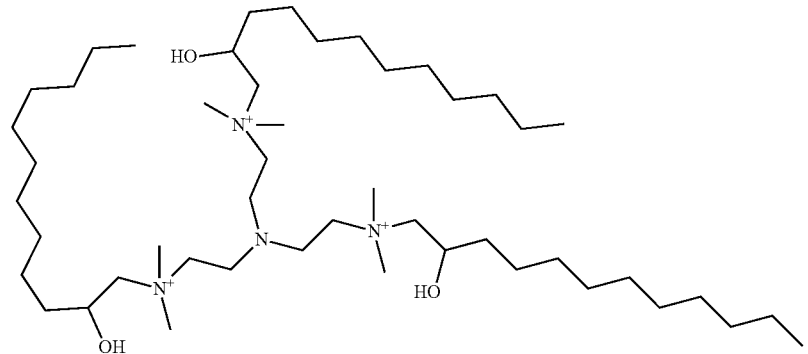 [SMILES: CCCCCCCCCCC(O)C[N+](C)(C)CCN(CC[N+](C)(C)CC(O)CCCCCCCCCC)CC[N+](C)(C)CC(O)CCCCCCCCCC]
3-C12-
amide
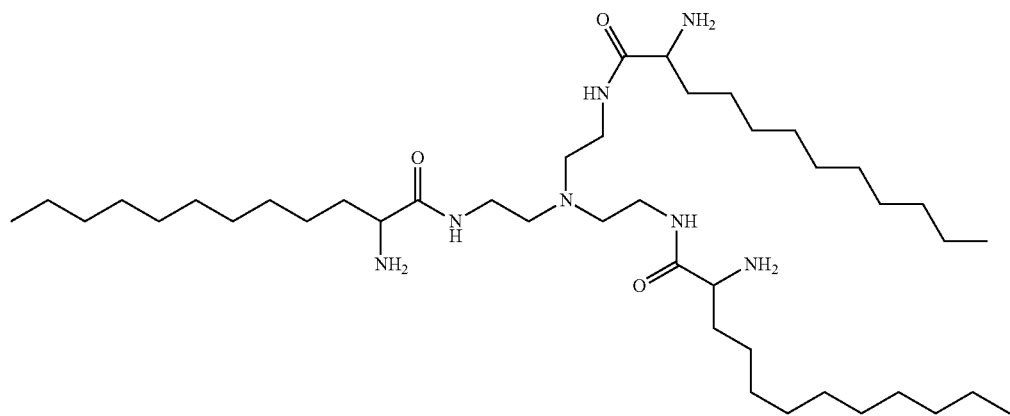 [SMILES: CCCCCCCCCCC(N)C(=O)NCCN(CCNC(=O)C(N)CCCCCCCCCC)CCNC(=O)C(N)CCCCCCCCCC]
3-C12-
amide
mono-
methyl
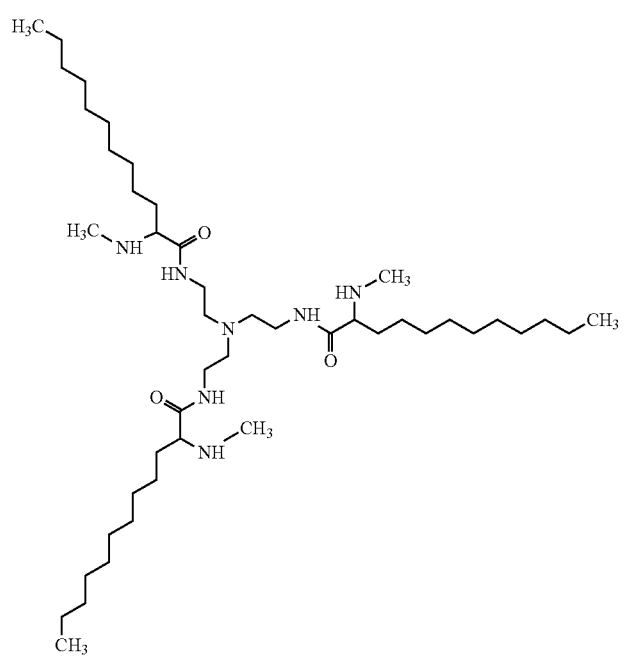 [SMILES: CCCCCCCCCCC(NC)C(=O)NCCN(CCNC(=O)C(CCCCCCCCCC)NC)CCNC(=O)C(CCCCCCCCCC)NC]

| | |
|---|---|
| 3-C12-amide dimethyl | 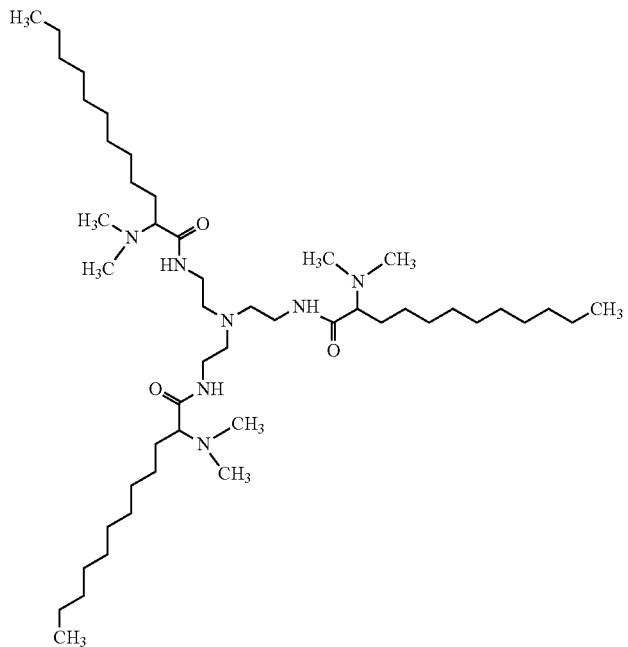 [SMILES: CCCCCCCCCCC(C(=O)NCCN(CCNC(=O)C(CCCCCCCCCC)N(C)C)CCNC(=O)C(CCCCCCCCCC)N(C)C)N(C)C] |
| Rev-PEG(10)-3-C12—OH | 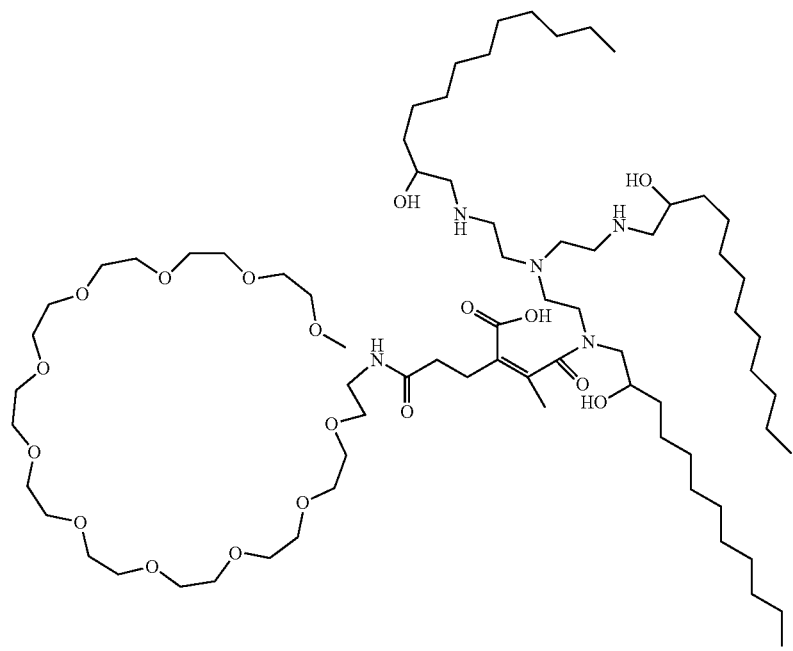 [SMILES: CCCCCCCCCCC(O)CNCCN(CCNCC(O)CCCCCCCCCC)CCN(CC(O)CCCCCCCCCC)C(=O)/C(C)=C(/CCC(=O)NCCOCCOCCOCCOCCOCCOCCOCCOCCOCCOCCOC)C(=O)O] |
| Rev-PEG(10)-DLin-pAbenzoic | 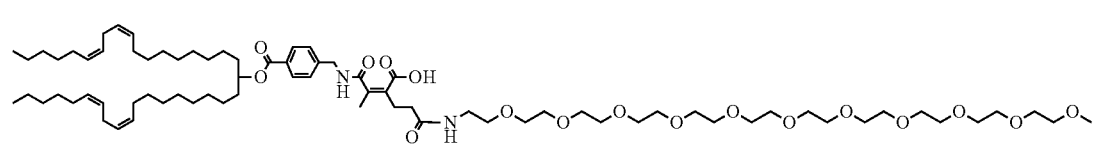 [SMILES: CCCCC/C=C\C/C=C\CCCCCCCCC(CCCCCCCC/C=C\C/C=C\CCCCC)OC(=O)c1ccc(CNC(=O)/C(C)=C(/CCC(=O)NCCOCCOCCOCCOCCOCCOCCOCCOCCOCCOCCOC)C(=O)O)cc1] |

-continued
3C12-amide-TMA cat.
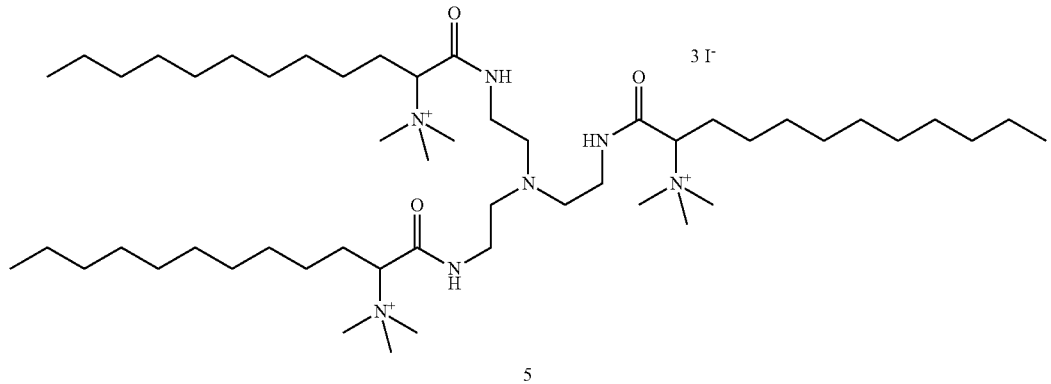 [SMILES: CCCCCCCCCCC(C(=O)NCCN(CCNC(=O)C(CCCCCCCCCC)[N+](C)(C)C)CCNC(=O)C(CCCCCCCCCC)[N+](C)(C)C)[N+](C)(C)C]
5
3C12-amide-DMA
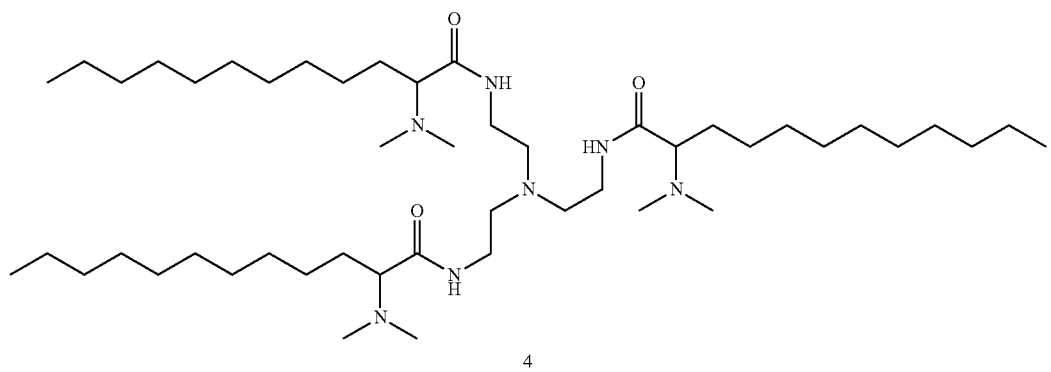 [SMILES: CCCCCCCCCCC(C(=O)NCCN(CCNC(=O)C(CCCCCCCCCC)N(C)C)CCNC(=O)C(CCCCCCCCCC)N(C)C)N(C)C]
4
3C12-amide-NH2
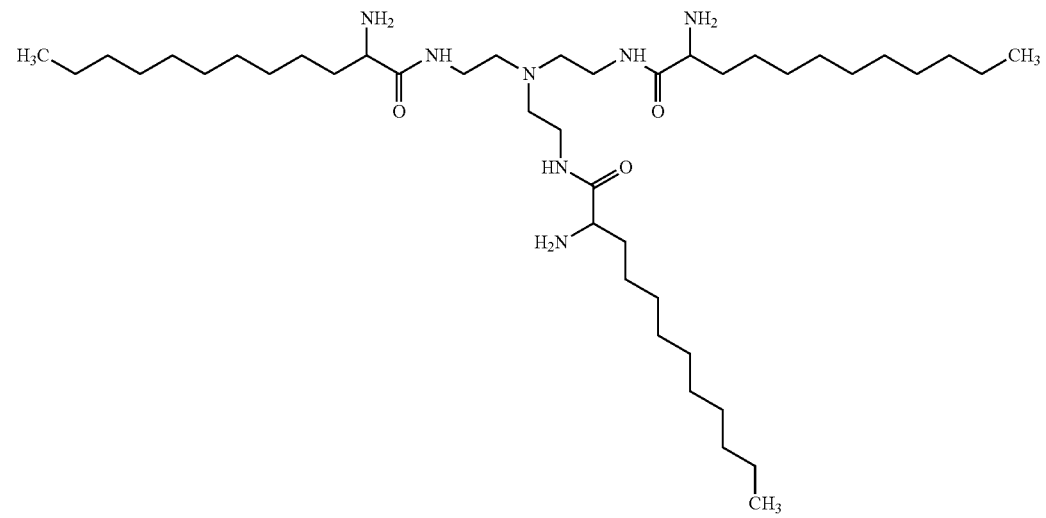 [SMILES: CCCCCCCCCCC(N)C(=O)NCCN(CCNC(=O)C(N)CCCCCCCCCC)CCNC(=O)C(N)CCCCCCCCCC]

3C12-amide-OH
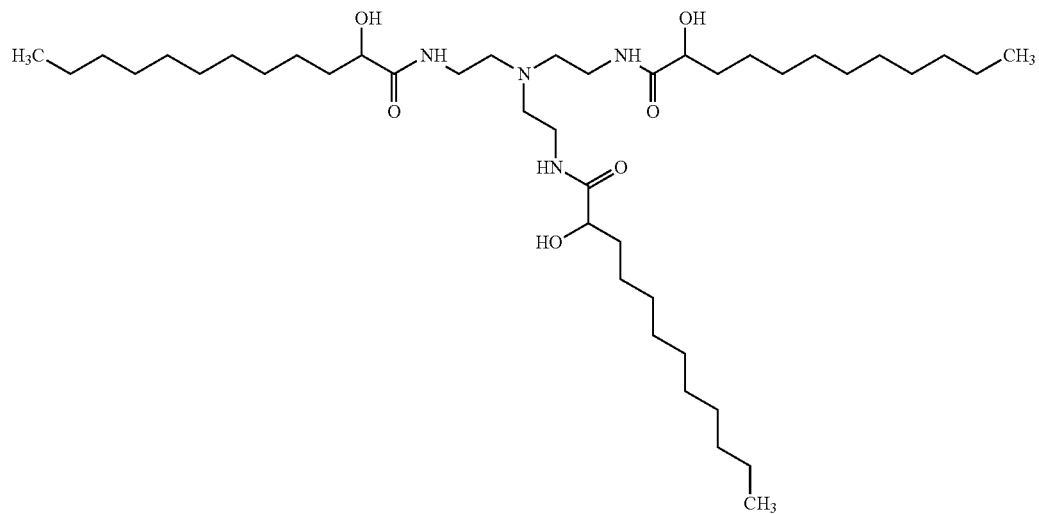 [SMILES: CCCCCCCCCCC(O)C(=O)NCCN(CCNC(=O)C(O)CCCCCCCCCC)CCNC(=O)C(O)CCCCCCCCCC]
3C12-Ester-OH
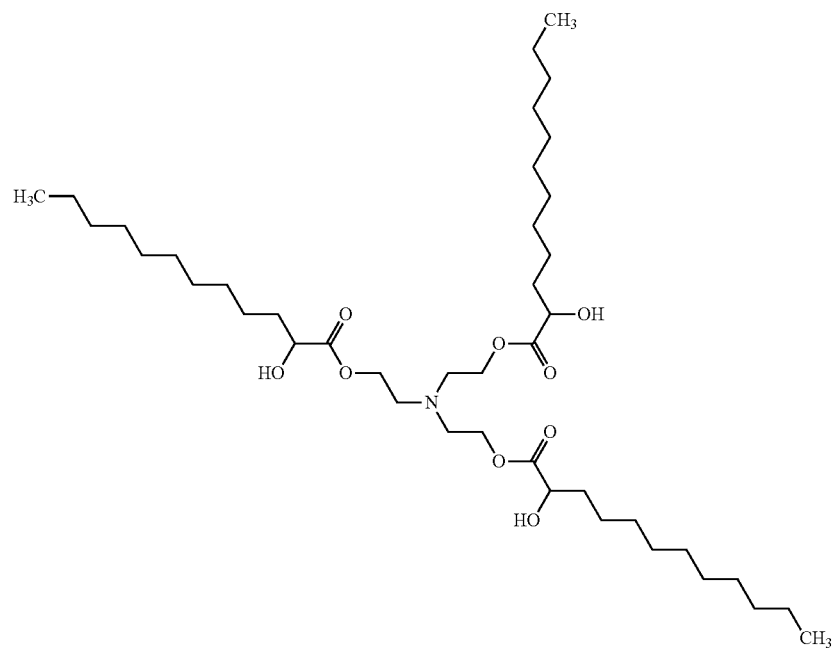 [SMILES: CCCCCCCCCCC(O)C(=O)OCCN(CCOC(=O)C(O)CCCCCCCCCC)CCOC(=O)C(O)CCCCCCCCCC]

3C12 Ester-amin
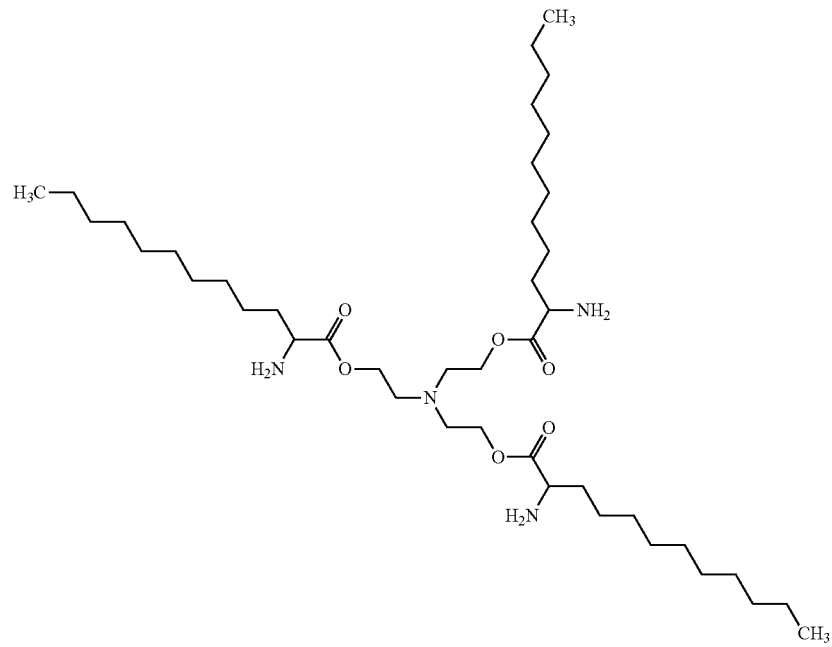
3C12-Ester-DMA
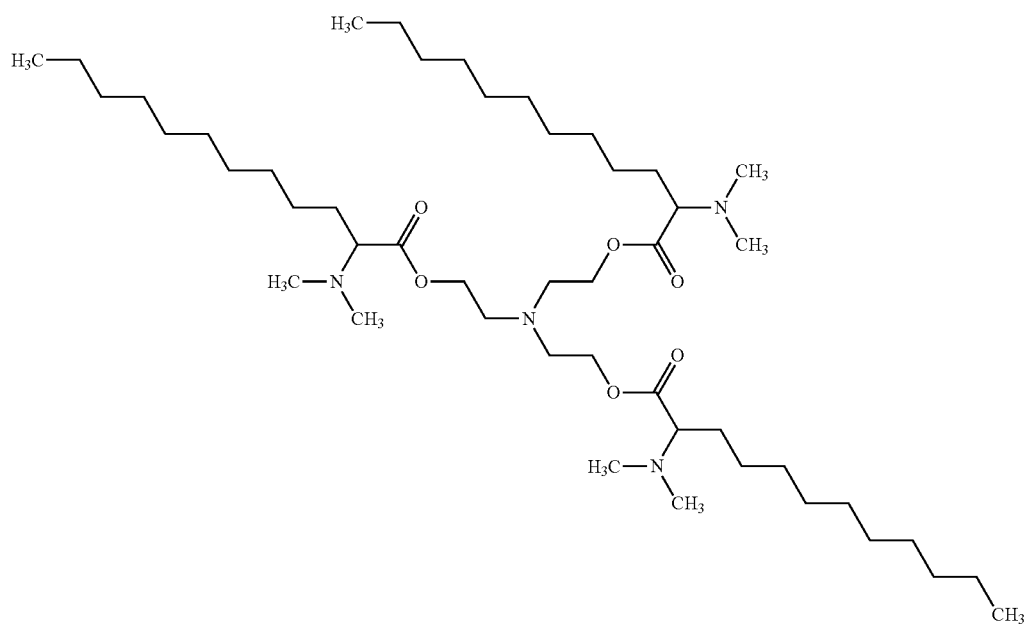 [SMILES: CCCCCCCCCCC(C(=O)OCCN(CCOC(=O)C(CCCCCCCCCC)N(C)C)CCOC(=O)C(CCCCCCCCCC)N(C)C)N(C)C]

| | |
|---|---|
| 2C12-Amid-DMA | 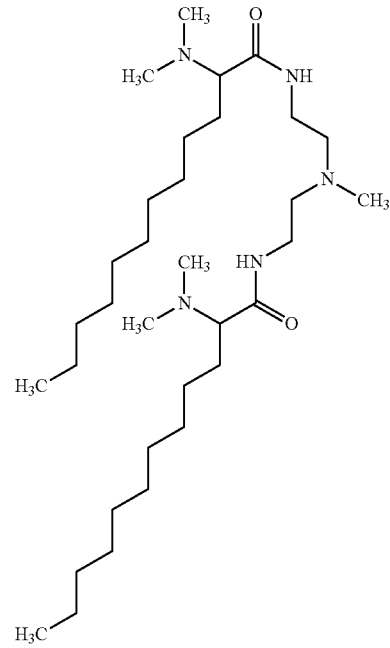 [SMILES: CCCCCCCCCCC(C(=O)NCCN(C)CCNC(=O)C(CCCCCCCCCC)N(C)C)N(C)C] |
| 3C12-lin-amid-DMA | 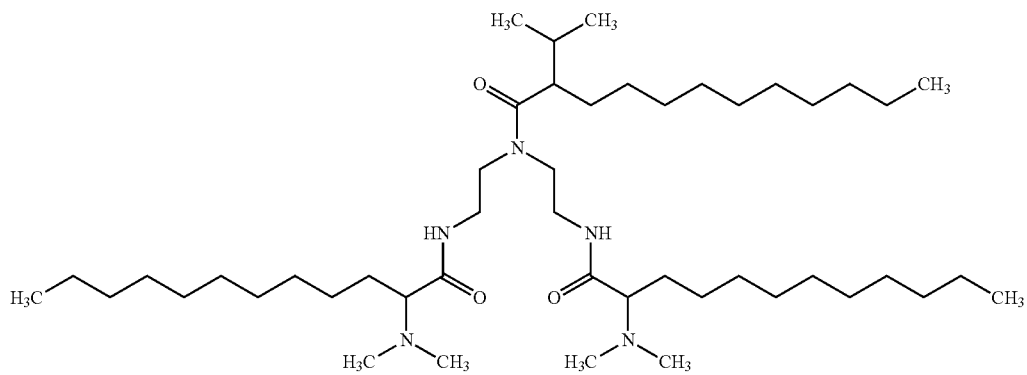 [SMILES: CCCCCCCCCCC(C(=O)N(CCNC(=O)C(CCCCCCCCCC)N(C)C)CCNC(=O)C(CCCCCCCCCC)N(C)C)C(C)C] |
| 2C12-sperm-amid-DMA | 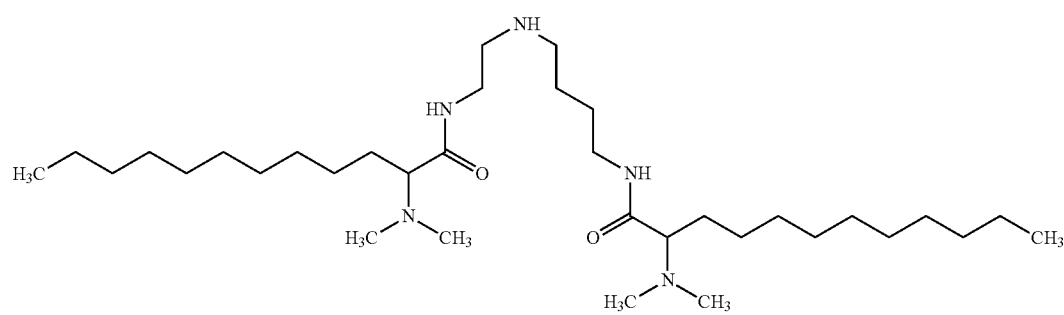 [SMILES: CCCCCCCCCCC(C(=O)NCCCCNCCNC(=O)C(CCCCCCCCCC)N(C)C)N(C)C] |

| | |
|---|---|
| 3C12-sperm-amid-DMA | 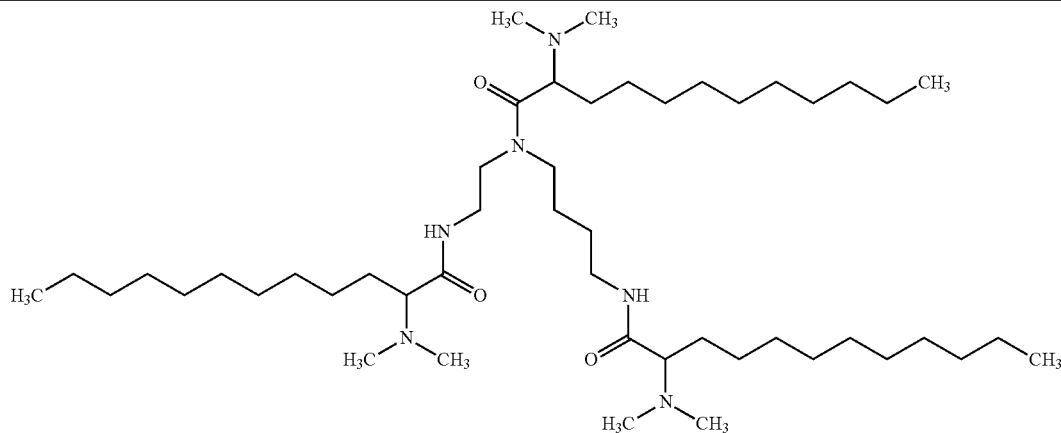 |

The biologically active cargo material comprised in the composition of the invention, or in the nanoparticle(s) of the invention as described below, is preferably a nucleic acid compound or complex. The nucleic acid compound comprised in the composition may be any type of nucleic acid or nucleic acid derivative. In some of the preferred embodiments, the nucleic acid compound is selected from chemically modified or unmodified DNA, single stranded or double stranded DNA, coding or non-coding DNA, optionally selected from a plasmid, (short) oligodesoxynucleotide (i.e. a (short) DNA oligonucleotide), genomic DNA, DNA primers, DNA probes, immunostimulatory DNA, aptamer, or any combination thereof. Alternatively, or in addition, such a nucleic acid molecule may be selected e.g. from any PNA (peptide nucleic acid). Further alternatively, or in addition, and also according to a particularly preferred embodiment, the nucleic acid is selected from chemically modified or unmodified RNA, single-stranded or double-stranded RNA, coding or non-coding RNA, optionally selected from messenger RNA (mRNA), (short) oligoribonucleotide (i.e. a (short) RNA oligonucleotide), viral RNA, replicon RNA, transfer RNA (tRNA), ribosomal RNA (rRNA), immunostimulatory RNA (isRNA), microRNA, small interfering RNA (siRNA), small nuclear RNA (snRNA), small-hairpin RNA (shRNA) or a riboswitch, an RNA aptamer, an RNA decoy, an antisense RNA, a ribozyme, or any combination thereof. Preferably, the nucleic acid molecule of the complex is an RNA. More preferably, the nucleic acid molecule of the complex is a (linear) single-stranded RNA, even more preferably an mRNA or an immunostimulatory RNA.

Optionally, the biologically active cargo material is a combination of more than one nucleic acid compounds.

Described from a different angle, the nucleic acid may be a single- or a double-stranded nucleic acid compound or complex. Strictly speaking, a double-stranded nucleic acid could also be considered as a combination of two nucleic acid compounds (i.e. the two antiparallel strands) which form a nucleic acid complex due to their association by non-covalent bonds. However, like in common technical language, a double-stranded nucleic acid may also be described as one compound or molecule. The nucleic acid may also be a partially double-stranded or partially single stranded nucleic acid, comprising two strands which are at least partially self-complementary. Such partially double-stranded or partially single stranded nucleic acid molecules are typically formed by a longer and a shorter single-stranded nucleic acid molecule or by two single stranded nucleic acid molecules, which are about equal in length, wherein one single-stranded nucleic acid molecule is in part complementary to the other single-stranded nucleic acid molecule and both thus form a double-stranded nucleic acid molecule in this region, i.e. a partially double-stranded or partially single stranded nucleic acid (molecule). Preferably, the nucleic acid compound is a single-stranded nucleic acid. Furthermore, the nucleic acid compound may be a circular or linear nucleic acid, preferably a linear nucleic acid.

Optionally, the nucleic acid may be an artificial nucleic acid. An "artificial nucleic acid molecule" or "artificial nucleic acid" may typically be understood to be a nucleic acid molecule, e.g. a DNA or an RNA, that does not occur naturally. In other words, an artificial nucleic acid molecule may be understood as a non-natural nucleic acid molecule. Such nucleic acid molecule may be non-natural due to its individual sequence (which does not occur naturally) and/or due to other modifications, e.g. structural modifications of nucleotides which do not occur naturally. An artificial nucleic acid molecule may be a DNA molecule, an RNA molecule or a hybrid-molecule comprising DNA and RNA portions. Typically, artificial nucleic acid molecules may be designed and/or generated by genetic engineering methods to correspond to a desired artificial sequence of nucleotides (heterologous sequence). In this context an artificial sequence is usually a sequence that may not occur naturally, i.e. it differs from the wild type sequence by at least one nucleotide. The term "wild type" may be understood as a sequence occurring in nature. Further, the term "artificial nucleic acid molecule" is not restricted to mean "one single molecule" but is, typically, understood to comprise an ensemble of identical molecules. Accordingly, it may relate to a plurality of identical molecules contained in an aliquot.

In a further embodiment, the sequences (protein, or respectively nucleic acid) which are defined in the present invention comprise or consist of a sequence (protein, or respectively nucleic acid) having a sequence identity of at least 5%, 10%, 20%, 30%, 40%, 50%, 60%, 70%, 80%, 85%, 86%, 87%, 88%, 89%, 90%, 91%, 92%, 93%, 94%, 95%, 96%, 97%, 98%, or 99% to said sequence (protein, or respectively nucleic acid).

A combination of two or more different nucleic acids may be useful, for example, in the case of a composition comprising a nucleic acid (such as an RNA) encoding the heavy chain of an antibody as well as a nucleic acid encoding the light chain of the same antibody. Another example is the combination of two or more nucleic acids to affect the part of an organism's immune system referred to as the CRISPR/Cas system (CRISPR: clustered regularly interspaced short palindromic repeats; Cas: CRISPR associated protein).

A yet further example is the combination of a guide RNA (gRNA) with an encoding nucleic acid within the composition or nanoparticle of the invention.

Coding Nucleic Acids

The nucleic acid may encode a protein or a peptide, which may be selected, without being restricted thereto, e.g. from therapeutically active proteins or peptides, selected e.g. from antigens, e.g. tumour antigens, pathogenic antigens (e.g. selected, from animal antigens, from viral antigens, from protozoal antigens, from bacterial antigens), allergenic antigens, autoimmune antigens, or further antigens, from allergens, from antibodies, from immunostimulatory proteins or peptides, from antigen-specific T-cell receptors, or from any other protein or peptide suitable for a specific (therapeutic) application, wherein the coding nucleic acid may be transported into a cell, a tissue or an organism and the protein may be expressed subsequently in this cell, tissue or organism.

Bicistronic nucleic acid or RNA and multicistronic nucleic acid or RNA: A bicistronic or multicistronic nucleic acid or RNA is typically a nucleic acid or an RNA, preferably an mRNA, that typically may have two (bicistronic) or more (multicistronic) coding regions. A coding region in this context is a sequence of codons that is translatable into a peptide or protein.

According to certain embodiments of the present invention, the nucleic acid is mono-, bi-, or multicistronic, preferably as defined herein. The coding sequences in a bi- or multicistronic nucleic acid molecule preferably encode distinct proteins or peptides as defined herein or a fragment or variant thereof. Preferably, the coding sequences encoding two or more proteins or peptides may be separated in the bi- or multicistronic nucleic acid by at least one IRES (internal ribosomal entry site) sequence, as defined below. Thus, the term "encoding two or more proteins or peptides" may mean, without being limited thereto, that the bi- or even multicistronic nucleic acid, may encode e.g. at least two, three, four, five, six or more (preferably different) proteins or peptides and/or proteins or peptides or their fragments or variants within the definitions provided herein. More preferably, without being limited thereto, the bi- or even multicistronic nucleic acid, may encode, for example, at least two, three, four, five, six or more (preferably different) proteins or peptides as defined herein or their fragments or variants as defined herein. In this context, a so-called IRES (internal ribosomal entry site) sequence as defined above can function as a sole ribosome binding site, but it can also serve to provide a bi- or even multicistronic nucleic acid as defined above, which encodes several proteins or peptides which are to be translated by the ribosomes independently of one another. Examples of IRES sequences, which can be used according to the invention, are those from picornaviruses (e.g. FMDV), pestiviruses (CFFV), polioviruses (PV), encephalomyocarditis viruses (ECMV), foot and mouth disease viruses (FMDV), hepatitis C viruses (HCV), classical swine fever viruses (CSFV), mouse leukoma virus (MLV), simian immunodeficiency viruses (SIV) or cricket paralysis viruses (CrPV).

According to a further embodiment, the at least one coding sequence of the nucleic acid sequence according to the invention may encode at least two, three, four, five, six, seven, eight and more proteins or peptides (or fragments and derivatives thereof) as defined herein linked with or without an amino acid linker sequence, wherein said linker sequence can comprise rigid linkers, flexible linkers, cleavable linkers (e.g., self-cleaving peptides) or a combination thereof. Therein, the proteins or peptides may be identical or different or a combination thereof. Particular proteins or peptides combinations can be encoded by said nucleic acid encoding at least two proteins or peptides as explained herein (also referred to herein as 'multi-antigen-constructs/nucleic acid').

It has to be noted that in the context of the invention, certain combinations of coding sequences (e.g., comprising at least two different proteins) may be generated by any combination of mono-, bi-, and multicistronic nucleic acids and/or multi-antigen-constructs/nucleic acid to obtain a poly- or even multivalent nucleic acid mixture.

In particular preferred aspects, the encoded peptides or proteins are selected from human, viral, bacterial, protozoan proteins or peptides.

a) Therapeutically Active Proteins

In the context of the present invention, therapeutically active proteins or peptides may be encoded by the nucleic acid comprised in the nanoparticle of the invention. Therapeutically active proteins are defined herein as proteins which have an effect on healing, prevent prophylactically or treat therapeutically a disease, preferably as defined herein, or are proteins of which an individual is in need of, e.g. a native or modified native protein which individual's organism does not produce, or only produces in insufficient quantities. These may be selected from any naturally occurring or synthetically designed recombinant or isolated protein known to a skilled person. Without being restricted thereto, therapeutically active proteins may comprise proteins capable of stimulating or inhibiting the signal transduction in the cell, e.g. cytokines, lymphokines, monokines, growth factors, receptors, signal transduction molecules, transcription factors, etc.; anticoagulants; antithrombins; antiallergic proteins; apoptotic factors or apoptosis related proteins, therapeutic active enzymes and any protein connected with any acquired disease or any hereditary disease.

b) Antigens

The nucleic acid may alternatively encode an antigen. According to the present invention, the term "antigen" refers to a substance which is recognised by the immune system and is capable of triggering an antigen-specific immune response, e.g. by formation of antibodies or antigen-specific T-cells as part of an adaptive immune response. In this context, an antigenic epitope, fragment or peptide of a protein means particularly B cell and T cell epitopes which may be recognized by B cells, antibodies or T cells, respectively.

In the context of the present invention, the antigen encoded by the nucleic acid typically represent any antigen, antigenic epitope or antigenic peptide falling under the above definition, and is preferably a protein and peptide antigen, e.g. a tumour antigen, allergenic antigen, autoimmune self-antigen, pathogenic antigen, etc. In particular, the antigen may be one derived from another organism that the host organism (e.g. a human subject) itself, such as a viral antigen, a bacterial antigen, a fungal antigen, a protozooal antigen, an animal antigen, an allergenic antigen etc. Allergenic antigens, also referred to as allergy antigens or allergens, are typically antigens which may cause an allergy in a human subject.

Alternatively, the antigen as encoded by the nucleic acid may be derived from the host itself. Examples for such antigens include tumour antigens, self-antigens or autoantigens, such as autoimmune self-antigens, but also (non-self) antigens as defined herein which have originally been derived from cells outside the host organism, but which have been fragmented or degraded inside the host organism, tissue or cell, e.g. by protease degradation or other types of metabolism.

One class of antigens also preferred in the context of the present invention is that of tumour antigens. Among the preferred tumour antigens are those that are located on the surface of a tumour cell. Tumour antigens may also represent proteins which are overexpressed in tumour cells compared to a normal cell. Furthermore, tumour antigens also include antigens expressed in cells which are not, or which were originally not, themselves tumour cells but associated with a tumour. For example, antigens which are connected with formation or reformation of tumour-supplying blood vessels, in particular those which are associated with neovascularisation, such growth factors like VEGF or bFGF, are also of interest. Antigens associated with a tumour also include antigens from cells or tissues typically embedding the tumour. Furthermore, certain other proteins or peptides may be (over) expressed and occur in increased concentrations in the body fluids of patients that have developed a tumour. These substances are also referred to as tumour antigens or tumour-associated antigens even though they are, strictly speaking, not antigens in that they do not induce an immune response.

Tumour antigens may be divided further into tumour-specific antigens (TSAs) and tumour-associated antigens (TAAs). TSAs can only be presented by tumour cells and not by healthy cells. They typically result from a tumour-specific mutation. TAAs, which are more common, are usually produced by both tumour and healthy cells. These antigens are recognised by the immune system and the antigen-presenting cell can be destroyed by cytotoxic T cells. Additionally, tumour antigens can also occur on the surface of the tumour in the form of, e.g., a mutated receptor. In this case, they can also be recognised by antibodies.

If the encoded antigen is an allergen, such antigen may be selected from antigens of any source, such as from animals, plants, molds, fungi, bacteria etc. Plant-derived allergens may, for example, be allergens from pollen. Again, the nucleic acid incorporated in the nanoparticle may encode the native antigen or a fragment or epitope thereof.

c) Antibodies

According to a further embodiment, the nucleic acid compound encodes an antibody or an antibody fragment. The antibody or a fragment thereof is selected from the group consisting of (i) a single-chain antibody, (ii) a single-chain antibody fragment, (iii) a multiple-chain antibody, and (iv) a multiple-chain antibody fragment.

In general, an antibody consists of a light chain and a heavy chain both having variable and constant domains. The light chain consists of an N-terminal variable domain, $V_L$, and a C-terminal constant domain, $C_L$. In contrast, the heavy chain of the IgG antibody, for example, is comprised of an N-terminal variable domain, $V_H$, and three constant domains, $C_H1$, $C_H2$ and $C_H3$.

In one of the preferred embodiments, the antibody is selected from full-length antibodies. Such an antibody may be any recombinantly produced or naturally occurring antibody, in particular an antibody suitable for therapeutic, diagnostic or scientific purposes, or an antibody which is associated with a disease, such as an immunological disease or cancer. The term "antibody" is used in its broadest sense and specifically covers monoclonal and polyclonal antibodies (including agonist, antagonist, and blocking or neutralising antibodies) and antibody species with polyepitopic specificity. The antibody may belong to any class of antibodies, such as IgM, IgD, IgG, IgA and IgE antibodies. Moreover, the antibody may resemble an antibody generated by immunisation in a host organism, or a recombinantly engineered version thereof, a chimeric antibody, a human antibody, a humanised antibody, a bispecific antibody, an intrabody.

Moreover, the nucleic acid compound may also encode an antibody fragment, variant, adduct or derivative of an antibody, such as single-chain variable fragment, a diabody or a triabody. The antibody fragment is preferably selected from Fab, Fab', F(ab')$_2$, Fc, Facb, pFc', Fd and Fv fragments of the aforementioned types of antibodies. In general, antibody fragments are known in the art. For example, a Fab ("fragment, antigen binding") fragment is composed of one constant and one variable domain of each of the heavy and the light chain. The two variable domains bind the epitope on specific antigens. The two chains are connected via a disulfide linkage. A scFv ("single chain variable fragment") fragment, for example, typically consists of the variable domains of the light and heavy chains. The domains are linked by an artificial linkage, in general a polypeptide linkage such as a peptide composed of 15-25 glycine, proline and/or serine residues.

In one embodiment, the biologically active cargo material comprises a combination of at least two distinct RNAs, wherein one RNA encodes a heavy chain of an antibody or a fragment thereof and another RNA encodes the corresponding light chain of the antibody or a fragment thereof.

In a further embodiment, the biologically active cargo material comprises a combination of at least two distinct RNAs, wherein one RNA encodes a heavy chain variable region of an antibody or a fragment thereof and another RNA encodes the corresponding light chain variable region of the antibody or a fragment thereof.

Moreover, it is preferred that the different chains of the antibody or antibody fragment are encoded by a multicistronic nucleic acid, also referred to as polycistronic nucleic acid. Alternatively, the different strains of the antibody or antibody fragment are encoded by several monocistronic nucleic acids.

According to a further embodiment, the present invention comprises the use of at least one nucleic acid molecule for the preparation of a biologically active cargo material. If more than one nucleic acid molecule is used, the complexed nucleic acid molecules may be different, i.e. thereby forming a mixture of at least two distinct (complexed) nucleic acid molecules.

In one embodiment, the biologically active cargo material comprises (i) a nucleic acid molecule encoding a CRISPR related protein; and/or (ii) one or more guide RNA(s) sequence(s).

The term "CRISPR related protein" includes but is not limited to CAS9 (CRISPR-Associated Protein 9), CSY4, dCAS9, and dCAS9-effector domain (activator and/or inhibitor domain) fusion proteins. The CRISPR related protein can be from any number of species including but not limited to *Streptococcus pyogenes, Listeria innocua*, and *Streptococcus thermophilus*.

The term "guide RNA (gRNA)", also referred to as "artificial guide RNA", "single guide RNA", "small guide RNA" or "sgRNA", describes an RNA including a typically 20-25 nucleotides long sequence that is complementary to one strand of the 5'UTR of the gene of interest upstream of the transcription start site. A description of sgRNA design can be found in e.g. Mali et al., 2013, Science 339:823-826. The artificial sgRNA targets a gene of interest, directing the CRISPR related protein encoded by the artificial polynucleotide to interact with the gene of interest, e.g., a gene where modulation of transcription is desired. The gene of interest is selected depending on the application.

In one embodiment, a single nucleic acid molecule of the invention comprised in the composition or in the nanoparticle(s) of the invention comprises a single nucleic acid molecule encoding said CRISPR related protein and simultaneously said guide RNA(s).

In a further embodiment, the biologically active cargo material comprises a combination of more than one nucleic acid molecule. In another embodiment, more than one nucleic acid molecules of the invention comprise said nucleic acid molecule encoding a CRISPR related protein and said guide RNA(s). In this case, the biologically active cargo material comprises two distinct RNA which express both a Cas9 protein and the target-specific gRNA.

siRNA

In a further preferred embodiment, the nucleic acid compound incorporated in the nanoparticle of the invention is in the form of dsRNA, preferably siRNA. A dsRNA, or a siRNA, is of interest particularly in connection with the phenomenon of RNA interference. The in vitro technique of RNA interference (RNAi) is based on double-stranded RNA molecules (dsRNA) which trigger the sequence-specific suppression of gene expression (Zamore (2001) Nat. Struct. Biol. 9: 746-750; Sharp (2001) Genes Dev. 5:485-490; Hannon (2002) Nature 41: 244-251). In the transfection of mammalian cells with long dsRNA, the activation of protein kinase R and RnaseL brings about unspecific effects, such as, for example, an interferon response (Stark et al. (1998) Annu. Rev. Biochem. 67: 227-264; He and Katze (2002) Viral Immunol. 15: 95-119). These unspecific effects are avoided when shorter, for example 21- to 23-mer, so-called siRNA (small interfering RNA), is used, because unspecific effects are not triggered by siRNA that is shorter than 30 bp (Elbashir et al. (2001) Nature 411: 494-498).

The nucleic acid may, for example, be a double-stranded RNA (dsRNA) having a length from about 17 to about 29 base pairs, and preferably from about 19 to about 25 base pairs. The dsRNA is preferably at least 90%, more preferably at least 95%, such as 100%, (regarding the nucleotides of a dsRNA) complementary to a section of the nucleic acid sequence of a therapeutically relevant protein or antigen as described hereinbefore, either a coding or a non-coding section, preferably a coding section. 90% complementary means that, with a length of a dsRNA of, for example, 20 nucleotides, this contains not more than 2 nucleotides without complementarity with the corresponding section of the mRNA encoding the respective protein. Also preferred is a double-stranded RNA whose sequence is wholly complementary with a section of the nucleic acid of a therapeutically relevant protein or antigen described hereinbefore.

In one embodiment, the dsRNA has the general structure $5'-(N_{17-29})-3'$, and preferably the general structure $5'-(N_{19-25})-3'$, or $5'-(N_{19-24})-3'$, or $5'-(N_{21-23})-3'$, respectively, wherein each N is a nucleotide, and wherein the nucleotide sequence is complementary to a section of the mRNA that corresponds to a therapeutically relevant protein or antigen described hereinbefore. In principle, all the sections having a length of from 17 to 29, preferably from 19 to 25, base pairs that occur in the coding region of the mRNA can serve as target sequence for a dsRNA herein. Equally, dsRNAs used as nucleic acid can also be directed against nucleotide sequences of a (therapeutically relevant) protein or antigen described (as active ingredient) hereinbefore that do not lie in the coding region, in particular in the 5' non-coding region of the mRNA, for example, therefore, against non-coding regions of the mRNA having a regulatory function. The target sequence of the dsRNA used as nucleic acid can therefore lie in the translated and untranslated region of the mRNA and/or in the region of the control elements of a protein or antigen described hereinbefore. The target sequence of a dsRNA used as nucleic acid can also lie in the overlapping region of untranslated and translated sequence; in particular, the target sequence can comprise at least one nucleotide upstream of the start triplet of the coding region of the mRNA.

Immunostimulatory Nucleic Acids a) Immunostimulatory CpG Nucleic Acids

According to another embodiment, the nucleic acid incorporated in the nanoparticle of the invention is an immunostimulatory CpG nucleic acid, in particular a CpG-RNA or a CpG-DNA, which preferably induces an innate immune response. Examples of potentially suitable immunostimulatory CpG nucleic acids include, without limitation, single-stranded CpG-DNA (ss CpG-DNA), double-stranded CpG-DNA (dsDNA), single-stranded CpG-RNA (ss CpG-RNA), and double-stranded CpG-RNA (ds CpG-RNA). Preferably, the CpG nucleic acid is a CpG-RNA, in particular a single-stranded CpG-RNA (ss CpG-RNA). That preferred length of the CpG nucleic acid in terms of nucleotides or base pairs is similar to that preferred for siRNA, as described above. Preferably, the CpG motifs are unmethylated.

b) Immunostimulatory RNA (isRNA)

According to a further alternative, the nucleic acid incorporated as biologically active cargo material in the nanoparticle of the invention may be in the form of a of an immunostimulatory RNA (isRNA), which preferably elicits an innate immune response.

Such isRNA may be a double-stranded RNA, a single-stranded RNA, or a partially double-stranded RNA, or a short RNA oligonucleotide. In one of the preferred embodiments, it is a single-stranded RNA.

Moreover, the isRNA may be circular or linear. In one of the preferred embodiments, a linear isRNA is used, such as a linear single-stranded RNA, or a long single-stranded RNA.

Moreover, the isRNA may be a coding or non-coding RNA. According to one of the preferred embodiments, a non-coding RNA is used as isRNA, such as a non-coding single-stranded RNA, a non-coding linear RNA, a non-coding linear single-stranded RNA, or a non-coding long linear single-stranded RNA.

According to one further preferred embodiment, the isRNA carries a triphosphate at its 5'-end, as is the case for in vitro transcribed RNA. This preference applies to all aforementioned types of linear isRNA.

Again, the isRNA used as biologically active cargo material according to the invention may be selected from any type or class of RNA, whether naturally occurring or synthetic, which is capable of inducing an innate immune response, and/or which is capable of enhancing or supporting an adaptive immune response induced by an antigen.

In this context, an immune response may occur in various ways. A substantial factor for a suitable adaptive immune response is the stimulation of certain T-cell sub-populations. T-lymphocytes are typically divided into two sub-populations, the T-helper 1 (Th1) cells and the T-helper 2 (Th2) cells, with which the immune system is capable of destroying intracellular (Th1) and extracellular (Th2) pathogens, such as antigens. The two Th cell populations differ in the pattern of the effector proteins (cytokines) produced by them. Thus, Th1 cells assist the cellular immune response by activation of macrophages and cytotoxic T-cells. Th2 cells, on the other hand, promote the humoral immune response by stimulation of B-cells for conversion into plasma cells and by formation of antibodies (e.g. against antigens). The Th1/Th2 ratio is therefore of great importance in the induction and maintenance of an adaptive immune response.

In the context of the present invention, it is preferred that the Th1/Th2 ratio of the adaptive immune response is shifted towards the cellular response (Th1 response), i.e. a cellular immune response is induced or enhanced. For example, the innate immune system which may support an adaptive immune response may be activated by ligands of toll-like receptors (TLRs). TLRs are a family of highly conserved pattern recognition receptor (PRR) polypeptides that recognise pathogen-associated molecular patterns (PAMPs) and play a critical role in innate immunity in mammals. Currently, at least thirteen family members have been identified and designated as toll-like receptors TLR1, TLR2, TLR3, TLR4, TLR5, TLR6, TLR7, TLR8, TLR9, TLR10, TLR11, TLR12 and TLR13. Furthermore, a number of specific TLR ligands have been identified. It was found that unmethylated bacterial DNA and synthetic analogs thereof (CpG DNA) are ligands for TLR9 (Hemmi H et al. (2000) Nature 408:740-5; Bauer S et al. (2001) Proc Natl Acad Sci USA 98, 9237-42). Furthermore, it has been reported that ligands for certain TLRs include certain nucleic acid molecules and that certain types of RNA are immunostimulatory in a sequence-independent or sequence-dependent manner, wherein these various immunostimulatory RNAs may stimulate TLR3, TLR7, or TLR8, or intracellular receptors such as RIG-I, MDA-5 and others. Lipford et al. determined certain G,U-containing oligoribonucleotides as immunostimulatory by acting via TLR7 and TLR8 (see WO 03/086280). The immunostimulatory G,U-containing oligoribonucleotides described by Lipford et al. were believed to be derivable from RNA sources including ribosomal RNA, transfer RNA, messenger RNA, and viral RNA.

The isRNA used in the context of the invention may thus comprise any RNA sequence known to be immunostimulatory, including, without being limited thereto, RNA sequences representing and/or encoding ligands of TLRs, such as the murine family members TLR1 to TLR13, or more preferably selected from human family members TLR1 to TLR10, in particular TLR7 or TLR8; or ligands for intracellular receptors for RNA such as RIG-I or MDA-5 (see e.g. Meylan, E., Tschopp, J. (2006): Toll-like receptors and RNA helicases: Two parallel ways to trigger antiviral responses. Mol. Cell 22, 561-569).

Without being limited thereto, the isRNA may include ribosomal RNA (rRNA), transfer RNA (tRNA), messenger RNA (mRNA), and viral RNA (vRNA). It may comprise up to about 5000 nucleotides, such as from about 5 to about 5000 nucleotides, or from about 5 to about 1000, or from about 500 to about 5000, or from about 5 to about 500, or from about 5 to about 250, or from about 5 to about 100, or from about 5 to about 50 or or from about 5 to about 30 nucleotides, respectively.

According to a further preferred aspect of this embodiment, the isRNA comprises or consists of a nucleic acid of formula V or VI:

$(N_uG_lX_mG_nN_v)_a$ (formula V)

wherein:

G is guanosine (guanine), uridine (uracil) or an analogue of guanosine (guanine) or uridine (uracil), preferably guanosine (guanine) or an analogue thereof;

X is guanosine (guanine), uridine (uracil), adenosine (adenine), thymidine (thymine), cytidine (cytosine), or an analogue of these nucleotides (nucleosides), preferably uridine (uracil) or an analogue thereof;

N is a nucleic acid sequence having a length of about 4 to 50, preferably of about 4 to 40, more preferably of about 4 to 30 or 4 to 20 nucleic acids, each N independently being selected from guanosine (guanine), uridine (uracil), adenosine (adenine), thymidine (thymine), cytidine (cytosine) or an analogue of these nucleotides (nucleosides);

a is an integer from 1 to 20, preferably from 1 to 15, most preferably from 1 to 10;

l is an integer from 1 to 40, wherein if l=1, G is guanosine (guanine) or an analogue thereof, and if l>1, at least 50% of these nucleotides (nucleosides) are guanosine (guanine) or an analogue thereof;

m is an integer and is at least 3; wherein if m=3, X is uridine (uracil) or an analogue thereof, and if m>3, at least 3 successive uridines (uracils) or analogues of uridine (uracil) occur;

n is an integer from 1 to 40, wherein if n=1, G is guanosine (guanine) or an analogue thereof, and if n>1, at least 50% of these nucleotides (nucleosides) are guanosine (guanine) or an analogue thereof;

u, v are independently from each other an integer from 0 to 50, wherein preferably if u=0, v≥1, or if v=0, u≥1;

wherein the nucleic acid molecule of formula V has a length of at least 50 nucleotides, preferably of at least 100 nucleotides, more preferably of at least 150 nucleotides, even more preferably of at least 200 nucleotides and most preferably of at least 250 nucleotides;

$(N_uC_lX_mC_nN_v)_a$ (formula VI)

wherein:

C is cytidine (cytosine), uridine (uracil) or an analogue of cytidine (cytosine) or uridine (uracil), preferably cytidine (cytosine) or an analogue thereof;

X is guanosine (guanine), uridine (uracil), adenosine (adenine), thymidine (thymine), cytidine (cytosine) or an analogue of the above-mentioned nucleotides (nucleosides), preferably uridine (uracil) or an analogue thereof;

N is each a nucleic acid sequence having a length of about 4 to 50, preferably of about 4 to 40, more preferably of about 4 to 30 or 4 to 20 nucleic acids, each N being independently selected from guanosine (guanine), uridine (uracil), adenosine (adenine), thymidine (thymine), cytidine (cytosine) or an analogue of these nucleotides (nucleosides);

a is an integer from 1 to 20, preferably from 1 to 15, most preferably from 1 to 10;

l is an integer from 1 to 40, wherein if l=1, C is cytidine (cytosine) or an analogue thereof, and if l>1, at least 50% of these nucleotides (nucleosides) are cytidine (cytosine) or an analogue thereof;

m is an integer and is at least 3; wherein if m=3, X is uridine (uracil) or an analogue thereof, and if m>3, at least 3 successive uridines (uracils) or analogues of uridine (uracil) occur;

n is an integer from 1 to 40, wherein if n=1, C is cytidine (cytosine) or an analogue thereof, and if n>1, at least 50% of these nucleotides (nucleosides) are cytidine (cytosine) or an analogue thereof;

u, v are independently from each other an integer from 0 to 50, wherein preferably if u=0, v≥1, or if v=0, u≥1;

wherein the nucleic acid molecule of formula VI has a length of at least 50 nucleotides, preferably of at least 100 nucleotides, more preferably of at least 150 nucleotides, even more preferably of at least 200 nucleotides and most preferably of at least 250 nucleotides.

For formula VI, any of the definitions given above for elements N (i.e. $N_u$ and $N_v$) and X ($X_m$), particularly the core structure as defined above, as well as for integers a, l, m, n, u and v, similarly apply to elements of formula V correspondingly, wherein in formula VI the core structure is defined by $C_lX_mC_n$. The definition of bordering elements $N_u$ and $N_v$ is identical to the definitions given above for $N_u$ and $N_v$.

According to a very particularly preferred aspect of this embodiment, the nucleic acid molecule according to formula V may be selected from e.g. any of the following sequences:

```
                                             (SEQ ID NO: 1)
UAGCGAAGCUCUUGGACCUAGGUUUUUUUUUUUUUUGGGUGCGUUCCU

AGAAGUACACG (SEQ ID NO: 2)
UAGCGAAGCUCUUGGACCUAGGUUUUUUUUUUUUUUGGGUGCGUUCCU

AGAAGUACACGAUCGCUUCGAGAACCUGGAUCCAAAAAAAAAAAAAAC

CCACGCAAGGAUCUUCAUGUGC (SEQ ID NO: 3)
GGGAGAAAGCUCAAGCUUGGAGCAAUGCCCGCACAUUGAGGAAACCGAG

UUGCAUAUCUCAGAGUAUUGGCCCCCGUGUAGGUUAUUCUUGACAGACA

GUGGAGCUUAUUCACUCCCAGGAUCCGAGUCGCAUACUACGGUACUGGU

GACAGACCUAGGUCGUCAGUUGACCAGUCCGCCACUAGACGUGAGUCCG

UCAAAGCAGUUAGAUGUUACACUCUAUUAGAUC (SEQ ID NO: 4)
GGGAGAAAGCUCAAGCUUGGAGCAAUGCCCGCACAUUGAGGAAACCGAG

UUGCAUAUCUCAGAGUAUUGGCCCCCGUGUAGGUUAUUCUUGACAGACA

GUGGAGCUUAUUCACUCCCAGGAUCCGAGUCGCAUACUACGGUACUGGU

GACAGACCUAGGUCGUCAGUUGACCAGUCCGCCACUAGACGUGAGUCCG

UCAAAGCAGUUAGAUGUUACACUCUAUUAGAUCUCGGAUUACAGCUGGA

AGGAGCAGGAGUAGUGUUCUUGCUCUAAGUACCGAGUGUGCCCAAUACC

CGAUCAGCUUAUUAACGAACGGCUCCUCCUCUUAGACUGCAGCGUAAGU

GCGGAAUCUGGGGAUCAAAUUACUGACUGCCUGGAUUACCCUCGGACAU

AUAACCUUGUAGCACGCUGUUGCUGUAUAGGUGACCAACGCCCACUCGA

GUAGACCAGCUCUCUUAGUCCGGACAAUGAUAGGAGGCGCGGUCAAUCU

ACUUCUGGCUAGUUAAGAAUAGGCUGCACCGACCUCUAUAAGUAGCGUG

UCCUCUAG (SEQ ID NO: 5)
GGGAGAAAGCUCAAGCUUGGAGCAAUGCCCGCACAUUGAGGAAACCGAG

UUGCAUAUCUCAGAGUAUUGGCCCCCGUGUAGGUUAUUCUUGACAGACA

GUGGAGCUUAUUCACUCCCAGGAUCCGAGUCGCAUACUACGGUACUGGU

GACAGACCUAGGUCGUCAGUUGACCAGUCCGCCACUAGACGUGAGUCCG

UCAAAGCAGUUAGAUGUUACACUCUAUUAGAUCUCGGAUUACAGCUGGA

AGGAGCAGGAGUAGUGUUCUUGCUCUAAGUACCGAGUGUGCCCAAUACC

CGAUCAGCUUAUUAACGAACGGCUCCUCCUCUUAGACUGCAGCGUAAGU

GCGGAAUCUGGGGAUCAAAUUACUGACUGCCUGGAUUACCCUCGGACAU

AUAACCUUGUAGCACGCUGUUGCUGUAUAGGUGACCAACGCCCACUCGA

GUAGACCAGCUCUCUUAGUCCGGACAAUGAUAGGAGGCGCGGUCAAUCU

ACUUCUGGCUAGUUAAGAAUAGGCUGCACCGACCUCUAUAAGUAGCGUG

UCCUCUAGAGCUACGCAGGUUCGCAAUAAAAGCGUUGAUUAGUGUGCAU

AGAACAGACCUCUUAUUCGGUGAAACGCCAGAAUGCUAAAUUCCAAUAA

CUCUUCCCAAAACGCGUACGGCCGAAGACGCGCGCUUAUCUUGUGUACG

UUCUCGCACAUGGAAGAAUCAGCGGGCAUGGUGGUAGGGCAAUAGGGGA

GCUGGGUAGCAGCGAAAAAGGGCCCCUGCGCACGUAGCUUCGCUGUUCG

UCUGAAACAACCCGGCAUCCGUUGUAGCGAUCCCGUUAUCAGUGUUAUU

CUUGUGCGCACUAAGAUUCAUGGUGUAGUCGACAAUAACAGCGUCUUGG

CAGAUUCUGGUCACGUGCCCUAUGCCCGGGCUUGUGCCUCUCAGGUGCA

CAGCGAUACUUAAAGCCUUCAAGGUACUCGACGUGGGUACCGAUUCGUG

ACACUUCCUAAGAUUAUUCCACUGUGUUAGCCCCGCACCGCCGACCUAA

ACUGGUCCAAUGUAUACGCAUUCGCUGAGCGGAUCGAUAAUAAAAGCUU

GAAUU (SEQ ID NO: 6)
GGGAGAAAGCUCAAGCUUAUCCAAGUAGGCUGGUCACCUGUACAACGUA

GCCGGUAUUUUUUUUUUUUUUUUUUUUUGACCGUCUCAAGGUCCAAGU

UAGUCUGCCUAUAAAGGUGCGGAUCCACAGCUGAUGAAAGACUUGUGCG

GUACGGUUAAUCUCCCCUUUUUUUUUUUUUUUUUUUUAGUAAAUGCGU

CUACUGAAUCCAGCGAUGAUGCUGGCCCAGAUC (SEQ ID NO: 7)
GGGAGAAAGCUCAAGCUUAUCCAAGUAGGCUGGUCACCUGUACAACGUA

GCCGGUAUUUUUUUUUUUUUUUUUUUUUGACCGUCUCAAGGUCCAAGU

UAGUCUGCCUAUAAAGGUGCGGAUCCACAGCUGAUGAAAGACUUGUGCG

GUACGGUUAAUCUCCCCUUUUUUUUUUUUUUUUUUUUAGUAAAUGCGU

CUACUGAAUCCAGCGAUGAUGCUGGCCCAGAUCUUCGACCACAAGUGCA

UAUAGUAGUCAUCGAGGGUCGCCUUUUUUUUUUUUUUUUUUUUUGGC

CCAGUUCUGAGACUUCGCUAGAGACUACAGUUACAGCUGCAGUAGUAAC

CACUGCGGCUAUUGCAGGAAAUCCCGUUCAGGUUUUUUUUUUUUUUUU

UUUUCCGCUCACUAUGAUUAAGAACCAGGUGGAGUGUCACUGCUCUCGA

GGUCUCACGAGAGCGCUCGAUACAGUCCUUGGAAGAAUCUUUUUUUUUU

UUUUUUUUUUUGUGCGACGAUCACAGAGAACUUCUAUUCAUGCAGGUC

UGCUCUAG (SEQ ID NO: 8)
GGGAGAAAGCUCAAGCUUAUCCAAGUAGGCUGGUCACCUGUACAACGUA

GCCGGUAUUUUUUUUUUUUUUUUUUUUUGACCGUCUCAAGGUCCAAGU

UAGUCUGCCUAUAAAGGUGCGGAUCCACAGCUGAUGAAAGACUUGUGCG

GUACGGUUAAUCUCCCCUUUUUUUUUUUUUUUUUUUUAGUAAAUGCGU

CUACUGAAUCCAGCGAUGAUGCUGGCCCAGAUCUUCGACCACAAGUGCA
```

-continued

```
UAUAGUAGUCAUCGAGGGUCGCCUUUUUUUUUUUUUUUUUUUUUGGC

CCAGUUCUGAGACUUCGCUAGAGACUACAGUUACAGCUGCAGUAGUAAC

CACUGCGGCUAUUGCAGGAAAUCCCGUUCAGGUUUUUUUUUUUUUUUU

UUUUCCGCUCACUAUGAUUAAGAACCAGGUGGAGUGUCACUGCUCUCGA

GGUCUCACGAGAGCGCUCGAUACAGUCCUUGGAAGAAUCUUUUUUUUUU

UUUUUUUUUUUUGUGCGACGAUCACAGAGAACUUCUAUUCAUGCAGGUC

UGCUCUAGAACGAACUGACCUGACGCCUGAACUUAUGAGCGUGCGUAUU

UUUUUUUUUUUUUUUUUUUCCUCCCAACAAAUGUCGAUCAAUAGCUG

GGCUGUUGGAGACGCGUCAGCAAAUGCCGUGGCUCCAUAGGACGUGUAG

ACUUCUAUUUUUUUUUUUUUUUUUUUCCCGGGACCACAAAUAAUAUU

CUUGCUUGGUUGGGCGCAAGGGCCCCGUAUCAGGUCAUAAACGGGUACA

UGUUGCACAGGCUCCUUUUUUUUUUUUUUUUUUUUUCGCUGAGUUAU

UCCGGUCUCAAAAGACGGCAGACGUCAGUCGACAACACGGUCUAAAGCA

GUGCUACAAUCUGCCGUGUUCGUGUUUUUUUUUUUUUUUUUUUUGUGAA

CCUACACGGCGUGCACUGUAGUUCGCAAUUCAUAGGGUACCGGCUCAGA

GUUAUGCCUUGGUUGAAAACUGCCCAGCAUACUUUUUUUUUUUUUUUU

UUUCAUAUUCCCAUGCUAAGCAAGGGAUGCCGCGAGUCAUGUUAAGCUU

GAAUU
```

According to another very particularly preferred embodiment, the nucleic acid molecule according to formula VI may be selected from e.g. any of the following sequences:

```
                                           (SEQ ID NO: 9)
UAGCGAAGCUCUUGGACCUACCUUUUUUUUUUUUUUCCCUGCGUUCCUA

GAAGUACACG
```
or
```
                                          (SEQ ID NO: 10)
UAGCGAAGCUCUUGGACCUACCUUUUUUUUUUUUUUCCCUGCGUUCCU

AGAAGUACACGAUCGCUUCGAGAACCUGGAUGGAAAAAAAAAAAAAAG

GGACGCAAGGAUCUUCAUGUGC
```

In a further embodiment, the nucleic acid compound used as biologically active cargo material according to the present invention is in the form of a chemically modified nucleic acid, or is a stabilised nucleic acid, preferably a stabilised RNA or DNA, such as a RNA that is essentially resistant to in vivo degradation by an exo- or endonuclease.

Chemical Modifications:

The terms "modification(s)", "chemical modification(s)", "modified" and the like with respect to a nucleic acid, as used herein, may refer to chemical modifications comprising backbone modifications as well as sugar modifications or base modifications. The respective product of the modification may, for example, be termed a "modified nucleic acid" or a "chemically modified nucleic acid".

A backbone modification in connection with the present invention is a modification in which phosphates of the backbone of the nucleotides contained in a nucleic acid compound, preferably an mRNA, are chemically modified. A sugar modification is a chemical modification of the sugar of the nucleotides of the nucleic acid. Furthermore, a base modification in connection with the present invention is a chemical modification of the base moiety of the nucleotides of the artificial nucleic acid, preferably an mRNA. In this context, nucleotide analogues or modifications are preferably selected from those nucleotide analogues which are applicable for transcription and/or translation.

Sugar Modifications:

As said, the nucleosides and nucleotides can be modified in the sugar moiety. For example, the 2'-hydroxyl group (OH) can be modified or replaced with a number of different "oxy" or "deoxy" substituents. Examples of "oxy"-2'-hydroxyl group modifications include, but are not limited to, alkoxy or aryloxy (—OR, e.g., R=H, alkyl, cycloalkyl, aryl, aralkyl, heteroaryl or sugar); polyethyleneglycols (PEG), —O(CH$_2$CH$_2$O)nCH$_2$CH$_2$OR; "locked" nucleic acids (LNA) in which the 2'-hydroxyl is connected, e.g., by a methylene bridge, to the 4'-carbon of the same ribose sugar; and amino groups (—O-amino, wherein the amino group, e.g., NRR, can be alkylamino, dialkylamino, heterocyclyl, arylamino, diarylamino, heteroarylamino, or diheteroaryl amino, ethylene diamine, polyamino) or aminoalkoxy.

"Deoxy" modifications include hydrogen, amino (e.g. NH$_2$; alkylamino, dialkylamino, heterocyclyl, arylamino, diaryl amino, heteroaryl amino, diheteroaryl amino, or amino acid); or the amino group can be attached to the sugar through a linker, wherein the linker comprises one or more of the atoms C, N, and O.

The sugar group can also contain one or more carbons that possess the opposite stereochemical configuration than that of the corresponding carbon in ribose. Thus, an artificial nucleic acid, preferably an mRNA, can include nucleotides containing, for instance, arabinose as the sugar.

Backbone Modifications

The phosphate groups of the backbone of the nucleic acid compound can be modified by replacing one or more of the oxygen atoms with a different substituent. Further, the modified nucleosides and nucleotides can include the full replacement of an unmodified phosphate moiety with a modified phosphate as described herein. Examples of modified phosphate groups include, but are not limited to, phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulfur. The phosphate linker can also be modified by the replacement of a linking oxygen with nitrogen (bridged phosphoroamidates), sulfur (bridged phosphorothioates) and carbon (bridged methylene-phosphonates).

Base Modifications:

Optionally, the modification may relate to a nucleobase moiety of the nucleic acid compound. Examples of nucleobases found in a nucleic acid such as RNA include, but are not limited to, adenine, guanine, cytosine and uracil. For example, the nucleosides and nucleotides described herein can be chemically modified on the major groove face. In some embodiments, the major groove chemical modifications can include an amino group, a thiol group, an alkyl group, or a halo group.

In particularly preferred embodiments of the present invention, the base modifications are selected from 2-amino-6-chloropurineriboside-5'-triphosphate, 2-aminopurine-riboside-5'-triphosphate; 2-aminoadenosine-5'-triphosphate, 2'-amino-2'-deoxycytidine-triphosphate, 2-thiocytidine-5'-triphosphate, 2-thiouridine-5'-triphosphate, 2'-fluorothymidine-5'-triphosphate, 2'-O-methyl inosine-5'-triphosphate 4-thiouridine-5'-triphosphate, 5-aminoallylcytidine-5'-triphosphate, 5-aminoallyluridine-5'-triphosphate, 5-bromocytidine-5'-triphosphate, 5-bromouridine-5'-triphosphate, 5-bromo-2'-deoxycytidine-5'-triphosphate, 5-bromo-2'-deoxyuridine-5'-triphosphate, 5-iodocytidine-5'-triphosphate, 5-iodo-2'-deoxycytidine-5'-triphosphate, 5-iodouridine-5'-triphosphate, 5-iodo-2'-deoxyuridine-5'-triphosphate, 5-methylcytidine-5'-triphosphate, 5-methyluridine-5'-triphosphate, 5-propynyl-2'-deoxycytidine-5'-triphosphate, 5-propynyl-2'-deoxyuridine-5'-triphosphate, 6-azacytidine-5'-triphosphate, 6-azauridine-5'-triphosphate, 6-chloropurineriboside-5'-triphosphate, 7-deazaadenosine-5'-triphosphate, 7-deazaguanosine-5'-triphosphate, 8-azaadenosine-5'-triphosphate, 8-azidoadenosine-5'-triphosphate, benzimidazole-riboside-5'-triphosphate, N1-methyladenosine-5'-triphosphate, N1-methylguanosine-5'-triphosphate, N6-methyladenosine-5'-triphosphate, O6-methylguanosine-5'-triphosphate, pseudouridine-5'-triphosphate, or puromycin-5'-triphosphate, xanthosine-5'-triphosphate. Particular preference is given to nucleotides for base modifications selected from the group of base-modified nucleotides consisting of 5-methylcytidine-5'-triphosphate, 7-deazaguanosine-5'-triphosphate, 5-bromocytidine-5'-triphosphate, and pseudouridine-5'-triphosphate.

In some embodiments, modified nucleosides include pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine.

In some embodiments, modified nucleosides include 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine.

In other embodiments, modified nucleosides include 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine.

In other embodiments, modified nucleosides include inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methyl-inosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

In some embodiments, the nucleotide can be modified on the major groove face and can include replacing hydrogen on C-5 of uracil with a methyl group or a halo group.

In specific embodiments, a modified nucleoside is 5'-O-(1-thiophosphate)-adenosine, 5'-O-(1-thiophosphate)-cytidine, 5'-O-(1-thiophosphate)-guanosine, 5'-O-(1-thiophosphate)-uridine or 5'-O-(1-thiophosphate)-pseudouridine.

In further specific embodiments, a modified nucleic acid compound, preferably an mRNA, may comprise nucleoside modifications selected from 6-aza-cytidine, 2-thio-cytidine, α-thio-cytidine, pseudo-iso-cytidine, 5-aminoallyl-uridine, 5-iodo-uridine, N1-methyl-pseudouridine, 5,6-dihydrouridine, α-thio-uridine, 4-thio-uridine, 6-aza-uridine, 5-hydroxy-uridine, deoxy-thymidine, 5-methyl-uridine, pyrrolo-cytidine, inosine, α-thio-guanosine, 6-methyl-guanosine, 5-methyl-cytdine, 8-oxo-guanosine, 7-deaza-guanosine, N1-methyl-adenosine, 2-amino-6-chloro-purine, N6-methyl-2-amino-purine, pseudo-iso-cytidine, 6-chloro-purine, N6-methyl-adenosine, α-thio-adenosine, 8-azido-adenosine, 7-deaza-adenosine.

In one embodiment, the nucleic acid exhibits a lipid modification. Such a lipid-modified nucleic acid or RNA as defined herein typically further comprises at least one linker covalently linked with that nucleic acid or RNA, and at least one lipid covalently linked with the respective linker. Alternatively, the lipid-modified nucleic acid comprises at least one nucleic acid as defined herein and at least one (bifunctional) lipid covalently linked (without a linker) with that nucleic acid. According to a third alternative, the lipid-modified nucleic acid comprises an nucleic acid molecule as defined herein, at least one linker covalently linked with that RNA, and at least one lipid covalently linked with the respective linker, and also at least one (bifunctional) lipid covalently linked (without a linker) with that nucleic acid. In this context, it is particularly preferred that the lipid modification is present at the terminal ends of a linear nucleic acid sequence.

According to another preferred embodiment of the invention, a modified nucleic acid sequence as defined herein, particularly a modified RNA as defined herein can be modified by the addition of a so-called '5' cap' structure, which preferably stabilizes the nucleic acid as described herein. A 5'-cap is an entity, typically a modified nucleotide entity, which generally "caps" the 5'-end of a mature RNA. A 5'-cap may typically be formed by a modified nucleotide, particularly by a derivative of a guanine nucleotide. Preferably, the 5'-cap is linked to the 5'-terminus via a 5'-5'-triphosphate linkage. A 5'-cap may be methylated, e.g. m7GpppN, wherein N is the terminal 5' nucleotide of the nucleic acid carrying the 5'-cap, typically the 5'-end of an RNA. m7GpppN is the 5'-cap structure, which naturally occurs in RNA transcribed by polymerase II and is therefore preferably not considered as modification comprised in a modified RNA in this context. Accordingly, a modified RNA sequence of the present invention may comprise a m7GpppN as 5'-cap, but additionally the modified RNA sequence typically comprises at least one further modification as defined herein.

Further examples of 5'cap structures include glyceryl, inverted deoxy abasic residue (moiety), 4',5' methylene nucleotide, 1-(beta-D-erythrofuranosyl) nucleotide, 4'-thio nucleotide, carbocyclic nucleotide, 1,5-anhydrohexitol nucleotide, L-nucleotides, alpha-nucleotide, modified base nucleotide, threo-pentofuranosyl nucleotide, acyclic 3',4'- seco nucleotide, acyclic 3,4-dihydroxybutyl nucleotide, acyclic 3,5 dihydroxypentyl nucleotide, 3'-3'-inverted nucleotide moiety, 3'-3'-inverted abasic moiety, 3'-2'-inverted nucleotide moiety, 3'-2'-inverted abasic moiety, 1,4-butanediol phosphate, 3'-phosphoramidate, hexylphosphate, aminohexyl phosphate, 3'-phosphate, 3'phosphorothioate, phosphorodithioate, or bridging or non-bridging methylphosphonate moiety. These modified 5'-cap structures are regarded as at least one modification in this context.

Particularly preferred modified 5'-cap structures are cap1 (methylation of the ribose of the adjacent nucleotide of m7G), cap2 (additional methylation of the ribose of the $2^{nd}$ nucleotide downstream of the m7G), cap3 (additional methylation of the ribose of the $3^{rd}$ nucleotide downstream of the m7G), cap4 (methylation of the ribose of the 4th nucleotide downstream of the m7G), ARCA (anti-reverse cap analogue, modified ARCA (e.g. phosphothioate modified ARCA), inosine, N1-methyl-guanosine, 2'-fluoro-guanosine, 7-deaza-guanosine, 8-oxo-guanosine, 2-amino-guanosine, LNA-guanosine, and 2-azido-guanosine. Accordingly, the RNA according to the invention preferably comprises a 5'-cap structure.

In a preferred embodiment, the 5'-cap structure is added co-transcriptionally using cap-analogues as defined herein in an RNA in vitro transcription reaction as defined herein. In another embodiment, the 5'-cap structure is added via enzymatic capping using capping enzymes (e.g. vaccinia virus capping enzymes).

Optionally, a nucleic acid may be selected which represents an mRNA that is essentially resistant to in vivo degradation by an exo- or endonucleases. Such stabilisation can be effected, for example, by chemically modifying the phosphates of the backbone. Sugar or base modifications may be additionally used. mRNA may also be stabilised against degradation by RNases by the addition of a so-called "5' cap" structure. Particular preference is given in this connection to an G(5')ppp(5')G or a m7G(5')ppp(5')N as the 5'cap structures (N being A, G, C, or U). According to another example, the mRNA may exhibit a poly-A tail on the 3' terminus of typically about 10 to about 200 adenosine nucleotides, preferably of about 10 to about 100 adenosine nucleotides, or about 20 to about 100 adenosine nucleotides or even about 40 to about 80 adenosine nucleotides. According to a further example, the mRNA may have a poly-C tail on the 3' terminus of typically about 10 to about 200 cytosine nucleotides, preferably about 10 to about 100 cytosine nucleotides, or about 20 to about 70 cytosine nucleotides, or about 20 to about 60 or even about 10 to about 40 cytosine nucleotides.

According to another embodiment, the nucleic acid sequence of the present invention may be modified, and thus stabilized, by modifying the guanosine/cytosine (G/C) content of the nucleic acid sequence.

In a particularly preferred embodiment of the present invention, the G/C content of the coding sequence of the nucleic acid sequence of the present invention is modified, particularly increased, compared to the G/C content of the coding sequence of the respective wild-type nucleic acid sequence, i.e. the unmodified nucleic acid. The amino acid sequence encoded by the nucleic acid is preferably not modified as compared to the amino acid sequence encoded by the respective wild-type nucleic acid. This modification of the nucleic acid sequence of the present invention is based on the fact that the sequence of any nucleic acid region, particularly the sequence of any RNA region to be translated is important for efficient translation of that nucleic acid, particularly of that RNA. Thus, the composition of the nucleic acid and the sequence of various nucleotides are important. In particular, in case of RNA, sequences having an increased G (guanosine)/C (cytosine) content are more stable than sequences having an increased A (adenosine)/U (uracil) content. According to the invention, the codons of the nucleic acid are therefore varied compared to the respective wild-type nucleic acid, while retaining the translated amino acid sequence, such that they include an increased amount of G/C nucleotides. In respect to the fact that several codons code for one and the same amino acid (so-called degeneration of the genetic code), the most favourable codons for the stability can be determined (so-called alternative codon usage). Depending on the amino acid to be encoded by the nucleic acid, there are various possibilities for modification of the nucleic acid sequence, compared to its wild-type sequence.

The following modifications may apply for RNA molecules, but may also be transferrable to DNA molecules: In the case of amino acids, which are encoded by codons, containing exclusively G or C nucleotides, no modification of the codon is necessary. Thus, the codons for Pro (CCC or CCG), Arg (CGC or CGG), Ala (GCC or GCG) and Gly (GGC or GGG) require no modification, since no A or U is present. In contrast, codons which contain A and/or U nucleotides can be modified by substitution of other codons, which code for the same amino acids but contain no A and/or U. Examples of these are: the codons for Pro can be modified from CCU or CCA to CCC or CCG; the codons for Arg can be modified from CGU or CGA or AGA or AGG to CGC or CGG; the codons for Ala can be modified from GCU or GCA to GCC or GCG; the codons for Gly can be modified from GGU or GGA to GGC or GGG. In other cases, although A or U nucleotides cannot be eliminated from the codons, it is however possible to decrease the A and U content by using codons which contain a lower content of A and/or U nucleotides. Examples of these are: the codons for Phe can be modified from UUU to UUC; the codons for Leu can be modified from UUA, UUG, CUU or CUA to CUC or CUG; the codons for Ser can be modified from UCU or UCA or AGU to UCC, UCG or AGC; the codon for Tyr can be modified from UAU to UAC; the codon for Cys can be modified from UGU to UGC; the codon for His can be modified from CAU to CAC; the codon for Gln can be modified from CAA to CAG; the codons for Ile can be modified from AUU or AUA to AUC; the codons for Thr can be modified from ACU or ACA to ACC or ACG; the codon for Asn can be modified from AAU to AAC; the codon for Lys can be modified from AAA to AAG; the codons for Val can be modified from GUU or GUA to GUC or GUG; the codon for Asp can be modified from GAU to GAC; the codon for Glu can be modified from GAA to GAG; the stop codon UAA can be modified to UAG or UGA. In the case of the codons for Met (AUG) and Trp (UGG), on the other hand, there is no possibility of sequence modification. The substitutions listed above can be used either individually or in all possible combinations to increase the G/C content of the RNA sequence of the present invention compared to its particular wild-type RNA (i.e. the original sequence). Thus, for example, all codons for Thr occurring in the wild-type sequence can be modified to ACC (or ACG). Preferably, however, for example, combinations of the above substitution possibilities are used:

substitution of all codons coding for Thr in the original sequence (wild-type RNA) to ACC (or ACG) and substitution of all codons originally coding for Ser to UCC (or UCG or AGC); substitution of all codons coding for Ile in the original sequence to AUC and substitution of all codons originally coding for Lys to AAG and substitution of all codons originally coding for Tyr to UAC; substitution of all codons coding for Val in the original sequence to GUC (or GUG) and substitution of all codons originally coding for Glu to GAG and substitution of all codons originally coding for Ala to GCC (or GCG) and substitution of all codons originally coding for Arg to CGC (or CGG); substitution of all codons coding for Val in the original sequence to GUC (or GUG) and substitution of all codons originally coding for Glu to GAG and substitution of all codons originally coding for Ala to GCC (or GCG) and substitution of all codons originally coding for Gly to GGC (or GGG) and substitution of all codons originally coding for Asn to AAC; substitution of all codons coding for Val in the original sequence to GUC (or GUG) and substitution of all codons originally coding for Phe to UUC and substitution of all codons originally coding for Cys to UGC and substitution of all codons originally coding for Leu to CUG (or CUC) and substitution of all codons originally coding for Gln to CAG and substitution of all codons originally coding for Pro to CCC (or CCG); etc.

According to a specific embodiment at least 5%, 10%, 20%, 30%, 40%, 50%, 60%, more preferably at least 70%, even more preferably at least 80% and most preferably at least 90%, 95% or even 100% of the substitutable codons in the region coding for a peptide or protein as defined herein or a fragment or variant thereof or the whole sequence of the wild type RNA sequence are substituted, thereby increasing the G/C content of said sequence. In this context, it is particularly preferable to increase the G/C content of the RNA sequence of the present invention, preferably of the at least one coding sequence of the RNA sequence according to the invention, to the maximum (i.e. 100% of the substitutable codons) as compared to the wild-type sequence. According to the invention, a further preferred modification of the RNA sequence of the present invention is based on the finding that the translation efficiency is also determined by a different frequency in the occurrence of tRNAs in cells. Thus, if so-called "rare codons" are present in the RNA sequence of the present invention to an increased extent, the corresponding modified RNA sequence is translated to a significantly poorer degree than in the case where codons coding for relatively "frequent" tRNAs are present. According to the invention, in the modified RNA sequence of the present invention, the region which codes for a peptide or protein as defined herein or a fragment or variant thereof is modified compared to the corresponding region of the wild-type RNA sequence such that at least one codon of the wild-type sequence, which codes for a tRNA which is relatively rare in the cell, is exchanged for a codon, which codes for a tRNA which is relatively frequent in the cell and carries the same amino acid as the relatively rare tRNA. By this modification, the sequence of the RNA of the present invention is modified such that codons for which frequently occurring tRNAs are available are inserted. In other words, according to the invention, by this modification all codons of the wild-type sequence, which code for a tRNA which is relatively rare in the cell, can in each case be exchanged for a codon, which codes for a tRNA which is relatively frequent in the cell and which, in each case, carries the same amino acid as the relatively rare tRNA. Which tRNAs occur relatively frequently in the cell and which, in contrast, occur relatively rarely is known to a person skilled in the art; cf. e.g. Akashi, Curr. Opin. Genet. Dev. 2001, 11(6): 660-666. The codons, which use for the particular amino acid the tRNA which occurs the most frequently, e.g. the Gly codon, which uses the tRNA, which occurs the most frequently in the (human) cell, are particularly preferred. According to the invention, it is particularly preferable to link the sequential G/C content which is increased, in particular maximized, in the modified RNA sequence of the present invention, with the "frequent" codons without modifying the amino acid sequence of the protein encoded by the coding sequence of the RNA sequence. This preferred embodiment allows provision of a particularly efficiently translated and stabilized (modified) RNA sequence of the present invention. The determination of a modified RNA sequence of the present invention as described above (increased G/C content; exchange of tRNAs) can be carried out using the computer program explained in WO 02/098443—the disclosure content of which is included in its full scope in the present invention. Using this computer program, the nucleotide sequence of any desired RNA sequence can be modified with the aid of the genetic code or the degenerative nature thereof such that a maximum G/C content results, in combination with the use of codons which code for tRNAs occurring as frequently as possible in the cell, the amino acid sequence coded by the modified RNA sequence preferably not being modified compared to the non-modified sequence. Alternatively, it is also possible to modify only the G/C content or only the codon usage compared to the original sequence. The source code in Visual Basic 6.0 (development environment used: Microsoft Visual Studio Enterprise 6.0 with Servicepack 3) is also described in WO 02/098443. In a further preferred embodiment of the present invention, the A/U content in the environment of the ribosome binding site of the RNA sequence of the present invention is increased compared to the A/U content in the environment of the ribosome binding site of its respective wild-type RNA. This modification (an increased A/U content around the ribosome binding site) increases the efficiency of ribosome binding to the RNA. An effective binding of the ribosomes to the ribosome binding site (e.g. to the Kozak sequence) in turn has the effect of an efficient translation of the RNA. According to a further embodiment of the present invention, the RNA sequence of the present invention may be modified with respect to potentially destabilizing sequence elements. Particularly, the coding sequence and/or the 5' and/or 3' untranslated region of this RNA sequence may be modified compared to the respective wild-type RNA such that it contains no destabilizing sequence elements, the encoded amino acid sequence of the modified RNA sequence preferably not being modified compared to its respective wild-type RNA. It is known that, for example in sequences of eukaryotic RNAs, destabilizing sequence elements (DSE) occur, to which signal proteins bind and regulate enzymatic degradation of RNA in vivo. For further stabilization of the modified RNA sequence, optionally in the region which encodes at least one peptide or protein as defined herein or a fragment or variant thereof, one or more such modifications compared to the corresponding region of the wild-type RNA can therefore be carried out, so that no or substantially no destabilizing sequence elements are contained there. According to the invention, DSE present in the untranslated regions (3'- and/or 5'-UTR) can also be eliminated from the RNA sequence of the present invention by such modifications. Such destabilizing sequences are e.g. AU-rich sequences (AURES), which occur in 3'-UTR sections of numerous unstable RNAs (Caput et al., Proc. Natl. Acad. Sci. USA 1986, 83: 1670 to 1674). The RNA sequence of the present invention is therefore preferably modified compared to the respective wild-type RNA such that the RNA sequence of the present invention contains no such destabilizing sequences. This also applies to those sequence motifs which are recognized by possible endonucleases, e.g. the sequence GAACAAG, which is contained in the 3'-UTR segment of the gene encoding the transferrin receptor (Binder et al., EMBO J. 1994, 13: 1969 to 1980). These sequence motifs are also preferably removed in the RNA sequence of the present invention.

According to another preferred embodiment, the mRNA used in the context of the invention has a modified the G/C content, preferably in its coding region, which means that the G/C content is modified, particularly increased, compared to the G/C content of the coding region of its corresponding wild-type mRNA, preferably without changing the encoded amino acid sequence. For example, the G/C content of the coding region may be increased by at least 7%, or by at least 15%, or by at least 20%, compared to that of the wild-type mRNA which codes for an antigen, antigenic protein or antigenic peptide as described herein, or a fragment or variant thereof. According to a specific embodiment, at least 5%, 10%, 20%, 30%, 40%, 50%, 60%, 70%, or 80%, such as 90% or more, 95% or more, or even 100% of the substitutable codons in the coding region or in the whole sequence are substituted to increase the G/C content. In this context, 100% substitution means that essentially all substitutable codons of the coding region are substituted, which is one of the preferred embodiments of the invention. In another preferred embodiment, an mRNA is used wherein the coding region is modified such that at least one codon of the wild-type sequence which codes for a tRNA which is relatively rare in the cell is exchanged for a codon which codes for a tRNA which is relatively frequent in the cell but encodes the same amino acid as the relatively rare tRNA. tRNAs that occur relatively rarely or frequently in the cell are known to a person skilled in the art; cf. e.g. Akashi, Curr. Opin. Genet. Dev. 2001, 11(6): 660-666. The most frequently occurring tRNAs for a particular amino acid are particularly preferred.

According to another embodiment, the nucleic acid sequence of the present invention, may be modified, and thus stabilized, by adapting the sequences to the human codon usage.

According to the invention, a further preferred modification of the nucleic acid sequence of the present invention is based on the finding that codons encoding the same amino acid typically occur at different frequencies. According to the invention, in the modified nucleic acid sequence of the present invention, the coding sequence as defined herein is preferably modified compared to the corresponding coding sequence of the respective wild-type nucleic acid such that the frequency of the codons encoding the same amino acid corresponds to the naturally occurring frequency of that codon according to the human codon usage as e.g. shown in Table B.

For example, in the case of the amino acid alanine (Ala) present in an amino acid sequence encoded by the at least one coding sequence of the a nucleic acid sequence according to the invention, the wild type coding sequence is preferably adapted in a way that the codon "GCC" is used with a frequency of 0.40, the codon "GCT" is used with a frequency of 0.28, the codon "GCA" is used with a frequency of 0.22 and the codon "GCG" is used with a frequency of 0.10 etc. (see Table B).

TABLE

Human codon usage table

| Amino acid | Codon | Fraction | /1000 |
| --- | --- | --- | --- |
| Ala | GCG | 0.10 | 7.4 |
| Ala | GCA | 0.22 | 15.8 |
| Ala | GCT | 0.28 | 18.5 |
| Ala | GCC* | 0.40 | 27.7 |
| Cys | TGT | 0.42 | 10.6 |
| Cys | TGC* | 0.58 | 12.6 |
| Asp | GAT | 0.44 | 21.8 |
| Asp | GAC* | 0.56 | 25.1 |
| Glu | GAG* | 0.59 | 39.6 |
| Glu | GAA | 0.41 | 29.0 |
| Phe | TTT | 0.43 | 17.6 |
| Phe | TTC* | 0.57 | 20.3 |
| Gly | GGG | 0.23 | 16.5 |
| Gly | GGA | 0.26 | 16.5 |
| Gly | GGT | 0.18 | 10.8 |
| Gly | GGC* | 0.33 | 22.2 |
| His | CAT | 0.41 | 10.9 |
| His | CAC* | 0.59 | 15.1 |
| Ile | ATA | 0.14 | 7.5 |
| Ile | ATT | 0.35 | 16.0 |
| Ile | ATC* | 0.52 | 20.8 |
| Lys | AAG* | 0.60 | 31.9 |
| Lys | AAA | 0.40 | 24.4 |
| Leu | TTG | 0.12 | 12.9 |
| Leu | TTA | 0.06 | 7.7 |
| Leu | CTG* | 0.43 | 39.6 |
| Leu | CTA | 0.07 | 7.2 |
| Leu | CTT | 0.12 | 13.2 |
| Leu | CTC | 0.20 | 19.6 |
| Met | ATG* | 1 | 22.0 |
| Asn | AAT | 0.44 | 17.0 |
| Asn | AAC* | 0.56 | 19.1 |
| Pro | CCG | 0.11 | 6.9 |
| Pro | CCA | 0.27 | 16.9 |
| Pro | CCT | 0.29 | 17.5 |
| Pro | CCC* | 0.33 | 19.8 |
| Gln | CAG* | 0.73 | 34.2 |
| Gln | CAA | 0.27 | 12.3 |
| Arg | AGG | 0.22 | 12.0 |
| Arg | AGA* | 0.21 | 12.1 |
| Arg | CGG | 0.19 | 11.4 |
| Arg | CGA | 0.10 | 6.2 |
| Arg | CGT | 0.09 | 4.5 |
| Arg | CGC | 0.19 | 10.4 |
| Ser | AGT | 0.14 | 12.1 |
| Ser | AGC* | 0.25 | 19.5 |
| Ser | TCG | 0.06 | 4.4 |
| Ser | TCA | 0.15 | 12.2 |
| Ser | TCT | 0.18 | 15.2 |
| Ser | TCC | 0.23 | 17.7 |
| Thr | ACG | 0.12 | 6.1 |
| Thr | ACA | 0.27 | 15.1 |
| Thr | ACT | 0.23 | 13.1 |
| Thr | ACC* | 0.38 | 18.9 |
| Val | GTG* | 0.48 | 28.1 |
| Val | GTA | 0.10 | 7.1 |
| Val | GTT | 0.17 | 11.0 |
| Val | GTC | 0.25 | 14.5 |
| Trp | TGG* | 1 | 13.2 |
| Tyr | TAT | 0.42 | 12.2 |
| Tyr | TAC* | 0.58 | 15.3 |
| Stop | TGA* | 0.61 | 1.6 |
| Stop | TAG | 0.17 | 0.8 |
| Stop | TAA | 0.22 | 1.0 |

*most frequent codon

As described above it is preferred according to the invention, that all codons of the wild-type sequence which code for a tRNA, which is relatively rare in the cell, are exchanged for a codon which codes for a tRNA, which is relatively frequent in the cell and which, in each case, carries the same amino acid as the relatively rare tRNA. Therefore it is particularly preferred that the most frequent codons are used for each encoded amino acid (see Table B, most frequent codons are marked with asterisks). Such an optimization procedure increases the codon adaptation index (CAI) and ultimately maximises the CAI. In the context of the invention, sequences with increased or maximized CAI are typically referred to as "codon-optimized" sequences and/or CAI increased and/or maximized sequences. According to a preferred embodiment, the nucleic acid sequence of the present invention comprises at least one coding sequence, wherein the coding sequence/sequence is codon-optimized as described herein. More preferably, the codon adaptation index (CAI) of the at least one coding sequence is at least 0.5, at least 0.8, at least 0.9 or at least 0.95. Most preferably, the codon adaptation index (CAI) of the at least one coding sequence is 1.

For example, in the case of the amino acid alanine (Ala) present in the amino acid sequence encoded by the at least one coding sequence of the nucleic acid sequence according to the invention, the wild type coding sequence is adapted in a way that the most frequent human codon "GCC" is always used for said amino acid, or for the amino acid Cysteine (Cys), the wild type sequence is adapted in a way that the most frequent human codon "TGC" is always used for said amino acid etc.

According to another embodiment, the nucleic acid sequence of the present invention may be modified by modifying, preferably increasing, the cytosine (C) content of the nucleic acid sequence, preferably of the coding sequence of the nucleic acid sequence, more preferably the coding sequence of the RNA sequence.

In a particularly preferred embodiment of the present invention, the C content of the coding sequence of the nucleic acid sequence of the present invention is modified, preferably increased, compared to the C content of the coding sequence of the respective wild-type nucleic acid, i.e. the unmodified nucleic acid. The amino acid sequence encoded by the at least one coding sequence of the nucleic acid sequence of the present invention is preferably not modified as compared to the amino acid sequence encoded by the respective wild-type nucleic acid.

In a preferred embodiment of the present invention, the modified nucleic acid, particularly the modified RNA sequence is modified such that at least 10%, 20%, 30%, 40%, 50%, 60%, 70% or 80%, or at least 90% of the theoretically possible maximum cytosine-content or even a maximum cytosine-content is achieved.

In further preferred embodiments, at least 10%, 20%, 30%, 40%, 50%, 60%, 70%, 80%, 90% or even 100% of the codons of the target nucleic acid, particularly the modified RNA wild type sequence, which are "cytosine content optimizable" are replaced by codons having a higher cytosine-content than the ones present in the wild type sequence.

In a further preferred embodiment, some of the codons of the wild type coding sequence may additionally be modified such that a codon for a relatively rare tRNA in the cell is exchanged by a codon for a relatively frequent tRNA in the cell, provided that the substituted codon for a relatively frequent tRNA carries the same amino acid as the relatively rare tRNA of the original wild type codon. Preferably, all of the codons for a relatively rare tRNA are replaced by a codon for a relatively frequent tRNA in the cell, except codons encoding amino acids, which are exclusively encoded by codons not containing any cytosine, or except for glutamine (Gln), which is encoded by two codons each containing the same number of cytosines.

In a further preferred embodiment of the present invention, the modified target nucleic acid, preferably the RNA is modified such that at least 80%, or at least 90% of the theoretically possible maximum cytosine-content or even a maximum cytosine-content is achieved by means of codons, which code for relatively frequent tRNAs in the cell, wherein the amino acid sequence remains unchanged.

Due to the naturally occurring degeneracy of the genetic code, more than one codon may encode a particular amino acid. Accordingly, 18 out of 20 naturally occurring amino acids are encoded by more than one codon (with Tryp and Met being an exception), e.g. by 2 codons (e.g. Cys, Asp, Glu), by three codons (e.g. Ile), by 4 codons (e.g. Al, Gly, Pro) or by 6 codons (e.g. Leu, Arg, Ser). However, not all codons encoding the same amino acid are utilized with the same frequency under in vivo conditions. Depending on each single organism, a typical codon usage profile is established.

The term 'cytosine content-optimizable codon' as used within the context of the present invention refers to codons, which exhibit a lower content of cytosines than other codons encoding the same amino acid. Accordingly, any wild type codon, which may be replaced by another codon encoding the same amino acid and exhibiting a higher number of cytosines within that codon, is considered to be cytosine-optimizable (C-optimizable). Any such substitution of a C-optimizable wild type codon by the specific C-optimized codon within a wild type coding sequence increases its overall C-content and reflects a C-enriched modified nucleic acid sequence. According to a preferred embodiment, the nucleic acid sequence, particularly the RNA sequence of the present invention, preferably the at least one coding sequence of the nucleic acid sequence of the present invention comprises or consists of a C-maximized RNA sequence containing C-optimized codons for all potentially C-optimizable codons. Accordingly, 100% or all of the theoretically replaceable C-optimizable codons are preferably replaced by C-optimized codons over the entire length of the coding sequence.

In this context, cytosine-content optimizable codons are codons, which contain a lower number of cytosines than other codons coding for the same amino acid.

Any of the codons GCG, GCA, GCU codes for the amino acid Ala, which may be exchanged by the codon GCC encoding the same amino acid, and/or the codon UGU that codes for Cys may be exchanged by the codon UGC encoding the same amino acid, and/or the codon GAU which codes for Asp may be exchanged by the codon GAC encoding the same amino acid, and/or the codon that UUU that codes for Phe may be exchanged for the codon UUC encoding the same amino acid, and/or any of the codons GGG, GGA, GGU that code Gly may be exchanged by the codon GGC encoding the same amino acid, and/or the codon CAU that codes for His may be exchanged by the codon CAC encoding the same amino acid, and/or any of the codons AUA, AUU that code for Ile may be exchanged by the codon AUC, and/or any of the codons UUG, UUA, CUG, CUA, CUU coding for Leu may be exchanged by the codon CUC encoding the same amino acid, and/or the codon AAU that codes for Asn may be exchanged by the codon AAC encoding the same amino acid, and/or any of the codons CCG, CCA, CCU coding for Pro may be exchanged by the codon CCC encoding the same amino acid, and/or any of the codons AGG, AGA, CGG, CGA, CGU coding for Arg may be exchanged by the codon CGC encoding the same amino acid, and/or any of the codons AGU, AGC, UCG, UCA, UCU coding for Ser may be exchanged by the codon UCC encoding the same amino acid, and/or any of the codons ACG, ACA, ACU coding for Thr may be exchanged by the codon ACC encoding the same amino acid, and/or any of the codons GUG, GUA, GUU coding for Val may be exchanged by the codon GUC encoding the same amino acid, and/or the codon UAU coding for Tyr may be exchanged by the codon UAC encoding the same amino acid.

In any of the above instances, the number of cytosines is increased by 1 per exchanged codon. Exchange of all non C-optimized codons (corresponding to C-optimizable codons) of the coding sequence results in a C-maximized coding sequence. In the context of the invention, at least 70%, preferably at least 80%, more preferably at least 90%, of the non C-optimized codons within the at least one coding sequence of the RNA sequence according to the invention are replaced by C-optimized codons.

It may be preferred that for some amino acids the percentage of C-optimizable codons replaced by C-optimized codons is less than 70%, while for other amino acids the percentage of replaced codons is higher than 70% to meet the overall percentage of C-optimization of at least 70% of all C-optimizable wild type codons of the coding sequence.

Preferably, in a C-optimized RNA sequence of the invention, at least 50% of the C-optimizable wild type codons for any given amino acid are replaced by C-optimized codons, e.g. any modified C-enriched RNA sequence preferably contains at least 50% C-optimized codons at C-optimizable wild type codon positions encoding any one of the above mentioned amino acids Ala, Cys, Asp, Phe, Gly, His, Ile, Leu, Asn, Pro, Arg, Ser, Thr, Val and Tyr, preferably at least 60%.

In this context codons encoding amino acids, which are not cytosine content-optimizable and which are, however, encoded by at least two codons, may be used without any further selection process. However, the codon of the wild type sequence that codes for a relatively rare tRNA in the cell, e.g. a human cell, may be exchanged for a codon that codes for a relatively frequent tRNA in the cell, wherein both code for the same amino acid. Accordingly, the relatively rare codon GAA coding for Glu may be exchanged by the relative frequent codon GAG coding for the same amino acid, and/or the relatively rare codon AAA coding for Lys may be exchanged by the relative frequent codon AAG coding for the same amino acid, and/or the relatively rare codon CAA coding for Gln may be exchanged for the relative frequent codon CAG encoding the same amino acid.

In this context, the amino acids Met (AUG) and Trp (UGG), which are encoded by only one codon each, remain unchanged. Stop codons are not cytosine-content optimized, however, the relatively rare stop codons amber, ochre (UAA, UAG) may be exchanged by the relatively frequent stop codon opal (UGA).

The single substitutions listed above may be used individually as well as in all possible combinations in order to optimize the cytosine-content of the modified nucleic acid sequence compared to the wild type nucleic acid sequence.

Accordingly, the at least one coding sequence as defined herein may be changed compared to the coding sequence of the respective wild type nucleic acid in such a way that an amino acid encoded by at least two or more codons, of which one comprises one additional cytosine, such a codon may be exchanged by the C-optimized codon comprising one additional cytosine, wherein the amino acid is preferably unaltered compared to the wild type sequence.

According to a further preferred embodiment, the nucleic acid sequence, particularly the RNA sequence of the present invention may contain a poly-A tail on the 3' terminus of typically about 10 to 200 adenosine nucleotides, preferably about 10 to 100 adenosine nucleotides, more preferably about 40 to 80 adenosine nucleotides or even more preferably about 50 to 70 adenosine nucleotides.

Preferably, the poly(A) sequence in the RNA sequence of the present invention is derived from a DNA template by RNA in vitro transcription. Alternatively, the poly(A) sequence may also be obtained in vitro by common methods of chemical-synthesis without being necessarily transcribed from a DNA-progenitor. Moreover, poly(A) sequences, or poly(A) tails may be generated by enzymatic polyadenylation of the RNA according to the present invention using commercially available polyadenylation kits and corresponding protocols known in the art.

Alternatively, the RNA as described herein optionally comprises a polyadenylation signal, which is defined herein as a signal, which conveys polyadenylation to a (transcribed) RNA by specific protein factors (e.g. cleavage and polyadenylation specificity factor (CPSF), cleavage stimulation factor (CstF), cleavage factors I and II (CF I and CF II), poly(A) polymerase (PAP)). In this context, a consensus polyadenylation signal is preferred comprising the NN(U/T)ANA consensus sequence. In a particularly preferred aspect, the polyadenylation signal comprises one of the following sequences: AA(U/T)AAA or A(U/T)(U/T)AAA (wherein uridine is usually present in RNA and thymidine is usually present in DNA).

According to a further preferred embodiment, the nucleic acid sequence, particularly the RNA sequence of the present invention may contain a poly(C) tail on the 3' terminus of typically about 10 to 200 cytosine nucleotides, preferably about 10 to 100 cytosine nucleotides, more preferably about 20 to 70 cytosine nucleotides or even more preferably about 20 to 60 or even 10 to 40 cytosine nucleotides. Preferably, the poly(C) sequence in the RNA sequence of the present invention is derived from a DNA template by RNA in vitro transcription.

In a preferred embodiment, the nucleic acid sequence, particularly the RNA sequence according to the invention comprises at least one 5'- or 3'-UTR element. In this context, an UTR element comprises or consists of a nucleic acid sequence, which is derived from the 5'- or 3'-UTR of any naturally occurring gene or which is derived from a fragment, a homolog or a variant of the 5'- or 3'-UTR of a gene. Preferably, the 5'- or 3'-UTR element used according to the present invention is heterologous to the at least one coding sequence of the RNA sequence of the invention. Even if 5'- or 3'-UTR elements derived from naturally occurring genes are preferred, also synthetically engineered UTR elements may be used in the context of the present invention.

The term '3'UTR element' typically refers to a nucleic acid sequence, which comprises or consists of a nucleic acid sequence that is derived from a 3'UTR or from a variant of a 3'UTR. A 3'UTR element in the sense of the present invention may represent the 3'UTR of a nucleic acid molecule, particularly of an RNA or DNA, preferably an mRNA. Thus, in the sense of the present invention, preferably, a 3'UTR element may be the 3'UTR of an RNA, preferably of an mRNA, or it may be the transcription template for a 3'UTR of an RNA. Thus, a 3'UTR element preferably is a nucleic acid sequence which corresponds to the 3'UTR of an RNA, preferably to the 3'UTR of an mRNA, such as an mRNA obtained by transcription of a genetically engineered vector construct. Preferably, the 3'UTR element fulfils the function of a 3'UTR or encodes a sequence which fulfils the function of a 3'UTR.

Preferably, the at least one 3'UTR element comprises or consists of a nucleic acid sequence derived from the 3'UTR of a chordate gene, preferably a vertebrate gene, more preferably a mammalian gene, most preferably a human gene, or from a variant of the 3'UTR of a chordate gene, preferably a vertebrate gene, more preferably a mammalian gene, most preferably a human gene.

Preferably, the nucleic acid sequence, particularly the RNA sequence of the present invention comprises a 3'UTR element, which may be derivable from a gene that relates to an RNA with an enhanced half-life (that provides a stable RNA), for example a 3'UTR element as defined and described below. Preferably, the 3' UTR element is a nucleic acid sequence derived from a 3' UTR of a gene, which preferably encodes a stable RNA, or from a homolog, a fragment or a variant of said gene In a particularly preferred embodiment, the 3'UTR element comprises or consists of a nucleic acid sequence, which is derived from a 3'UTR of a gene selected from the group consisting of an albumin gene, an alpha-globin gene, a beta-globin gene, a tyrosine hydroxylase gene, a lipoxygenase gene, and a collagen alpha gene, such as a collagen alpha 1(I) gene, or from a variant of a 3'UTR of a gene selected from the group consisting of an albumin gene, an alpha-globin gene, a beta-globin gene, a tyrosine hydroxylase gene, a lipoxygenase gene, and a collagen alpha gene, such as a collagen alpha 1(I) gene according to SEQ ID NOs: 1369-1390 of the patent application WO2013/143700, whose disclosure is incorporated herein by reference, or from a homolog, a fragment or a variant thereof. In a particularly preferred embodiment, the 3'UTR element comprises or consists of a nucleic acid sequence which is derived from a 3'UTR of an albumin gene, preferably a vertebrate albumin gene, more preferably a mammalian albumin gene, most preferably a human albumin gene.

In this context it is particularly preferred that the RNA sequence according to the invention comprises a 3'-UTR element comprising a corresponding RNA sequence derived from the nucleic acids according to SEQ ID NOs: 1369-1390 of the patent application WO2013/143700 or a fragment, homolog or variant thereof.

In another particularly preferred embodiment, the 3'UTR element comprises or consists of a nucleic acid sequence which is derived from a 3'UTR of an alpha- or beta-globin gene, preferably a vertebrate alpha- or beta-globin gene, more preferably a mammalian alpha- or beta-globin gene, most preferably a human alpha- or beta-globin gene.

The term 'a nucleic acid sequence which is derived from the 3'UTR of a [ . . . ] gene' preferably refers to a nucleic acid sequence which is based on the 3'UTR sequence of a [ . . . ] gene or on a part thereof, such as on the 3'UTR of an albumin gene, an alpha-globin gene, a beta-globin gene, a tyrosine hydroxylase gene, a lipoxygenase gene, or a collagen alpha gene, such as a collagen alpha 1(I) gene, preferably of an albumin gene or on a part thereof. This term includes sequences corresponding to the entire 3'UTR sequence, i.e. the full length 3'UTR sequence of a gene, and sequences corresponding to a fragment of the 3'UTR sequence of a gene, such as an albumin gene, alpha-globin gene, beta-globin gene, tyrosine hydroxylase gene, lipoxygenase gene, or collagen alpha gene, such as a collagen alpha 1(I) gene, preferably of an albumin gene.

The term 'a nucleic acid sequence which is derived from a variant of the 3'UTR of a [ . . . ] gene' preferably refers to a nucleic acid sequence, which is based on a variant of the 3'UTR sequence of a gene, such as on a variant of the 3'UTR of an albumin gene, an alpha-globin gene, a beta-globin gene, a tyrosine hydroxylase gene, a lipoxygenase gene, or a collagen alpha gene, such as a collagen alpha 1(I) gene, or on a part thereof as described above. This term includes sequences corresponding to the entire sequence of the variant of the 3'UTR of a gene, i.e. the full length variant 3'UTR sequence of a gene, and sequences corresponding to a fragment of the variant 3'UTR sequence of a gene. A fragment in this context preferably consists of a continuous stretch of nucleotides corresponding to a continuous stretch of nucleotides in the full-length variant 3'UTR, which represents at least 20%, preferably at least 30%, more preferably at least 40%, more preferably at least 50%, even more preferably at least 60%, even more preferably at least 70%, even more preferably at least 80%, and most preferably at least 90% of the full-length variant 3'UTR. Such a fragment of a variant, in the sense of the present invention, is preferably a functional fragment of a variant as described herein.

According to a preferred embodiment, the nucleic acid sequence, particularly the RNA sequence according to the invention comprises a 5'-cap structure and/or at least one 3'-untranslated region element (3'-UTR element), preferably as defined herein. More preferably, the RNA further comprises a 5'-UTR element as defined herein.

In a particularly preferred embodiment the RNA sequence comprises, preferably in 5'- to 3'-direction:

a.) a 5'-CAP structure, preferably m7GpppN;

b.) at least one coding sequence encoding at least one antigenic peptide or protein derived from a protein of interest or peptide of interest or a fragment or variant thereof, or a fragment or variant thereof, c.) a 3'-UTR element comprising or consisting of a nucleic acid sequence which is derived from an alpha globin gene, a homolog, a fragment or a variant thereof;

d.) optionally, a poly(A) sequence, preferably comprising 64 adenosines;

e.) optionally, a poly(C) sequence, preferably comprising 30 cytosines; and

In a particularly preferred embodiment, the at least one nucleic acid sequence, in particular, the RNA sequence comprises at least one 5'-untranslated region element (5'-UTR element). Preferably, the at least one 5'-UTR element comprises or consists of a nucleic acid sequence, which is derived from the 5'-UTR of a TOP gene or which is derived from a fragment, homolog or variant of the 5'-UTR of a TOP gene.

It is particularly preferred that the 5'-UTR element does not comprise a TOP-motif or a 5'-TOP, as defined above.

In some embodiments, the nucleic acid sequence of the 5'-UTR element, which is derived from a 5'-UTR of a TOP gene, terminates at its 3'-end with a nucleotide located at position 1, 2, 3, 4, 5, 6, 7, 8, 9 or 10 upstream of the start codon (e.g. A(U/T)G) of the gene or RNA it is derived from. Thus, the 5'-UTR element does not comprise any part of the protein coding sequence. Thus, preferably, the only protein coding part of the at least one nucleic acid sequence, particularly of the RNA sequence, is provided by the coding sequence.

The nucleic acid sequence derived from the 5'-UTR of a TOP gene is preferably derived from a eukaryotic TOP gene, preferably a plant or animal TOP gene, more preferably a chordate TOP gene, even more preferably a vertebrate TOP gene, most preferably a mammalian TOP gene, such as a human TOP gene.

For example, the 5'-UTR element is preferably selected from 5'-UTR elements comprising or consisting of a nucleic acid sequence, which is derived from a nucleic acid sequence selected from the group consisting of SEQ ID NOs: 1-1363, SEQ ID NO: 1395, SEQ ID NO: 1421 and SEQ ID NO: 1422 of the patent application WO2013/143700, whose disclosure is incorporated herein by reference, from the homologs of SEQ ID NOs: 1-1363, SEQ ID NO: 1395, SEQ ID NO: 1421 and SEQ ID NO: 1422 of the patent application WO2013/143700, from a variant thereof, or preferably from a corresponding RNA sequence. The term "homologs of SEQ ID NOs: 1-1363, SEQ ID NO: 1395, SEQ ID NO: 1421 and SEQ ID NO: 1422 of the patent application WO2013/143700" refers to sequences of other species than *Homo sapiens*, which are homologous to the sequences according to SEQ ID NOs: 1-1363, SEQ ID NO: 1395, SEQ ID NO. 1421 and SEQ ID NO: 1422 of the patent application WO2013/143700.

In a preferred embodiment, the 5'-UTR element of the nucleic acid sequence, particularly of the RNA sequence according to the invention comprises or consists of a nucleic acid sequence, which is derived from a nucleic acid sequence extending from nucleotide position 5 (i.e. the nucleotide that is located at position 5 in the sequence) to the nucleotide position immediately 5' to the start codon (located at the 3' end of the sequences), e.g. the nucleotide position immediately 5' to the ATG sequence, of a nucleic acid sequence selected from SEQ ID NOs: 1-1363, SEQ ID NO: 1395, SEQ ID NO: 1421 and SEQ ID NO: 1422 of the patent application WO2013/143700, from the homologs of SEQ ID NOs: 1-1363, SEQ ID NO: 1395, SEQ ID NO: 1421 and SEQ ID NO: 1422 of the patent application WO2013/143700 from a variant thereof, or a corresponding RNA sequence. It is particularly preferred that the 5' UTR element is derived from a nucleic acid sequence extending from the nucleotide position immediately 3' to the 5'-TOP to the nucleotide position immediately 5' to the start codon (located at the 3' end of the sequences), e.g. the nucleotide position immediately 5' to the ATG sequence, of a nucleic acid sequence selected from SEQ ID NOs: 1-1363, SEQ ID NO: 1395, SEQ ID NO: 1421 and SEQ ID NO: 1422 of the patent application WO2013/143700, from the homologs of SEQ ID NOs: 1-1363, SEQ ID NO: 1395, SEQ ID NO: 1421 and SEQ ID NO: 1422 of the patent application WO2013/143700, from a variant thereof, or a corresponding RNA sequence.

In a particularly preferred embodiment, the 5'-UTR element comprises or consists of a nucleic acid sequence, which is derived from a 5'-UTR of a TOP gene encoding a ribosomal protein or from a variant of a 5'-UTR of a TOP gene encoding a ribosomal protein. For example, the 5'-UTR element comprises or consists of a nucleic acid sequence, which is derived from a 5'-UTR of a nucleic acid sequence according to any of SEQ ID NOs: 67, 170, 193, 244, 259, 554, 650, 675, 700, 721, 913, 1016, 1063, 1120, 1138, and 1284-1360 of the patent application WO2013/143700, a corresponding RNA sequence, a homolog thereof, or a variant thereof as described herein, preferably lacking the 5'-TOP motif. As described above, the sequence extending from position 5 to the nucleotide immediately 5' to the ATG (which is located at the 3'end of the sequences) corresponds to the 5'-UTR of said sequences.

Preferably, the 5'-UTR element comprises or consists of a nucleic acid sequence, which is derived from a 5'-UTR of a TOP gene encoding a ribosomal Large protein (RPL) or from a homolog or variant of a 5'-UTR of a TOP gene encoding a ribosomal Large protein (RPL). For example, the 5'-UTR element comprises or consists of a nucleic acid sequence, which is derived from a 5'-UTR of a nucleic acid sequence according to any of SEQ ID NOs: 67, 259, 1284-1318, 1344, 1346, 1348-1354, 1357, 1358, 1421 and 1422 of the patent application WO2013/143700, a corresponding RNA sequence, a homolog thereof, or a variant thereof as described herein, preferably lacking the 5'-TOP motif.

In a particularly preferred embodiment, the 5'-UTR element comprises or consists of a nucleic acid sequence which is derived from the 5'-UTR of a ribosomal protein Large 32 gene, preferably from a vertebrate ribosomal protein Large 32 (L32) gene, more preferably from a mammalian ribosomal protein Large 32 (L32) gene, most preferably from a human ribosomal protein Large 32 (L32) gene, or from a variant of the 5'UTR of a ribosomal protein Large 32 gene, preferably from a vertebrate ribosomal protein Large 32 (L32) gene, more preferably from a mammalian ribosomal protein Large 32 (L32) gene, most preferably from a human ribosomal protein Large 32 (L32) gene, wherein preferably the 5'-UTR element does not comprise the 5'-TOP of said gene.

Accordingly, in a particularly preferred embodiment, the 5'-UTR element comprises or consists of a nucleic acid sequence, which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID NO: 13 (5'-UTR of human ribosomal protein Large 32 lacking the 5' terminal oligopyrimidine tract: GGCGCTGCCTACGGAGGTGGCAGC-CATCTCCTTCTCGGCATC; corresponding to SEQ ID No. 1368 of the patent application WO 2013/143700) or preferably to a corresponding RNA sequence, or wherein the at least one 5'UTR element comprises or consists of a fragment of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence of the above described sequences, wherein, preferably, the fragment is as described above, i.e. being a continuous stretch of nucleotides representing at least 20% etc. of the full-length 5'UTR. Preferably, the fragment exhibits a length of at least about 20 nucleotides or more, preferably of at least about 30 nucleotides or more, more preferably of at least about 40 nucleotides or more. Preferably, the fragment is a functional fragment as described herein.

In some embodiments, the RNA sequence according to the invention comprises a 5'-UTR element, which comprises or consists of a nucleic acid sequence, which is derived from the 5'-UTR of a vertebrate TOP gene, such as a mammalian, e.g. a human TOP gene, selected from RPSA, RPS2, RPS3, RPS3A, RPS4, RPS5, RPS6, RPS7, RPS8, RPS9, RPS10, RPS11, RPS12, RPS13, RPS14, RPS15, RPS15A, RPS16, RPS17, RPS18, RPS19, RPS20, RPS21, RPS23, RPS24, RPS25, RPS26, RPS27, RPS27A, RPS28, RPS29, RPS30, RPL3, RPL4, RPL5, RPL6, RPL7, RPL7A, RPL8, RPL9, RPL10, RPL10A, RPL11, RPL12, RPL13, RPL13A, RPL14, RPL15, RPL17, RPL18, RPL18A, RPL19, RPL21, RPL22, RPL23, RPL23A, RPL24, RPL26, RPL27, RPL27A, RPL28, RPL29, RPL30, RPL31, RPL32, RPL34, RPL35, RPL35A, RPL36, RPL36A, RPL37, RPL37A, RPL38, RPL39, RPL40, RPL41, RPLP0, RPLP1, RPLP2, RPLP3, RPLP0, RPLP1, RPLP2, EEF1A1, EEF1B2, EEF1D, EEF1G, EEF2, EIF3E, EIF3F, EIF3H, EIF2S3, EIF3C, EIF3K, EIF3EIP, EIF4A2, PABPC1, HNRNPA1, TPT1, TUBB1, UBA52, NPM1, ATP5G2, GNB2L1, NME2, UQCRB, or from a homolog or variant thereof, wherein preferably the 5'-UTR element does not comprise a TOP-motif or the 5'-TOP of said genes, and wherein optionally the 5'-UTR element starts at its 5'-end with a nucleotide located at position 1, 2, 3, 4, 5, 6, 7, 8, 9 or 10 downstream of the 5'-terminal oligopyrimidine tract (TOP) and wherein further optionally the 5'UTR element which is derived from a 5'-UTR of a TOP gene terminates at its 3'-end with a nucleotide located at position 1, 2, 3, 4, 5, 6, 7, 8, 9 or 10 upstream of the start codon (A(U/T)G) of the gene it is derived from.

In further particularly preferred embodiments, the 5'-UTR element comprises or consists of a nucleic acid sequence, which is derived from the 5'-UTR of a ribosomal protein Large 32 gene (RPL32), a ribosomal protein Large 35 gene (RPL35), a ribosomal protein Large 21 gene (RPL21), an ATP synthase, H+ transporting, mitochondrial F1 complex, alpha subunit 1, cardiac muscle (ATP5A1) gene, an hydroxysteroid (17-beta) dehydrogenase 4 gene (HSD17B4), an androgen-induced 1 gene (AIG1), cytochrome c oxidase subunit VIc gene (COX6C), or a N-acylsphingosine amidohydrolase (acid ceramidase) 1 gene (ASAH1) or from a variant thereof, preferably from a vertebrate ribosomal protein Large 32 gene (RPL32), a vertebrate ribosomal protein Large 35 gene (RPL35), a vertebrate ribosomal protein Large 21 gene (RPL21), a vertebrate ATP synthase, H+ transporting, mitochondrial F1 complex, alpha subunit 1, cardiac muscle (ATP5A1) gene, a vertebrate hydroxysteroid (17-beta) dehydrogenase 4 gene (HSD17B4), a vertebrate androgen-induced 1 gene (AIG1), a vertebrate cytochrome c oxidase subunit VIc gene (COX6C), or a vertebrate N-acylsphingosine amidohydrolase (acid ceramidase) 1 gene (ASAH1) or from a variant thereof, more preferably from a mammalian ribosomal protein Large 32 gene (RPL32), a ribosomal protein Large 35 gene (RPL35), a ribosomal protein Large 21 gene (RPL21), a mammalian ATP synthase, H+ transporting, mitochondrial F1 complex, alpha subunit 1, cardiac muscle (ATP5A1) gene, a mammalian hydroxysteroid (17-beta) dehydrogenase 4 gene (HSD17B4), a mammalian androgen-induced 1 gene (AIG1), a mammalian cyto-chrome c oxidase subunit VIc gene (COX6C), or a mammalian N-acylsphingosine ami-dohydrolase (acid ceramidase) 1 gene (ASAH1) or from a variant thereof, most preferably from a human ribosomal protein Large 32 gene (RPL32), a human ribosomal protein Large 35 gene (RPL35), a human ribosomal protein Large 21 gene (RPL21), a human ATP synthase, H+ transporting, mitochondrial F1 complex, alpha subunit 1, cardiac muscle (ATP5A1) gene, a human hydroxysteroid (17-beta) dehydrogenase 4 gene (HSD17B4), a human androgen-induced 1 gene (AIG1), a human cytochrome c oxidase subunit VIc gene (COX6C), or a human N-acylsphingosine amidohydrolase (acid ceramidase) 1 gene (ASAH1) or from a variant thereof, wherein preferably the 5'UTR element does not comprise the 5'TOP of said gene.

Accordingly, in a particularly preferred embodiment, the 5'-UTR element comprises or consists of a nucleic acid sequence, which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID NOs: 1412-1420 of the patent application WO2013/143700, or a corresponding RNA sequence or wherein the at least one 5'UTR element comprises or consists of a fragment of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according SEQ ID NOs: 1412-1420 of the patent application WO2013/143700, wherein, preferably, the fragment is as described above, i.e. being a continuous stretch of nucleotides representing at least 20% etc. of the full-length 5'UTR. Preferably, the fragment exhibits a length of at least about 20 nucleotides or more, preferably of at least about 30 nucleotides or more, more preferably of at least about 40 nucleotides or more. Preferably, the fragment is a functional fragment as described herein.

Accordingly, in a particularly preferred embodiment, the 5'-UTR element comprises or consists of a nucleic acid sequence, which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID NO: 14 (5'-UTR of ATP5A1 lacking the 5' terminal oligopyrimidine tract: GCGGCTCGGCCAT-TTTGTCCCAGTCAGTCCG-GAGGCTGCGGCTGCAGAAGTACCGCCTGCG-GAGTAACTG CAAAG; corresponding to SEQ ID NO: 1414 of the patent application WO 2013/143700) or preferably to a corresponding RNA sequence, or wherein the at least one 5'UTR element comprises or consists of a fragment of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence as described above, wherein, preferably, the fragment is as described above, i.e. being a continuous stretch of nucleotides representing at least 20% etc. of the full-length 5'UTR. Preferably, the fragment exhibits a length of at least about 20 nucleotides or more, preferably of at least about 30 nucleotides or more, more preferably of at least about 40 nucleotides or more. Preferably, the fragment is a functional fragment as described herein.

Preferably, the at least one 5'-UTR element and the at least one 3'UTR element act synergistically to increase protein production from the at least one RNA sequence as described above.

According to a particularly preferred embodiment the RNA sequence according to the invention comprises, preferably in 5'- to 3'-direction:

a.) a 5'-cap structure, preferably m7GpppN;

b.) a 5'-UTR element which comprises or consists of a nucleic acid sequence which is derived from the 5'-UTR of a TOP gene, a homolog, a fragment or a variant thereof;

c.) at least one coding sequence encoding at least one antigenic peptide or protein derived from a protein of interest or peptide of interest or a fragment or variant thereof, d.) a 3'-UTR element comprising or consisting of a nucleic acid sequence which is derived from a gene providing a stable RNA, a homolog, a fragment or a variant thereof;

e.) optionally, a poly(A) sequence preferably comprising 64 adenosines; and f.) optionally, a poly(C) sequence, preferably comprising 30 cytosines.

In a particularly preferred embodiment, the nucleic acid sequence, particularity the RNA sequence used according to the invention comprises a histone stem-loop sequence/structure. Such histone stem-loop sequences are preferably selected from histone stem-loop sequences as disclosed in WO 2012/019780, the disclosure of which is incorporated herewith by reference.

A histone stem-loop sequence, suitable to be used within the present invention, is preferably selected from at least one of the following formulae VII or VIII:

formula VII (stem-loop sequence without stem bordering elements):

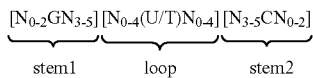

formula VIII (stem-loop sequence with stem bordering elements):

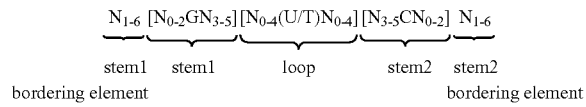

wherein:

stem1 or stem2 bordering elements $N_{1-6}$ is a consecutive sequence of 1 to 6, preferably of 2 to 6, more preferably of 2 to 5, even more preferably of 3 to 5, most preferably of 4 to 5 or 5 N, wherein each N is independently from another selected from a nucleotide selected from A, U, T, G and C, or a nucleotide analogue thereof;

stem1 $[N_{0-2} GN_{3-5}]$ is reverse complementary or partially reverse complementary with element stem2, and is a consecutive sequence between of 5 to 7 nucleotides;

wherein $N_{0-2}$ is a consecutive sequence of 0 to 2, preferably of 0 to 1, more preferably of 1 N, wherein each N is independently from another selected from a nucleotide selected from A, U, T, G and C or a nucleotide analogue thereof;

wherein $N_{3-5}$ is a consecutive sequence of 3 to 5, preferably of 4 to 5, more preferably of 4 N, wherein each N is independently from another selected from a nucleotide selected from A, U, T, G and C or a nucleotide analogue thereof, and wherein G is guanosine or an analogue thereof, and may be optionally replaced by a cytidine or an analogue thereof, provided that its complementary nucleotide cytidine in stem2 is replaced by guanosine;

loop sequence $[N_{0-4}(U/T)N_{0-4}]$ is located between elements stem1 and stem2, and is a consecutive sequence of 3 to 5 nucleotides, more preferably of 4 nucleotides;

wherein each $N_{0-4}$ is independent from another a consecutive sequence of 0 to 4, preferably of 1 to 3, more preferably of 1 to 2 N, wherein each N is independently from another selected from a nucleotide selected from A, U, T, G and C or a nucleotide analogue thereof; and wherein U/T represents uridine, or optionally thymidine;

stem2 $[N_{3-5}CN_{0-2}]$ is reverse complementary or partially reverse complementary with element stem1, and is a consecutive sequence between of 5 to 7 nucleotides;

wherein $N_{3-5}$ is a consecutive sequence of 3 to 5, preferably of 4 to 5, more preferably of 4 N, wherein each N is independently from another selected from a nucleotide selected from A, U, T, G and C or a nucleotide analogue thereof;

wherein $N_{0-2}$ is a consecutive sequence of 0 to 2, preferably of 0 to 1, more preferably of 1 N, wherein each N is independently from another selected from a nucleotide selected from A, U, T, G or C or a nucleotide analogue thereof; and wherein C is cytidine or an analogue thereof, and may be optionally replaced by a guanosine or an analogue thereof provided that its complementary nucleoside guanosine in stem1 is replaced by cytidine;

wherein stem1 and stem2 are capable of base pairing with each other forming a reverse complementary sequence, wherein base pairing may occur between stem1 and stem2, e.g. by Watson-Crick base pairing of nucleotides A and U/T or G and C or by non-Watson-Crick base pairing e.g. wobble base pairing, reverse Watson-Crick base pairing, Hoogsteen base pairing, reverse Hoogsteen base pairing or are capable of base pairing with each other forming a partially reverse complementary sequence, wherein an incomplete base pairing may occur between stem1 and stem2, on the basis that one or more bases in one stem do not have a complementary base in the reverse complementary sequence of the other stem.

According to a further preferred embodiment, the nucleic acid sequence, particularly the RNA sequence may comprise at least one histone stem-loop sequence according to at least one of the following specific formulae VIIa or VIIIa:

formula VIIa (stem-loop sequence without stem bordering elements):

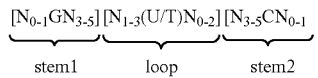

formula VIIIa (stem-loop sequence with stem bordering elements):

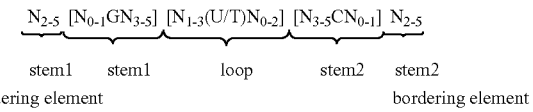

wherein N, C, G, T and U are as defined above.

According to a further more particularly preferred embodiment, the at least one nucleic acid, preferably the at least one RNA may comprise at least one histone stem-loop sequence according to at least one of the following specific formulae VIIb or VIIIb:

formula VIIb (stem-loop sequence without stem bordering elements):

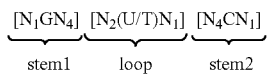

formula VIIIb (stem-loop sequence with stem bordering elements):

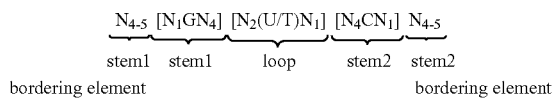

wherein N, C, G, T and U are as defined above.

A particularly preferred histone stem-loop sequence is the sequence CAAAGGCTCTTTTCAGAGCCACCA (according to SEQ ID NO: 15) or more preferably the corresponding RNA sequence CAAAGGCUCUUUUCAGAGCCACCA (according to SEQ ID NO: 16).

Any of the above modifications may be applied to the nucleic acid sequence, in particular, to the DNA and/or RNA sequence of the present invention, and further to any DNA or RNA as used in the context of the present invention and may be, if suitable or necessary, be combined with each other in any combination, provided, these combinations of modifications do not interfere with each other in the respective nucleic acid sequence. A person skilled in the art will be able to take his choice accordingly.

The nucleic acid sequence according to the invention, particularly the RNA sequence according to the present invention which comprises at least one coding sequence as defined herein, may preferably comprise a 5' UTR and/or a 3' UTR preferably containing at least one histone stem-loop. The 3' UTR of the RNA sequence according to the invention preferably comprises also a poly(A) and/or a poly(C) sequence as defined herein. The single elements of the 3' UTR may occur therein in any order from 5' to 3' along the sequence of the RNA sequence of the present invention. In addition, further elements as described herein, may also be contained, such as a stabilizing sequence as defined herein (e.g. derived from the UTR of a globin gene), IRES sequences, etc. Each of the elements may also be repeated in the RNA sequence according to the invention at least once (particularly in di- or multicistronic constructs), preferably twice or more. As an example, the single elements may be present in the nucleic acid sequence, particularly in the RNA sequence according to the invention in the following order:

5'-coding sequence-histone stem-loop-poly(A)/(C) sequence-3'; or

5'-coding sequence-poly(A)/(C) sequence-histone stem-loop-3'; or

5'-coding sequence-histone stem-loop-polyadenylation signal-3'; or

5'-coding sequence-polyadenylation signal-histone stem-loop-3'; or

5'-coding sequence-histone stem-loop-histone stem-loop-poly(A)/(C) sequence-3'; or 5'-coding sequence-histone stem-loop-histone stem-loop-polyadenylation signal-3'; or 5'-coding sequence-stabilizing sequence-poly(A)/(C) sequence-histone stem-loop-3'; or 5'-coding sequence-stabilizing sequence-poly(A)/(C) sequence-poly(A)/(C) sequence-histone stem-loop-3'; etc.

According to a further embodiment, the nucleic acid sequence used in the present invention, particularly the RNA sequence, preferably comprises at least one of the following structural elements: a 5'- and/or 3'-untranslated region element (UTR element), particularly a 5'-UTR element, which preferably comprises or consists of a nucleic acid sequence which is derived from the 5'-UTR of a TOP gene or from a fragment, homolog or a variant thereof, or a 5'- and/or 3'-UTR element which may preferably be derivable from a gene that provides a stable RNA or from a homolog, fragment or variant thereof; a histone-stem-loop structure, preferably a histone-stem-loop in its 3' untranslated region; a 5'-cap structure; a poly-A tail; or a poly(C) sequence.

In a particularly preferred embodiment the nucleic acid sequence, in particular, the RNA sequence comprises, preferably in 5'- to 3'-direction:

a.) a 5'-CAP structure, preferably m7GpppN;

b.) at least one coding sequence encoding at least one antigenic peptide of interest or protein of interest or a fragment or variant thereof;

c.) a 3'-UTR element comprising or consisting of a nucleic acid sequence which is derived from an alpha globin gene, a homolog, a fragment or a variant thereof;

d.) optionally, a poly(A) sequence, preferably comprising 64 adenosines;

e.) optionally, a poly(C) sequence, preferably comprising 30 cytosines; and f.) optionally, a histone stem-loop, preferably comprising the RNA sequence according to SEQ ID NO: 16.

According to another particularly preferred embodiment the nucleic acid sequence, in particular, the RNA sequence used according to the invention comprises, preferably in 5'- to 3'-direction:

a.) a 5'-CAP structure, preferably m7GpppN;

b.) a 5'-UTR element which comprises or consists of a nucleic acid sequence which is derived from the 5'-UTR of a TOP gene, a homolog, a fragment or a variant thereof;

c.) at least one coding sequence encoding at least one antigenic peptide of interest or protein of interest or a fragment or variant thereof, d.) a 3'-UTR element comprising or consisting of a nucleic acid sequence which is derived from a gene providing a stable RNA;

e.) optionally, a poly(A) sequence preferably comprising 64 adenosines;

f.) optionally, a poly(C) sequence, preferably comprising 30 cytosines; and optionally, a histone stem-loop, preferably comprising the RNA sequence according to SEQ ID NO: 16.

Nucleic acids used according to the present invention may be prepared by any method known in the art, including synthetic methods such as e.g. solid phase synthesis, as well as in vitro methods, such as in vitro transcription reactions or in vivo reactions, such as in vivo propagation of DNA plasmids in bacteria.

According to another preferred embodiment, the nucleic acid is in the form of a coding nucleic acid, preferably an mRNA, which additionally or alternatively encodes a secretory signal peptide. Such signal peptides typically exhibit a length of about 15 to 30 amino acids and are preferably located at the N-terminus of the encoded peptide, without being limited thereto. Signal peptides, as defined herein, preferably allow the transport of the encoded protein or peptide to a specific cell region or into a specific cellular compartment, such as to the cell surface, the endoplasmic reticulum (ER) or the endosomal-lysosomal compartment.

Proteins or peptides encoded by the nucleic acid may represent fragments or variants of naturally occurring proteins. Such fragments or variants may typically comprise a sequence having a sequence identity with one of the above mentioned proteins or peptides or sequences of their encoding nucleic acid sequences of at least 5%, 10%, 20%, 30%, 40%, 50%, 60%, preferably at least 70%, more preferably at least 80%, equally more preferably at least 85%, even more preferably at least 90% and most preferably at least 95% or even 97%, to the entire wild-type sequence, either on nucleic acid level or on amino acid level.

"Fragments" of proteins or peptides in the context of the present invention may comprise a sequence of an protein or peptide as defined herein, which is, with regard to its amino acid sequence or its encoded nucleic acid sequence, N-terminally, C-terminally and/or intrasequentially truncated compared to the amino acid sequence of the native protein or its encoded nucleic acid sequence. Such truncation may occur either on the amino acid level or on the nucleic acid level. A sequence identity with respect to such a fragment may therefore refer to the entire protein or peptide or to the entire coding nucleic acid sequence. The same applies accordingly to nucleic acids.

Such fragments of proteins or peptides may comprise a sequence of about 6 to about 20 or more amino acids, which includes fragments as processed and presented by MHC class I molecules, preferably having a length of about 8 to about 10 amino acids, e.g. 8, 9, or 10, (or even 6, 7, 11, or 12 amino acids), as well as fragments as processed and presented by MHC class II molecules, preferably having a length of about 13 or more amino acids, e.g. 13, 14, 15, 16, 17, 18, 19, 20 or even more amino acids, wherein these fragments may be selected from any part of the amino acid sequence. These fragments are typically recognized by T-cells in form of a complex consisting of the peptide fragment and an MHC molecule, i.e. the fragments are typically not recognised in their native form.

The fragments of proteins or peptides may also comprise epitopes of those proteins or peptides. Epitopes (also called "antigen determinants"), in the context of the present invention, are typically fragments located on the outer surface of native proteins or peptides, preferably having 5 to 15 amino acids, more preferably having 5 to 12 amino acids, 6 to 9 amino acids, which may be recognised by antibodies or B-cell receptors in their native form. Such epitopes may furthermore be selected from any of the herein mentioned variants of such proteins or peptides. In this context, antigenic determinants can be conformational or discontinuous epitopes which are composed of segments of the proteins or peptides that are discontinuous in the amino acid sequence of the proteins or peptides, but are brought together in the three-dimensional structure or continuous or linear epitopes which are composed of a single polypeptide chain.

"Variants" of proteins or peptides as defined herein may be encoded by the nucleic acid, wherein nucleotides encoding the protein or peptide are replaced such that the encoded amino acid sequence is changed. Thereby a protein or peptide with one or more mutations is generated, such as with one or more substituted, inserted and/or deleted amino acids. Preferably, these fragments and/or variants have the same biological function or specific activity compared to the full-length native protein, e.g. its specific antigenic property.

In one embodiment, the weight ratio of the cationic peptide or polymer to the nucleic acid compound is at least about 1. For example, it may be in the range from about 1 to about 20, or from about 1 to about 15, such as about 2±1, 3±1, 4±1, 5±1, 6±1, 7±1, 8±1, 9±1, 10±1, 11±1, 12±1, 13±1, 14±1.

Expressed in terms of nmol of cationic lipidoid per µg nucleic acid compound, this amount is preferably not higher than about 40 nmol/µg. In another embodiment, this ratio is not more than about 15 nmol/µg, and in particular not more than 10 nmol/µg. In some specific embodiments, the amount is even much lower, such as about 2 nmol/µg or less, or about 1.5 nmol/µg or less, or even about 1 nmol/µg or less, such as in the range from about 0.05 to about 2 nmol/µg, or from about 0.1 to about 1.5 nmol/µg, or from about 0.25 to about 1.0 nmol/µg, or from about 0.3 to about 0.8 nmol/µg, such as about 0.4 nmol/µg, respectively.

In one embodiment, the weight ratio of the cationic peptide or polymer to the nucleic acid compound is at least about 1, and/or the ratio of the lipidoid to the nucleic acid compound is not higher than about 15 nmol/µg Not only is the amount of lipidoid relatively low in relation to the nucleic acid cargo, but also relative to the cationic peptide or polymer. It is generally preferred that the weight ratio of the lipidoid to the cationic peptide or polymer is not higher than about 1:10, or not more than about 1:20, or 1:30, or 1:40, respectively. In another preferred embodiment, the respective ratio is not higher than about 1:50, and/or the ratio of the lipidoid to the nucleic acid is not higher than about 2 nmol/µg.

The composition may also be characterised by the N/P ratio, which is according to the invention defined as the mole ratio of the nitrogen atoms ("N") of the basic groups of the cationic peptide or polymer to the phosphate groups ("P") of the nucleic acid compound which is used as cargo; unless it is clear from the context that a different N/P ratio is meant. In one embodiment, the N/P ratio from about 0.1 to about 20, or from about 0.2 to about 15, or from about 2 to about 15, or from about 2 to about 12.

The N/P ratio may be calculated on the basis that, for example, 1 µg RNA typically contains about 3 nmol phosphate residues, provided that the RNA exhibits a statistical distribution of bases. The "N"-value of the peptide or polymer may be calculated on the basis of its molecular weight, or its average molecular weight in case the peptide or polymer has a molecular weight distribution, and the relative content of cationic or cationisable groups. In a further preferred embodiment, the N/P ratio is in the range from about 0.2 to about 15, or in the range from about 0.2 to about 13, or from about 0.3 to about 12, or from about 0.5 to about 10, or from about 0.6 to about 8, respectively.

In one embodiment, the N/P ratio is selected in the range from about 2 to about 15, or from about 2 to about 12. A composition according to the invention which exhibits such N/P ratio is particularly suitable for a use comprising the intravenous administration of the composition.

As mentioned above, the amount of lipidoid in the composition of the invention as well as in the nanoparticle(s) is typically much lower than in conventional lipid-based carriers for nucleic acids as cargo.

In theory, the amount of lipidoid may also be expressed in terms of an N/P-ratio. In this case, the "N" represents the moles of the basic groups of the lipidoid, whereas the "P" refers the phosphate groups of the nucleic acid which is used as cargo. In the compositions of the invention, and accordingly also in the nanoparticles of the invention, this lipidoid-related N/P-ratio is preferably not higher than about 3, in particular not higher than about 2. Also preferred are lipidoid-related N/P-ratios in the range of 1 or less, such as from about 0.01 to about 1, or from about 0.02 to about 0.8, or from about 0.05 to about 0.6, or from about 0.1 to about 0.5, respectively.

The composition of the invention may comprise further constituents, such as one or more inactive ingredients, auxiliary agents or excipients. In one embodiment, the composition comprises one or more compounds independently selected from targeting agents, cell penetrating agents, and stealth agents.

As used herein, a targeting agent is a compound that has affinity to a target, such as a target located on or at the surface of a target cell, or an intracellular target. For example, the targeting agent may represent an antibody, an antibody fragment, or a small molecular agent having affinity to a target of interest. Optionally, such agent may be incorporated within the cationic peptide or polymer. In other cases, such agent may be incorporated in the composition as an additional constituent without covalent attachment to any of the carrier compounds.

The same applies to the optional cell penetrating agent and/or stealth agent. As used herein, cell penetrating agents include cell-penetrating peptides (CPPs), as well as any other compounds with a similar biological or biomimetic function, i.e. to facilitate the uptake of cargo into cells. A stealth agent, in the context of the invention, means a compound or material which, when attached to a cargo molecule or particle, leads to a longer circulation time in the bloodstream of a subject to which it is injected, e.g. by intravenous injection or infusion. An example for a stealth agent is a pegylated lipid whose lipid domain is capable of functioning as an anchor to the nanoparticle by e.g. interacting with a hydrophobic group of the lipidoid, whereas its polyethyleneglycol (PEG) domain may impart "stealth" properties, which means that the cargo material shows decreased interaction with a subject's immune system while circulating in the bloodstream, which is typically associated with a prolonged elimination half life from the blood, as well as reduced immunogenicity and antigenicity.

Examples of useful pegylated lipids include 1-(monomethoxy-polyethyleneglycol)-2,3-dimyristoylglycerol (PEG-DMG), N-[(methoxy poly(ethylene glycol)$_{2000}$) carbamoyl]-1,2-dimyristyloxypropyl-3-amine (PEG-C-DMA), or 1,2-diacyal-sn-glycero-3-phosphoethanolamine-N-[methoxy(polyethylene glycol)]; in case of the latter, acyl may mean e.g. myristoyl, palmitoyl, stearoyl, or oleoyl, and the polyethylene glycol is typically polyethylene glycol-350 to polyethylene glycol-5000, in particular polyethylene glycol-750, polyethylene glycol-1000, polyethylene glycol-2000, and polyethylene glycol-3000.

In the composition of the invention, the constituents, i.e. the cationic peptide or polymer, the lipidoid, and the nucleic acid compound may be incorporated in one or more nanoparticles. In other words, the composition may comprise one or more nanoparticles comprising the cationic peptide or polymer, the lipidoid, and the nucleic acid compound. Alternatively, the composition may comprise one or more nanoparticles comprising at least the cationic peptide or polymer and the nucleic acid compound. In these embodiments, each of the constituents may be selected as described above, including all options and preferences with respect to these features.

Typically, such nanoparticles are formed when the cationic peptide or polymer and optionally also the lipidoid are combined with a nucleic acid compound, which may together form a carrier-cargo complex as described in further detail below. However, it is also possible that two components, i.e. the polymer or peptide and the nucleic acid compound, interact such as to form colloidal structures which resemble nanoparticles, whereas the lipidoid is not or not fully incorporated within such complex or nanoparticle.

A "nanoparticle", as used herein, is a submicron particle having any structure or morphology. Submicron particles may also be referred to as colloids, or colloidal. With respect to the material on which the nanoparticle is based, and to the structure or morphology, a nanoparticle may be classified, for example, as a nanocapsule, a vesicle, a liposome, a lipid nanoparticle, a micelle, a crosslinked micelle, a lipoplex, a polyplex, a mixed or hybrid complex, to mention only a few of the possible designations of specific types of nanoparticles.

According to this aspect, the invention is also directed to the above-defined nanoparticle as such, as well as to a plurality of such nanoparticles, in particular to a plurality of the preferred nanoparticles as described in more detail below.

In one of the preferred embodiments, the nanoparticle comprises a complex formed by the nucleic acid compound and the cationic peptide or polymer and/or the lipidoid. In a further specific embodiment, the nanoparticle essentially consists of these constituents (a), (b) and (c). In yet another specific embodiment, the nanoparticle essentially consists of (a) one or more cationic peptides and/or polymers; (b) one or more lipidoids; (c) one or more nucleic acid compounds; and optionally (d) one or more compounds independently selected from targeting agents, cell penetrating agents, and stealth agents. Again, also for these embodiments, the options and preferences that have been described above with respect to the individual constituent are fully applicable.

In one of the preferred embodiments, the nanoparticle(s) of the invention comprise a complex of the cationic peptide or polymer and the cationic lipidoid; or a complex of the cationic peptide or polymer and/or the cationic lipidoid with the nucleic acid compound. In other words, the nanoparticles may comprise a complex, or even substantially represent a complex, which complex may be composed of any two members, or all three members, of (a) the cationic peptide or polymer;
(b) the cationic lipidoid; and/or
(c) the nucleic acid compound.

A "complex", as used herein, is an association of molecules into larger units held together by forces that are weaker than covalent chemical bonds. Such complex may also be referred to as an association complex. The forces by which a complex is held together are often hydrogen bonds, also known as hydrogen bridges, London forces, and/or dipolar attraction. A complex involving a lipid or lipidoid and a nucleic acid is often referred to as a lipoplex, and a complex between a polymer and a nucleic acid is known as a polyplex.

In the presence of both a cationic peptide or polymer and a lipidoid as provided according to the invention, the nucleic acid may form a hybrid complex having characteristics of a lipoplex and of a polyplex at the same time. Without wishing to be bound by theory, the inventors assume that such hybrid complexes, if formed in the composition or nanoparticle of the invention, could be particularly stable in that they combine various types of interaction between the cargo and the different types of carriers, involving different domains or regions of the cargo molecules. On the other hand, it is also considered possible that the complexation of the nucleic acid compound, when carrying out the invention, is primarily achieved by the cationic peptide or protein, in particular if only relatively small amounts of the lipidoid are used, and that the presence of the lipidoid predominantly effect the fate of the complex once it has been taken up by a living cell. In any case, the invention is not limited by any theory, and any complex formed from two or more constituents as defined herein should be understood as a complex according to the present invention.

In one of the preferred embodiments, the nanoparticle of the invention substantially consists of a cargo-carrier complex as defined above. In this specific context, the expression "substantially consists of" should not be understood such as to exclude the presence of minor amounts of auxiliary materials in the nanoparticles such as solvents, cosolvents, surfactants, isotonising agents and the like.

Alternatively, at least about 50 wt.-% of the nanoparticles in the composition of the invention consist of the cationic peptide or polymer, the lipidoid, and the biologically active cargo material, or at least 60 wt.-% thereof, at least 70 wt.-% thereof, at least 80 wt.-% thereof, at least 85 wt.-% thereof, at least 90 wt.-% thereof, or at least 95 wt.-% thereof, respectively.

In the context of the invention, a "biologically active cargo material" generically refers to a compound, or mixture or combination of compounds, which is intended to be delivered to a subject, or to an organ, tissue, or cell of a subject, by means of a formulation, carrier, vector or vehicle, in order to achieve a desired biologic effect, such as a pharmacological effect, including any type of prophylactic, therapeutic, diagnostic, or ameliorating effect. The delivery of biologically active cargo material is the purpose of administering a product comprising such material, whereas the formulation, or carrier, vector or vehicle, which may in some cases also be considered as biologically active, are primarily the means for delivering the cargo material. Unless different meanings are evident from the context, the expressions "biologically active cargo material", "biologically active compound", "cargo material", "cargo" and the like are used synonymously. The composition of the invention, as well as the nanoparticles of the invention, comprises as a biologically active cargo material at least one nucleic acid compound, or a nucleic acid-based material. Optionally, one or more other active ingredients which may or may not represent a nucleic acid compound may be present and also form part of the cargo.

A "carrier", or "vehicle", as used herein, may generically mean any compound, construct or material being part of a formulation which aids, enables, or improves the delivery of the biologically active compound or material. It may be biologically substantially inert, or it may be biologically active in that it interacts substantially with tissues, cells or subcellular components of the subject and, for example, enhance the uptake of the biologically active cargo material. In the context of the invention, the terms may also be applied to the lipidoid, to the cationic peptide or polymer, or to the combination or mixture of both.

A "formulation", with respect to a biologically active compound that is incorporated in it and administered by means of the formulation, is any product which is pharmaceutically acceptable in terms of its composition and manufacturing method which comprises at least one biologically active compound and one excipient, carrier, vehicle or other auxiliary material.

As mentioned, the composition of the invention may comprise further constituents, such as one or more compounds independently selected from targeting agents, cell penetrating agents, and stealth agents, as described above. Any of these additional constituents may optionally be incorporated in the nanoparticle(s).

As used herein, a targeting agent is a compound that has affinity to a target, such as a target located on or at the surface of a target cell, or an intracellular target. For example, the targeting agent may represent an antibody, an antibody fragment, or a small molecular agent having affinity to a target of interest. As discussed in the context of the compound with moiety P or disulfide-linked multimer thereof, such agent may optionally be incorporated within such compound. In other cases, such agent may be incorporated in the nanoparticle as an additional constituent without covalent attachment to any of the carrier compounds.

The same applies to the optional cell penetrating agent and/or stealth agent. As used herein, cell penetrating agents include cell-penetrating peptides (CPPs) as defined above, as well as any other compounds with a similar biological or biomimetic function, i.e. to facilitate the uptake of cargo into cells. A stealth agent, in the context of the invention, means a compound or material which, when incorporated in the nanoparticle comprising the cationic lipidoid, the compound comprising moiety P or disulfide-linked multimer thereof, and the nucleic acid cargo, leads to a longer circulation time of the nanoparticle in the bloodstream of a subject to which the nanoparticle is injected, e.g. by intravenous injection or infusion. An example for a stealth agent is a pegylated lipid whose lipid domain is capable of functioning as an anchor to the nanoparticle by e.g. interacting with a hydrophobic group of the lipidoid, whereas its polyethyleneglycol (PEG) domain may impart "stealth" properties to the nanoparticle, which means that the nanoparticle shows decreased interaction with a subject's immune system while circulating in the bloodstream, which is typically associated with a prolonged elimination half life of the nanoparticle from the blood, as well as reduced immunogenicity and antigenicity.

Examples of useful pegylated lipids include 1-(monomethoxy-polyethyleneglycol)-2,3-dimyristoylglycerol (PEG-DMG), N-[(methoxy poly(ethylene glycol)$_{2000}$) carbamoyl]-1,2-dimyristyloxypropyl-3-amine (PEG-C-DMA), or 1,2-diacyal-sn-glycero-3-phosphoethanolamine-N-[methoxy(polyethylene glycol)]; in case of the latter, acyl may mean e.g. myristoyl, palmitoyl, stearoyl, or oleoyl, and the polyethylene glycol is typically polyethylene glycol-350 to polyethylene glycol-5000, in particular polyethylene glycol-750, polyethylene glycol-1000, polyethylene glycol-2000, and polyethylene glycol-3000.

Other neutral lipids do not normally have to be incorporated in the composition, or in the nanoparticle(s), of the invention. This is a further advantage of the present invention, and in contrast to most known lipid carrier systems suitable for the complexation and delivery of nucleic acid cargo which do require the incorporation of—typically even substantial amounts of—a so-called helper lipid. As used herein, helper lipids are non-cationic or cationisable (unless zwitterionic) phospholipids or steroids that may contribute to the stability of lipid nanoparticles in combination with nucleic acids. Accordingly, it is one of the preferred embodiments of the invention that the nanoparticle, as well as the composition of the invention, is free of such helper lipids.

The nanoparticles have a hydrodynamic diameter as determined by dynamic laser scattering of not more than about 1,000 nm. More preferably, their hydrodynamic diameter is not higher than about 800 nm, such as in the range from about 30 nm to about 800 nm. In other preferred embodiments, the hydrodynamic diameter is in the range from about 50 nm to about 300 nm, or from about 60 nm to about 250 nm, from about 60 nm to about 150 nm, or from about 60 nm to about 120 nm, respectively. While these are preferred diameters of individual nanoparticles, this does not exclude the presence of nanoparticles of other diameters in the composition of the invention. However, the invention is preferably practised with compositions in which many—or even most—of the nanoparticles exhibit such diameters.

Moreover, the composition according to the invention which comprises a plurality of such nanoparticles may also be characterised by the mean hydrodynamic diameter as determined by dynamic laser scattering, which is also preferably not higher than 800 nm, such as in the range from about 30 nm to about 800 nm. In the context of the hydrodynamic diameter, the "mean" should be understood as the Z-average, also known as the cumulants mean. Obviously, the measurement by dynamic laser scattering must also be conducted with an appropriate dispersant and at an appropriate dilution, following the recommendations of the manufacturer of the analytic equipment that is used. Particularly preferred is a mean hydrodynamic diameter in the range from about 50 nm to about 300 nm, or from about 60 nm to about 250 nm, from about 60 nm to about 150 nm, or from about 60 nm to about 120 nm, respectively.

The nanoparticles may further be characterised by their electrokinetic potential, which may be expressed by means of the zeta potential. In preferred embodiments, the zeta potential is in the range from about 0 mV to about 50 mV, or from about 0 mV to about 10 mV, respectively. In other preferred embodiments, the zeta potential is positive, i.e. higher than 0 mV, but not higher than 50 mV, or 40 mV, or 30 mV, or 20 mV, or 10 mV, respectively.

In further embodiments, the zeta potential is in the range from about 0 mV to about
−50 mV, or from about 0 mV to about −10 mV, respectively. In another embodiment, the zeta potential is negative, i.e. lower than 0 mV, but not lower than −50 mV, or −40 mV, or −30 mV, or −20 mV, or −10 mV, respectively.

In another embodiment, the zeta potential is in the range of 0 mV to −50 mV for particles having an N/P ratio of under 1 (particularly suitable for local administration). In a further embodiment, the zeta potential is in the range of 0 mV to +50 mV for particles having an N/P ratio of over 1 (particularly suitable for intravenous or other intravascular applications).

The amount of the cationic compound comprising the cationic moiety P, or of the disulfide-linked multimer thereof, should be selected taking the amount of the nucleic acid cargo into account. In one of the preferred embodiments, these amounts are selected such as to result in an N/P ratio in the range from about 0.1 to about 20. In this context, the N/P ratio is defined as the mole ratio of the nitrogen atoms ("N") of the basic nitrogen-containing groups of the compound comprising moiety P or the disulfide-linked multimer thereof to the phosphate groups ("P") of the nucleic acid which is used as cargo. The N/P ratio may be calculated on the basis that, for example, 1 µg RNA typically contains about 3 nmol phosphate residues, provided that the RNA exhibits a statistical distribution of bases. The "N"-value of the peptide or polymer may be calculated on the basis of its molecular weight, or its average molecular weight in case the peptide or polymer has a molecular weight distribution, and the relative content of cationic or cationisable groups. In a further preferred embodiment, the N/P ratio is in the range from about 0.2 to about 15, or in the range from about 0.2 to about 13, or from about 0.3 to about 12, or from about 0.5 to about 10, or from about 0.6 to about 8, respectively.

In one embodiment, the N/P ratio is selected in the range from about 2 to about 15, or from about 2 to about 12. A composition according to the invention which exhibits such N/P ratio is particularly suitable for a use comprising the intravenous administration of the composition.

As mentioned above, the amount of cationic lipidoid in the composition of the invention as well as in the nanoparticle(s) is typically much lower than in conventional lipidoid-based carriers for nucleic acids as cargo. The present invention may be practised with as little as about 0.1 to about 10% of the typical amount of lipidoids used in lipoplexes or lipidoid nanoparticles that have been proposed for the delivery of e.g. RNA and the transfection of cells. Without wishing to be bound by theory, the inventors assume that such low amount of lipidoid has been pivotal in achieving the high tolerability of the composition of the invention.

The amount of lipidoid may also be expressed in terms of an N/P-ratio. In this case, the "N" represents the moles of the basic groups of the cationic lipidoid, whereas the "P" refers the phosphate groups of the nucleic acid which is used as cargo. In the compositions of the invention, and accordingly also in the nanoparticles of the invention, this lipidoid-related N/P-ratio is preferably not higher than about 3, in particular not higher than about 2. Also preferred are lipidoid-related N/P-ratios in the range from about 0.016 to about 0.650, or from about 0.032 to about 0.484, or from about 0.080 to about 0.323, or from about 0.968 to about 0.258, such as about 0.129, respectively.

Not only is the amount of cationic lipidoid relatively low in relation to the cargo, but also relative to the peptide or polymer carrier, i.e. to the amount of the compound comprising moiety P or the multimer thereof. It is generally preferred that the weight ratio of the cationic lipidoid to the compound comprising moiety P or disulfide-linked multimer thereof is not higher than about 1:10, or not more than about 1:20, or 1:30, or 1:40, respectively. In another preferred embodiment, the respective ratio is not higher than about 1:50.

The nanoparticles may be prepared by a method comprising the step of combining (i) one or more cationic peptides and/or polymers; (ii) one or more lipidoids as defined above, optionally dissolved in an appropriate solvent (e.g. ethanol, DMSO); and (iii) one or more nucleic acid compounds, the combining being conducted in the presence of an aqueous liquid such as to allow the formation of a nanoparticle or a plurality of nanoparticles. In order to enable good mixing of the different agents, the lipidoid may be mixed with the cationic complexation partner prior to mixing with the nucleic acid. The mixing can be conducted by an suitable mixing device (e.g. laminar flow combination utilizing a T or Y valve; microfluidic devices or simple addition to a stirred solution).

The composition, the nanoparticles or the composition comprising the nanoparticles of the invention which comprises the cationic peptide or polymer, the lipidoid, the nucleic acid compound as cargo and/or one or more inactive ingredients, and in particular the composition which comprises the nanoparticles as describe above, is preferably formulated and processed such as to be suitable for administration to a subject, in particular to an animal or to a human subject. Preferably, the composition is sterile.

In this respect, the composition may also be referred to as a pharmaceutical composition. This is a general preference which may be applied to any of the options and preferences described herein with respect to the constituents and other features of the composition or the nanoparticles. In other words, the invention is also directed e.g. to a pharmaceutical composition as defined herein where the nucleic acid compound is a coding nucleic acid which encodes at least one peptide or protein. For example, the coding nucleic acid may encode a therapeutically active protein or an antigen. The invention is further directed to a vaccine comprising such pharmaceutical composition wherein the coding nucleic acid encodes at least one antigen. In this context, the vaccine may consist of the pharmaceutical composition, or it may comprise it along with other constituents.

The inventive pharmaceutical composition, the nanoparticles or the composition comprising the nanoparticles may be administered orally, parenterally, by inhalation spray, topically, rectally, nasally, buccally, vaginally or via an implanted reservoir. The term parenteral, as used herein, includes subcutaneous, intravenous, intramuscular, intra-articular, intra-synovial, intrasternal, intrathecal, intrahepatic, intralesional, intracranial, transdermal, intradermal, intrapulmonal, intraperitoneal, intracardial, intraarterial, and sublingual injection or infusion techniques. In some embodiments, the inventive pharmaceutical composition, the nanoparticles or the composition comprising the nanoparticles may be administered by ocular delivery. In a specific embodiment, the inventive pharmaceutical composition, the nanoparticles or the composition comprising the nanoparticles is administered by subretinal or intravitreal injection. In a preferred embodiment, the inventive pharmaceutical composition, the nanoparticles or the composition comprising the nanoparticles is administered by intravitreal injection. In another preferred embodiment, the inventive pharmaceutical composition the nanoparticles or the composition comprising the nanoparticles is administered by subretinal injection.

The present invention may also be used to treat a subject who is suffering from or susceptible to an ocular disease, disorder or condition. As used herein, an "ocular disease, disorder or condition" refers to a disease, disorder or condition affecting the eye and/or vision. In some embodiments, an ocular disease, disorder or condition may be caused by a protein deficiency or dysfunctions in the eye or parts of the anatomy associated with vision. Exemplary ocular diseases, disorders or conditions include, but are not limited to, age-related macular degeneration (AMD), pigmentary uveitis (PU), branch retinal vein occlusion (BRVO), central retinal vein occlusion (CRVO), diabetic macular edema (DME), cystoid macular edema (CME), uveitic macular edema (UME), cytomegalovirus (CMV) retinitis, endophthalmitis, inflammation, glaucoma, macular degeneration, scleritis, choriotetinitis, and uveitis.

In various embodiments, the present invention may be used to deliver an mRNA encoding a protein that is deficient in any of the ocular diseases, disorders or conditions described herein.

Preferably, the inventive pharmaceutical composition, the nanoparticles or the composition comprising the nanoparticles may be administered by parenteral injection, more preferably by subcutaneous, intravenous, intramuscular, intra-articular, intra-synovial, intrasternal, intrathecal, intrahepatic, intralesional, intracranial, transdermal, intradermal, intrapulmonal, intraperitoneal, intracardial, intraarterial, intravitreal, subretinal, intracameral, subconjunctival, sub-tenon, retrobulbar, topical, and/or posterior juxtascleral administration, administration into the ciliary muscle and sublingual injection or via infusion techniques. Particularly preferred is intradermal and intramuscular injection. Sterile injectable forms of the inventive pharmaceutical compositions may be aqueous or oleaginous suspension. These suspensions may be formulated according to techniques known in the art using suitable dispersing or wetting agents and suspending agents.

The inventive pharmaceutical composition, the nanoparticles or the composition comprising the nanoparticles as defined herein may also be administered orally in any orally acceptable dosage form including, but not limited to, capsules, tablets, aqueous suspensions or solutions.

The inventive pharmaceutical composition, the nanoparticles or the composition comprising the nanoparticles may also be administered topically, especially when the target of treatment includes areas or organs readily accessible by topical application, e.g. including diseases of the skin or of any other accessible epithelial tissue. Suitable topical formulations are readily prepared for each of these areas or organs. For topical applications, the inventive pharmaceutical composition may be formulated in a suitable ointment, containing the nucleic acid as defined herein suspended or dissolved in one or more carriers.

The inventive pharmaceutical composition, the nanoparticles or the composition comprising the nanoparticles typically comprises a "safe and effective amount" of the components of the inventive pharmaceutical composition, particularly of the nucleic acid sequence(s) as defined herein. As used herein, a "safe and effective amount" means an amount of the nucleic acid sequence(s) as defined herein as such that is sufficient to significantly induce a positive modification of a disease or disorder as defined herein. At the same time, however, a "safe and effective amount" is small enough to avoid serious side-effects and to permit a sensible relationship between advantage and risk. The determination of these limits typically lies within the scope of sensible medical judgment.

Accordingly, the vaccine according to the invention is based on the same components as the (pharmaceutical) composition described herein. Insofar, it may be referred to the description of the (pharmaceutical) composition as provided herein. Preferably, the vaccine according to the invention comprises at least one nucleic acid comprising at least one nucleic acid sequence as defined herein and a pharmaceutically acceptable carrier. In embodiments, where the vaccine comprises more than one nucleic acid, particularly more than one mRNA sequence (such as a plurality of RNA sequences according to the invention, wherein each preferably encodes a distinct antigenic peptide or protein), the vaccine may be provided in physically separate form and may be administered by separate administration steps. The vaccine according to the invention may correspond to the (pharmaceutical) composition as described herein, especially where the mRNA sequences are provided by one single composition. However, the inventive vaccine may also be provided physically separated. For instance, in embodiments, wherein the vaccine comprises more than one mRNA sequences/species, these RNA species may be provided such that, for example, two, three, four, five or six separate compositions, which may contain at least one mRNA species/sequence each (e.g. three distinct mRNA species/sequences), each encoding distinct antigenic peptides or proteins, are provided, which may or may not be combined. Also, the inventive vaccine may be a combination of at least two distinct compositions, each composition comprising at least one mRNA encoding at least one of the antigenic peptides or proteins defined herein. Alternatively, the vaccine may be provided as a combination of at least one mRNA, preferably at least two, three, four, five, six or more mRNAs, each encoding one of the antigenic peptides or proteins defined herein. The vaccine may be combined to provide one single composition prior to its use or it may be used such that more than one administration is required to administer the distinct mRNA sequences/species encoding any of the antigenic peptides or proteins as defined herein. If the vaccine contains at least one mRNA sequence, typically at least two mRNA sequences, encoding the antigen combinations defined herein, it may e.g. be administered by one single administration (combining all mRNA species/sequences), by at least two separate administrations. Accordingly; any combination of mono-, bi- or multicistronic mRNAs encoding the at least one antigenic peptide or protein or any combination of antigens as defined herein (and optionally further antigens), provided as separate entities (containing one mRNA species) or as combined entity (containing more than one mRNA species), is understood as a vaccine according to the present invention.

As with the (pharmaceutical) composition according to the present invention, the entities of the vaccine may be provided in liquid and or in dry (e.g. lyophilized) form. They may contain further components, in particular further components allowing for its pharmaceutical use. The vaccine or the (pharmaceutical) composition may, e.g., additionally contain a pharmaceutically acceptable carrier and/or further auxiliary substances and additives.

The vaccine or (pharmaceutical) composition typically comprises a safe and effective amount of the nucleic acid, particularly mRNA according to the invention as defined herein, encoding an antigenic peptide or protein as defined herein or a fragment or variant thereof or a combination of antigens, preferably as defined herein. As used herein, "safe and effective amount" means an amount of the mRNA that is sufficient to significantly induce a positive modification of cancer or a disease or disorder related to cancer. At the same time, however, a "safe and effective amount" is small enough to avoid serious side-effects, that is to say to permit a sensible relationship between advantage and risk. The determination of these limits typically lies within the scope of sensible medical judgment. In relation to the vaccine or (pharmaceutical) composition of the present invention, the expression "safe and effective amount" preferably means an amount of the mRNA (and thus of the encoded antigen) that is suitable for stimulating the adaptive immune system in such a manner that no excessive or damaging immune reactions are achieved but, preferably, also no such immune reactions below a measurable level. Such a "safe and effective amount" of the mRNA of the (pharmaceutical) composition or vaccine as defined herein may furthermore be selected in dependence of the type of mRNA, e.g. monocistronic, bi- or even multicistronic mRNA, since a bi- or even multicistronic mRNA may lead to a significantly higher expression of the encoded antigen(s) than the use of an equal amount of a monocistronic mRNA. A "safe and effective amount" of the mRNA of the (pharmaceutical) composition or vaccine as defined above will furthermore vary in connection with the particular condition to be treated and also with the age and physical condition of the patient to be treated, the severity of the condition, the duration of the treatment, the nature of the accompanying therapy, of the particular pharmaceutically acceptable carrier used, and similar factors, within the knowledge and experience of the accompanying doctor. The vaccine or composition according to the invention can be used according to the invention for human and also for veterinary medical purposes, as a pharmaceutical composition or as a vaccine.

In a preferred embodiment, the nucleic acid, particularly the mRNA of the (pharmaceutical) composition, vaccine or kit of parts according to the invention is provided in lyophilized form. Preferably, the lyophilized mRNA is reconstituted in a suitable buffer, advantageously based on an aqueous carrier, prior to administration, e.g. Ringer-Lactate solution, which is preferred, Ringer solution, a phosphate buffer solution. In a preferred embodiment, the (pharmaceutical) composition, the vaccine or the kit of parts according to the invention contains at least one, two, three, four, five, six or more mRNAs, preferably mRNAs which are provided separately in lyophilized form (optionally together with at least one further additive) and which are preferably reconstituted separately in a suitable buffer (such as Ringer-Lactate solution) prior to their use so as to allow individual administration of each of the (monocistronic) mRNAs.

The vaccine or (pharmaceutical) composition according to the invention may typically contain a pharmaceutically acceptable carrier. The expression "pharmaceutically acceptable carrier" as used herein preferably includes the liquid or non-liquid basis of the inventive vaccine. If the inventive vaccine is provided in liquid form, the carrier will be water, typically pyrogen-free water; isotonic saline or buffered (aqueous) solutions, e.g phosphate, citrate etc. buffered solutions. Particularly for injection of the inventive vaccine, water or preferably a buffer, more preferably an aqueous buffer, may be used, containing a sodium salt, preferably at least 50 mM of a sodium salt, a calcium salt, preferably at least 0.01 mM of a calcium salt, and optionally a potassium salt, preferably at least 3 mM of a potassium salt. According to a preferred embodiment, the sodium, calcium and, optionally, potassium salts may occur in the form of their halogenides, e.g. chlorides, iodides, or bromides, in the form of their hydroxides, carbonates, hydrogen carbonates, or sulfates, etc. Without being limited thereto, examples of sodium salts include e.g. NaCl, NaI, NaBr, Na2CO3, NaHCO$_3$, Na2SO4, examples of the optional potassium salts include e.g. KCl, KI, KBr, K2CO3, KHCO3, K2SO4, and examples of calcium salts include e.g. CaCl2, CaI2, CaBr2, CaCO3, CaSO4, Ca(OH)2. Furthermore, organic anions of the aforementioned cations may be contained in the buffer. According to a more preferred embodiment, the buffer suitable for injection purposes as defined above, may contain salts selected from sodium chloride (NaCl), calcium chloride (CaCl2) and optionally potassium chloride (KCl), wherein further anions may be present additional to the chlorides. CaCl2 can also be replaced by another salt like KCl. Typically, the salts in the injection buffer are present in a concentration of at least 50 mM sodium chloride (NaCl), at least 3 mM potassium chloride (KCl) and at least 0.01 mM calcium chloride (CaCl2). The injection buffer may be hypertonic, isotonic or hypotonic with reference to the specific reference medium, i.e. the buffer may have a higher, identical or lower salt content with reference to the specific reference medium, wherein preferably such concentrations of the afore mentioned salts may be used, which do not lead to damage of cells due to osmosis or other concentration effects. Reference media are e.g. in "in vivo" methods occurring liquids such as blood, lymph, cytosolic liquids, or other body liquids, or e.g. liquids, which may be used as reference media in "in vitro" methods, such as common buffers or liquids. Such common buffers or liquids are known to a skilled person. Ringer-Lactate solution is particularly preferred as a liquid basis.

However, one or more compatible solid or liquid fillers or diluents or encapsulating compounds may be used as well, which are suitable for administration to a person. The term "compatible" as used herein means that the constituents of the inventive vaccine are capable of being mixed with the nucleic acid, particularly the mRNA according to the invention as defined herein, in such a manner that no interaction occurs, which would substantially reduce the pharmaceutical effectiveness of the inventive vaccine under typical use conditions. Pharmaceutically acceptable carriers, fillers and diluents must, of course, have sufficiently high purity and sufficiently low toxicity to make them suitable for administration to a person to be treated. Some examples of compounds which can be used as pharmaceutically acceptable carriers, fillers or constituents thereof are sugars, such as, for example, lactose, glucose, trehalose and sucrose; starches, such as, for example, corn starch or potato starch; dextrose; cellulose and its derivatives, such as, for example, sodium carboxymethylcellulose, ethylcellulose, cellulose acetate; powdered tragacanth; malt; gelatin; tallow; solid glidants, such as, for example, stearic acid, magnesium stearate; calcium sulfate; vegetable oils, such as, for example, groundnut oil, cottonseed oil, sesame oil, olive oil, corn oil and oil from theobroma; polyols, such as, for example, polypropylene glycol, glycerol, sorbitol, mannitol and polyethylene glycol; alginic acid.

The choice of a pharmaceutically acceptable carrier is determined, in principle, by the manner, in which the pharmaceutical composition or vaccine according to the invention is administered. The composition or vaccine can be administered, for example, systemically or locally. Routes for systemic administration in general include, for example, transdermal, oral, parenteral routes, including subcutaneous, intravenous, intramuscular, intraarterial, intradermal and intraperitoneal injections, intraocular, intravitreal, subretinal, intracameral, subconjunctival, subtenon, retrobulbar, topical, and/or posterior juxtascleral administration, administration into the ciliary muscle and/or intranasal administration routes. Routes for local administration in general include, for example, topical administration routes but also intradermal, transdermal, subcutaneous, or intramuscular injections or intralesional, intracranial, intrapulmonal, intracardial, and sublingual injections. More preferably, composition or vaccines according to the present invention may be administered by an intradermal, subcutaneous, or intramuscular route, preferably by injection, which may be needle-free and/or needle injection. Compositions/vaccines are therefore preferably formulated in liquid or solid form. The suitable amount of the vaccine or composition according to the invention to be administered can be determined by routine experiments, e.g. by using animal models. Such models include, without implying any limitation, rabbit, sheep, mouse, rat, dog and non-human primate models. Preferred unit dose forms for injection include sterile solutions of water, physiological saline or mixtures thereof. The pH of such solutions should be adjusted to about 7.4. Suitable carriers for injection include hydrogels, devices for controlled or delayed release, polylactic acid and collagen matrices. Suitable pharmaceutically acceptable carriers for topical application include those which are suitable for use in lotions, creams, gels and the like. If the inventive composition or vaccine is to be administered perorally, tablets, capsules and the like are the preferred unit dose form. The pharmaceutically acceptable carriers for the preparation of unit dose forms which can be used for oral administration are well known in the prior art. The choice thereof will depend on secondary considerations such as taste, costs and storability, which are not critical for the purposes of the present invention, and can be made without difficulty by a person skilled in the art.

The inventive vaccine or composition can additionally contain one or more auxiliary substances in order to further increase the immunogenicity. A synergistic action of the nucleic acid contained in the inventive composition and of an auxiliary substance, which may be optionally be co-formulated (or separately formulated) with the inventive vaccine or composition as described above, is preferably achieved thereby. Depending on the various types of auxiliary substances, various mechanisms may play a role in this respect.

Further additives which may be included in the inventive vaccine or composition are emulsifiers, such as, for example, Tween; wetting agents, such as, for example, sodium lauryl sulfate; colouring agents; taste-imparting agents, pharmaceutical carriers; tablet-forming agents; stabilizers; antioxidants; preservatives.

The inventive vaccine or composition can also additionally contain any further compound, which is known to be immune-stimulating due to its binding affinity (as ligands) to human Toll-like receptors TLR1, TLR2, TLR3, TLR4, TLR5, TLR6, TLR7, TLR8, TLR9, TLR10, or due to its binding affinity (as ligands) to murine Toll-like receptors TLR1, TLR2, TLR3, TLR4, TLR5, TLR6, TLR7, TLR8, TLR9, TLR10, TLR11, TLR12 or TLR13.

Another class of compounds, which may be added to an inventive vaccine or composition in this context, may be CpG nucleic acids, in particular CpG-RNA or CpG-DNA. A CpG-RNA or CpG-DNA can be a single-stranded CpG-DNA (ss CpG-DNA), a double-stranded CpG-DNA (dsDNA), a single-stranded CpG-RNA (ss CpG-RNA) or a double-stranded CpG-RNA (ds CpG-RNA). The CpG nucleic acid is preferably in the form of CpG-RNA, more preferably in the form of single-stranded CpG-RNA (ss CpG-RNA). The CpG nucleic acid preferably contains at least one or more (mitogenic) cytosine/guanine dinucleotide sequence(s) (CpG motif(s)). According to a first preferred alternative, at least one CpG motif contained in these sequences, that is to say the C (cytosine) and the G (guanine) of the CpG motif, is unmethylated. All further cytosines or guanines optionally contained in these sequences can be either methylated or unmethylated. According to a further preferred alternative, however, the C (cytosine) and the G (guanine) of the CpG motif can also be present in methylated form.

As used herein, the term 'inventive composition' may refer to the inventive composition comprising at least one artificial nucleic acid. Likewise, the term 'inventive vaccine', as used in this context, may refer to an inventive vaccine, which is based on the artificial nucleic acid, i.e. which comprises at least one artificial nucleic acid or which comprises the inventive composition comprising said artificial nucleic acid.

The composition may be designed as a ready-to-use injectable formulation. For example, it may be formulated as a sterile liquid suitable for injection. In this case, it may be provided as a sterile aqueous solution, or a sterile aqueous suspension of nanoparticles, preferably with a pH in the range from about 4 to about 9, or more preferably from about 4.5 to about 8.5. The osmolality of such liquid composition is preferably from about 150 to about 500 mOsmol/kg, and more preferably from about 200 to about 400 mOsmol/kg. If the composition is to be injected intravenously, the pH may also be in the range from about 4.5 to about 8, or from about 5 to about 7.5; and the osmolality may in this case preferably be selected in the range from about 220 to about 350 mOsmol/kg, or from about 250 to about 330 mOsmol/kg, respectively.

Alternatively, the composition may be formulated as a concentrated form which requires dilution or even reconstitution before use. For example, it may be in the form of a liquid concentrate, which could be an aqueous and/or organic liquid formulation which requires dilution with an aqueous solvent or diluent. If the liquid concentrate comprises an organic solvent, such solvent is preferably selected from water-miscible organic solvents with relatively low toxicity such as ethanol or propylene glycol.

In one of the preferred embodiments, the composition of the invention is provided as a dry formulation for reconstitution with a liquid carrier such as to generate a liquid formulation suitable for injection. In particular, the dry formulation may be a sterile powder or lyophilised form for reconstitution with an aqueous liquid carrier.

In order to optimise its performance, stability or tolerability, the composition may optionally comprise pharmaceutical excipients as required or useful. Potentially useful excipients include acids, bases, osmotic agents, antioxidants, stabilisers, surfactants, synergists, colouring agents, thickening agents, bulking agents, and—if required—preservatives.

The invention is also directed to a kit, particularly kits of parts, comprising the constituents of the composition of the invention as defined herein. In other words, the invention provides a kit for preparing any such composition. The inventive pharmaceutical composition may e.g. occur in one or different parts of the kit, with the kit comprising a first kit component comprising the cationic peptide or polymer, and/or the lipidoid compound, and a second kit component comprising the nucleic acid compound.

For example, the first kit component may be provided as a sterile solid composition, such as a lyophilised form or powder, or as a sterile liquid composition. In addition to the cationic peptide or polymer and/or the lipidoid, the first kit component may comprise one or more inactive ingredients as described above. Similarly, the second kit component may be formulated, for example, as a sterile solid or liquid composition and also contain one or more additional inactive ingredients in addition to the nucleic acid compound. The composition of the invention is obtained by combining and optionally mixing the content of the two components. Optionally, the lipidoid may be accommodated in a third kit component rather in the first kit component along with the cationic peptide or polymer.

Alternatively, but also within the scope of the invention, a kit is provided which comprises a first kit component comprising at least one cationic peptide or polymer, at least one lipidoid, and at least one nucleic acid compound or at least one nucleic acid sequence or a vaccine comprising the nucleic acid sequence, formulated e.g. as a sterile solid or liquid formulation, said first kit component optionally comprising at least one other component as defined herein, such as the pharmaceutical carrier or vehicle; and a second kit component comprising a liquid carrier for dissolving or dispersing the content of the first kit component such as to obtain a composition of the invention as described above. Again, the kit components are preferably provided in sterile form, whether solid or liquid, and each of them may comprise one or more additional excipient, or inactive ingredient.

In case the kit or kit of parts comprises a plurality of nucleic acid sequences, one component of the kit can comprise only one, several or all nucleic acid sequences comprised in the kit. In an alternative embodiment every/each nucleic acid sequence may be comprised in a different/separate component of the kit such that each component forms a part of the kit. Also, more than one nucleic acid may be comprised in a first component as part of the kit, whereas one or more other (second, third etc.) components (providing one or more other parts of the kit) may either contain one or more than one nucleic acids, which may be identical or partially identical or different from the first component.

Optionally, any of the kit components described above are formulated to represent concentrates, whether in solid or liquid form, and may be designed to be diluted by a biocompatible or physiologically tolerable liquid carrier which may optionally not part of the kit, such as sterile saline solution, sterile buffer, or other solutions that are frequently used as liquid diluents for injectable drugs.

In this context of injectable formulations, the expression "liquid carrier" typically means a well-tolerated aqueous injectable liquid composition having a physiologically acceptable composition, pH and osmolality.

The kit or kit of parts may furthermore contain technical instructions with information on the administration and dosage of the nucleic acid sequence, the inventive pharmaceutical composition or of any of its components or parts, e.g. if the kit is prepared as a kit of parts.

The nanoparticles, the kit and the composition as described above are particularly useful to deliver nucleic acid cargo to living cells such as to transfect the cells with the nucleic acid. This may serve a scientific research purpose, a diagnostic application or a therapy. In one of the preferred embodiments, the nanoparticle(s) or the composition is used as a medicament.

As used herein, a "medicament" means any compound, material, composition or formulation which is useful for the prophylaxis, prevention, treatment, cure, palliative treatment, amelioration, management, improvement, delay, stabilisation, or the prevention or delay of reoccurrence or spreading of a disease or condition, including the prevention, treatment or amelioration of any symptom of a disease or condition.

In order to be suitable for use as a diagnostic or as a medicine in vivo, the composition of the invention may be provided in liquid form, wherein each constituent may be independently incorporated in dissolved or dispersed (e.g. suspended or emulsified) form. For example, the composition may be in the form of a sterile aqueous solution which is suitable for administration to a subject by injection. In another preferred embodiment, the composition is formulated as a sterile solid composition, such as a sterile powder or lyophilised form for reconstitution with an aqueous liquid carrier.

In a further preferred embodiment, the nanoparticle(s) and/or the composition as described herein are used in the prophylaxis, treatment and/or amelioration of a disease associated with a peptide or protein deficiency. Accordingly, the invention is also directed to the use of the nanoparticle(s) and/or the composition for the manufacture of a medicament for the prophylaxis, treatment and/or amelioration of a disease associated with a peptide or protein deficiency. Moreover, the invention provides a method of treating a subject in risk of, or being affected by, a disease or condition associated with a peptide or protein deficiency, which method includes the administration of the nanoparticle(s) and/or the composition to that subject.

The present invention furthermore provides several applications and uses of the artificial nucleic acid, the inventive composition comprising at least one artificial nucleic acid, the inventive polypeptides as described herein, the inventive composition comprising at least one inventive polypeptide or the inventive vaccine or of kits comprising same. In particular, the inventive (pharmaceutical) composition(s) or the inventive vaccine may be used for human and also for veterinary medical purposes, preferably for human medical purposes, as a pharmaceutical composition in general or as a vaccine.

In a further aspect, the invention provides the artificial nucleic acid, the inventive composition comprising at least one artificial nucleic acid, the inventive polypeptides as described herein, the inventive composition comprising at least one inventive polypeptide, the inventive vaccine or the inventive kit or kit of parts for use in a method of prophylactic (pre-exposure prophylaxis or post-exposure prophylaxis) and/or therapeutic treatment of e.g. virus infections. Consequently, in a further aspect, the present invention is directed to the first medical use of the artificial nucleic acid, the inventive composition comprising at least one artificial nucleic acid as disclosed herein, the inventive polypeptides as described herein, the inventive composition comprising at least one inventive polypeptide, the inventive vaccine or the inventive kit or kit of parts as defined herein as a medicament. Particularly, the invention provides the use of an artificial nucleic acid comprising at least one coding region encoding at least one polypeptide comprising at least one e.g. virus protein or peptide as defined herein, or a fragment or variant thereof as described herein for the preparation of a medicament.

According to another aspect, the present invention is directed to the second medical use of the artificial nucleic acid as disclosed herein, the inventive composition comprising at least one artificial nucleic acid as disclosed herein, the inventive polypeptides as described herein, the inventive composition comprising at least one inventive polypeptide, the inventive vaccine or the inventive kit or kit of parts for the treatment of an infection with e.g. a virus or a disease or disorders related to an infection.

The inventive composition or the inventive vaccine, in particular the inventive composition comprising at least one artificial nucleic acid as disclosed herein, the inventive polypeptides as described herein or the inventive composition comprising at least one inventive polypeptide, can be administered, for example, systemically or locally. Routes for systemic administration in general include, for example, transdermal, oral, parenteral routes, including subcutaneous, intravenous, intramuscular, intraarterial, intradermal and intraperitoneal injections, intracameral, subconjunctival, subtenon, retrobulbar, topical, and/or posterior juxtascleral administration, administration into the ciliary muscle and/or intranasal administration routes. Routes for local administration in general include, for example, topical administration routes but also intradermal, transdermal, subcutaneous, or intramuscular injections or intralesional, intracranial, intrapulmonal, intracardial, and sublingual injections. More preferably, vaccines may be administered by an intradermal, subcutaneous, or intramuscular route. Inventive vaccines are therefore preferably formulated in liquid (or sometimes in solid) form. Preferably, the inventive vaccine may be administered by conventional needle injection or needle-free jet injection. In a preferred embodiment the inventive vaccine or composition may be administered by jet injection as defined herein, preferably intramuscularly or intradermally, more preferably intradermally.

In a preferred embodiment, a single dose of the artificial nucleic acid, composition or vaccine comprises a specific amount of the artificial nucleic acid as disclosed herein. Preferably, the artificial nucleic acid is provided in an amount of at least 40 µg per dose, preferably in an amount of from 40 to 700 µg per dose, more preferably in an amount of from 80 to 400 µg per dose. More specifically, in the case of intradermal injection, which is preferably carried out by using a conventional needle, the amount of the inventive artificial nucleic acid comprised in a single dose is typically at least 200 µg, preferably from 200 µg to 1.000 µg, more preferably from 300 µg to 850 µg, even more preferably from 300 µg to 700 µg. In the case of intradermal injection, which is preferably carried out via jet injection (e.g. using a Tropis device), the amount of the artificial nucleic acid comprised in a single dose is typically at least 80 µg, preferably from 80 µg to 700 µg, more preferably from 80 µg to 400 µg. Moreover, in the case of intramuscular injection, which is preferably carried out by using a conventional needle or via jet injection, the amount of the artificial nucleic acid comprised in a single dose is typically at least 80 µg, preferably from 80 µg to 1.000 µg, more preferably from 80 µg to 850 µg, even more preferably from 80 µg to 700 µg.

The immunization protocol for the treatment or prophylaxis of e.g. a virus infection, i.e the immunization of a subject against e.g. a virus, typically comprises a series of single doses or dosages of the inventive composition or the inventive vaccine. A single dosage, as used herein, refers to the initial/first dose, a second dose or any further doses, respectively, which are preferably administered in order to "boost" the immune reaction.

According to a preferred embodiment, the artificial nucleic acid as disclosed herein, the inventive composition comprising at least one artificial nucleic acid as disclosed herein, the inventive polypeptides as described herein, the inventive composition comprising at least one inventive polypeptide, the inventive vaccine or the inventive kit or kit of parts is provided for use in treatment or prophylaxis, preferably treatment or prophylaxis of e.g. a virus infection or a related disorder or disease, wherein the treatment or prophylaxis comprises the administration of a further active pharmaceutical ingredient. More preferably, in the case of the inventive vaccine or composition, which is based on the inventive artificial nucleic acid, a polypeptide may be co-administered as a further active pharmaceutical ingredient. For example, at least one e.g. virus protein or peptide as described herein, or a fragment or variant thereof, may be co-administered in order to induce or enhance an immune response. Likewise, in the case of the inventive vaccine or composition, which is based on the inventive polypeptide as described herein, an artificial nucleic acid as described herein may be co-administered as a further active pharmaceutical ingredient. For example, an artificial nucleic acid as described herein encoding at least one polypeptide as described herein may be co-administered in order to induce or enhance an immune response.

A further component of the inventive vaccine or composition may be an immunotherapeutic agent that can be selected from immunoglobulins, preferably IgGs, monoclonal or polyclonal antibodies, polyclonal serum or sera, etc, most preferably immunoglobulins directed against e.g. a virus. Preferably, such a further immunotherapeutic agent may be provided as a peptide/protein or may be encoded by a nucleic acid, preferably by a DNA or an RNA, more preferably an mRNA. Such an immunotherapeutic agent allows providing passive vaccination additional to active vaccination triggered by the inventive artificial nucleic acid or by the inventive polypeptide.

In a further aspect the invention provides a method of treating or preventing a disorder, wherein the disorder is preferably an infection with e.g. a virus or a disorder related to an infection with e.g. a virus, wherein the method comprises administering to a subject in need thereof the artificial nucleic acid as disclosed herein, the inventive composition comprising at least one artificial nucleic acid as disclosed herein, the inventive polypeptides as described herein, the inventive composition comprising at least one inventive polypeptide, the inventive vaccine or the inventive kit or kit of parts.

In particular, such a method may preferably comprise the steps of:

a) providing the artificial nucleic acid as disclosed herein, the inventive composition comprising at least one artificial nucleic acid as disclosed herein, the inventive polypeptides as described herein, the inventive composition comprising at least one inventive polypeptide, the inventive vaccine or the inventive kit or kit of parts;

b) applying or administering the artificial nucleic acid as disclosed herein, the inventive composition comprising at least one artificial nucleic acid as disclosed herein, the inventive polypeptides as described herein, the inventive composition comprising at least one inventive polypeptide, the inventive vaccine or the inventive kit or kit of parts to a tissue or an organism;

c) optionally administering immunoglobuline (IgGs) against e.g. the virus.

According to a further aspect, the present invention also provides a method for expression of at least one polypeptide comprising e.g. at least one virus, or a fragment or variant thereof, wherein the method preferably comprises the following steps:

a) providing the inventive artificial nucleic acid comprising at least one coding region encoding at least one polypeptide comprising e.g. at least one virus, or a fragment or variant thereof, preferably as defined herein, or a composition comprising said artificial nucleic acid; and b) applying or administering the inventive artificial nucleic acid or the inventive composition comprising said artificial nucleic acid to an expression system, e.g. to a cell-free expression system, a cell (e.g. an expression host cell or a somatic cell), a tissue or an organism.

The method may be applied for laboratory, for research, for diagnostic, for commercial production of peptides or proteins and/or for therapeutic purposes. In this context, typically after preparing the inventive artificial nucleic acid as defined herein or of the inventive composition or vaccine as defined herein, it is typically applied or administered to a cell-free expression system, a cell (e.g. an expression host cell or a somatic cell), a tissue or an organism, e.g. in naked or complexed form or as a (pharmaceutical) composition or vaccine as described herein, preferably via transfection or by using any of the administration modes as described herein. The method may be carried out in vitro, in vivo or ex vivo. The method may furthermore be carried out in the context of the treatment of a specific disease, particularly in the treatment of infectious diseases, or a related disorder.

In this context, in vitro is defined herein as transfection or transduction of the inventive artificial nucleic acid as defined herein or of the inventive composition or vaccine as defined herein into cells in culture outside of an organism; in vivo is defined herein as transfection or transduction of the inventive artificial nucleic acid or of the inventive composition or vaccine into cells by application of the inventive mRNA or of the inventive composition to the whole organism or individual and ex vivo is defined herein as transfection or transduction of the inventive artificial nucleic acid or of the inventive composition or vaccine into cells outside of an organism or individual and subsequent application of the transfected cells to the organism or individual.

Likewise, according to another aspect, the present invention also provides the use of the inventive artificial nucleic acid as defined herein or of the inventive composition or vaccine as defined herein, preferably for diagnostic or therapeutic purposes, for expression of e.g. an encoded virus antigenic peptide or protein, e.g. by applying or administering the inventive artificial nucleic acid as defined herein or of the inventive composition or vaccine as defined herein, e.g. to a cell-free expression system, a cell (e.g. an expression host cell or a somatic cell), a tissue or an organism. The use may be applied for a (diagnostic) laboratory, for research, for diagnostics, for commercial production of peptides or proteins and/or for therapeutic purposes. In this context, typically after preparing the inventive artificial nucleic acid as defined herein or of the inventive composition or vaccine as defined herein, it is typically applied or administered to a cell-free expression system, a cell (e.g. an expression host cell or a somatic cell), a tissue or an organism, preferably in naked form or complexed form, or as a (pharmaceutical) composition or vaccine as described herein, preferably via transfection or by using any of the administration modes as described herein. The use may be carried out in vitro, in vivo or ex vivo. The use may furthermore be carried out in the context of the treatment of a specific disease, particularly in the treatment of e.g. a virus infection or a related disorder.

In a particularly preferred embodiment, the invention provides the artificial nucleic acid, the inventive composition or the inventive vaccine for use as defined herein, preferably for use as a medicament, for use in treatment or prophylaxis, preferably treatment or prophylaxis of a e.g. a virus infection or a related disorder, or for use as a vaccine.

The composition or vaccine may be administered by conventional needle injection or needle-free jet injection, e.g. into, adjacent to and/or in close proximity to tumor tissue. In a preferred embodiment, the inventive composition or the inventive pharmaceutical composition is administered by jet injection. Jet injection refers to a needle-free injection method, wherein a fluid comprising the inventive composition and, optionally, further suitable excipients is forced through an orifice, thus generating an ultra-fine liquid stream of high pressure that is capable of penetrating mammalian skin. In principle, the liquid stream forms a hole in the skin, through which the liquid stream is pushed into the target tissue, e.g. tumor tissue. Accordingly, jet injection may be used e.g. for intratumoral application of the inventive composition.

In other embodiments, the inventive composition or the inventive pharmaceutical composition may be administered orally, parenterally, by inhalation spray, topically, rectally, nasally, buccally, vaginally or via an implanted reservoir. The term parenteral as used herein includes subcutaneous, intravenous, intramuscular, intraarticular, intranodal, intrasynovial, intrasternal, intrathecal, intrahepatic, intralesional, intracranial, transdermal, intradermal, intrapulmonal, intraperitoneal, intracardial, intraarterial, intracameral, subconjunctival, subtenon, retrobulbar, topical, and/or posterior juxtascleral administration, administration into the ciliary muscle, and sublingual injection or infusion techniques.

Further particularly preferred administration routes are intradermal and intramuscular injection.

Despite, the inventive pharmaceutical composition may comprise further components for facilitating administration and uptake of components of the pharmaceutical composition. Such further components may be an appropriate carrier or vehicle, antibacterial and/or antiviral agents.

A further component of the inventive pharmaceutical composition may be an immunotherapeutic agent that can be selected from immunoglobulins, preferably IgGs, monoclonal or polyclonal antibodies, polyclonal serum or sera, etc. Preferably, such a further immunotherapeutic agent may be provided as a peptide/protein or may be encoded by a nucleic acid, preferably by a DNA or an RNA, more preferably an mRNA.

The inventive pharmaceutical composition typically comprises a "safe and effective amount" of the components of the inventive pharmaceutical composition, particularly of the RNA molecule(s) as defined herein. As used herein, a "safe and effective amount" means an amount of the RNA molecule(s) as defined herein as such that is sufficient to significantly induce a positive modification of e.g. a tumor or cancer disease. At the same time, however, a "safe and effective amount" is small enough to avoid serious side-effects and to permit a sensible relationship between advantage and risk. The determination of these limits typically lies within the scope of sensible medical judgment.

The inventive pharmaceutical composition may be used for human and also for veterinary medical purposes, preferably for human medical purposes, as a pharmaceutical composition in general.

The present invention furthermore provides several applications and uses of the nucleic acid sequence as defined herein, of the inventive composition comprising a plurality of nucleic acid sequences as defined herein, of the inventive pharmaceutical composition, comprising the nucleic acid sequence as defined herein or of kits comprising same.

According to one specific aspect, the present invention is directed to the first medical use of the nucleic acid sequence as defined herein or of the inventive composition comprising a plurality of nucleic acid sequences as defined herein as a medicament, particularly in gene therapy, preferably for the treatment of diseases as defined herein.

According to another aspect, the present invention is directed to the second medical use of the nucleic acid sequence as defined herein or of the inventive composition comprising a plurality of nucleic acid sequences as defined herein, for the treatment of diseases as defined herein, preferably to the use of the nucleic acid sequence as defined herein, of the inventive composition comprising a plurality of nucleic acid sequences as defined herein, of a pharmaceutical composition comprising same or of kits comprising same for the preparation of a medicament for the prophylaxis, treatment and/or amelioration of diseases as defined herein. Preferably, the pharmaceutical composition is used or to be administered to a patient in need thereof for this purpose.

Preferably, diseases as mentioned herein are preferably selected from infectious diseases, neoplasms (e.g. cancer or tumor diseases), diseases of the blood and blood-forming organs, endocrine, nutritional and metabolic diseases, diseases of the nervous system, diseases of the circulatory system, diseases of the respiratory system, diseases of the digestive system, diseases of the skin and subcutaneous tissue, diseases of the musculoskeletal system and connective tissue, and diseases of the genitourinary system.

In this context particularly preferred are inherited diseases selected from: 1p36 deletion syndrome; 18p deletion syndrome; 21-hydroxylase deficiency; 45,X (Turner syndrome); 47,XX,+21 (Down syndrome); 47,XXX (triple X syndrome); 47,XXY (Klinefelter syndrome); 47,XY,+21 (Down syndrome); 47,XYY syndrome; 5-ALA dehydratase-deficient porphyria (ALA dehydratase deficiency); 5-aminolaevulinic dehydratase deficiency porphyria (ALA dehydratase deficiency); 5p deletion syndrome (Cri du chat) 5p-syndrome (Cri du chat); A-T (ataxia-telangiectasia); AAT (alpha-1 antitrypsin deficiency); Absence of vas deferens (congenital bilateral absence of vas deferens); Absent vasa (congenital bilateral absence of vas deferens); aceruloplasminemia; ACG2 (achondrogenesis type II); ACH (achondroplasia); Achondrogenesis type II; achondroplasia; Acid beta-glucosidase deficiency (Gaucher disease type 1); Acrocephalosyndactyly (Apert) (Apert syndrome); acrocephalosyndactyly, type V (Pfeiffer syndrome); Acrocephaly (Apert syndrome); Acute cerebral Gaucher's disease (Gaucher disease type 2); acute intermittent porphyria; ACY2 deficiency (Canavan disease); AD (Alzheimer's disease); Adelaide-type craniosynostosis (Muenke syndrome); Adenomatous Polyposis Coli (familial adenomatous polyposis); Adenomatous Polyposis of the Colon (familial adenomatous polyposis); ADP (ALA dehydratase deficiency); adenylosuccinate lyase deficiency; Adrenal gland disorders (21-hydroxylase deficiency); Adrenogenital syndrome (21-hydroxylase deficiency); Adrenoleukodystrophy; AIP (acute intermittent porphyria); AIS (androgen insensitivity syndrome); AKU (alkaptonuria); ALA dehydratase porphyria (ALA dehydratase deficiency); ALA-D porphyria (ALA dehydratase deficiency); ALA dehydratase deficiency; Alcaptonuria (alkaptonuria); Alexander disease; alkaptonuria; Alkaptonuric ochronosis (alkaptonuria); alpha-1 antitrypsin deficiency; alpha-1 proteinase inhibitor (alpha-1 antitrypsin deficiency); alpha-1 related emphysema (alpha-1 antitrypsin deficiency); Alpha-galactosidase A deficiency (Fabry disease); ALS (amyotrophic lateral sclerosis); Alstrom syndrome; ALX (Alexander disease); Alzheimer disease; Amelogenesis Imperfecta; Amino levulinic acid dehydratase deficiency (ALA dehydratase deficiency); Aminoacylase 2 deficiency (Canavan disease); amyotrophic lateral sclerosis; Anderson-Fabry disease (Fabry disease); androgen insensitivity syndrome; Anemia; Anemia, hereditary sideroblastic (X-linked sideroblastic anemia); Anemia, sex-linked hypochromic sideroblastic (X-linked sideroblastic anemia); Anemia, splenic, familial (Gaucher disease); Angelman syndrome; Angiokeratoma Corporis Diffusum (Fabry's disease); Angiokeratoma diffuse (Fabry's disease); Angiomatosis retinae (von Hippel-Lindau disease); ANH1 (X-linked sideroblastic anemia); APC resistance, Leiden type (factor V Leiden thrombophilia); Apert syndrome; AR deficiency (androgen insensitivity syndrome); AR-CMT2 ee (Charcot-Mare-Tooth disease, type 2); Arachnodactyly (Marfan syndrome); ARN-SHL (Nonsyndromic deafness autosomal recessive); Arthro-ophthalmopathy, hereditary progressive (Stickler syndrome COL2A1); Arthrochalasis multiplex congenita (Ehlers-Danlos syndrome arthrochalasia type); AS (Angelman syndrome); Asp deficiency (Canavan disease); Aspa deficiency (Canavan disease); Aspartoacylase deficiency (Canavan disease); ataxia-telangiectasia; Autism-Dementia-Ataxia-Loss of Purposeful Hand Use syndrome (Rett syndrome); autosomal dominant juvenile ALS (amyotrophic lateral sclerosis, type 4); Autosomal dominant opitz G/BBB syndrome (22q11.2 deletion syndrome); autosomal recessive form of juvenile ALS type 3 (Amyotrophic lateral sclerosis type 2); Autosomal recessive nonsyndromic hearing loss (Nonsyndromic deafness autosomal recessive); Autosomal Recessive Sensorineural Hearing Impairment and Goiter (Pendred syndrome); AxD (Alexander disease); Ayerza syndrome (primary pulmonary hypertension); B variant of the Hexosaminidase GM2 gangliosidosis (Sandhoff disease); BANF (neurofibromatosis 2); Beare-Stevenson cutis gyrata syndrome; Benign paroxysmal peritonitis (Mediterranean fever, familial); Benjamin syndrome; beta thalassemia; BH4 Deficiency (tetrahydrobiopterin deficiency); Bilateral Acoustic Neurofibromatosis (neurofibromatosis 2); biotinidase deficiency; bladder cancer; Bleeding disorders (factor V Leiden thrombophilia); Bloch-Sulzberger syndrome (incontinentia pigmenti); Bloom syndrome; Bone diseases;

Bone marrow diseases (X-linked sideroblastic anemia); Bonnevie-Ullrich syndrome (Turner syndrome); Bourneville disease (tuberous sclerosis); Bourneville phakomatosis (tuberous sclerosis); Brain diseases (prion disease); breast cancer; Birt-Hogg-Dubé syndrome; Brittle bone disease (osteogenesis imperfecta); Broad Thumb-Hallux syndrome (Rubinstein-Taybi syndrome); Bronze Diabetes (hemochromatosis); Bronzed cirrhosis (hemochromatosis); Bulbospinal muscular atrophy, X-linked (Kennedy disease); Burger-Grutz syndrome (lipoprotein lipase deficiency, familial); CADASIL; CGD Chronic Granulomatous Disorder; Camptomelic dysplasia; Canavan disease; Cancer; Cancer Family syndrome (hereditary nonpolyposis colorectal cancer); Cancer of breast (breast cancer); Cancer of the bladder (bladder cancer); Carboxylase Deficiency, Multiple, Late-Onset (biotinidase deficiency); Cardiomyopathy (Noonan syndrome); Cat cry syndrome (Cri du chat); CAVD (congenital bilateral absence of vas deferens); Caylor cardiofacial syndrome (22q11.2 deletion syndrome); CBAVD (congenital bilateral absence of vas deferens); Celiac Disease; CEP (congenital erythropoietic porphyria); Ceramide trihexosidase deficiency (Fabry disease); Cerebelloretinal Angiomatosis, familial (von Hippel-Lindau disease); Cerebral arteriopathy with subcortical infarcts and leukoencephalopathy (CADASIL); Cerebral autosomal dominant ateriopathy with subcortical infarcts and leukoencephalopathy (CADASIL); Cerebral sclerosis (tuberous sclerosis); Cerebroatrophic Hyperammonemia (Rett syndrome); Cerebroside Lipidosis syndrome (Gaucher disease); CF (cystic fibrosis); CH (congenital hypothyroidism); Charcot disease (amyotrophic lateral sclerosis); Charcot-Marie-Tooth disease; Chondrodystrophia (achondroplasia); Chondrodystrophy syndrome (achondroplasia); Chondrodystrophy with sensorineural deafness (otospondylomegaepiphyseal dysplasia); Chondrogenesis imperfecta (achondrogenesis, type II); Choreoathetosis self-mutilation hyperuricemia syndrome (Lesch-Nyhan syndrome); Classic Galactosemia (galactosemia); Classical Ehlers-Danlos syndrome (Ehlers-Danlos syndrome classical type); Classical Phenylketonuria (phenylketonuria); Cleft lip and palate (Stickler syndrome); Cloverleaf skull with thanatophoric dwarfism (Thanatophoric dysplasia type 2); CLS (Coffin-Lowry syndrome); CMT (Charcot-Marie-Tooth disease); Cockayne syndrome; Coffin-Lowry syndrome; collagenopathy, types II and XI; Colon Cancer, familial Nonpolyposis (hereditary nonpolyposis colorectal cancer); Colon cancer, familial (familial adenomatous polyposis); Colorectal Cancer; Complete HPRT deficiency (Lesch-Nyhan syndrome); Complete hypoxanthine-guanine phosphoribosy transferase deficiency (Lesch-Nyhan syndrome); Compression neuropathy (hereditary neuropathy with liability to pressure palsies); Congenital adrenal hyperplasia (21-hydroxylase deficiency); congenital bilateral absence of vas deferens (Congenital absence of the vas deferens); Congenital erythropoietic porphyria; Congenital heart disease; Congenital hypomyelination (Charcot-Marie-Tooth disease Type 1/Charcot-Marie-Tooth disease Type 4); Congenital hypothyroidism; Congenital methemoglobinemia (Methemoglobinemia Congenital methaemoglobinaemia); Congenital osteosclerosis (achondroplasia); Congenital sideroblastic anaemia (X-linked sideroblastic anemia); Connective tissue disease; Conotruncal anomaly face syndrome (22q11.2 deletion syndrome); Cooley's Anemia (beta thalassemia); Copper storage disease (Wilson disease); Copper transport disease (Menkes disease); Coproporphyria, hereditary (hereditary coproporphyria); Coproporphyrinogen oxidase deficiency (hereditary coproporphyria); Cowden syndrome; CPO deficiency (hereditary coproporphyria); CPRO deficiency (hereditary coproporphyria); CPX deficiency (hereditary coproporphyria); Craniofacial dysarthrosis (Crouzon syndrome); Craniofacial Dysostosis (Crouzon syndrome); Cretinism (congenital hypothyroidism); Creutzfeldt-Jakob disease (prion disease); Cri du chat (Crohn's disease, fibrostenosing); Crouzon syndrome; Crouzon syndrome with acanthosis nigricans (Crouzonodermoskeletal syndrome); Crouzonodermoskeletal syndrome; CS (Cockayne syndrome)(Cowden syndrome); Curschmann-Batten-Steinert syndrome (myotonic dystrophy); cutis gyrata syndrome of Beare-Stevenson (Beare-Stevenson cutis gyrata syndrome); Disorder Mutation Chromosome; D-glycerate dehydrogenase deficiency (hyperoxaluria, primary); Dappled metaphysis syndrome (spondyloepimetaphyseal dysplasia, Strudwick type); DAT—Dementia Alzheimer's type (Alzheimer disease); Genetic hypercalciuria (Dent's disease); DBMD (muscular dystrophy, Duchenne and Becker types); Deafness with goiter (Pendred syndrome); Deafness-retinitis pigmentosa syndrome (Usher syndrome); Deficiency disease, Phenylalanine Hydroxylase (phenylketonuria); Degenerative nerve diseases; de Grouchy syndrome 1 (De Grouchy Syndrome); Dejerine-Sottas syndrome (Charcot-Marie-Tooth disease); Delta-aminolevulinate dehydratase deficiency porphyria (ALA dehydratase deficiency); Dementia (CADASIL); demyelinogenic leukodystrophy (Alexander disease); Dermatosparactic type of Ehlers-Danlos syndrome (Ehlers-Danlos syndrome dermatosparaxis type); Dermatosparaxis (Ehlers-Danlos syndrome dermatosparaxis type); developmental disabilities; dHMN (Amyotrophic lateral sclerosis type 4); DHMN-V (distal spinal muscular atrophy, type V); DHTR deficiency (androgen insensitivity syndrome); Diffuse Globoid Body Sclerosis (Krabbe disease); DiGeorge syndrome; Dihydrotestosterone receptor deficiency (androgen insensitivity syndrome); distal spinal muscular atrophy, type V; DM1 (Myotonic dystrophy type1); DM2 (Myotonic dystrophy type2); Down syndrome; DSMAV (distal spinal muscular atrophy, type V); DSN (Charcot-Marie-Tooth disease type 4); DSS (Charcot-Marie-Tooth disease, type 4); Duchenne/Becker muscular dystrophy (muscular dystrophy, Duchenne and Becker types); Dwarf, achondroplastic (achondroplasia); Dwarf, thanatophoric (thanatophoric dysplasia); Dwarfism; Dwarfism-retinal atrophy-deafness syndrome (Cockayne syndrome); dysmyelinogenic leukodystrophy (Alexander disease); Dystrophia myotonica (myotonic dystrophy); dystrophia retinae pigmentosa-dysostosis syndrome (Usher syndrome); Early-Onset familial alzheimer disease (EOFAD) (Alzheimer disease); EDS (Ehlers-Danlos syndrome); Ehlers-Danlos syndrome; Ekman-Lobstein disease (osteogenesis imperfecta); Entrapment neuropathy (hereditary neuropathy with liability to pressure palsies); Epiloia (tuberous sclerosis); EPP (erythropoietic protoporphyria); Erythroblastic anemia (beta thalassemia); Erythrohepatic protoporphyria (erythropoietic protoporphyria); Erythroid 5-aminolevulinate synthetase deficiency (X-linked sideroblastic anemia); Erythropoietic porphyria (congenital erythropoietic porphyria); Erythropoietic protoporphyria; Erythropoietic uroporphyria (congenital erythropoietic porphyria); Eye cancer (retinoblastoma FA—Friedreich ataxia); Fabry disease; Facial injuries and disorders; Factor V Leiden thrombophilia; FALS (amyotrophic lateral sclerosis); familial acoustic neuroma (neurofibromatosis type II); familial adenomatous polyposis; familial Alzheimer disease (FAD) (Alzheimer disease); familial amyotrophic lateral sclerosis (amyotrophic lateral sclerosis); familial dysautonomia; familial fat-induced hypertriglyceridemia (lipoprotein lipase deficiency, familial); familial hemochromatosis (hemochromatosis); familial LPL deficiency (lipoprotein lipase deficiency, familial); familial nonpolyposis colon cancer (hereditary nonpolyposis colorectal cancer); familial paroxysmal polyserositis (Mediterranean fever, familial); familial PCT (porphyria cutanea tarda); familial pressure sensitive neuropathy (hereditary neuropathy with liability to pressure palsies); familial primary pulmonary hypertension (FPPH) (primary pulmonary hypertension); Familial Turner syndrome (Noonan syndrome); familial vascular leukoencephalopathy (CADASIL); FAP (familial adenomatous polyposis); FD (familial dysautonomia); Female pseudo-Turner syndrome (Noonan syndrome); Ferrochelatase deficiency (erythropoietic protoporphyria); ferroportin disease (Haemochromatosis type 4); Fever (Mediterranean fever, familial); FG syndrome; FGFR3-associated coronal synostosis (Muenke syndrome); Fibrinoid degeneration of astrocytes (Alexander disease); Fibrocystic disease of the pancreas (cystic fibrosis); FMF (Mediterranean fever, familial); Folling disease (phenylketonuria); fra(X) syndrome (fragile X syndrome); fragile X syndrome; Fragilitas ossium (osteogenesis imperfecta); FRAXA syndrome (fragile X syndrome); FRDA (Friedreich's ataxia); Friedreich ataxia (Friedreich's ataxia); Friedreich's ataxia; FXS (fragile X syndrome); G6PD deficiency; Galactokinase deficiency disease (galactosemia); Galactose-1-phosphate uridyl-transferase deficiency disease (galactosemia); galactosemia; Galactosylceramidase deficiency disease (Krabbe disease); Galactosylceramide lipidosis (Krabbe disease); galactosylcerebrosidase deficiency (Krabbe disease); galactosylsphingosine lipidosis (Krabbe disease); GALC deficiency (Krabbe disease); GALT deficiency (galactosemia); Gaucher disease; Gaucher-like disease (pseudo-Gaucher disease); GBA deficiency (Gaucher disease type 1); GD (Gaucher's disease); Genetic brain disorders; genetic emphysema (alpha-1 antitrypsin deficiency); genetic hemochromatosis (hemochromatosis); Giant cell hepatitis, neonatal (Neonatal hemochromatosis); GLA deficiency (Fabry disease); Glioblastoma, retinal (retinoblastoma); Glioma, retinal (retinoblastoma); globoid cell leukodystrophy (GCL, GLD) (Krabbe disease); globoid cell leukoencephalopathy (Krabbe disease); Glucocerebrosidase deficiency (Gaucher disease); Glucocerebrosidosis (Gaucher disease); Glucosyl cerebroside lipidosis (Gaucher disease); Glucosylceramidase deficiency (Gaucher disease); Glucosylceramide beta-glucosidase deficiency (Gaucher disease); Glucosylceramide lipidosis (Gaucher disease); Glyceric aciduria (hyperoxaluria, primary); Glycine encephalopathy (Nonketotic hyperglycinemia); Glycolic aciduria (hyperoxaluria, primary); GM2 gangliosidosis, type 1 (Tay-Sachs disease); Goiter-deafness syndrome (Pendred syndrome); Graefe-Usher syndrome (Usher syndrome); Gronblad-Strandberg syndrome (pseudoxanthoma elasticum); Guenther porphyria (congenital erythropoietic porphyria); Gunther disease (congenital erythropoietic porphyria); Haemochromatosis (hemochromatosis); Hallgren syndrome (Usher syndrome); Harlequin Ichthyosis; Hb S disease (sickle cell anemia); HCH (hypochondroplasia); HCP (hereditary coproporphyria); Head and brain malformations; Hearing disorders and deafness; Hearing problems in children; HEF2A (hemochromatosis type 2); HEF2B (hemochromatosis type 2); Hematoporphyria (porphyria); Heme synthetase deficiency (erythropoietic protoporphyria); Hemochromatoses (hemochromatosis); hemochromatosis; hemoglobin M disease (methemoglobinemia beta-globin type); Hemoglobin S disease (sickle cell anemia); hemophilia; HEP (hepatoerythropoietic porphyria); hepatic AGT deficiency (hyperoxaluria, primary); hepatoerythropoietic porphyria; Hepatolenticular degeneration syndrome (Wilson disease); Hereditary arthro-ophthalmopathy (Stickler syndrome); Hereditary coproporphyria; Hereditary dystopic lipidosis (Fabry disease); Hereditary hemochromatosis (HHC) (hemochromatosis); Hereditary Inclusion Body Myopathy (skeletal muscle regeneration); Hereditary iron-loading anemia (X-linked sideroblastic anemia); Hereditary motor and sensory neuropathy (Charcot-Marie-Tooth disease); Hereditary motor neuronopathy (spinal muscular atrophy); Hereditary motor neuronopathy, type V (distal spinal muscular atrophy, type V); Hereditary Multiple Exostoses; Hereditary nonpolyposis colorectal cancer; Hereditary periodic fever syndrome (Mediterranean fever, familial); Hereditary Polyposis Coli (familial adenomatous polyposis); Hereditary pulmonary emphysema (alpha-1 antitrypsin deficiency); Hereditary resistance to activated protein C (factor V Leiden thrombophilia); Hereditary sensory and autonomic neuropathy type III (familial dysautonomia); Hereditary spastic paraplegia (infantile-onset ascending hereditary spastic paralysis); Hereditary spinal ataxia (Friedreich ataxia); Hereditary spinal sclerosis (Friedreich ataxia); Herrick's anemia (sickle cell anemia); Heterozygous OSMED (Weissenbacher-Zweymüller syndrome); Heterozygous otospondylomegaepiphyseal dysplasia (Weissenbacher-Zweymüller syndrome); HexA deficiency (Tay-Sachs disease); Hexosaminidase A deficiency (Tay-Sachs disease); Hexosaminidase alpha-subunit deficiency (variant B) (Tay-Sachs disease); HFE-associated hemochromatosis (hemochromatosis); HGPS (Progeria); Hippel-Lindau disease (von Hippel-Lindau disease); HLAH (hemochromatosis); HMN V (distal spinal muscular atrophy, type V); HMSN (Charcot-Marie-Tooth disease); HNPCC (hereditary nonpolyposis colorectal cancer); HNPP (hereditary neuropathy with liability to pressure palsies); homocystinuria; Homogentisic acid oxidase deficiency (alkaptonuria); Homogentisic acidura (alkaptonuria); Homozygous porphyria cutanea tarda (hepatoerythropoietic porphyria); HP1 (hyperoxaluria, primary); HP2 (hyperoxaluria, primary); HPA (hyperphenylalaninemia); HPRT—Hypoxanthine-guanine phosphoribosyltransferase deficiency (Lesch-Nyhan syndrome); HSAN type III (familial dysautonomia); HSAN3 (familial dysautonomia); HSN-III (familial dysautonomia); Human dermatosparaxis (Ehlers-Danlos syndrome dermatosparaxis type); Huntington's disease; Hutchinson-Gilford progeria syndrome (progeria); Hyperandrogenism, nonclassic type, due to 21-hydroxylase deficiency (21-hydroxylase deficiency); Hyperchylomicronemia, familial (lipoprotein lipase deficiency, familial); hyperglycinemia with ketoacidosis and leukopenia (propionic acidemia); Hyperlipoproteinemia type I (lipoprotein lipase deficiency, familial); hyperoxaluria, primary; hyperphenylalaninaemia (hyperphenylalaninemia); hyperphenylalaninemia; Hypochondrodysplasia (hypochondroplasia); hypochondrogenesis; hypochondroplasia; Hypochromic anemia (X-linked sideroblastic anemia); Hypocupremia, congenital; Menkes syndrome); hypoxanthine phosphoribosyltransferse (HPRT) deficiency (Lesch-Nyhan syndrome); IAHSP (infantile-onset ascending hereditary spastic paralysis); idiopathic hemochromatosis (hemochromatosis, type 3); Idiopathic neonatal hemochromatosis (hemochromatosis, neonatal); Idiopathic pulmonary hypertension (primary pulmonary hypertension); Immune system disorders (X-linked severe combined immunodeficiency); Incontinentia Pigmenti; Infantile cerebral Gaucher's disease (Gaucher disease type 2); Infantile Gaucher disease (Gaucher disease type 2); infantile-onset ascending hereditary spastic paralysis; Infertility; inherited emphysema (alpha-1 antitrypsin deficiency);

Inherited human transmissible spongiform encephalopathies (prion disease); inherited tendency to pressure palsies (hereditary neuropathy with liability to pressure palsies); Insley-Astley syndrome (otospondylomegaepiphyseal dysplasia); Intermittent acute porphyria syndrome (acute intermittent porphyria); Intestinal polyposis-cutaneous pigmentation syndrome (Peutz-Jeghers syndrome); IP (incontinentia pigmenti); Iron storage disorder (hemochromatosis); Isodicentric 15 (idic15); Isolated deafness (nonsyndromic deafness); Jackson-Weiss syndrome; JH (Haemochromatosis type 2); Joubert syndrome; JPLS (Juvenile Primary Lateral Sclerosis); juvenile amyotrophic lateral sclerosis (Amyotrophic lateral sclerosis type 2); Juvenile gout, choreoathetosis, mental retardation syndrome (Lesch-Nyhan syndrome); juvenile hyperuricemia syndrome (Lesch-Nyhan syndrome); JWS (Jackson-Weiss syndrome); KD (X-linked spinal-bulbar muscle atrophy); Kennedy disease (X-linked spinal-bulbar muscle atrophy); Kennedy spinal and bulbar muscular atrophy (X-linked spinal-bulbar muscle atrophy); Kerasin histiocytosis (Gaucher disease); Kerasin lipoidosis (Gaucher disease); Kerasin thesaurismosis (Gaucher disease); ketotic glycinemia (propionic acidemia); ketotic hyperglycinemia (propionic acidemia); Kidney diseases (hyperoxaluria, primary); Klinefelter syndrome; Klinefelter's syndrome; Kniest dysplasia; Krabbe disease; Lacunar dementia (CADASIL); Langer-Saldino achondrogenesis (achondrogenesis, type II); Langer-Saldino dysplasia (achondrogenesis, type II); Late-onset Alzheimer disease (Alzheimer disease type 2); Late-onset familial Alzheimer disease (AD2) (Alzheimer disease type 2); late-onset Krabbe disease (LOKD) (Krabbe disease); Learning Disorders (Learning disability); Lentiginosis, perioral (Peutz-Jeghers syndrome); Lesch-Nyhan syndrome; Leukodystrophies; leukodystrophy with Rosenthal fibers (Alexander disease); Leukodystrophy, spongiform (Canavan disease); LFS (Li-Fraumeni syndrome); Li-Fraumeni syndrome; Lipase D deficiency (lipoprotein lipase deficiency, familial); LIPD deficiency (lipoprotein lipase deficiency, familial); Lipidosis, cerebroside (Gaucher disease); Lipidosis, ganglioside, infantile (Tay-Sachs disease); Lipoid histiocytosis (kerasin type) (Gaucher disease); lipoprotein lipase deficiency, familial; Liver diseases (galactosemia); Lou Gehrig disease (amyotrophic lateral sclerosis); Louis-Bar syndrome (ataxia-telangiectasia); Lynch syndrome (hereditary nonpolyposis colorectal cancer); Lysyl-hydroxylase deficiency (Ehlers-Danlos syndrome kyphoscoliosis type); Machado-Joseph disease (Spinocerebellar ataxia type 3); Male breast cancer (breast cancer); Male genital disorders; Male Turner syndrome (Noonan syndrome); Malignant neoplasm of breast (breast cancer); malignant tumor of breast (breast cancer); Malignant tumor of urinary bladder (bladder cancer); Mammary cancer (breast cancer); Marfan syndrome 15; Marker X syndrome (fragile X syndrome); Martin-Bell syndrome (fragile X syndrome); McCune-Albright syndrome; McLeod syndrome; MEDNIK; Mediterranean Anemia (beta thalassemia); Mediterranean fever, familial; Mega-epiphyseal dwarfism (otospondylomegaepiphyseal dysplasia); Menkea syndrome (Menkes syndrome); Menkes syndrome; Mental retardation with osteocartilaginous abnormalities (Coffin-Lowry syndrome); Metabolic disorders; Metatropic dwarfism, type II (Kniest dysplasia); Metatropic dysplasia type II (Kniest dysplasia); Methemoglobinemia beta-globin type; methylmalonic acidemia; MFS (Marfan syndrome); MHAM (Cowden syndrome); MK (Menkes syndrome); Micro syndrome; Microcephaly; MMA (methylmalonic acidemia); MNK (Menkes syndrome); Monosomy 1p36 syndrome (1p36 deletion syndrome); monosomy X (Turner syndrome); Motor neuron disease, amyotrophic lateral sclerosis (amyotrophic lateral sclerosis); Movement disorders; Mowat-Wilson syndrome; Mucopolysaccharidosis (MPS I); Mucoviscidosis (cystic fibrosis); Muenke syndrome; Multi-Infarct dementia (CADASIL); Multiple carboxylase deficiency, late-onset (biotinidase deficiency); Multiple hamartoma syndrome (Cowden syndrome); Multiple neurofibromatosis (neurofibromatosis); Muscular dystrophy; Muscular dystrophy, Duchenne and Becker type; Myotonia atrophica (myotonic dystrophy); Myotonia dystrophica (myotonic dystrophy); myotonic dystrophy; Myxedema, congenital (congenital hypothyroidism); Nance-Insley syndrome (otospondylomegaepiphyseal dysplasia); Nance-Sweeney chondrodysplasia (otospondylomegaepiphyseal dysplasia); NBIA1 (pantothenate kinase-associated neurodegeneration); Neill-Dingwall syndrome (Cockayne syndrome); Neuroblastoma, retinal (retinoblastoma); Neurodegeneration with brain iron accumulation type 1 (pantothenate kinase-associated neurodegeneration); Neurofibromatosis type I; Neurofibromatosis type II; Neurologic diseases; Neuromuscular disorders; neuronopathy, distal hereditary motor, type V (Distal spinal muscular atrophy type V); neuronopathy, distal hereditary motor, with pyramidal features (Amyotrophic lateral sclerosis type 4); NF (neurofibromatosis); Niemann-Pick (Niemann-Pick disease); Noack syndrome (Pfeiffer syndrome); Nonketotic hyperglycinemia (Glycine encephalopathy); Non-neuronopathic Gaucher disease (Gaucher disease type 1); Non-phenylketonuric hyperphenylalaninemia (tetrahydrobiopterin deficiency); nonsyndromic deafness; Noonan syndrome; Norrbottnian Gaucher disease (Gaucher disease type 3); Ochronosis (alkaptonuria); Ochronotic arthritis (alkaptonuria); OI (osteogenesis imperfecta); OSMED (otospondylomegaepiphyseal dysplasia); osteogenesis imperfecta; Osteopsathyrosis (osteogenesis imperfecta); Osteosclerosis congenita (achondroplasia); Oto-spondylomegaepiphyseal dysplasia (otospondylomegaepiphyseal dysplasia); otospondylomegaepiphyseal dysplasia; Oxalosis (hyperoxaluria, primary); Oxaluria, primary (hyperoxaluria, primary); pantothenate kinase-associated neurodegeneration; Patau Syndrome (Trisomy 13); PBGD deficiency (acute intermittent porphyria); PCC deficiency (propionic acidemia); PCT (porphyria cutanea tarda); PDM (Myotonic dystrophy type 2); Pendred syndrome; Periodic disease (Mediterranean fever, familial); Periodic peritonitis (Mediterranean fever, familial); Periorificial lentiginosis syndrome (Peutz-Jeghers syndrome); Peripheral nerve disorders (familial dysautonomia); Peripheral neurofibromatosis (neurofibromatosis 1); Peroneal muscular atrophy (Charcot-Marie-Tooth disease); peroxisomal alanine:glyoxylate aminotransferase deficiency (hyperoxaluria, primary); Peutz-Jeghers syndrome; Pfeiffer syndrome; Phenylalanine hydroxylase deficiency disease (phenylketonuria); phenylketonuria; Pheochromocytoma (von Hippel-Lindau disease); Pierre Robin syndrome with fetal chondrodysplasia (Weissenbacher-Zweymüller syndrome); Pigmentary cirrhosis (hemochromatosis); PJS (Peutz-Jeghers syndrome); PKAN (pantothenate kinase-associated neurodegeneration); PKU (phenylketonuria); Plumboporphyria (ALA deficiency porphyria); PMA (Charcot-Marie-tooth disease); polyostotic fibrous dysplasia (McCune-Albright syndrome); polyposis coli (familial adenomatous polyposis); polyposis, hamartomatous intestinal (Peutz-Jeghers syndrome); polyposis, intestinal, II (Peutz-Jeghers syndrome); polyps-and-spots syndrome (Peutz-Jeghers syndrome); Porphobilinogen synthase deficiency (ALA deficiency porphyria); porphyria; porphyrin disorder (porphyria); PPH (primary pulmonary hypertension); PPOX deficiency (variegate porphyria); Prader-Labhart-Willi syndrome (Prader-Willi syndrome); Prader-Willi syndrome; presenile and senile dementia (Alzheimer disease); primary hemochromatosis (hemochromatosis); primary hyperuricemia syndrome (Lesch-Nyhan syndrome); primary pulmonary hypertension; primary senile degenerative dementia (Alzheimer disease); prion disease; procollagen type EDS VII, mutant (Ehlers-Danlos syndrome arthrochalasia type); progeria (Hutchinson Gilford Progeria Syndrome); Progeria-like syndrome (Cockayne syndrome); progeroid nanism (Cockayne syndrome); progressive chorea, chronic hereditary (Huntington) (Huntington's disease); progressive muscular atrophy (spinal muscular atrophy); progressively deforming osteogenesis imperfecta with normal sclerae (Osteogenesis imperfecta type III); PROMM (Myotonic dystrophy type 2); propionic academia; propionyl-CoA carboxylase deficiency (propionic acidemia); protein C deficiency; protein S deficiency; protoporphyria (erythropoietic protoporphyria); protoporphyrinogen oxidase deficiency (variegate porphyria); proximal myotonic dystrophy (Myotonic dystrophy type 2); proximal myotonic myopathy (Myotonic dystrophy type 2); pseudo-Gaucher disease; pseudo-Ullrich-Turner syndrome (Noonan syndrome); pseudoxanthoma elasticum; psychosine lipidosis (Krabbe disease); pulmonary arterial hypertension (primary pulmonary hypertension); pulmonary hypertension (primary pulmonary hypertension); PWS (Prader-Willi syndrome); PXE—pseudoxanthoma elasticum (pseudoxanthoma elasticum); Rb (retinoblastoma); Recklinghausen disease, nerve (neurofibromatosis 1); Recurrent polyserositis (Mediterranean fever, familial); Retinal disorders; Retinitis pigmentosa-deafness syndrome (Usher syndrome); Retinoblastoma; Rett syndrome; RFALS type 3 (Amyotrophic lateral sclerosis type 2); Ricker syndrome (Myotonic dystrophy type 2); Riley-Day syndrome (familial dysautonomia); Roussy-Levy syndrome (Charcot-Marie-Tooth disease); RSTS (Rubinstein-Taybi syndrome); RTS (Rett syndrome) (Rubinstein-Taybi syndrome); RTT (Rett syndrome); Rubinstein-Taybi syndrome; Sack-Barabas syndrome (Ehlers-Danlos syndrome, vascular type); SADDAN; sarcoma family syndrome of Li and Fraumeni (Li-Fraumeni syndrome); sarcoma, breast, leukemia, and adrenal gland (SBLA) syndrome (Li-Fraumeni syndrome); SBLA syndrome (Li-Fraumeni syndrome); SBMA (X-linked spinal-bulbar muscle atrophy); SCD (sickle cell anemia); Schwannoma, acoustic, bilateral (neurofibromatosis 2); SCIDX1 (X-linked severe combined immunodeficiency); sclerosis tuberosa (tuberous sclerosis); SDAT (Alzheimer disease); SED congenita (spondyloepiphyseal dysplasia congenita); SED Strudwick (spondyloepimetaphyseal dysplasia, Strudwick type); SEDc (spondyloepiphyseal dysplasia congenita); SEMD, Strudwick type (spondyloepimetaphyseal dysplasia, Strudwick type); senile dementia (Alzheimer disease type 2); severe achondroplasia with developmental delay and acanthosis nigricans (SADDAN); Shprintzen syndrome (22q11.2 deletion syndrome); sickle cell anemia; skeleton-skin-brain syndrome (SADDAN); Skin pigmentation disorders; SMA (spinal muscular atrophy); SMED, Strudwick type (spondyloepimetaphyseal dysplasia, Strudwick type); SMED, type I (spondyloepimetaphyseal dysplasia, Strudwick type); Smith Lemli Opitz Syndrome; South-African genetic porphyria (variegate porphyria); spastic paralysis, infantile onset ascending (infantile-onset ascending hereditary spastic paralysis); Speech and communication disorders; sphingolipidosis, Tay-Sachs (Tay-Sachs disease); spinal-bulbar muscular atrophy; spinal muscular atrophy; spinal muscular atrophy, distal type V (Distal spinal muscular atrophy type V); spinal muscular atrophy, distal, with upper limb predominance (Distal spinal muscular atrophy type V); spinocerebellar ataxia; spondyloepimetaphyseal dysplasia, Strudwick type; spondyloepiphyseal dysplasia congenital; spondyloepiphyseal dysplasia (collagenopathy, types II and XI); spondylometaepiphyseal dysplasia congenita, Strudwick type (spondyloepimetaphyseal dysplasia, Strudwick type); spondylometaphyseal dysplasia (SMD) (spondyloepimetaphyseal dysplasia, Strudwick type); spondylometaphyseal dysplasia, Strudwick type (spondyloepimetaphyseal dysplasia, Strudwick type); spongy degeneration of central nervous system (Canavan disease); spongy degeneration of the brain (Canavan disease); spongy degeneration of white matter in infancy (Canavan disease); sporadic primary pulmonary hypertension (primary pulmonary hypertension); SSB syndrome (SADDAN); steely hair syndrome (Menkes syndrome); Steinert disease (myotonic dystrophy); Steinert myotonic dystrophy syndrome (myotonic dystrophy); Stickler syndrome; stroke (CADASIL); Strudwick syndrome (spondyloepimetaphyseal dysplasia, Strudwick type); subacute neuronopathic Gaucher disease (Gaucher disease type 3); Swedish genetic porphyria (acute intermittent porphyria); Swedish porphyria (acute intermittent porphyria); Swiss cheese cartilage dysplasia (Kniest dysplasia); Tay-Sachs disease; TD—thanatophoric dwarfism (thanatophoric dysplasia); TD with straight femurs and cloverleaf skull (thanatophoric dysplasia Type 2); Telangiectasia, cerebello-oculocutaneous (ataxia-telangiectasia); Testicular feminization syndrome (androgen insensitivity syndrome); tetrahydrobiopterin deficiency; TFM—testicular feminization syndrome (androgen insensitivity syndrome); thalassemia intermedia (beta thalassemia); Thalassemia Major (beta thalassemia); thanatophoric dysplasia; thiamine-responsive megaloblastic anemia with diabetes mellitus and sensorineural deafness; Thrombophilia due to deficiency of cofactor for activated protein C, Leiden type (factor V Leiden thrombophilia); Thyroid disease; Tomaculous neuropathy (hereditary neuropathy with liability to pressure palsies); Total HPRT deficiency (Lesch-Nyhan syndrome); Total hypoxanthine-guanine phosphoribosyl transferase deficiency (Lesch-Nyhan syndrome); Tourette's Syndrome; Transmissible dementias (prion disease); Transmissible spongiform encephalopathies (prion disease); Treacher Collins syndrome; Trias fragilitis ossium (osteogenesis imperfecta Type I); triple X syndrome; Triplo X syndrome (triple X syndrome); Trisomy 21 (Down syndrome); Trisomy X (triple X syndrome); Troisier-Hanot-Chauffard syndrome (hemochromatosis); TS (Turner syndrome); TSD (Tay-Sachs disease); TSEs (prion disease); tuberose sclerosis (tuberous sclerosis); tuberous sclerosis; Turner syndrome; Turner syndrome in female with X chromosome (Noonan syndrome); Turner's phenotype, karyotype normal (Noonan syndrome); Turner's syndrome (Turner syndrome); Turner-like syndrome (Noonan syndrome); Type 2 Gaucher disease (Gaucher disease type 2); Type 3 Gaucher disease (Gaucher disease type 3); UDP-galactose-4-epimerase deficiency disease (galactosemia); UDP glucose 4-epimerase deficiency disease (galactosemia); UDP glucose hexose-1-phosphate uridylyltransferase deficiency (galactosemia); Ullrich-Noonan syndrome (Noonan syndrome); Ullrich-Turner syndrome (Turner syndrome); Undifferentiated deafness (nonsyndromic deafness); UPS deficiency (acute intermittent porphyria); Urinary bladder cancer (bladder cancer); UROD deficiency (porphyria cutanea tarda); Uroporphyrinogen decarboxylase deficiency (porphyria cutanea tarda); Uroporphyrinogen synthase deficiency (acute intermittent porphyria); UROS deficiency (congenital erythropoietic porphyria); Usher syndrome; UTP hexose-1-phosphate uridylyltransferase deficiency (galactosemia); Van Bogaert-Bertrand syndrome (Canavan disease); Van der Hoeve syndrome (osteogenesis imperfecta Type I); variegate porphyria; Velocardiofacial syndrome (22q11.2 deletion syndrome); VHL syndrome (von Hippel-Lindau disease); Vision impairment and blindness (Alstrom syndrome); Von Bogaert-Bertrand disease (Canavan disease); von Hippel-Lindau disease; Von Recklenhausen-Applebaum disease (hemochromatosis); von Recklinghausen disease (neurofibromatosis 1); VP (variegate porphyria); Vrolik disease (osteogenesis imperfecta); Waardenburg syndrome; Warburg Sjo Fledelius Syndrome (Micro syndrome); WD (Wilson disease); Weissenbacher-Zweymüller syndrome; Wilson disease; Wilson's disease (Wilson disease); Wolf-Hirschhorn syndrome; Wolff Periodic disease (Mediterranean fever, familial); WZS (Weissenbacher-Zweymüller syndrome); Xeroderma Pigmentosum; X-linked mental retardation and macroorchidism (fragile X syndrome); X-linked primary hyperuricemia (Lesch-Nyhan syndrome); X-linked severe combined immunodeficiency; X-linked sideroblastic anemia; X-linked spinal-bulbar muscle atrophy (Kennedy disease); X-linked uric aciduria enzyme defect (Lesch-Nyhan syndrome); X-SCID (X-linked severe combined immunodeficiency); XLSA (X-linked sideroblastic anemia); XSCID (X-linked severe combined immunodeficiency); XXX syndrome (triple X syndrome); XXXX syndrome (48, XXXX); XXXXX (syndrome (49, XXXXX); XXY syndrome (Klinefelter syndrome); XXY trisomy (Klinefelter syndrome); XYY karyotype (47,XYY syndrome); XYY syndrome (47,XYY syndrome); and YY syndrome (47,XYY syndrome).

In a further preferred aspect, the nucleic acid sequence as defined herein or the inventive composition comprising a plurality of nucleic acid sequences as defined herein may be used for the preparation of a pharmaceutical composition, particularly for purposes as defined herein, preferably for the use in gene therapy in the treatment of diseases as defined herein.

The inventive pharmaceutical composition may furthermore be used in gene therapy particularly in the treatment of a disease or a disorder, preferably as defined herein.

The present invention furthermore provides several applications and uses of the inventive RNA containing composition, or the pharmaceutical composition, or the vaccine, or the kit or kit of parts as defined herein. In one embodiment, the composition or the pharmaceutical composition or the kit or kit of parts may be used as a medicament, namely for treatment of tumor or cancer diseases. In this context the treatment is preferably done by intratumoral application, especially by injection into tumor tissue. According to another aspect, the present invention is directed to the second medical use of the RNA containing composition or the pharmaceutical composition, or the vaccine, or the kit or kit of parts as described above, wherein these subject matters are used for preparation of a medicament particularly for intratumoral application (administration) for treatment of tumor or cancer diseases.

Preferably, diseases as mentioned herein are selected from tumor or cancer diseases which preferably include e.g. Acute lymphoblastic leukemia, Acute myeloid leukemia, Adrenocortical carcinoma, AIDS-related cancers, AIDS-related lymphoma, Anal cancer, Appendix cancer, Astrocytoma, Basal cell carcinoma, Bile duct cancer, Bladder cancer, Bone cancer, Osteosarcoma/Malignant fibrous histiocytoma, Brainstem glioma, Brain tumor, cerebellar astrocytoma, cerebral astrocytoma/malignant glioma, ependymoma, medulloblastoma, supratentorial primitive neuroectodermal tumors, visual pathway and hypothalamic glioma, Breast cancer, Bronchial adenomas/carcinoids, Burkitt lymphoma, childhood Carcinoid tumor, gastrointestinal Carcinoid tumor, Carcinoma of unknown primary, primary Central nervous system lymphoma, childhood Cerebellar astrocytoma, childhood Cerebral astrocytoma/Malignant glioma, Cervical cancer, Childhood cancers, Chronic lymphocytic leukemia, Chronic myelogenous leukemia, Chronic myeloproliferative disorders, Colon Cancer, Cutaneous T-cell lymphoma, Desmoplastic small round cell tumor, Endometrial cancer, Ependymoma, Esophageal cancer, Ewing's sarcoma in the Ewing family of tumors, Childhood Extracranial germ cell tumor, Extragonadal Germ cell tumor, Extrahepatic bile duct cancer, Intraocular melanoma, Retinoblastoma, Gallbladder cancer, Gastric (Stomach) cancer, Gastrointestinal Carcinoid Tumor, Gastrointestinal stromal tumor (GIST), extracranial, extragonadal, or ovarian Germ cell tumor, Gestational trophoblastic tumor, Glioma of the brain stem, Childhood Cerebral Astrocytoma, Childhood Visual Pathway and Hypothalamic Glioma, Gastric carcinoid, Hairy cell leukemia, Head and neck cancer, Heart cancer, Hepatocellular (liver) cancer, Hodgkin lymphoma, Hypopharyngeal cancer, childhood Hypothalamic and visual pathway glioma, Intraocular Melanoma, Islet Cell Carcinoma (Endocrine Pancreas), Kaposi sarcoma, Kidney cancer (renal cell cancer), Laryngeal Cancer, Leukemias, acute lymphoblastic Leukemia, acute myeloid Leukemia, chronic lymphocytic Leukemia, chronic myelogenous Leukemia, hairy cell Leukemia, Lip and Oral Cavity Cancer, Liposarcoma, Liver Cancer, Non-Small Cell Lung Cancer, Small Cell Lung Cancer, Lymphomas, AIDS-related Lymphoma, Burkitt Lymphoma, cutaneous T-Cell Lymphoma, Hodgkin Lymphoma, Non-Hodgkin Lymphomas, Primary Central Nervous System Lymphoma, Waldenström Macroglobulinemia, Malignant Fibrous Histiocytoma of Bone/Osteosarcoma, Childhood Medulloblastoma, Melanoma, Intraocular (Eye) Melanoma, Merkel Cell Carcinoma, Adult Malignant Mesothelioma, Childhood Mesothelioma, Metastatic Squamous Neck Cancer with Occult Primary, Mouth Cancer, Childhood Multiple Endocrine Neoplasia Syndrome, Multiple Myeloma/Plasma Cell Neoplasm, Mycosis Fungoides, Myelodysplastic Syndromes, Myelodysplastic/Myeloproliferative Diseases, Chronic Myelogenous Leukemia, Adult Acute Myeloid Leukemia, Childhood Acute Myeloid Leukemia, Multiple Myeloma (Cancer of the Bone-Marrow), Chronic Myeloproliferative Disorders, Nasal cavity and paranasal sinus cancer, Nasopharyngeal carcinoma, Neuroblastoma, Oral Cancer, Oropharyngeal cancer, Osteosarcoma/malignant fibrous histiocytoma of bone, Ovarian cancer, Ovarian epithelial cancer (Surface epithelial-stromal tumor), Ovarian germ cell tumor, Ovarian low malignant potential tumor, Pancreatic cancer, islet cell Pancreatic cancer, Paranasal sinus and nasal cavity cancer, Parathyroid cancer, Penile cancer, Pharyngeal cancer, Pheochromocytoma, Pineal astrocytoma, Pineal germinoma, childhood Pineoblastoma and supratentorial primitive neuroectodermal tumors, Pituitary adenoma, Plasma cell neoplasia/Multiple myeloma, Pleuropulmonary blastoma, Primary central nervous system lymphoma, Prostate cancer, Rectal cancer, Renal cell carcinoma (kidney cancer), Cancer of the Renal pelvis and ureter, Retinoblastoma, childhood Rhabdomyosarcoma, Salivary gland cancer, Sarcoma of the Ewing family of tumors, Kaposi Sarcoma, soft tissue Sarcoma, uterine Sarcoma, Sézary syndrome, Skin cancer (nonmelanoma), Skin cancer (melanoma), Merkel cell Skin carcinoma, Small intestine cancer, Squamous cell carcinoma, metastatic Squamous neck cancer with occult primary, childhood Supratentorial primitive neuroectodermal tumor, Testicular cancer, Throat cancer, childhood Thymoma, Thymoma and Thymic carcinoma, Thyroid cancer, childhood Thyroid cancer, Transitional cell cancer of the renal pelvis and ureter, gestational Trophoblastic tumor, Urethral cancer, endometrial Uterine cancer, Uterine sarcoma, Vaginal cancer, childhood Visual pathway and hypothalamic glioma, Vulvar cancer, Waldenström macroglobulinemia, and childhood Wilms tumor (kidney cancer).

Especially preferred examples of tumors or cancers that are suitable for intratumoral administration are prostate cancer, lung cancer, breast cancer, brain cancer, head and neck cancer, thyroid cancer, colon cancer, stomach cancer, liver cancer, pancreas cancer, ovary cancer, skin cancer, urinary bladder, uterus and cervix.

According to a specific embodiment, the medicament may be administered to the patient as a single dose or as several doses. In certain embodiments, the medicament may be administered to a patient as a single dose followed by a second dose later and optionally even a third, fourth (or more) dose subsequent thereto et cetera.

Preferably, the inventive composition is provided in an amount of at least 40 µg RNA per dose. More specifically, the amount of the mRNA comprised in a single dose is typically at least 200 µg, preferably from 200 µg to 1.000 µg, more preferably from 300 µg to 850 µg, even more preferably from 300 µg to 700 µg.

In another embodiment, the nucleotide acid molecule of the inventive composition, preferably the mRNA molecule, encodes at least one epitope of at least one antigen. In preferred embodiments of the invention the at least one antigen is selected from the group consisting of an antigen from a pathogen associated with infectious diseases, an antigen associated with allergies, an antigen associated with autoimmune diseases, and an antigen associated with cancer or tumor diseases, or a fragment, variant and/or derivative of said antigen.

Preferably the at least one antigen is derived from a pathogen, preferably a viral, bacterial, fungal or protozoan pathogen, preferably selected from the list consisting of: Rabies virus, Ebolavirus, Marburgvirus, Hepatitis B virus, human Papilloma virus (hPV), *Bacillus anthracis*, Respiratory syncytial virus (RSV), Herpes simplex virus (HSV), Dengue virus, Rotavirus, Influenza virus, human immunodeficiency virus (HIV), Yellow Fever virus, *Mycobacterium tuberculosis, Plasmodium, Staphylococcus aureus, Chlamydia trachomatis*, Cytomegalovirus (CMV) and Hepatitis B virus (HBV).

In this context the mRNA of the inventive composition may encode for a protein or a peptide, which comprises at least one epitope of a pathogenic antigen or a fragment, variant or derivative thereof. Such pathogenic antigens are derived from pathogenic organisms, in particular bacterial, viral or protozoological (multicellular) pathogenic organisms, which evoke an immunological reaction by subject, in particular a mammalian subject, more particularly a human. More specifically, pathogenic antigens are preferably surface antigens, e.g. proteins (or fragments of proteins, e.g. the exterior portion of a surface antigen) located at the surface of the virus or the bacterial or protozoological organism.

Pathogenic antigens are peptide or protein antigens preferably derived from a pathogen associated with infectious disease which are preferably selected from antigens derived from the pathogens *Acinetobacter baumannii, Anaplasma* genus, *Anaplasma phagocytophilum, Ancylostoma braziliense, Ancylostoma duodenale, Arcanobacterium haemolyticum, Ascaris lumbricoides, Aspergillus* genus, Astroviridae, *Babesia* genus, *Bacillus anthracis, Bacillus cereus, Bartonella henselae*, BK virus, *Blastocystis hominis, Blastomyces dermatitidis, Bordetella pertussis, Borrelia burgdorferi, Borrelia* genus, *Borrelia* spp, *Brucella* genus, *Brugia malayi*, Bunyaviridae family, *Burkholderia cepacia* and other *Burkholderia* species, *Burkholderia mallei, Burkholderia pseudomallei*, Caliciviridae family, *Campylobacter* genus, *Candida albicans, Candida* spp, *Chlamydia trachomatis, Chlamydophila pneumoniae, Chlamydophila psittaci*, CJD prion, *Clonorchis sinensis, Clostridium botulinum, Clostridium difficile, Clostridium perfringens, Clostridium perfringens, Clostridium* spp, *Clostridium tetani, Coccidioides* spp, coronaviruses, *Corynebacterium diphtheriae, Coxiella burnetii*, Crimean-Congo hemorrhagic fever virus, *Cryptococcus neoformans, Cryptosporidium* genus, Cytomegalovirus (CMV), Dengue viruses (DEN-1, DEN-2, DEN-3 and DEN-4), *Dientamoeba fragilis*, Ebolavirus (EBOV), *Echinococcus* genus, *Ehrlichia chaffeensis, Ehrlichia ewingii, Ehrlichia* genus, *Entamoeba histolytica, Enterococcus* genus, *Enterovirus* genus, Enteroviruses, mainly Coxsackie A virus and *Enterovirus* 71 (EV71), *Epidermophyton* spp, Epstein-Barr Virus (EBV), *Escherichia coli* O157:H7, O111 and O104:H4, *Fasciola hepatica* and *Fasciola gigantica*, FFI prion, Filarioidea superfamily, Flaviviruses, *Francisella tularensis, Fusobacterium* genus, *Geotrichum candidum, Giardia intestinalis, Gnathostoma* spp, GSS prion, Guanarito virus, *Haemophilus ducreyi, Haemophilus influenzae, Helicobacter pylori*, Henipavirus (Hendra virus Nipah virus), Hepatitis A Virus, Hepatitis B Virus (HBV), Hepatitis C Virus (HCV), Hepatitis D Virus, Hepatitis E Virus, Herpes simplex virus 1 and 2 (HSV-1 and HSV-2), *Histoplasma capsulatum*, HIV (Human immunodeficiency virus), *Hortaea werneckii*, Human bocavirus (HBoV), Human herpesvirus 6 (HHV-6) and Human herpesvirus 7 (HHV-7), Human metapneumovirus (hMPV), Human papillomavirus (HPV), Human parainfluenza viruses (HPIV), Japanese encephalitis virus, JC virus, Junin virus, *Kingella kingae, Klebsiella granulomatis*, Kuru prion, Lassa virus, *Legionella pneumophila, Leishmania* genus, *Leptospira* genus, *Listeria monocytogenes*, Lymphocytic choriomeningitis virus (LCMV), Machupo virus, *Malassezia* spp, Marburg virus, Measles virus, *Metagonimus yokagawai*, Microsporidia phylum, *Molluscum contagiosum* virus (MCV), Mumps virus, *Mycobacterium leprae* and *Mycobacterium lepromatosis, Mycobacterium tuberculosis, Mycobacterium ulcerans, Mycoplasma pneumoniae, Naegleria fowleri, Necator americanus, Neisseria gonorrhoeae, Neisseria meningitidis, Nocardia asteroides, Nocardia* spp, *Onchocerca volvulus, Orientia tsutsugamushi*, Orthomyxoviridae family (Influenza), *Paracoccidioides brasiliensis, Paragonimus* spp, *Paragonimus westermani*, Parvovirus B19, *Pasteurella* genus, *Plasmodium* genus, *Pneumocystis jirovecii*, Poliovirus, Rabies virus, Respiratory syncytial virus (RSV), Rhinovirus, rhinoviruses, *Rickettsia akari, Rickettsia* genus, *Rickettsia prowazekii, Rickettsia rickettsii, Rickettsia typhi*, Rift Valley fever virus, Rotavirus, Rubella virus, Sabia virus, *Salmonella* genus, *Sarcoptes scabiei*, SARS coronavirus, *Schistosoma* genus, *Shigella* genus, Sin Nombre virus, Hantavirus, *Sporothrix schenckii, Staphylococcus* genus, *Staphylococcus* genus, *Streptococcus agalactiae, Streptococcus pneumoniae, Streptococcus pyogenes, Strongyloides stercoralis, Taenia* genus, *Taenia solium*, Tick-borne encephalitis virus (TBEV), *Toxocara canis* or *Toxocara cati, Toxoplasma gondii, Treponema pallidum, Trichinella spiralis, Trichomonas vaginalis, Trichophyton* spp, *Trichuris trichiura, Trypano-* soma brucei, Trypanosoma cruzi, Ureaplasma urealyticum, Varicella zoster virus (VZV), Varicella zoster virus (VZV), Variola major or Variola minor, vCJD prion, Venezuelan equine encephalitis virus, Vibrio cholerae, West Nile virus, Western equine encephalitis virus, Wuchereria bancrofti, Yellow fever virus, Yersinia enterocolitica, Yersinia pestis, and Yersinia pseudotuberculosis.

Furthermore, the pathogenic antigen (antigen derived from a pathogen associated with infectious disease) may be preferably selected from the following antigens: Outer membrane protein A OmpA, biofilm associated protein Bap, transport protein MucK (Acinetobacter baumannii, Acinetobacter infections)); variable surface glycoprotein VSG, microtubule-associated protein MAPP15, trans-sialidase TSA (Trypanosoma brucei, African sleeping sickness (African trypanosomiasis)); HIV p24 antigen, HIV envelope proteins (Gp120, Gp41, Gp160), polyprotein GAG, negative factor protein Nef, trans-activator of transcription Tat (HIV (Human immunodeficiency virus), AIDS (Acquired immunodeficiency syndrome)); galactose-inhibitable adherence protein GIAP, 29 kDa antigen Eh29, Gal/GalNAc lectin, protein CRT, 125 kDa immunodominant antigen, protein M17, adhesin ADH112, protein STIRP (Entamoeba histolytica, Amoebiasis); Major surface proteins 1-5 (MSP1a, MSP1b, MSP2, MSP3, MSP4, MSP5), type IV secreotion system proteins (VirB2, VirB7, VirB11, VirD4) (Anaplasma genus, Anaplasmosis); protective Antigen PA, edema factor EF, lethal facotor LF, the S-layer homology proteins SLH (Bacillus anthracis, Anthrax); acranolysin, phospholipase D, collagen-binding protein CbpA (Arcanobacterium haemolyticum, Arcanobacterium haemolyticum infection); nucleocapsid protein NP, glycoprotein precursor GPC, glycoprotein GP1, glycoprotein GP2 (Junin virus, Argentine hemorrhagic fever); chitin-protein layer proteins, 14 kDa surface antigen A14, major sperm protein MSP, MSP polymerization-organizing protein MPOP, MSP fiber protein 2 MFP2, MSP polymerization-activating kinase MPAK, ABA-1-like protein ALB, protein ABA-1, cuticulin CUT-1 (Ascaris lumbricoides, Ascariasis); 41 kDa allergen Asp v13, allergen Asp f3, major conidial surface protein rodlet A, protease Pep1p, GPI-anchored protein Gel1p, GPI-anchored protein Crf1p (Aspergillus genus, Aspergillosis); family VP26 protein, VP29 protein (Astroviridae, Astrovirus infection); Rhoptry-associated protein 1 RAP-1, merozoite surface antigens MSA-1, MSA-2 (a1, a2, b, c), 12D3, 11C5, 21B4, P29, variant erythrocyte surface antigen VESA1, Apical Membrane Antigen 1 AMA-1 (Babesia genus, Babesiosis); hemolysin, enterotoxin C, PXO1-51, glycolate oxidase, ABC-transporter, penicillin-bingdn protein, zinc transporter family protein, pseudouridine synthase Rsu, plasmid replication protein RepX, oligoendopeptidase F, prophage membrane protein, protein HemK, flagellar antigen H, 28.5-kDa cell surface antigen (Bacillus cereus, Bacillus cereus infection); large T antigen LT, small T antigen, capsid protein VP1, capsid protein VP2 (BK virus, BK virus infection); 29 kDa-protein, caspase-3-like antigens, glycoproteins (Blastocystis hominis, Blastocystis hominis infection); yeast surface adhesin WI-1 (Blastomyces dermatitidis, Blastomycosis); nucleoprotein N, polymerase L, matrix protein Z, glycoprotein GP (Machupo virus, Bolivian hemorrhagic fever); outer surface protein A OspA, outer surface protein OspB, outer surface protein OspC, decorin binding protein A DbpA, decorin binding protein B DbpB, flagellar filament 41 kDa core protein Fla, basic membrane protein A precursor BmpA (Immunodominant antigen P39), outer surface 22 kDa lipoprotein precursor (antigen IPLA7), variable surface lipoprotein vlsE (Borrelia genus, Borrelia infection); Botulinum neurotoxins BoNT/A1, BoNT/A2, BoNT/A3, BoNT/B, BoNT/C, BoNT/D, BoNT/E, BoNT/F, BoNT/G, recombinant botulinum toxin F Hc domain FHc (Clostridium botulinum, Botulism (and Infant botulism)); nucleocapsid, glycoprotein precursor (Sabia virus, Brazilian hemorrhagic fever); copper/Zinc superoxide dismutase SodC, bacterioferritin Bfr, 50S ribosomal protein RplL, OmpA-like transmembrane domain-containing protein Omp31, immunogenic 39-kDa protein M5 P39, zinc ABC transporter periplasmic zinc-bnding protein znuA, periplasmic immunogenic protein Bp26, 30S ribosomal protein S12 RpsL, glyceraldehyde-3-phosphate dehydrogenase Gap, 25 kDa outer-membrane immunogenic protein precursor Omp25, invasion protein B IalB, trigger factor Tig, molecular chaperone DnaK, putative peptidyl-prolyl cis-trans isomerase SurA, lipoprotein Omp19, outer membrane protein MotY Omp16, conserved outer membrane protein D15, malate dehydrogenase Mdh, component of the Type-IV secretion system (T4SS) VirJ, lipoprotein of unknown function BAB1_0187 (Brucella genus, Brucellosis); members of the ABC transporter family (LolC, OppA, and PotF), putative lipoprotein releasing system transmembrane protein LolC/E, flagellin FliC, Burkholderia intracellular motility A BimA, bacterial Elongation factor-Tu EF-Tu, 17 kDa OmpA-like protein, boaA coding protein, boaB coding protein (Burkholderia cepacia and other Burkholderia species, Burkholderia infection); mycolyl-transferase Ag85A, heat-shock protein Hsp65, protein TB10.4, 19 kDa antigen, protein PstS3, heat-shock protein Hsp70 (Mycobacterium ulcerans, Buruli ulcer); norovirus major and minor viral capsid proteins VP1 and VP2, genome polyprotein, Sapoviurus capsid protein VP1, protein Vp3, geome polyprotein (Caliciviridae family, Calicivirus infection (Norovirus and Sapovirus)); major outer membrane protein PorA, flagellin FlaA, surface antigen CjaA, fibronectin binding protein CadF, aspartate/glutamate-binding ABC transporter protein Peb1A, protein FspA1, protein FspA2 (Campylobacter genus, Campylobacteriosis); glycolytic enzyme enolase, secreted aspartyl proteinases SAP1-10, glycophosphatidylinositol (GPI)-linked cell wall protein, protein Hyr1, complement receptor 3-related protein CR3-RP, adhesin Als3p, heat shock protein 90 kDa hsp90, cell surface hydrophobicity protein CSH (usually Candida albicans and other Candida species, Candidiasis); 17-kDa antigen, protein P26, trimeric autotransporter adhesins TAAs, Bartonella adhesin A BadA, variably expressed outer-membrane proteins Vomps, protein Pap3, protein HbpA, envelope-associated protease HtrA, protein OMP89, protein GroEL, protein LalB, protein OMP43, dihydrolipoamide succinyltransferase SucB (Bartonella henselae, Cat-scratch disease); amastigote surface protein-2, amastigote-specific surface protein SSP4, cruzipain, trans-sialidase TS, trypomastigote surface glycoprotein TSA-1, complement regulatory protein CRP-10, protein G4, protein G2, paraxonemal rod protein PAR2, paraflagellar rod component Par1, mucin-Associated Surface Proteins MPSP (Trypanosoma cruzi, Chagas Disease (American trypanosomiasis)); envelope glycoproteins (gB, gC, gE, gH, gI, gK, gL) (Varicella zoster virus (VZV), Chickenpox); major outer membrane protein MOMP, probable outer membrane protein PMPC, outer membrane complex protein B OmcB, heat shock proteins Hsp60 HSP10, protein IncA, proteins from the type III secretion system, ribonucleotide reductase small chain protein NrdB, plasmid protein Pgp3, chlamydial outer protein N CopN, antigen CT521, antigen CT425, antigen CT043, antigen TC0052, antigen TC0189, antigen TC0582, antigen TC0660, antigen TC0726, antigen TC0816, antigen TC0828 (Chlamydia trachomatis, Chlamydia); low calcium response protein E LCrE, chlamydial outer protein N CopN, serine/threonine-protein kinase PknD, acyl-carrier-protein S-malonyltransferase FabD, single-stranded DNA-binding protein Ssb, major outer membrane protein MOMP, outer membrane protein 2 Omp2, polymorphic membrane protein family (Pmp1, Pmp2, Pmp3, Pmp4, Pmp5, Pmp6, Pmp7, Pmp8, Pmp9, Pmp10, Pmp11, Pmp12, Pmp13, Pmp14, Pmp15, Pmp16, Pmp17, Pmp18, Pmp19, Pmp20, Pmp21) (*Chlamydophila pneumoniae, Chlamydophila pneumoniae* infection); cholera toxin B CTB, toxin coregulated pilin A TcpA, toxin coregulated pilin TcpF, toxin co-regulated pilus biosynthesis ptrotein F TcpF, cholera enterotoxin subunit A, cholera enterotoxin subunit B, Heat-stable enterotoxin ST, mannose-sensitive hemagglutinin MSHA, outer membrane protein U Porin ompU, Poring B protein, polymorphic membrane protein-D (*Vibrio cholerae*, Cholera); propionyl-CoA carboxylase PCC, 14-3-3 protein, prohibitin, cysteine proteases, glutathione transferases, gelsolin, cathepsin L proteinase CatL, Tegumental Protein 20.8 kDa TP20.8, tegumental protein 31.8 kDa TP31.8, lysophosphatidic acid phosphatase LPAP, (*Clonorchis sinensis*, Clonorchiasis); surface layer proteins SLPs, glutamate dehydrogenase antigen GDH, toxin A, toxin B, cysteine protease Cwp84, cysteine protease Cwp13, cysteine protease Cwp19, Cell Wall Protein CwpV, flagellar protein FliC, flagellar protein FliD (*Clostridium difficile, Clostridium difficile* infection); rhinoviruses: capsid proteins VP1, VP2, VP3, VP4; coronaviruses: spike proteins S, envelope proteins E, membrane proteins M, nucleocapsid proteins N (usually rhinoviruses and coronaviruses, Common cold (Acute viral rhinopharyngitis; Acute coryza)); prion protein Prp (CJD prion, Creutzfeldt-Jakob disease (CJD)); envelope protein Gc, envelope protein Gn, nucleocapsid proteins (Crimean-Congo hemorrhagic fever virus, Crimean-Congo hemorrhagic fever (CCHF)); virulence-associated DEAD-box RNA helicase VAD1, galactoxylomannan-protein GalXM, glucuronoxylomannan GXM, mannoprotein MP (*Cryptococcus neoformans*, Cryptococcosis); acidic ribosomal protein P2 CpP2, mucin antigens Muc1, Muc2, Muc3 Muc4, Muc5, Much, Muc7, surface adherence protein CP20, surface adherence protein CP23, surface protein CP12, surface protein CP21, surface protein CP40, surface protein CP60, surface protein CP15, surface-associated glycopeptides gp40, surface-associated glycopeptides gp15, oocyst wall protein AB, profilin PRF, apyrase (*Cryptosporidium* genus, Cryptosporidiosis); fatty acid and retinol binding protein-1 FAR-1, tissue inhibitor of metalloproteinase TIMP (TMP), cysteine proteinase ACEY-1, cysteine proteinase ACCP-1, surface antigen Ac-16, secreted protein 2 ASP-2, metalloprotease 1 MTP-1, aspartyl protease inhibitor API-1, surface-associated antigen SAA-1, adult-specific secreted factor Xa serine protease inhibitor anticoagulant AP, cathepsin D-like aspartic protease ARR-1 (usually *Ancylostoma braziliense*; multiple other parasites, Cutaneous larva migrans (CLM)); cathepsin L-like proteases, 53/25-kDa antigen, 8 kDa family members, cysticercus protein with a marginal trypsin-like activity TsAg5, oncosphere protein TSOL18, oncosphere protein TSOL45-1A, lactate dehydrogenase A LDHA, lactate dehydrogenase B LDHB (*Taenia solium*, Cysticercosis); pp65 antigen, membrane protein pp15, capsid-proximal tegument protein pp150, protein M45, DNA polymerase UL54, helicase UL105, glycoprotein gM, glycoprotein gN, glcoprotein H, glycoprotein B gB, protein UL83, protein UL94, protein UL99 (Cytomegalovirus (CMV), Cytomegalovirus infection); capsid protein C, pre-membrane protein prM, membrane protein M, envelope protein E (domain I, domain II, domain II), protein NS1, protein NS2A, protein NS2B, protein NS3, protein NS4A, protein 2K, protein NS4B, protein NS5 (Dengue viruses (DEN-1, DEN-2, DEN-3 and DEN-4)-Flaviviruses, Dengue fever); 39 kDa protein (*Dientamoeba fragilis*, Dientamoebiasis); diphtheria toxin precursor Tox, diphteria toxin DT, pilin-specific sortase SrtA, shaft pilin protein SpaA, tip pilin protein SpaC, minor pilin protein SpaB, surface-associated protein DIP1281 (*Corynebacterium diphtheriae*, Diphtheria); glycoprotein GP, nucleoprotein NP, minor matrix protein VP24, major matrix protein VP40, transcription activator VP30, polymerase cofactor VP35, RNA polymerase L (Ebolavirus (EBOV), Ebola hemorrhagic fever); prion protein (vCJD prion, Variant Creutzfeldt-Jakob disease (vCJD, nvCJD)); UvrABC system protein B, protein Flp1, protein Flp2, protein Flp3, protein TadA, hemoglobin receptor HgbA, outer membrane protein TdhA, protein CpsRA, regulator CpxR, protein SapA, 18 kDa antigen, outer membrane protein NcaA, protein LspA, protein LspA1, protein LspA2, protein LspB, outer membrane component DsrA, lectin DltA, lipoprotein Hlp, major outer membrane protein OMP, outer membrane protein OmpA2 (*Haemophilus ducreyi*, Chancroid); aspartyl protease 1 Pep1, phospholipase B PLB, alpha-mannosidase 1 AMN1, glucanosyltransferase GEL1, urease URE, peroxisomal matrix protein Pmp1, proline-rich antigen Pra, humal T-cell reative protein TcrP (*Coccidioides immitis* and *Coccidioides posadasii*, Coccidioidomycosis); allergen Tri r 2, heat shock protein 60 Hsp60, fungal actin Act, antigen Tri r2, antigen Tri r4, antigen Tri t1, protein IV, glycerol-3-phosphate dehydrogenase Gpd1, osmosensor HwSho1A, osmosensor HwSho1B, histidine kinase HwHhk7B, allergen Mala s 1, allergen Mala s 11, thioredoxin Trx Mala s 13, allergen Mala f, allergen Mala s (usually *Trichophyton* spp, *Epidermophyton* spp., *Malassezia* spp., *Hortaea werneckii*, Dermatophytosis); protein EG95, protein EG10, protein EG18, protein EgA31, protein EM18, antigen EPC1, antigen B, antigen 5, protein P29, protein 14-3-3, 8-kDa protein, myophilin, heat shock protein 20 HSP20, glycoprotein GP-89, fatty acid binding protein FAPB (*Echinococcus* genus, Echinococcosis); major surface protein 2 MSP2, major surface protein 4 MSP4, MSP variant SGV1, MSP variant SGV2, outer membrane protein OMP, outer membrane protein 19 OMP-19, major antigenic protein MAP1, major antigenic protein MAP1-2, major antigenic protein MAP1B, major antigenic protein MAP1-3, Erum2510 coding protein, protein GroEL, protein GroES, 30-kDA major outer membrane proteins, GE 100-kDa protein, GE 130-kDa protein, GE 160-kDa protein (*Ehrlichia* genus, Ehrlichiosis); secreted antigen SagA, sagA-like proteins SalA and SalB, collagen adhesin Scm, surface proteins Fms1 (EbpA(fm), Fms5 (EbpB(fm), Fms9 (EpbC(fm) and Fms10, protein EbpC(fm), 96 kDa immunoprotective glycoprotein G1 (*Enterococcus* genus, *Enterococcus* infection); genome polyprotein, polymerase 3D, viral capsid protein VP1, viral capsid protein VP2, viral capsid protein VP3, viral capsid protein VP4, protease 2A, protease 3C (*Enterovirus* genus, *Enterovirus* infection); outer membrane proteins OM, 60 kDa outer membrane protein, cell surface antigen OmpA, cell surface antigen OmpB (sca5), 134 kDa outer membrane protein, 31 kDa outer membrane protein, 29.5 kDa outer membrane protein, cell surface protein SCA4, cell surface protein Adr1 (RP827), cell surface protein Adr2 (RP828), cell surface protein SCA1, Invasion protein invA, cell division protein fts, secretion proteins sec Ofamily, virulence proteins virB, tlyA, tlyC, parvulin-like protein Plp, preprotein translocase SecA, 120-kDa surface protein antigen SPA, 138 kD complex antigen, major 100- kD protein (protein I), intracytoplasmic protein D, protective surface protein antigen SPA (*Rickettsia prowazekii*, Epidemic typhus); Epstein-Barr nuclear antigens (EBNA-1, EBNA-2, EBNA-3A, EBNA-3B, EBNA-3C, EBNA-leader protein (EBNA-LP)), latent membrane proteins (LMP-1, LMP-2A, LMP-2B), early antigen EBV-EA, membrane antigen EBV-MA, viral capsid antigen EBV-VCA, alkaline nuclease EBV-AN, glycoprotein H, glycoprotein gp350, glycoprotein gp110, glycoprotein gp42, glycoprotein gHgL, glycoprotein gB (Epstein-Barr Virus (EBV), Epstein-Barr Virus Infectious Mononucleosis); cpasid protein VP2, capsid protein VP1, major protein NS1 (Parvovirus B19, Erythema infectiosum (Fifth disease)); pp65 antigen, glycoprotein 105, major capsid protein, envelope glycoprotein H, protein U51 (Human herpesvirus 6 (HHV-6) and Human herpesvirus 7 (HHV-7), Exanthem subitum); thioredoxin-glutathione reductase TGR, cathepsins L1 and L2, Kunitz-type protein KTM, leucine aminopeptidase LAP, cysteine proteinase Fas2, saposin-like protein-2 SAP-2, thioredoxin peroxidases TPx, Prx-1, Prx-2, cathepsin 1 cysteine proteinase CL3, protease cathepsin L CL1, phosphoglycerate kinase PGK, 27-kDa secretory protein, 60 kDa protein HSP35alpha, glutathione transferase GST, 28.5 kDa tegumental antigen 28.5 kDa TA, cathepsin B3 protease CatB3, Type I cystatin stefin-1, cathepsin L5, cathepsin L1g and cathepsin B, fatty acid binding protein FABP, leucine aminopeptidases LAP (*Fasciola hepatica* and *Fasciola gigantica*, Fasciolosis); prion protein (FFI prion, Fatal familial insomnia (FFI)); venom allergen homolog-like protein VAL-1, abundant larval transcript ALT-1, abundant larval transcript ALT-2, thioredoxin peroxidase TPX, vespid allergen homologue VAH, thiordoxin peroxidase 2 TPX-2, antigenic protein SXP (peptides N, N1, N2, and N3), activation associated protein-1 ASP-1, Thioredoxin TRX, transglutaminase BmTGA, glutathione-S-transferases GST, myosin, vespid allergen homologue VAH, 175 kDa collagenase, glyceraldehyde-3-phosphate dehydrogenase GAPDH, cuticular collagen Col-4, secreted larval acidic proteins SLAPs, chitinase CHI-1, maltose binding protein MBP, glycolytic enzyme fructose-1,6-bisphosphate aldolase Fba, tropomyosin TMY-1, nematode specific gene product OvB20, onchocystatin CPI-2, Cox-2 (Filarioidea superfamily, Filariasis); phospholipase C PLC, heat-labile enterotoxin B, Iota toxin component Ib, protein CPE1281, pyruvate ferredoxin oxidoreductase, elongation factor G EF-G, perfringolysin O Pfo, glyceraldehyde-3-phosphate dehydrogenase GapC, Fructose-bisphosphate aldolase Alf2, *Clostridium perfringens* enterotoxin CPE, alpha toxin AT, alpha toxoid ATd, epsilon-toxoid ETd, protein HP, large cytotoxin TpeL, endo-beta-N-acetylglucosaminidase Naglu, phosphoglyceromutase Pgm (*Clostridium perfringens*, Food poisoning by *Clostridium perfringens*); leukotoxin lktA, adhesion FadA, outer membrane protein RadD, high-molecular weight arginine-binding protein (*Fusobacterium* genus, *Fusobacterium* infection); phospholipase C PLC, heat-labile enterotoxin B, Iota toxin component Ib, protein CPE1281, pyruvate ferredoxin oxidoreductase, elongation factor G EF-G, perfringolysin O Pfo, glyceraldehyde-3-phosphate dehydrogenase GapC, fructose-bisphosphate aldolase Alf2, *Clostridium perfringens* enterotoxin CPE, alpha toxin AT, alpha toxoid ATd, epsilon-toxoid ETd, protein HP, large cytotoxin TpeL, endo-beta-N-acetylglucosaminidase Naglu, phosphoglyceromutase Pgm (usually *Clostridium perfringens*; other *Clostridium* species, Gas gangrene (Clostridial myonecrosis)); lipase A, lipase B, peroxidase Dec1 (*Geotrichum candidum*, Geotrichosis); prion protein (GSS prion, Gerstmann-Sträussler-Scheinker syndrome (GSS)); cyst wall proteins CWP1, CWP2, CWP3, variant surface protein VSP, VSP1, VSP2, VSP3, VSP4, VSP5, VSP6, 56 kDa antigen, pyruvate ferredoxin oxidoreductase PFOR, alcohol dehydrogenase E ADHE, alpha-giardin, alpha8-giardin, alpha1-guiardin, beta-giardin, cystein proteases, glutathione-S-transferase GST, arginine deiminase ADI, fructose-1,6-bisphosphat aldolase FBA, *Giardia* trophozoite antigens GTA (GTA1, GTA2), ornithine carboxyl transferase OCT, striated fiber-asseblin-like protein SALP, uridine phosphoryl-like protein UPL, alpha-tubulin, beta-tubulin (*Giardia intestinalis*, Giardiasis); members of the ABC transporter family (LolC, OppA, and PotF), putative lipoprotein releasing system transmembrane protein LolC/E, flagellin FliC, *Burkholderia* intracellular motility A BimA, bacterial Elongation factor-Tu EF-Tu, 17 kDa OmpA-like protein, boaA coding protein (*Burkholderia mallei*, Glanders); cyclophilin CyP, 24 kDa third-stage larvae protien GS24, excretion-secretion products ESPs (40, 80, 120 and 208 kDa) (*Gnathostoma spinigerum* and *Gnathostoma hispidum*, Gnathostomiasis); pilin proteins, minor pilin-associated subunit pilC, major pilin subunit and variants pilE, pilS, phase variation protein porA, Porin B PorB, protein TraD, Neisserial outer membrane antigen H.8, 70 kDa antigen, major outer membrane protein PI, outer membrane proteins PIA and PIB, W antigen, surface protein A NspA, transferrin binding protein TbpA, transferrin binding protein TbpB, PBP2, mtrR coding protein, ponA coding protein, membrane permease FbpBC, FbpABC protein system, LbpAB proteins, outer membrane protein Opa, outer membrane transporter FetA, iron-repressed regulator MpeR (*Neisseria gonorrhoeae*, Gonorrhea); outer membrane protein A OmpA, outer membrane protein C OmpC, outer membrane protein K17 OmpK17 (*Klebsiella granulomatis*, Granuloma inguinale (Donovanosis)); fibronectin-binding protein Sfb, fibronectin/fibrinogen-binding protein FBP54, fibronectin-binding protein FbaA, M protein type 1 Emm1, M protein type 6 Emm6, immunoglobulin-binding protein 35 Sib35, Surface protein R28 Spr28, superoxide dismutase SOD, C5a peptidase ScpA, antigen I/II AgI/II, adhesin AspA, G-related alpha2-macroglobulin-binding protein GRAB, surface fibrillar protein M5 (*Streptococcus pyogenes*, Group A streptococcal infection); C protein β antigen, arginine deiminase proteins, adhesin BibA, 105 kDA protein BPS, surface antigens c, surface antigens R, surface antigens X, trypsin-resistant protein R1, trypsin-resistant protein R3, trypsin-resistant protein R4, surface immunogenic protein Sip, surface protein Rib, Leucine-rich repeats protein LrrG, serine-rich repeat protein Srr-2, C protein alpha-antigen Bca, Beta antigen Bag, surface antigen Epsilon, alpha-like protein ALP1, alpha-like protein ALP5 surface antigen delta, alpha-like protein ALP2, alpha-like protein ALP3, alpha-like protein ALP4, Cbeta protein Bac (*Streptococcus agalactiae*, Group B streptococcal infection); transferrin-binding protein 2 Tbp2, phosphatase P4, outer membrane protein P6, peptidoglycan-associated lipoprotein Pal, protein D, protein E, adherence and penetration protein Hap, outer membrane protein 26 Omp26, outer membrane protein P5 (Fimbrin), outer membrane protein D15, outer membrane protein OmpP2, 5'-nucleotidase NucA, outer membrane protein P1, outer membrane protein P2, outer membrane lipoprotein Pcp, Lipoprotein E, outer membrane protein P4, fuculokinase FucK, [Cu,Zn]-superoxide dismutase SodC, protease HtrA, protein O145, alpha-galactosylceramide (*Haemophilus influenzae, Haemophilus influenzae* infection); polymerase 3D, viral capsid protein VP1, viral capsid protein VP2, viral capsid protein VP3, viral capsid protein VP4, protease 2A, protease 3C (Enteroviruses, mainly Coxsackie A virus and *Enterovirus* 71 (EV71), Hand, foot and mouth disease (HFMD)); RNA polymerase L, protein L, glycoprotein Gn, glycoprotein Gc, nucleocapsid protein S, envelope glycoprotein G1, nucleoprotein NP, protein N, polyprotein M (Sin Nombre virus, Hantavirus, Hantavirus Pulmonary Syndrome (HPS)); heat shock protein HspA, heat shock protein HspB, citrate synthase GltA, protein UreB, heat shock protein Hsp60, neutrophil-activating protein NAP, catalase KatA, vacuolating cytotoxin VacA, urease alpha UreA, urease beta Ureb, protein Cpn10, protein groES, heat shock protein Hsp10, protein MopB, cytotoxicity-associated 10 kDa protein CAG, 36 kDa antigen, beta-lactamase HcpA, Beta-lactamase HcpB (*Helicobacter pylori, Helicobacter pylori* infection); integral membrane proteins, aggregation-prone proteins, O-antigen, toxin-antigens Stx2B, toxin-antigen Stx1B, adhesion-antigen fragment Int28, protein EspA, protein EspB, Intimin, protein Tir, protein IntC300, protein Eae (*Escherichia coli* O157:H7, O111 and O104:H4, Hemolytic-uremic syndrome (HUS)); RNA polymerase L, protein L, glycoprotein Gn, glycoprotein Gc, nucleocapsid protein S, envelope glycoprotein G1, nucleoprotein NP, protein N, polyprotein M (Bunyaviridae family, Hemorrhagic fever with renal syndrome (HFRS)); glycoprotein G, matrix protein M, nucleoprotein N, fusion protein F, polymerase L, protein W, proteinC, phosphoprotein p, non-structural protein V (Henipavirus (Hendra virus Nipah virus), Henipavirus infections); polyprotein, glycoproten Gp2, hepatitis A surface antigen HBAg, protein 2A, virus protein VP1, virus protein VP2, virus protein VP3, virus protein VP4, protein P1B, protein P2A, protein P3AB, protein P3D (Hepatitis A Virus, Hepatitis A); hepatitis B surface antigen HBsAg, Hepatitis B core antigen HbcAg, polymerase, protein Hbx, preS2 middle surface protein, surface protein L, large S protein, virus protein VP1, virus protein VP2, virus protein VP3, virus protein VP4 (Hepatitis B Virus (HBV), Hepatitis B); envelope glycoprotein E1 gp32 gp35, envelope glycoprotein E2 NS1 gp68 gp70, capsid protein C, core protein Core, polyprotein, virus protein VP1, virus protein VP2, virus protein VP3, virus protein VP4, antigen G, protein NS3, protein NS5A, (Hepatitis C Virus, Hepatitis C); virus protein VP1, virus protein VP2, virus protein VP3, virus protein VP4, large hepaptitis delta antigen, small hepaptitis delta antigen (Hepatitis D Virus, Hepatitis D); virus protein VP1, virus protein VP2, virus protein VP3, virus protein VP4, capsid protein E2 (Hepatitis E Virus, Hepatitis E); glycoprotein L UL1, uracil-DNA glycosylase UL2, protein UL3, protein UL4, DNA replication protein UL5, portal protein UL6, virion maturation protein UL7, DNA helicase UL8, replication origin-binding protein UL9, glycoprotein M UL10, protein UL11, alkaline exonuclease UL12, serine-threonine protein kinase UL13, tegument protein UL14, terminase UL15, tegument protein UL16, protein UL17, capsid protein VP23 UL18, major capsid protein VP5 UL19, membrane protein UL20, tegument protein UL21, Glycoprotein H (UL22), Thymidine Kinase UL23, protein UL24, protein UL25, capsid protein P40 (UL26, VP24, VP22A), glycoprotein B (UL27), ICP18.5 protein (UL28), major DNA-binding protein ICP8 (UL29), DNA polymerase UL30, nuclear matrix protein UL31, envelope glycoprotein UL32, protein UL33, inner nuclear membrane protein UL34, capsid protein VP26 (UL35), large tegument protein UL36, capsid assembly protein UL37, VP19C protein (UL38), ribonucleotide reductase (Large subunit) UL39, ribonucleotide reductase (Small subunit) UL40, tegument protein/virion host shutoff VHS protein (UL41), DNA polymerase processivity factor UL42, membrane protein UL43, glycoprotein C (UL44), membrane protein UL45, tegument proteins VP11/12 (UL46), tegument protein VP13/14 (UL47), virion maturation protein VP16 (UL48, Alpha-TIF), envelope protein UL49, dUTP diphosphatase UL50, tegument protein UL51, DNA helicase/primase complex protein UL52, glycoprotein K (UL53), transcriptional regulation protein IE63 (ICP27, UL54), protein UL55, protein UL56, viral replication protein ICP22 (1E68, US1), protein US2, serine/threonine-protein kinase US3, glycoprotein G (US4), glycoprotein J (US5), glycoprotein D (US6), glycoprotein I (US7), glycoprotein E (US8), tegument protein US9, capsid/tegument protein US10, Vmw21 protein (US11), ICP47 protein (IE12, US12), major transcriptional activator ICP4 (IE175, RS1), E3 ubiquitin ligase ICP0 (IE110), latency-related protein 1 LRP1, latency-related protein 2 LRP2, neurovirulence factor RL1 (ICP34.5), latency-associated transcript LAT (Herpes simplex virus 1 and 2 (HSV-1 and HSV-2), Herpes simplex); heat shock protein Hsp60, cell surface protein H1C, dipeptidyl peptidase type IV DppIV, M antigen, 70 kDa protein, 17 kDa histone-like protein (*Histoplasma capsulatum*, Histoplasmosis); fatty acid and retinol binding protein-1 FAR-1, tissue inhibitor of metalloproteinase TIMP (TMP), cysteine proteinase ACEY-1, cysteine proteinase ACCP-1, surface antigen Ac-16, secreted protein 2 ASP-2, metalloprotease 1 MTP-1, aspartyl protease inhibitor API-1, surface-associated antigen SAA-1, surface-associated antigen SAA-2, adult-specific secreted factor Xa, serine protease inhibitor anticoagulant AP, cathepsin D-like aspartic protease ARR-1, glutathione S-transferase GST, aspartic protease APR-1, acetylcholinesterase AChE (*Ancylostoma duodenale* and *Necator americanus*, Hookworm infection); protein NS1, protein NP1, protein VP1, protein VP2, protein VP3 (Human bocavirus (HBoV), Human bocavirus infection); major surface protein 2 MSP2, major surface protein 4 MSP4, MSP variant SGV1, MSP variant SGV2, outer membrane protein OMP, outer membrande protein 19 OMP-19, major antigenic protein MAP1, major antigenic protein MAP1-2, major antigenic protein MAP1B, major antigenic protein MAP1-3, Erum2510 coding protein, protein GroEL, protein GroES, 30-kDA major outer membrane proteins, GE 100-kDa protein, GE 130-kDa protein, GE 160-kDa protein (*Ehrlichia ewingii, Human ewingii* ehrlichiosis); major surface proteins 1-5 (MSP1a, MSP1b, MSP2, MSP3, MSP4, MSP5), type IV secreotion system proteins VirB2, VirB7, VirB11, VirD4 (*Anaplasma phagocytophilum*, Human granulocytic anaplasmosis (HGA)); protein NS1, small hydrophobic protein NS2, SH protein, fusion protein F, glycoprotein G, matrix protein M, matrix protein M2-1, matrix protein M2-2, phosphoprotein P, nucleoprotein N, polymerase L (Human metapneumovirus (hMPV), Human metapneumovirus infection); major surface protein 2 MSP2, major surface protein 4 MSP4, MSP variant SGV1, MSP variant SGV2, outer membrane protein OMP, outer membrande protein 19 OMP-19, major antigenic protein MAP1, major antigenic protein MAP1-2, major antigenic protein MAP1B, major antigenic protein MAP1-3, Erum2510 coding protein, protein GroEL, protein GroES, 30-kDA major outer membrane proteins, GE 100-kDa protein, GE 130-kDa protein, GE 160-kDa protein (*Ehrlichia chaffeensis*, Human monocytic ehrlichiosis); replication protein E1, regulatory protein E2, protein E3, protein E4, protein E5, protein E6, protein E7, protein E8, major capsid protein L1, minor capsid protein L2 (Human papillomavirus (HPV), Human papillomavirus (HPV) infection); fusion protein F, hemagglutinin-neuramidase HN, glycoprotein G, matrix protein M, phosphoprotein P, nucleoprotein N, polymerase L (Human parainfluenza viruses (HPIV), Human parainfluenza virus infection); Hemagglutinin (HA), Neuraminidase (NA), Nucleoprotein (NP), M1 protein, M2 protein, NS1 protein, NS2 protein (NEP protein: nuclear export protein), PA protein, PB1 protein (polymerase basic 1 protein), PB1-F2 protein and PB2 protein (Orthomyxoviridae family, Influenza virus (flu)); genome polyprotein, protein E, protein M, capsid protein C (Japanese encephalitis virus, Japanese encephalitis); RTX toxin, type IV pili, major pilus subunit PilA, regulatory transcription factors PilS and PilR, protein sigma54, outer membrane proteins (Kingella kingae, Kingella kingae infection); prion protein (Kuru prion, Kuru); nucleoprotein N, polymerase L, matrix protein Z, glycoprotein GP (Lassa virus, Lassa fever); peptidoglycan-associated lipoprotein PAL, 60 kDa chaperonin Cpn60 (groEL, HspB), type IV pilin PilE, outer membrane protein MIP, major outer membrane protein MompS, zinc metalloproteinase MSP (Legionella pneumophila, Legionellosis (Legionnaires' disease, Pontiac fever)); P4 nuclease, protein WD, ribonucleotide reductase M2, surface membrane glycoprotein Pg46, cysteine proteinase CP, glucose-regulated protein 78 GRP-78, stage-specific S antigen-like protein A2, ATPase F1, beta-tubulin, heat shock protein 70 Hsp70, KMP-11, glycoprotein GP63, protein BT1, nucleoside hydrolase NH, cell surface protein B1, ribosomal protein P1-like protein P1, sterol 24-c-methyltransferase SMT, LACK protein, histone H1, SPB1 protein, thiol specific antioxidant TSA, protein antigen STl1, signal peptidase SP, histone H2B, surface antigen PSA-2, cystein proteinase b Cpb (Leishmania genus, Leishmaniasis); major membrane protein I, serine-rich antigen-45 kDa, 10 kDa caperonin GroES, HSP kDa antigen, amino-oxononanoate synthase AONS, protein recombinase A RecA, Acetyl-/propionyl-coenzyme A carboxylase alpha, alanine racemase, 60 kDa chaperonin 2, ESAT-6-like protein EcxB (L-ESAT-6), protein Lsr2, protein ML0276, Heparin-binding hemagglutinin HBHA, heat-shock protein 65 Hsp65, mycP1 or ML0041 coding protein, htrA2 or ML0176 coding protein, htrA4 or ML2659 coding protein, gcp or ML0379 coding protein, clpC or ML0235 coding protein (Mycobacterium leprae and Mycobacterium lepromatosis, Leprosy); outer membrane protein LipL32, membrane protein LIC10258, membrane protein LP30, membrane protein LIC12238, Ompa-like protein Lsa66, surface protein LigA, surface protein LigB, major outer membrane protein OmpL1, outer membrane protein LipL41, protein LigAni, surface protein LcpA, adhesion protein LipL53, outer membrane protein UpL32, surface protein Lsa63, flagellin FlaB1, membran lipoprotein LipL21, membrane protein pL40, leptospiral surface adhesin Lsa27, outer membrane protein OmpL36, outer membrane protein OmpL37, outer membrane protein OmpL47, outer membrane protein OmpL54, acyltransferase LpxA (Leptospira genus, Leptospirosis); listeriolysin O precursor Hly (LLO), invasion-associated protein lap (P60), Listeriolysin regulatory protein PrfA, Zinc metalloproteinase Mpl, Phosphatidylinositol-specific phospholipase C PLC (PlcA, PlcB), o-acetyltransferase Oat, ABC-transporter permease Im.G_1771, adhesion protein LAP, LAP receptor Hsp60, adhesin LapB, haemolysin listeriolysin O LLO, protein ActA, Internalin A In1A, protein lnlB (Listeria monocytogenes, Listeriosis); outer surface protein A OspA, outer surface protein OspB, outer surface protein OspC, decorin binding protein A DbpA, decorin binding protein B DbpB, flagellar filament 41 kDa core protein Fla, basic membrane protein A BmpA (Immunodominant antigen P39), outer surface 22 kDa lipoprotein precursor (antigen IPLA7), variable surface lipoprotein vlsE (usually Borrelia burgdorferi and other Borrelia species, Lyme disease (Lyme borreliosis)); venom allergen homolog-like protein VAL-1, abundant larval transcript ALT-1, abundant larval transcript ALT-2, thioredoxin peroxidase TPX, vespid allergen homologue VAH, thiordoxin peroxidase 2 TPX-2, antigenic protein SXP (peptides N, N1, N2, and N3), activation associated protein-1 ASP-1, thioredoxin TRX, transglutaminase BmTGA, glutathione-S-transferases GST, myosin, vespid allergen homologue VAH, 175 kDa collagenase, glyceraldehyde-3-phosphate dehydrogenase GAPDH, cuticular collagen Col-4, Secreted Larval Acidic Proteins SLAPs, chitinase CHI-1, maltose binding protein MBP, glycolytic enzyme fructose-1,6-bisphosphate aldolase Fba, tropomyosin TMY-1, nematode specific gene product OvB20, onchocystatin CPI-2, protein Cox-2 (Wuchereria bancrofti and Brugia malayi, Lymphatic filariasis (Elephantiasis)); glycoprotein GP, matrix protein Z, polymerase L, nucleoprotein N (Lymphocytic choriomeningitis virus (LCMV), Lymphocytic choriomeningitis); thrombospondin-related anonymous protein TRAP, SSP2 Sporozoite surface protein 2, apical membrane antigen 1 AMA1, rhoptry membrane antigen RMA1, acidic basic repeat antigen ABRA, cell-traversal protein PF, protein Pvs25, merozoite surface protein 1 MSP-1, merozoite surface protein 2 MSP-2, ring-infected erythrocyte surface antigen RESALiver stage antigen 3 LSA-3, protein Eba-175, serine repeat antigen 5 SERA-5, circumsporozoite protein CS, merozoite surface protein 3 MSP3, merozoite surface protein 8 MSP8, enolase PF10, hepatocyte erythrocyte protein 17 kDa HEP17, erythrocyte membrane protein 1 EMP1, protein Kbetamerozoite surface protein 4/5 MSP 4/5, heat shock protein Hsp90, glutamate-rich protein GLURP, merozoite surface protein 4 MSP-4, protein STARP, circumsporozoite protein-related antigen precursor CRA (Plasmodium genus, Malaria); nucleoprotein N, membrane-associated protein VP24, minor nucleoprotein VP30, polymerase cofactor VP35, polymerase L, matrix protein VP40, envelope glycoprotein GP (Marburg virus, Marburg hemorrhagic fever (MHF)); protein C, matrix protein M, phosphoprotein P, non-structural protein V, hemagglutinin glycoprotein H, polymerase L, nucleoprotein N, fusion protein F (Measles virus, Measles); members of the ABC transporter family (LolC, OppA, and PotF), putative lipoprotein releasing system transmembrane protein LolC/E, flagellin FliC, Burkholderia intracellular motility A BimA, bacterial Elongation factor-Tu EF-Tu, 17 kDa OmpA-like protein, boaA coding protein, boaB coding protein (Burkholderia pseudomallei, Melioidosis (Whitmore's disease)); pilin proteins, minor pilin-associated subunit pilC, major pilin subunit and variants pilE, pilS, phase variation protein porA, Porin B PorB, protein TraD, Neisserial outer membrane antigen H.8, 70 kDa antigen, major outer membrane protein PI, outer membrane proteins PlA and PlB, W antigen, surface protein A NspA, transferrin binding protein TbpA, transferrin binding protein TbpB, PBP2, mtrR coding protein, ponA coding protein, membrane permease FbpBC, FbpABC protein system, LbpAB proteins, outer membrane protein Opa, outer membrane transporter FetA, iron-repressed regulator MpeR, factor H-binding protein fHbp, adhesin NadA, protein NhbA, repressor FarR (Neisseria meningitidis, Meningococcal disease); 66 kDa protein, 22 kDa protein (usually Metagonimus yokagawai, Metagonimiasis); polar tube proteins (34, 75, and 170 kDa in Glugea, 35, 55 and 150 kDa in Encephalitozoon), kinesin-related protein, RNA polymerase II largest subunit, similar of integral membrane protein YIPA, anti-silencing protein 1, heat shock transcription factor HSF, protein kinase, thymidine kinase, NOP-2 like nucleolar protein (Microsporidia phylum, Microsporidiosis); CASP8 and FADD-like apoptosis regulator, Glutathione peroxidase GPX1, RNA helicase NPH-II NPH2, Poly(A) polymerase catalytic subunit PAPL, Major envelope protein P43K, early transcription factor 70 kDa subunit VETFS, early transcription factor 82 kDa subunit VETFL, metalloendopeptidase G1-type, nucleoside triphosphatase I NPH1, replication protein A28-like MC134L, RNA polymease 7 kDa subunit RPO7 (*Molluscum contagiosum* virus (MCV), *Molluscum contagiosum* (MC)); matrix protein M, phosphoprotein P/V, small hydrophobic protein SH, nucleoprotein N, protein V, fusion glycoprotein F, hemagglutinin-neuraminidase HN, RNA polymerase L (Mumps virus, Mumps); Outer membrane proteins OM, cell surface antigen OmpA, cell surface antigen OmpB (sca5), cell surface protein SCA4, cell surface protein SCA1, intracytoplasmic protein D, crystalline surface layer protein SLP, protective surface protein antigen SPA (*Rickettsia typhi*, Murine typhus (Endemic typhus)); adhesin P1, adhesion P30, protein p116, protein P40, cytoskeletal protein HMW1, cytoskeletal protein HMW2, cytoskeletal protein HMW3, MPN152 coding protein, MPN426 coding protein, MPN456 coding protein, MPN-500coding protein (*Mycoplasma pneumoniae*, *Mycoplasma* pneumonia); NocA, Iron dependent regulatory protein, VapA, VapD, VapF, VapG, caseinolytic protease, filament tip-associated 43-kDa protein, protein P24, protein P61, 15-kDa protein, 56-kDa protein (usually *Nocardia asteroides* and other *Nocardia* species, Nocardiosis); venom allergen homolog-like protein VAL-1, abundant larval transcript ALT-1, abundant larval transcript ALT-2, thioredoxin peroxidase TPX, vespid allergen homologue VAH, thiordoxin peroxidase 2 TPX-2, antigenic protein SXP (peptides N, N1, N2, and N3), activation associated protein-1 ASP-1, Thioredoxin TRX, transglutaminase BmTGA, glutathione-S-transferases GST, myosin, vespid allergen homologue VAH, 175 kDa collagenase, glyceraldehyde-3-phosphate dehydrogenase GAPDH, cuticular collagen Col-4, Secreted Larval Acidic Proteins SLAPs, chitinase CHI-1, maltose binding protein MBP, glycolytic enzyme fructose-1,6-bisphosphate aldolase Fba, tropomyosin TMY-1, nematode specific gene product OvB20, onchocystatin CPI-2, Cox-2 (*Onchocerca volvulus*, Onchocerciasis (River blindness)); 43 kDa secreted glycoprotein, glycoprotein gp0, glycoprotein gp75, antigen Pb27, antigen Pb40, heat shock protein Hsp65, heat shock protein Hsp70, heat shock protein Hsp90, protein P10, triosephosphate isomerase TPI, N-acetyl-glucosamine-binding lectin Paracoccin, 28 kDa protein Pb28 (*Paracoccidioides brasiliensis*, Paracoccidioidomycosis (South American blastomycosis)); 28-kDa cruzipain-like cystein protease Pw28CCP (usually *Paragonimus westermani* and other *Paragonimus* species, Paragonimiasis); outer membrane protein OmpH, outer membrane protein Omp28, protein PM1539, protein PM0355, protein PM1417, repair protein MutL, protein BcbC, protein PM0305, formate dehydrogenase-N, protein PM0698, protein PM1422, DNA gyrase, lipoprotein PlpE, adhesive protein Cp39, heme aquisition system receptor HasR, 39 kDa capsular protein, iron-regulated OMP IROMP, outer membrane protein OmpA87, fimbrial protein Ptf, fimbrial subunit protein PtfA, transferrin binding protein Tbpl, esterase enzyme MesA, *Pasteurella multocida* toxin PMT, adhesive protein Cp39 (*Pasteurella* genus, Pasteurellosis); "filamentous hemagglutinin FhaB, adenylate cyclase CyaA, pertussis toxin subunit 4 precursor PtxD, pertactin precursor Prn, toxin subunit 1 PtxA, protein Cpn60, protein brkA, pertussis toxin subunit 2 precursor PtxB, pertussis toxin subunit 3 precursor PtxC, pertussis toxin subunit 5 precursor PtxE, pertactin Prn, protein Fim2, protein Fim3;" (*Bordetella pertussis*, Pertussis (Whooping cough)); "F1 capsule antigen, virulence-associated V antigen, secreted effector protein LcrV, V antigen, outer membrane protease Pla, secreted effector protein YopD, putative secreted protein-tyrosine phosphatase YopH, needle complex major subunit YscF, protein kinase YopO, putative autotransporter protein YapF, inner membrane ABC-transporter YbtQ (Irp7), putative sugar binding protein YP00612, heat shock protein 90 HtpG, putative sulfatase protein YdeN, outer-membrane lipoprotein carrier protein LolA, secretion chaperone YerA, putative lipoprotein YPO0420, hemolysin activator protein HpmB, pesticin/yersiniabactin outer membrane receptor Psn, secreted effector protein YopE, secreted effector protein YopF, secreted effector protein YopK, outer membrane protein YopN, outer membrane protein YopM, Coagulase/fibrinolysin precursor Pla;" (*Yersinia pestis*, Plague); protein PhpA, surface adhesin PsaA, pneumolysin Ply, ATP-dependent protease Clp, lipoate-protein ligase LplA, cell wall surface anchored protein psrP, sortase SrtA, glutamyl-tRNA synthetase GltX, choline binding protein A CbpA, pneumococcal surface protein A PspA, pneumococcal surface protein C PspC, 6-phosphogluconate dehydrogenase Gnd, iron-binding protein PiaA, Murein hydrolase LytB, proteon LytC, protease A1 (*Streptococcus pneumoniae*, Pneumococcal infection); major surface protein B, kexin-like protease KEX1, protein A12, 55 kDa antigen P55, major surface glycoprotein Msg (*Pneumocystis jirovecii, Pneumocystis* pneumonia (PCP)); genome polyprotein, polymerase 3D, viral capsid protein VP1, viral capsid protein VP2, viral capsid protein VP3, viral capsid protein VP4, protease 2A, protease 3C (Poliovirus, Poliomyelitis); protein Nfa1, exendin-3, secretory lipase, cathepsin B-like protease, cysteine protease, cathepsin, peroxiredoxin, protein Cry1Ac (usually *Naegleria fowleri*, Primary amoebic meningoencephalitis (PAM)); agnoprotein, large T antigen, small T antigen, major capsid protein VP1, minor capsid protein Vp2 (JC virus, Progressive multifocal leukoencephalopathy); low calcium response protein E LCrE, chlamydial outer protein N CopN, serine/threonine-protein kinase PknD, acyl-carrier-protein S-malonyltransferase FabD, single-stranded DNA-binding protein Ssb, major outer membrane protein MOMP, outer membrane protein 2 Omp2, polymorphic membrane protein family (Pmp1, Pmp2, Pmp3, Pmp4, Pmp5, Pmp6, Pmp7, Pmp8, Pmp9, Pmp10, Pmp11, Pmp12, Pmp13, Pmp14, Pmp15, Pmp16, Pmp17, Pmp18, Pmp19, Pmp20, Pmp21) (*Chlamydophila psittaci*, Psittacosis); outer membrane protein P1, heat shock protein B HspB, peptide ABC transporter, GTP-binding protein, protein IcmB, ribonuclease R, phosphatas SixA, protein DsbD, outer membrane protein TolC, DNA-binding protein PhoB, ATPase DotB, heat shock protein B HspB, membrane protein Com1, 28 kDa protein, DNA-3-methyladenine glycosidase I, pouter membrane protein OmpH, outer membrane protein AdaA, glycine cleavage system T-protein (*Coxiella burnetii*, Q fever); nucleoprotein N, large structural protein L, phophoprotein P, matrix protein M, glycoprotein G (Rabies virus, Rabies); fusionprotein F, nucleoprotein N, matrix protein M, matrix protein M2-1, matrix protein M2-2, phophoprotein P, small hydrophobic protein SH, major surface glycoprotein G, polymerase L, non-structural protein 1 NS1, non-structural protein 2 NS2 (Respiratory syncytial virus (RSV), Respiratory syncytial virus infection); genome polyprotein, polymerase 3D, viral capsid protein VP1, viral capsid protein VP2, viral capsid protein VP3, viral capsid protein VP4, protease 2A, protease 3C (Rhinovirus, Rhinovirus infection); outer membrane proteins OM, cell surface antigen OmpA, cell surface antigen OmpB (sca5), cell surface protein SCA4, cell surface protein SCA1, protein PS120, intracytoplasmic protein D, protective surface protein antigen SPA (*Rickettsia* genus, Rickettsial infection); outer membrane proteins OM, cell surface antigen OmpA, cell surface antigen OmpB (sca5), cell surface protein SCA4, cell surface protein SCA1, intracytoplasmic protein D (*Rickettsia akari*, Rickettsialpox); envelope glycoprotein GP, polymerase L, nucleoprotein N, non-structural protein NSS (Rift Valley fever virus, Rift Valley fever (RVF)); outer membrane proteins OM, cell surface antigen OmpA, cell surface antigen OmpB (sca5), cell surface protein SCA4, cell surface protein SCA1, intracytoplasmic protein D (*Rickettsia rickettsii*, Rocky mountain spotted fever (RMSF)); "non-structural protein 6 NS6, non-structural protein 2 NS2, intermediate capsid protein VP6, inner capsid protein VP2, non-structural protein 3 NS3, RNA-directed RNA polymerase L, protein VP3, non-structural protein 1 NS1, non-structural protein 5 NSS, outer capsid glycoprotein VP7, non-structural glycoprotein 4 NS4, outer capsid protein VP4" (Rotavirus, Rotavirus infection); polyprotein P200, glycoprotein E1, glycoprotein E2, protein NS2, capsid protein C (Rubella virus, Rubella); chaperonin GroEL (MopA), inositol phosphate phosphatase SopB, heat shock protein HslU, chaperone protein DnaJ, protein TviB, protein IroN, flagellin FliC, invasion protein SipC, glycoprotein gp43, outer membrane protein LamB, outer membrane protein PagC, outer membrane protein TolC, outer membrane protein NmpC, outer membrane protein FadL, transport protein SadA, transferase WgaP, effector proteins SifA, SteC, SseL, SseJ and SseF (*Salmonella* genus, Salmonellosis), protein 14, non-structural protein NS7b, non-structural protein NS8a, protein 9b, protein 3a, nucleoprotein N, non-structural protein NS3b, non-structural protein NS6, protein 7a, non-structural protein NS8b, membrane protein M, envelope small membrane protein EsM, replicase polyprotein 1a, spike glycoprotein S, replicase polyprotein 1ab; (SARS coronavirus, SARS (Severe Acute Respiratory Syndrome)); serin protease, Atypical *Sarcoptes* Antigen 1 ASA1, glutathione S-transferases GST, cystein protease, serine protease, apolipoprotein (*Sarcoptes scabiei*, Scabies); glutathione S-transferases GST, paramyosin, hemoglbinase SM32, major egg antigen, 14 kDa fatty acid-binding protein Sm14, major larval surface antigen P37, 22.6 kDa tegumental antigen, calpain CANP, triphospate isomerase Tim, surface protein 9B, outer capsid protein VP2, 23 kDa integral membrane protein Sm23, Cu/Zn-superoxide dismutase, glycoprotein Gp, myosin (*Schistosoma* genus, Schistosomiasis (Bilharziosis)); 60 kDa chaperonin, 56 kDa type-specific antigen, pyruvate phosphate dikinase, 4-hydroxybenzoate octaprenyltransferase (*Orientia tsutsugamushi*, Scrub typhus); dehydrogenase GuaB, invasion protein Spa32, invasin IpaA, invasin IpaB, invasin IpaC, invasin IpaD, invasin IpaH, invasin IpaJ (*Shigella* genus, Shigellosis (Bacillary dysentery)); protein P53, virion protein US10 homolog, transcriptional regulator IE63, transcriptional transactivator IE62, protease P33, alpha trans-inducing factor 74 kDa protein, deoxyuridine 5'-triphosphate nucleotidohydrolase, transcriptional transactivator IE4, membrane protein UL43 homolog, nuclear phosphoprotein UL3 homolog, nuclear protein UL4 homolog, replication origin-binding protein, membrane protein 2, phosphoprotein 32, protein 57, DNA polymerase processivity factor, portal protein 54, DNA primase, tegument protein UL14 homolog, tegument protein UL21 homolog, tegument protein UL55 homolog,tripartite terminase subunit UL33 homolog,tripartite terminase subunit UL15 homolog, capsid-binding protein 44, virion-packaging protein 43 (Varicella zoster virus (VZV), Shingles (Herpes zoster)); truncated 3-beta hydroxy-5-ene steroid dehydrogenase homolog, virion membrane protein A13, protein A19, protein A31, truncated protein A35 homolog, protein A37.5 homolog, protein A47, protein A49, protein A51, semaphorin-like protein A43, serine proteinase inhibitor 1, serine proteinase inhibitor 2, serine proteinase inhibitor 3, protein A6, protein B15, protein C1, protein C5, protein C6, protein F7, protein F8, protein F9, protein F11, protein F14, protein F15, protein F16 (Variola major or Variola minor, Smallpox (Variola)); adhesin/glycoprotein gp70, proteases (*Sporothrix schenckii*, Sporotrichosis); heme-iron binding protein IsdB, collagen adhesin Cna, clumping factor A ClfA, protein MecA, fibronectin-binding protein A FnbA, enterotoxin type A EntA, enterotoxin type B EntB, enterotoxin type C EntC1, enterotoxin type C EntC2, enterotoxin type D EntD, enterotoxin type E EntE, Toxic shock syndrome toxin-1 TSST-1, Staphylokinase, Penicillin binding protein 2a PBP2a (MecA), secretory antigen SssA (*Staphylococcus* genus, Staphylococcal food poisoning); heme-iron binding protein IsdB, collagen adhesin Cna, clumping factor A ClfA, protein MecA, fibronectin-binding protein A FnbA, enterotoxin type A EntA, enterotoxin type B EntB, enterotoxin type C EntC1, enterotoxin type C EntC2, enterotoxin type D EntD, enterotoxin type E EntE, Toxic shock syndrome toxin-1 TSST-1, Staphylokinase, Penicillin binding protein 2a PBP2a (MecA), secretory antigen SssA (*Staphylococcus* genus e.g. *aureus*, Staphylococcal infection); antigen Ss-IR, antigen NIE, strongylastacin, Na+-K+ ATPase Sseat-6, tropomysin SsTmy-1, protein LEC-5, 41 kDa antigen P5, 41-kDa larval protein, 31-kDa larval protein, 28-kDa larval protein (*Strongyloides stercoralis*, Strongyloidiasis); glycerophosphodiester phosphodiesterase GlpQ (Gpd), outer membrane protein TmpB, protein Tp92, antigen TpF1, repeat protein Tpr, repeat protein F TprF, repeat protein G TprG, repeat protein I TprI, repeat protein J TprJ, repeat protein K TprK, treponemal membrane protein A TmpA, lipoprotein, 15 kDa Tpp15, 47 kDa membrane antigen, miniferritin TpF1, adhesin Tp0751, lipoprotein TP0136, protein TpN17, protein TpN47, outer membrane protein TP0136, outer membrane protein TP0155, outer membrane protein TP0326, outer membrane protein TP0483, outer membrane protein TP0956 (*Treponema pallidum*, Syphilis); Cathepsin L-like proteases, 53/25-kDa antigen, 8 kDa family members, cysticercus protein with a marginal trypsin-like activity TsAg5, oncosphere protein TSOL18, oncosphere protein TSOL45-1A, lactate dehydrogenase A LDHA, lactate dehydrogenase B LDHB (*Taenia* genus, Taeniasis); tetanus toxin TetX, tetanus toxin C TTC, 140 kDa S layer protein, flavoprotein beta-subunit CT3, phospholipase (lecithinase), phosphocarrier protein HPr (*Clostridium tetani*, Tetanus (Lockjaw)); genome polyprotein, protein E, protein M, capsid protein C (Tick-borne encephalitis virus (TBEV), Tick-borne encephalitis); 58-kDa antigen, 68-kDa antigens, *Toxocara* larvae excretory-secretory antigen TES, 32-kDa glycoprotein, glycoprotein TES-70, glycoprotein GP31, excretory-secretory antigen TcES-57, perienteric fluid antigen Pe, soluble extract antigens Ex, excretory/secretory larval antigens ES, antigen TES-120, polyprotein allergen TBA-1, cathepsin L-like cysteine protease c-cpl-1, 26-kDa protein (*Toxocara canis* or *Toxocara cati*, Toxocariasis (Ocular Larva Migrans (OLM) and Visceral Larva Migrans (VLM))); microneme proteins (MIC1, MIC2, MIC3, MIC4, MIC5, MICE, MIC7, MIC8), rhoptry protein Rop2, rhoptry proteins (Rop1, Rop2, Rop3, Rop4, Rop5, Rop6, Rop7, Rop16, Rjop17), protein SR1, surface antigen P22, major antigen p24, major surface antigen p30, dense granule proteins (GRA1, GRA2, GRA3, GRA4, GRA5, GRA6, GRA7, GRA8, GRA9, GRA10), 28 kDa antigen, surface antigen SAG1, SAG2 related antigen, nucleoside-triphosphatase 1, nucleoside-triphosphatase 2, protein Stt3, HesB-like domain-containing protein, rhomboid-like protease 5, toxomepsin 1 (*Toxoplasma gondii*, Toxoplasmosis); 43 kDa secreted glycoprotein, 53 kDa secreted glycoprotein, paramyosin, antigen Ts21, antigen Ts87, antigen p46000, TSL-1 antigens, caveolin-1 CAV-1, 49 kDa newborn larva antigen, prosaposin homologue, serine protease, serine proteinase inhibitor, 45-kDa glycoprotein Gp45 (*Trichinella spiralis*, Trichinellosis); Myb-like transcriptional factors (Myb1, Myb2, Myb3), adhesion protein AP23, adhesion protein AP33, adhesin protein AP33-3, adhesins AP51, adhesin AP65, adhesion protein AP65-1, alpha-actinin, kinesin-associated protein, teneurin, 62 kDa proteinase, subtilisin-like serine protease SUB1, cysteine proteinase gene 3 CP3, alpha-enolase Eno1, cysteine proteinase CP30, heat shock proteins (Hsp70, Hsp60), immunogenic protein P270, (*Trichomonas vaginalis*, Trichomoniasis); beta-tubulin, 47-kDa protein, secretory leucocyte-like proteinase-1 SLP-1, 50-kDa protein TT50, 17 kDa antigen, 43/47 kDa protein (*Trichuris trichiura*, Trichuriasis (Whipworm infection)); protein ESAT-6 (EsxA), 10 kDa filtrate antigen EsxB, secreted antigen 85-B FBPB, fibronectin-binding protein A FbpA (Ag85A), serine protease PepA, PPE family protein PPE18, fibronectin-binding protein D FbpD, immunogenic protein MPT64, secreted protein MPT51, catalase-peroxidase-peroxynitritase T KATG, periplasmic phosphate-binding lipoprotein PSTS3 (PBP-3, Phos-1), iron-regulated heparin binding hemagglutinin Hbha, PPE family protein PPE14, PPE family protein PPE68, protein Mtb72F, protein Apa, immunogenic protein MPT63, periplasmic phosphate-binding lipoprotein PSTS1 (PBP-1), molecular chaperone DnaK, cell surface lipoprotein Mpt83, lipoprotein P23, phosphate transport system permease protein pstA, 14 kDa antigen, fibronectin-binding protein C FbpC1, Alanine dehydrogenase TB43, Glutamine synthetase 1, ESX-1 protein, protein CFP10, TB10.4 protein, protein MPT83, protein MTB12, protein MTBE, Rpf-like proteins, protein MTB32, protein MTB39, crystallin, heat-shock protein HSP65, protein PST-S (usually *Mycobacterium tuberculosis*, Tuberculosis); outer membrane protein FobA, outer membrane protein FobB, intracellular growth locus lglC1, intracellular growth locus IglC2, aminotransferase Wbtl, chaperonin GroEL, 17 kDa major membrane protein TUL4, lipoprotein LpnA, chitinase family 18 protein, isocitrate dehydrogenase, Nif3 family protein, type IV pili glycosylation protein, outer membrane protein tolC, FAD binding family protein, type IV pilin multimeric outer membrane protein, two component sensor protein KdpD, chaperone protein DnaK, protein TolQ (*Francisella tularensis*, Tularemia); "MB antigen, urease, protein GyrA, protein GyrB, protein ParC, protein ParE, lipid associated membrane proteins LAMP, thymidine kinase TK, phospholipase PL-A1, phospholipase PL-A2, phospholipase PL-C, surface-expressed 96-kDa antigen;" (*Ureaplasma urealyticum*, Ureaplasma urealyticum infection); non-structural polyprotein, structural polyprotein, capsid protein CP, protein E1, protein E2, protein E3, protease P1, protease P2, protease P3 (Venezuelan equine encephalitis virus, Venezuelan equine encephalitis); glycoprotein GP, matrix protein Z, polymerase L, nucleoprotein N (Guanarito virus, Venezuelan hemorrhagic fever); polyprotein, protein E, protein M, capsid protein C, protease NS3, protein NS1, protein NS2A, protein AS2B, protein NS4A, protein NS4B, protein NS5 (West Nile virus, West Nile Fever); capsid protein CP, protein E1, protein E2, protein E3, protease P2 (Western equine encephalitis virus, Western equine encephalitis); genome polyprotein, protein E, protein M, capsid protein C, protease NS3, protein NS1, protein NS2A, protein AS2B, protein NS4A, protein NS4B, protein NS5 (Yellow fever virus, Yellow fever); putative Yop targeting protein YobB, effector protein YopD, effector protein YopE, protein YopH, effector protein YopJ, protein translocation protein YopK, effector protein YopT, protein YpkA, flagellar biosyntheses protein FlhA, peptidase M48, potassium efflux system KefA, transcriptional regulatoer RovA, adhesin Ifp, translocator portein LcrV, protein PcrV, invasin Inv, outer membrane protein OmpF-like porin, adhesin YadA, protein kinase C, phospholipase C1, protein PsaA, mannosyltransferase-like protein WbyK, protein YscU, antigen YPMa (*Yersinia pseudotuberculosis*, Yersinia pseudotuberculosis infection); effector protein YopB, 60 kDa chaperonin, protein WbcP, tyrosin-protein phosphatase YopH, protein YopQ, enterotoxin, Galactoside permease, reductaase NrdE, protein YasN, Invasin Inv, adhesin YadA, outer membrane porin F OmpF, protein UspA1, protein EibA, protein Hia, cell surface protein Ail, chaperone SycD, protein LcrD, protein LcrG, protein LcrV, protein SycE, protein YopE, regulator protein TyeA, protein YopM, protein YopN, protein YopO, protein YopT, protein YopD, protease ClpP, protein MyfA, protein FilA, and protein PsaA (*Yersinia enterocolitica*, Yersiniosis) (in brackets is the particular pathogen or the family of pathogens of which the antigen(s) is/are derived and the infectious disease with which the pathogen is associated).

In particularly preferred embodiments the pathogenic antigen is selected from a) HIV p24 antigen, HIV envelope proteins (Gp120, Gp41, Gp160), polyprotein GAG, negative factor protein Nef, trans-activator of transcription Tat if the infectious disease is HIV, preferably an infection with Human immunodeficiency virus, b) major outer membrane protein MOMP, probable outer membrane protein PMPC, outer membrane complex protein B OmcB, heat shock proteins Hsp60 HSP10, protein IncA, proteins from the type III secretion system, ribonucleotide reductase small chain protein NrdB, plasmid protein Pgp3, chlamydial outer protein N CopN, antigen CT521, antigen CT425, antigen CT043, antigen TC0052, antigen TC0189, antigen TC0582, antigen TC0660, antigen TC0726, antigen TC0816, antigen TC0828 if the infectious disease is an infection with *Chlamydia trachomatis*, c) pp65 antigen, membrane protein pp15, capsid-proximal tegument protein pp150, protein M45, DNA polymerase UL54, helicase UL105, glycoprotein gM, glycoprotein gN, glcoprotein H, glycoprotein B gB, protein UL83, protein UL94, protein UL99 if the infectious disease is Cytomegalovirus infection, preferably an infection with Cytomegalovirus (CMV);

d) capsid protein C, premembrane protein prM, membrane protein M, envelope protein E (domain I, domain II, domain II), protein NS1, protein NS2A, protein NS2B, protein NS3, protein NS4A, protein 2K, protein NS4B, protein NS5 if the infectious disease is Dengue fever, preferably an infection with Dengue viruses (DEN-1, DEN-2, DEN-3 and DEN-4)-Flaviviruses;

e) hepatitis B surface antigen HBsAg, Hepatitis B core antigen HbcAg, polymerase, protein Hbx, preS2 middle surface protein, surface protein L, large S protein, virus protein VP1, virus protein VP2, virus protein VP3, virus protein VP4 if the infectious disease is Hepatits B, preferably an infection with Hepatitis B Virus (HBV);

f) replication protein E1, regulatory protein E2, protein E3, protein E4, protein ES, protein E6, protein E7, protein E8, major capsid protein L1, minor capsid protein L2 if the infectious disease is Human papillomavirus (HPV) infection, preferably an infection with Human papillomavirus (HPV);

g) fusion protein F, hemagglutinin-neuramidase HN, glycoprotein G, matrix protein M, phosphoprotein P, nucleoprotein N, polymerase L if the infectious disease is Human parainfluenza virus infection, preferably an infection with Human parainfluenza viruses (HPIV);

h) Hemagglutinin (HA), Neuraminidase (NA), Nucleoprotein (NP), M1 protein, M2 protein, NS1 protein, NS2 protein (NEP protein: nuclear export protein), PA protein, PB1 protein (polymerase basic 1 protein), PB1-F2 protein and PB2 protein (Orthomyxoviridae family, Influenza virus (flu));

i) nucleoprotein N, large structural protein L, phophoprotein P, matrix protein M, glycoprotein G if the infectious disease is Rabies, preferably an infection with Rabies virus;

j) fusionprotein F, nucleoprotein N, matrix protein M, matrix protein M2-1, matrix protein M2-2, phophoprotein P, small hydrophobic protein SH, major surface glycoprotein G, polymerase L, non-structural protein 1 NS1, non-structural protein 2 NS2 if the infectious disease is Respiratory syncytial virus infection, preferably an infection with Respiratory syncytial virus (RSV);

k) secretory antigen SssA (*Staphylococcus* genus, Staphylococcal food poisoning); secretory antigen SssA (*Staphylococcus* genus e.g. *aureus*, Staphylococcal infection); molecular chaperone DnaK, cell surface lipoprotein Mpt83, lipoprotein P23, phosphate transport system permease protein pstA, 14 kDa antigen, fibronectin-binding protein C FbpC1, Alanine dehydrogenase TB43, Glutamine synthetase 1, ESX-1 protein, protein CFP10, TB10.4 protein, protein MPT83, protein MTB12, protein MTB8, Rpf-like proteins, protein MTB32, protein MTB39, crystallin, heat-shock protein HSP65, protein PST-S if the infectious disease is Tuberculosis, preferably an infection with *Mycobacterium tuberculosis*;

or genome polyprotein, protein E, protein M, capsid protein C, protease NS3, protein NS1, protein NS2A, protein AS2B, protein NS4A, protein NS4B, protein NS5 if the infectious disease is Yellow fever, preferably an infection with Yellow fever virus.

EXAMPLES

The following examples are intended to further illustrate the invention. They are merely illustrative and not intended to limit the scope of the subject matter of the invention.

Example 1: Preparation of Compositions According to the Invention

For the following examples, a DNA sequence encoding Gaussia princeps luciferase (GpLuc) was prepared and used for subsequent RNA in vitro transcription reactions. The obtained mRNA constructs were used for further in vitro and in vivo experiments. The respective amino acid sequences and the mRNA sequences of GpLuc and PpLuc as well as preparation step details are provided below.

GpLuc, amino acid sequence (SEQ ID NO: 11):
MGVKVLFALICIAVAEAKPTENNEDFNIVAVASNFATTDLDADRGKLPGKK
LPLEVLKEMEANARKAGCTRGCLICLSHIKCTPKMKKFIPGRCHTYEGDKE
SAQGGIGEAIVDIPEIPGFKDLEPMEQFIAQVDLCVDCTTGCLKGLANVQC
SDLLKKWLPQRCATFASKIQGQVDKIKGAGGD GpLuc, mRNA sequence
(SEQ ID NO: 12), also labelled
R2851 herein:
GGGGCGCUGCCUACGGAGGUGGCAGCCAUCUCCUUCUCGGCAUCAAGCUUA
CCAUGGGCGUGAAGGUCCUGUUCGCCCUCAUCUGCAUCGCCGUGGCGGAGG
CCAAGCCCACCGAGAACAACGAGGACUUCAACAUCGUGGCCGUCGCCAGCA
ACUUCGCCACCACGGACCUGGACGCGGACCGGGGAAGCUGCCGGGCAAGA
AGCUCCCCUGGAGGUGCUGAAGGAGAUGGAGGCCAACGCCCGCAAGGCCG
GGUGCACCCGGGCUGCCUCAUCUGCCUGUCCCACAUCAAGUGCACCCCCA
AGAUGAAGAAGUUCAUCCCCGGGCGCUGCCACACCUACGAGGGCGACAAGG
AGAGCGCGCAGGGCGGGAUCGGCGAGGCCAUCGUGGACAUCCCGGAGAUCC
CCGGGUUCAAGGACCUGGAGCCCAUGGAGCAGUUCAUCGCCCAGGUCGACC
UCUGCGUGGACUGCACGACCGGCUGCCUGAAGGGGCUGGCCAACGUGCAGU
GCUCCGACCUCCUGAAGAAGUGGCUGCCCCAGCGGUGCGCCACCUUCGCGA
GCAAGAUCCAGGGCCAGGUCGACAAGAUCAAGGGCGCCGGGGGCGACUGAG
GACUAGUGCAUCACAUUUAAAAGCAUCUCAGCCUACCAUGAGAAUAAGAGA
AAGAAAAUGAAGAUCAAUAGCUUAUUCAUCUCUUUUUCUUUUUCGUUGGUG
UAAAGCCAACACCCUGUCUAAAAAACAUAAAUUUCUUUAAUCAUUUUGCCU
CUUUUCUCUGUGCUUCAAUUAAUAAAAAAUGGAAAGAACCUAGAUCUAAAA
AAAAAAAAAAAAAAAAAAAAAAAAAAAAAAAAAAAAAAAAAAAAAAAAAA
AAAAAAAAAUGCAUCCCCCCCCCCCCCCCCCCCCCCCCCCCCCAAAGGC
UCUUUUCAGAGCCACCAGAAUU PpLuc, amino acid sequence (SEQ ID NO: 18):
MEDAKNIKKGPAPFYPLEDGTAGEQLHKAMKRYALVPGTIAFTDAHIEVDI
TYAEYFEMSVRLAEAMKRYGLNTNHRIVVCSENSLQFFMPVLGALFIGVAV
APANDIYNERELLNSMGISQPTVVFVSKKGLQKILNVQKKLPIIQKIIIMD
SKTDYQGFQSMYTFVTSHLPPGFNEYDFVPESFDRDKTIALIMNSSGSTGL
PKGVALPHRTACVRFSHARDPIFGNQIIPDTAILSVVPFHHGFGMFTTLGY
LICGFRVVLMYRFEEELFLRSLQDYKIQSALLVPTLFSFFAKSTLIDKYDL
SNLHEIASGGAPLSKEVGEAVAKRFHLPGIRQGYGLTETTSAILITPEGDD
KPGAVGKVVPFFEAKVVDLDTGKTLGVNQRGELCVRGPMIMSGYVNNPEAT
NALIDKDGWLHSGDIAYVVDEDEHFFIVDRLKSLIKYKGYQVAPAELESIL
LQHPNIFDAGVAGLPDDDAGELPAAVVVLEHGKTMTEKEIVDYVASQVTTA
KKLRGGVVFVDEVPKGLTGKLDARKIREILIKAKKGGKIAV PpLuc, mRNA sequence (SEQ ID NO: 19):
GGGGCGCUGCCUACGGAGGUGGCAGCCAUCUCCUUCUCGGCAUCAAGCUUG

AGGAUGGAGGACGCCAAGAACAUCAAGAAGGGCCCGGCGCCCUUCUACCCG

CUGGAGGACGGGACCGCCGGCGAGCAGCUCCACAAGGCCAUGAAGCGGUAC

GCCCUGGUGCCGGGCACGAUCGCCUUCACCGACGCCCACAUCGAGGUCGAC

AUCACCUACGCGGAGUACUUCGAGAUGAGCGUGCGCCUGGCCGAGGCCAUG

AAGCGGUACGGCCUGAACACCAACCACCGGAUCGUGGUGUGCUCGGAGAAC

AGCCUGCAGUUCUUCAUGCCGGUGCUGGGCGCCCUCUUCAUCGGCGUGGCC

GUCGCCCCGGCGAACGACAUCUACAACGAGCGGGAGCUGCUGAACAGCAUG

GGGAUCAGCCAGCCGACCGUGGUGUUCGUGAGCAAGAAGGGCCUGCAGAAG

AUCCUGAACGUGCAGAAGAAGCUGCCCAUCAUCCAGAAGAUCAUCAUCAUG

GACAGCAAGACCGACUACCAGGGCUUCCAGUCGAUGUACACGUUCGUGACC

AGCCACCUCCCGCCGGGCUUCAACGAGUACGACUUCGUCCCGGAGAGCUUC

GACCGGGACAAGACCAUCGCCCUGAUCAUGAACAGCAGCGGCAGCACCGGC

CUGCCGAAGGGGUGGCCCUGCCGCACCGGACCGCCUGCGUGCGCUUCUCG

CACGCCCGGGACCCCAUCUUCGGCAACCAGAUCAUCCCGGACACCGCCAUC

CUGAGCGUGGUGCCGUUCCACCACGGCUUCGGCAUGUUCACGACCCUGGGC

UACCUCAUCUGCGGCUUCCGGGUGGUCCUGAUGUACCGGUUCGAGGAGGAG

CUGUUCCUGCGGAGCCUGCAGGACUACAAGAUCCAGAGCGCGCUGCUCGUG

CCGACCCUGUUCAGCUUCUUCGCCAAGAGCACCCUGAUCGACAAGUACGAC

CUGUCGAACCUGCACGAGAUCGCCAGCGGGGCGCCCCGCUGAGCAAGGAG

GUGGGCGAGGCCGUGGCCAAGCGGUUCCACCUCCCGGGCAUCCGCCAGGGC

UACGGCCUGACCGAGACCACGAGCGCGAUCCUGAUCACCCCGAGGGGGAC

GACAAGCCGGGCGCCGUGGGCAAGGUGGUCCCGUUCUUCGAGGCCAAGGUG

GUGGACCUGGACACCGGCAAGACCCUGGGCGUGAACCAGCGGGGCGAGCUG

UGCGUGCGGGGCCGAUGAUCAUGAGCGGCUACGUGAACAACCCGGAGGCC

ACCAACGCCCUCAUCGACAAGGACGGCUGGCUGCACAGCGGCGACAUCGCC

UACUGGGACGAGGACGAGCACUUCUUCAUCGUCGACCGGCUGAAGUCGCUG

AUCAAGUACAAGGGCUACCAGGUGGCGCCGGCCGAGCUGGAGAGCAUCCUG

CUCCAGCACCCCAACAUCUUCGACGCCGGCGUGGCCGGGCUGCCGGACGAC

GACGCCGGCGAGCUGCCGGCCGCGGUGGUGGUGCUGGAGCACGGCAAGACC

AUGACGGAGAAGGAGAUCGUCGACUACGUGGCCAGCCAGGUGACCACCGCC

AAGAAGCUGCGGGGCGGCGUGGUGUUCGUGGACGAGGUCCCGAAGGGCCUG

ACCGGGAAGCUCGACGCCCGGAAGAUCCGCGAGAUCCUGAUCAAGGCCAAG

AAGGGCGGCAAGAUCGCCGUGUAAGACUAGUGCAUCACAUUUAAAAGCAUC

UCAGCCUACCAUGAGAAUAAGAGAAAGAAAAUGAAGAUCAAUAGCUUAUUC

AUCUCUUUUCUUUUUCGUUGGUGUAAAGCCAACACCCUGUCUAAAAAACA

UAAAUUUCUUUAAUCAUUUUGCCUCUUUUCUCUGUGCUUCAAUUAAUAAAA

AAUGGAAAGAACCUAGAUCUAAAAAAAAAAAAAAAAAAAAAAAAAAAA

AAAAAAAAAAAAAAAAAAAAAAAAAAAAAAAAUGCAUCCCCCCCCCCCC

CCCCCCCCCCCCCCCCCAAAGGCUCUUUUCAGAGCCACCAGAAUU

Preparation of DNA and mRNA Constructs:

The DNA sequence encoding Gaussia princeps luciferase was prepared by modifying the wild type encoding DNA sequence by introducing a GC-optimized sequence for stabilization. Sequences were introduced into a derived pUC19 vector and modified to comprise stabilizing UTR sequences derived from 32L4-5'-UTR ribosomal 5'TOP UTR (32L4) and 3'UTR derived from albumin 7, a histone stem-loop sequence, a stretch of 64× adenosine at the 3'-terminal end (poly-A-tail) and a stretch of 30× cytosine at the 3'-terminal end (poly-C-tail) were introduced 3' of the coding sequence. The sequence contains following sequence elements: the coding sequence encoding Gaussia luciferase; stabilizing sequences derived from 32L4-5'-UTR ribosomal 5'TOP UTR (32L4); 64× adenosine at the 3'-terminal end (poly-A-tail); 5 nucleotides, 30× cytosine at the 3'-terminal end (poly-C-tail) and 5 additional nucleotides.

R2851 as mentioned in the present context resembles a GC-enriched mRNA sequence encoding for a Gaussia princeps luciferase having a poly(A)-sequence with 64 adenylates, followed by 5 nucleotides, followed by a poly (C)-sequence with 30 cytidylates and a histone stem-loop sequence followed by another 5 nucleotides.

RNA In Vitro Transcription:

The respective DNA plasmids were enzymatically linearized and transcribed in vitro using DNA dependent T7 RNA polymerase in the presence of a nucleotide mixture under respective buffer conditions. GpLuc mRNA was co-transcriptionally capped by adding a cap analog (m7GpppG) to the nucleotide mixture.

Purification of mRNA Constructs:

The obtained mRNA constructs were purified using PureMessenger® (CureVac, Tübingen, Germany; WO 2008/077592 A1) and used for the further experiments.

Preparation of Cationic Peptide/Polymer

PB83, a disulfide-linked polyethylene glycol/peptide conjugate was prepared as follows. An amount of 20 mg peptide (CHHHHHHRRRRHHHHHHC—$NH_2$) TFA salt was dissolved in 2 mL borate buffer pH 8.5 and stirred at room temperature for approximately 18 hours. Then, 12.6 mg PEG-SH 5000 (Sunbright) dissolved in N-methylpyrrolidone was added to the peptide solution and filled up to 3 mL with borate buffer pH 8.5. After 18 hours incubation at room temperature, the reaction mixture was purified and concentrated by centricon procedure (MWCO 10 kDa), washed against water and lyophilized. After lyophilisation, the lyophilisate was dissolved in ELGA water and the concentration was adjusted to 10 mg/mL. The obtained polyethylene glycol/peptide polymers (HO-PEG 5000-S-(S—CHHHHHHRRRRHHHHHHC-S-)$_7$-S-PEG 5000-OH) were used for further formulation experiments, and are hereinafter referred to as PB83.

Preparation of Lipidoids
The lipidoids

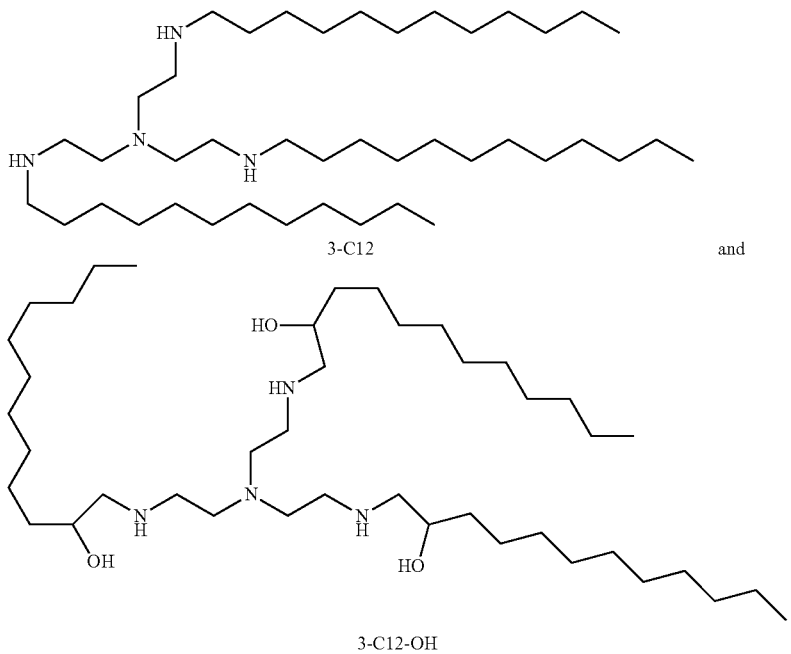

were prepared. Lipidoid 3-C12 may be obtained by acylation of tris(2-aminoethyl)amine with an activated lauric ($C_{12}$) acid derivative, followed by reduction of the amide. Alternatively, it may be prepared by reductive amination with the corresponding aldehyde. Lipidoid 3-C12-OH is prepared by addition of the terminal $C_{12}$ alkyl epoxide with the same oligoamine according to Love et al., pp. 1864-1869, PNAS, vol. 107 (2010), no. 5 (cf. compound C12-110).

The lipidoid 3-C12-OH-cat comprising the cation according to formula IX:

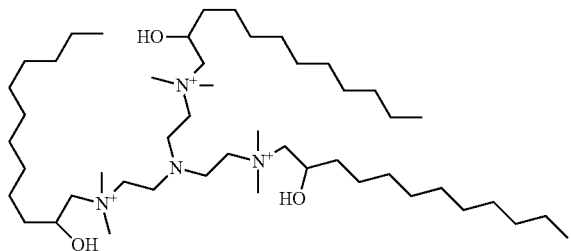

(formula IX)

was prepared from 3-C12-OH by reaction with activated methyl group such as methyl iodide.

Preparation of Compositions with Nanoparticles of Polymer-Lipidoid Complexed mRNA:

First, ringer lactate buffer (RiLa; alternatively e.g. saline (NaCl) or PBS buffer may be used), respective amounts of lipidoid, and respective amounts of a polymer (PB83) were mixed to prepare compositions comprising a lipidoid and a peptide or polymer. Then, the carrier compositions were used to assemble nanoparticles with the mRNA by mixing the mRNA with respective amounts of polymer-lipidoid carrier and allowing an incubation period of 10 minutes at room temperature such as to enable the formation of a complex between the lipidoid, polymer and mRNA. The nanoparticles were then used for further in in vitro and in vivo experiments. Relevant parameters in that context are the amount and kind of lipidoid, the amount and kind of polymer, and the N/P ratio.

In order to characterize the integrity of the obtained polymer-lipidoid complexed mRNA particles, RNA agarose gel shift assays were performed. In addition, size measurements were performed to evaluate whether the obtained nanoparticles have a uniform size profile.

For the RNA gel shift assay, a conventional RNA agarose gel was prepared and loaded with the respective polymer-lipidoid complexed mRNA particles. The gel bands were visualized using a bio imager. All tested polymer-lipidoid complexed mRNAs were analyzed and determined to be stable under the respective conditions (data not shown).

For determining the particle sizes, samples comprising polymer-lipidoid complexed mRNAs were diluted in ringer lactate (alternatively saline) to a final volume of 50 µL. The size measurement was performed using a Zetasizer® device.

The results of the gel shift assay and the particle size analysis showed that the obtained polymer-lipidoid-mRNA complexes were stable and uniform over a broad range of polymer-to-lipidoid ratios.

Figure 1B:
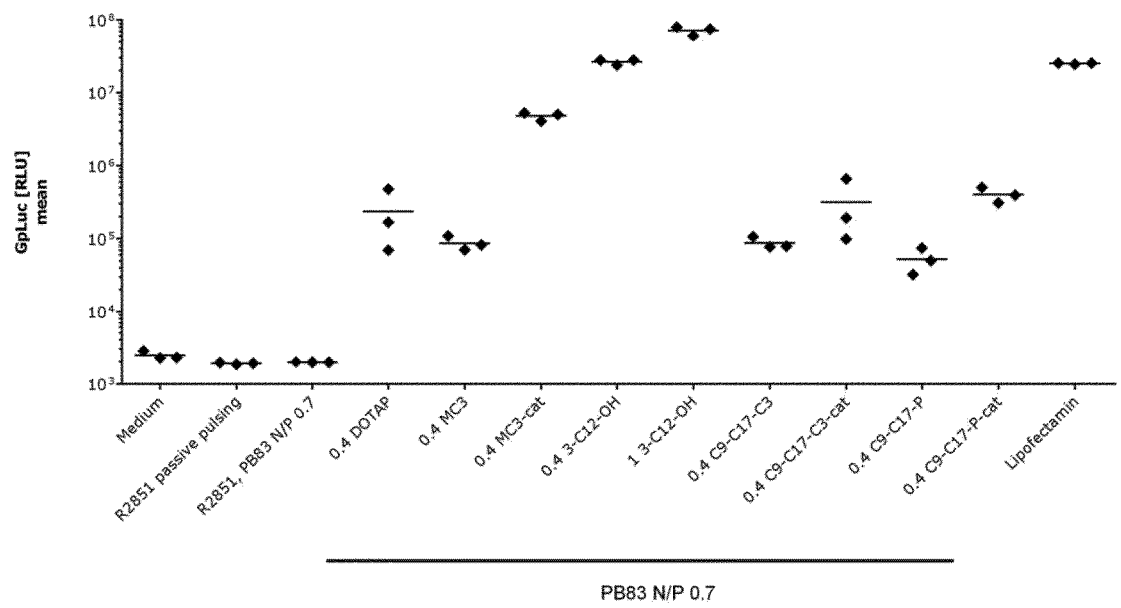
Figure 1C:
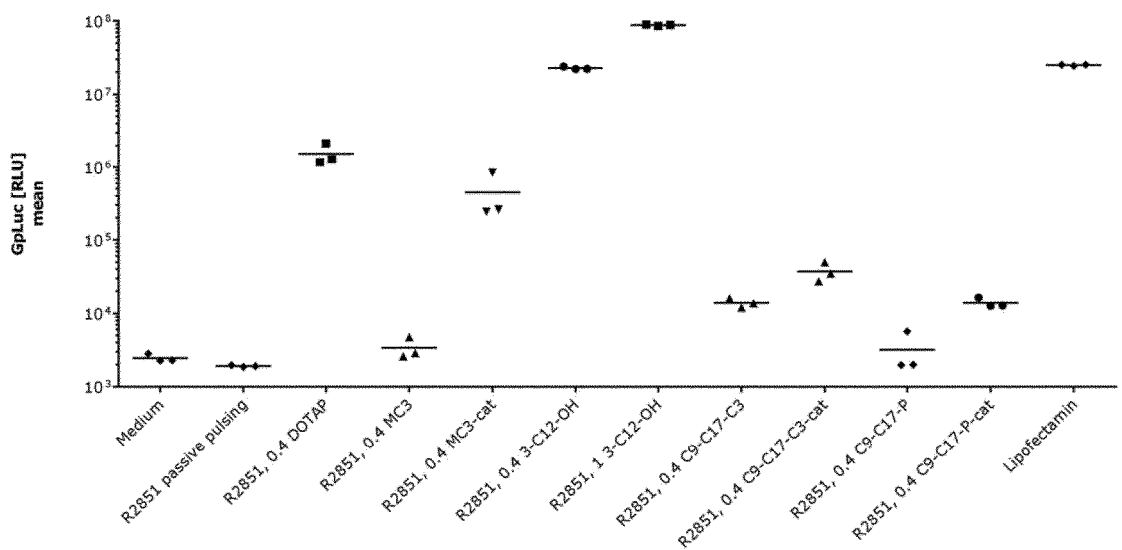

Example 2: Effect of Different Polymer-Lipidoid Formulations on Transfection Efficiency of Sol8 Muscle Cells In Vitro This example shows the transfection efficiency of various compositions according to the invention comprising GpLuc mRNA (SEQ ID NO: 12) compared to positive and negative controls in differentiated Sol8 cells. It was found that the addition of even small amounts of lipidoid (namely 3-C12 and 3-C12-OH) to a cationic polymer-peptide conjugate (PB83) leads to a profound increase of transfection efficiency as can be seen in FIGS. 1A to 1C.

Transfection of Sol8 Cells:

Sol8 is a myogenic cell line isolated by Daubas et al. from primary cultures of soleus muscle taken from the leg of a normal C3H mouse. A volume of 0.2 mL Sol8 cells (20.000 cells) were seeded in 96 well glass bottom plates (Softwell Hydrogel coated with collagen, elasticity E=12 kPa) on day 1. After removing the medium from each well, 100 µL DMEM medium (with 2% horse serum) was added to each well. Afterwards, on day 2, Sol8 cells were transfected with 100 µL transfection mix (in triplicates) of polymer-lipidoid complexes prepared according to Example 1) and respective controls (in triplicates), and cells were incubated at 37° C. and 5% $CO_2$ for 120 minutes. After incubation, 150 µL medium was exchanged with 150 µL fresh DMEM medium supplemented with 10% fetal calf serum. Twenty-four hours post transfection, i.e. on day 3, 10 µL of supernatant of each well was extracted and used for further luminescence analysis, which was performed as described below. Successful transfection with the cargo leads to the translation of the luciferase protein and to a secretion of Gp luciferase protein into the cell culture supernatant.

For luminescence analysis, a volume of 10 µL supernatant was transferred to a 96 well plate for GpLuc measurement. Then, coelenterazine working solution (100 µM) was prepared (1 mL coelenterazine stock solution (4.72 mM in EtOH) in 49 mL phosphate buffered saline supplemented with 5 mM NaCl, pH 7.2). A volume of 100 µL coelenterazine working solution was used as a substrate for GpLuc and measured after 5 seconds in a commercially available microplate reader.

Figure 2A:
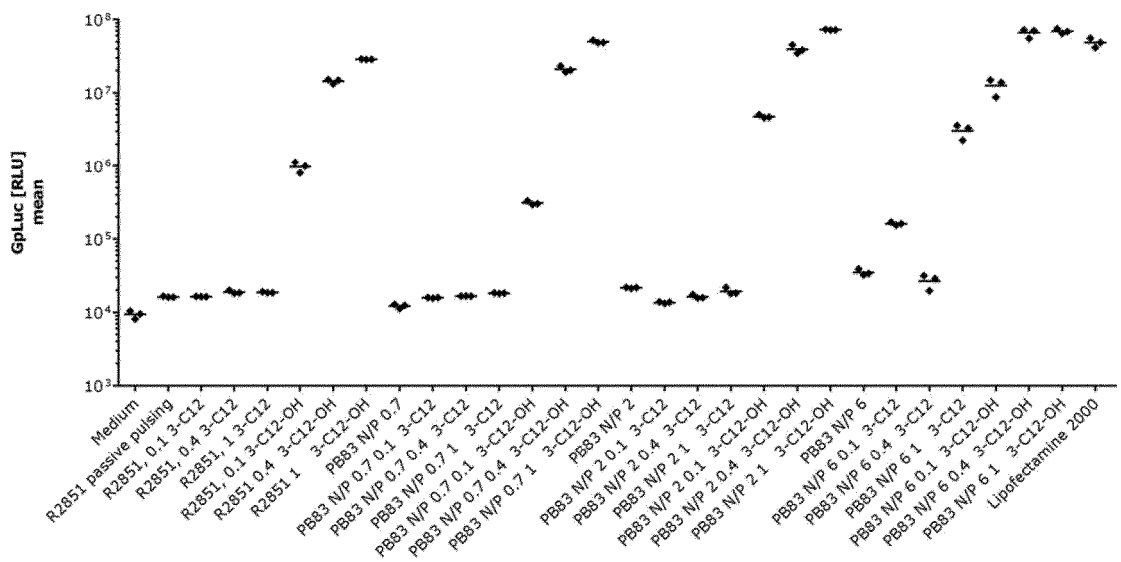
FIGS. 2A and 2B show the effect of the inventive polymer-lipidoid formulations on transfection efficiency of mRNA in HepG2 cells in vitro. In particular, the cationisable 3-C12 and 3-C12-OH and the permanently cationic 3-C12-OH-cat were compared. For further details, see Example 3.
Figure 2B:
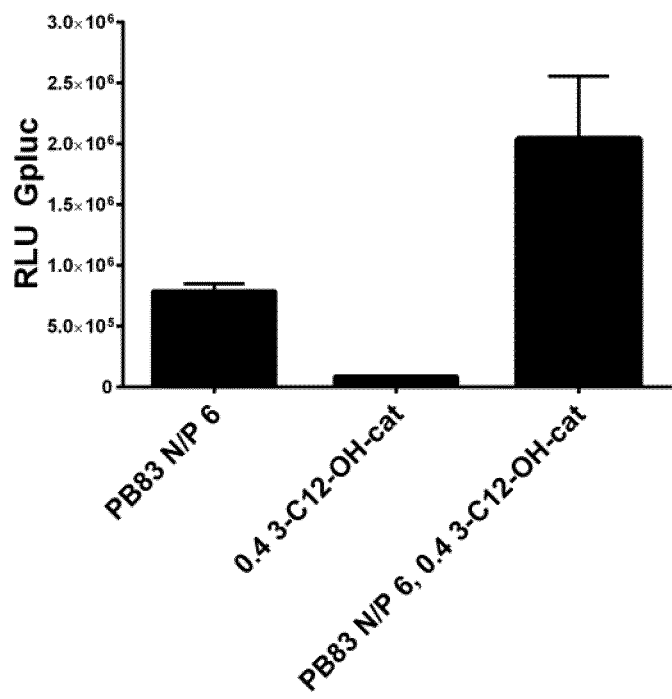

Example 3: Effect of Different Polymer-Lipidoid Formulations on Transfection Efficiency of HepG2 Cells In Vitro This example shows the transfection efficiency of various compositions according to the invention comprising GpLuc mRNA compared to positive and negative controls in HepG2 cells. It was found that the addition of even small amounts of lipidoid (3-C12; 3-C12-OH, or 3-C12-OH-cat) to a cationic polymer-peptide conjugate (PB83) leads to a profound increase of transfection efficiency, as can be seen in FIGS. 2A and 2B.

The experiments were conducted as described in the previous Example, except that HepG2 cells were transfected instead of Sol8 cells. A volume of 0.2 mL HepG2 cells (10.000 cells) were seeded in a 96 well tissue culture plate. After removing the medium from each well, 100 µL RPMI 1640 medium (with 1% Penicillin and 1% Streptomycin, 1% L-Glutamin) was added to each well. Afterwards, HepG2 cells were transfected with 100 µL transfection mix (in triplicates) of polymer-lipidoid mRNA complexes and respective controls (in triplicates), and cells were incubated at 37° C. and 5% $CO_2$ for 90 minutes. After incubation, 150 µL medium was exchanged with 150 µL fresh RPMI 1640 medium supplemented with 10% fetal calf serum. Twenty-four hours post transfection, 10 µL of supernatant of each well was extracted and used for further luminescence analysis.

Example 4: In Vitro Cytokine Stimulation in Human PBMCs

In this example, the intrinsic stimulation of the immune system evoked by the nanoparticles of the invention was evaluated. To assess the impact of the inventive formulation on immune stimulation, the release of cytokines interferon alpha (INFa) and tumor necrosis factor alpha (TNFa) in human peripheral blood mononuclear cells (PBMCs) after treatment with different polymer-lipid complexed GpLuc mRNA was measured.

Human peripheral blood mononuclear cells (PBMCs) from peripheral blood of healthy donors were isolated using a Ficoll gradient and washed subsequently with 1×PBS (phosphate-buffered saline). Isolated cells were seeded on 96 well microtiter plates (2×105 cells/well). The PBMCs were incubated for 24 h with 10 µL of the respective polymer-lipidoid complexed mRNA particles (prepared according to Example 1) or certain controls (e.g., naked RNA, Ringer Lactate buffer, CpG2216, RNAdjuvant®) in X-VIVO 15 Medium (Lonza) in triplicates. The immunostimulatory effect upon PBMC stimulation was measured by detecting the cytokine production using specific antibodies detecting human INFa.

ELISA microtiter plates (Nunc Maxisorb) were incubated overnight (o/n) with binding buffer (0.02% $NaN_3$, 15 mM $Na_2CO_3$, 15 mM $NaHCO_3$, pH 9.7), additionally containing a specific cytokine antibody. Cells were then blocked with 1×PBS, containing 1% BSA (bovine serum albumin). The cell supernatant was added and incubated for 4 h at 37° C. Subsequently, the microtiter plate was washed with 1×PBS, containing 0.05% Tween-20 and then incubated with a Biotin-labelled secondary antibody (BD Pharmingen, Heidelberg, Germany). Streptavidin-coupled horse radish peroxidase was added to the plate. Then, the plate was again washed with 1×PBS, containing 0.05% Tween-20, and ABTS (2,2'-azino-bis(3-ethyl-benzthiazoline-6-sulfonic acid) was added as a substrate. The amount of cytokine was determined by measuring the absorption at 405 nm (OD 405) using a standard curve with recombinant cytokines (BD Pharmingen, Heidelberg, Germany) with the Sunrise ELISA-Reader from Tecan (Crailsheim, Germany). In parallel, the GpLuc concentration in the cell culture supernatant was also determined.

Figure 3:
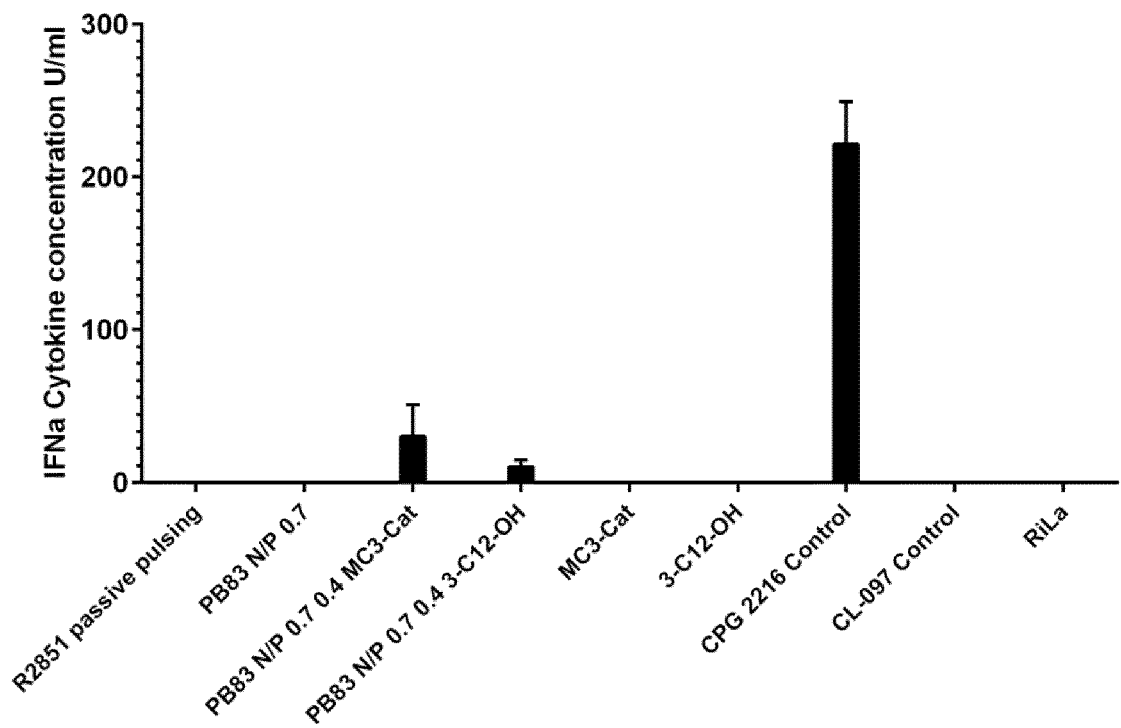
FIG. 3 shows the in vitro release of cytokine interferon alpha (INFa) in human peripheral blood mononuclear cells (PBMCs) after treatment with different polymer-lipid or lipidoid complexed GpLuc mRNA. For further details, see Example 4.

In result, the tested compositions did not stimulate the secretion of cytokines in human PBMCs as can be seen in FIG. 3, indicating that the nanoparticles of the invention only have a very minor intrinsic potential to stimulate the immune system in the absence of a potent positive control such as CpG oligodeoxynucleotide.

Example 5: Scanning Laser Ophthalmoscopy (SLO) Analysis of Rat Eyes 24 h after Subretinal Injection of Luciferase-mRNA mRNA complexes were prepared by mixing PpLuc mRNA (SEQ ID NO: 19) and cationic polymer-lipid or lipidoid solutions (e.g. MC3-cat or 3-C12-OH) at different charge ratios. Animals treated with Ringer's buffer served as controls. Lyophilized formulations were rehydrated with Ringer's buffer. The final mRNA concentration was 2.5 µg/µl. 2 doses of 2 µl were injected into each eye. 4 eyes (2 rats) were treated per group. Twentyfour hours after the treatment non-invasive Scanning Laser Ophthalmoscopy (SLO) was used to image the retina (data not shown). Luciferin solution was injected into the tail vein of the rats and the eyes were analyzed after an incubation time of 2 minutes for at least 10 minutes. During this time the rats additionally received a luciferin solution to sniff. For a detailed analysis, the animals were then sacrificed, their eyes removed and frozen. Subsequently, eye samples were analyzed for the levels of transfection. To that end the eyes were mechanically disrupted in a TissueLyser and lysed. Luciferase activity of each sample was assayed in a luminometer.

Figure 4:
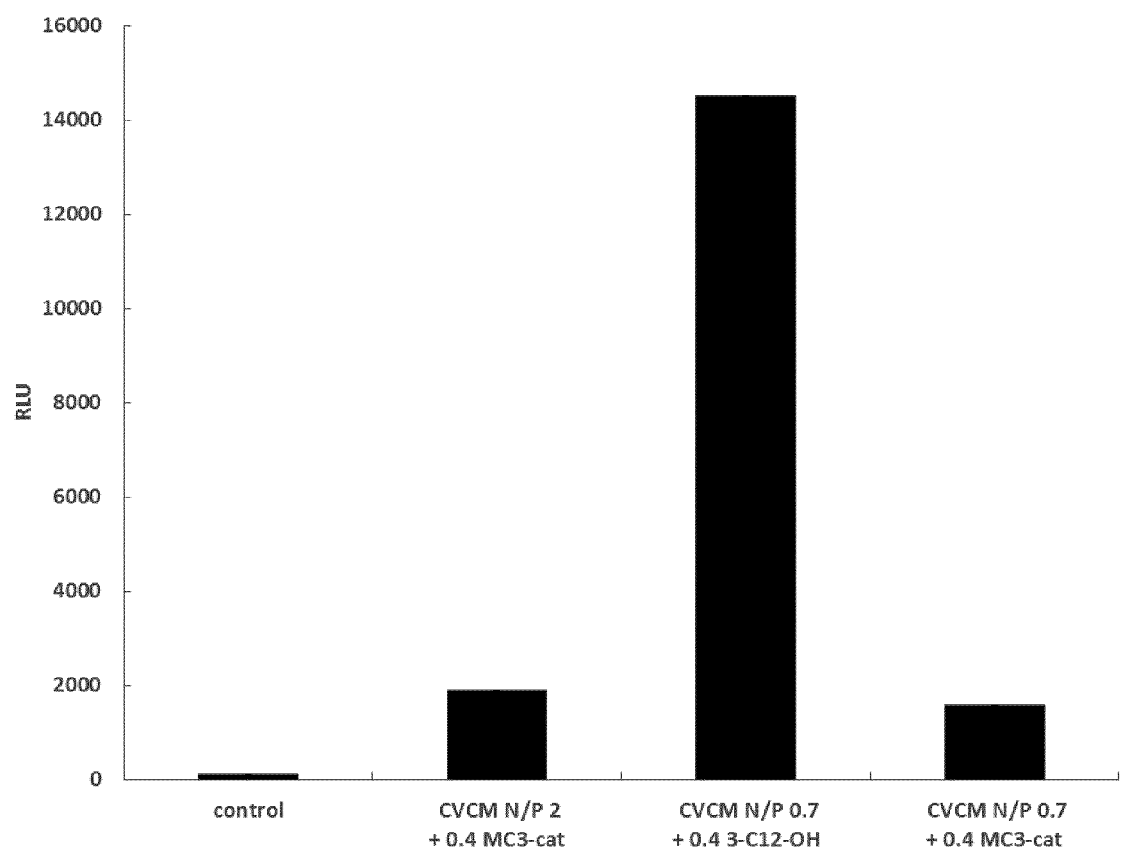
FIG. 4 shows the scanning laser ophthalmoscopy (SLO) analysis results of the subretinal injection of PpLuc mRNA (SEQ ID NO: 19) into rat eyes, 24 h after subretinal injection of the inventive polymer-lipid or polymer-lipidoid formulations, expressed as relative light units (RLU). For the injection regimen and further details, see Example 5.

The results of the subretinal injection of luciferase-mRNA (PpLuc mRNA) are shown in FIG. 4, expressed as relative light units (RLU).

Example 6: Induction of a Humoral and Cellular Immune Response after Intramuscular Vaccination of Mice Preparation of DNA and mRNA Constructs For the present example, a DNA sequence encoding the hemagglutinin (HA) protein of influenza A virus (A/Netherlands/602/2009(H1N1)) was prepared and used for subsequent in vitro transcription reactions. The respective mRNA sequence as well as further details on the vaccination regimen are provided below.

```
G/C-enriched mRNA sequence R2564 coding for the
hemagglutinin (HA) protein of influenza A virus
(A/Netherlands/602/2009(H1N1)) (SEQ ID NO 17):
GGGGCGCUGCCUACGGAGGUGGCAGCCAUCUCCUUCUCGGCAUCAAGCUUA
CCAUGAAGGCCAUCCUGGUGGUCCUCCUGUACACCUUCGCCACCGCGAACG
CCGACACGCUGUGCAUCGGCUACCACGCCAACAACAGCACCGACACCGUGG
ACACCGUGCUCGAGAAGAACGUCACGGUGACCCACUCCGUGAACCUGCUGG
AGGACAAGCACAACGGGAAGCUCUGCAAGCUGCGGGGCGUCGCCCCGCUGC
ACCUCGGGAAGUGCAACAUCGCCGGCUGGAUCCUGGGGAACCCGGAGUGCG
AGAGCCUGUCCACCGCGAGCUCCUGGAGCUACAUCGUGGAGACCUCCAGCU
CCGACAACGGCACGUGCUACCCCGGCGACUUCAUCGACUACGAGGAGCUCC
GCGAGCAGCUGAGCUCCGUGAGCUCCUUCGAGCGGUUCGAGAUCUUCCCCA
AGACCAGCUCCUGGCCCAACCACGACAGCAACAAGGGGGUCACCGCCGCCU
GCCCGCACGCCGGCGCGAAGUCCUUCUACAAGAACCUGAUCUGGCUCGUGA
AGAAGGGGAACAGCUACCCCAAGCUGUCCAAGAGCUACAUCAACGACAAGG
GCAAGGAGGUGCUGGUCCUCUGGGGGAUCCACCACCCCAGCACCUCCGCCG
ACCAGCAGAGCCUGUACCAGAACGCCGACGCCUACGUGUUCGUGGGCUCCA
GCCGCUACUCCAAGAAGUUCAAGCCCGAGAUCGCCAUCCGGCCGAAGGUCC
GCGACCAGGAGGGCCGGAUGAACUACUACUGGACGCUGGUGGAGCCCGGGG
ACAAGAUCACCUUCGAGGCGACCGGCAACCUCGUGGUCCCCCGCUACGCCU
UCGCCAUGGAGCGGAACGCCGGGAGCGGCAUCAUCAUCUCCGACACCCCCG
UGCACGACUGCAACACGACCUGCCAGACCCCGAAGGGCGCCAUCAACACCA
GCCUGCCCUUCCAGAACAUCCACCCCAUCACGAUCGGGAAGUGCCCCAAGU
ACGUGAAGUCCACCAAGCUGCGCCUCGCGACCGGCCUGCGGAACGUCCCGA
GCAUCCAGUCCCGCGGGCUGUUCGGCGCCAUCGCCGGGUUCAUCGAGGGCG
GCUGGACCGGGAUGGUGGACGGCUGGUACGGGUACCACCACCAGAACGAGC
AGGGCAGCGGGUACGCCGCCGACCUCAAGUCCACGCAGAACGCGAUCGACG
AGAUCACCAACAAGGUGAACAGCGUCAUCGAGAAGAUGAACACCCAGUUCA
CCGCCGUGGGCAAGGAGUUCAACCACCUGGAGAAGCGGAUCGAGAACCUGA
ACAAGAAGGUCGACGACGGCUUCCUCGACAUCUGGACGUACAACGCCGAGC
UGCUGGUGCUCCUGGAGAACGAGCGCACCCUGGACUACCACGACUCCAACG
UGAAGAACCUCUACGAGAAGGUCCGGAGCCAGCUGAAGAACAACGCCAAGG
AGAUCGGGAACGGCUGCUUCGAGUUCUACCACAAGUGCGACAACACCUGCA
UGGAGUCCGUGAAGAACGGGACCUACGACUACCCCAAGUACAGCGAGGAGG
CCAAGCUGAACCGCGAGGAGAUCGACGGCGUGAAGCUCGAGUCCACGCGGA
UCUACCAGAUCCUGGCGAUCUACAGCACCGUCGCCAGCUCCCUGGUGCUCG
UGGUCAGCCUGGGGGCCAUCUCCUUCUGGAUGUGCAGCAACGGCUCCCUGC
AGUGCCGCAUCUGCAUCUGACCACUAGUGCAUCACAUUUAAAAGCAUCUCA
GCCUACCAUGAGAAUAAGAGAAAGAAAAUGAAGAUCAAUAGCUUAUUCAUC
UCUUUUUCUUUUUCGUUGGUGUAAAGCCAACACCCUGUCUAAAAAACAUAA
AUUUCUUUAAUCAUUUUGCCUCUUUUCUCUGUGCUUCAAUUAAUAAAAAAU
GGAAAGAACCUAGAUCUAAAAAAAAAAAAAAAAAAAAAAAAAAAAAAAAAA
AAAAAAAAAAAAAAAAAAAAAAAAAAAAAAAAUGCAUCCCCCCCCCCCCCC
CCCCCCCCCCCCCCAAAGGCUCUUUUCAGAGCCACCAGAAUU
```

According to a first preparation, the DNA sequence coding for the above mentioned mRNA was prepared. The construct R2564 (SEQ ID NO: 17) was prepared by introducing a 5'-TOP-UTR derived from the ribosomal protein 32L, modifying the wild type coding sequence by introducing a GC-optimized sequence for stabilization, followed by a stabilizing sequence derived from the albumin-3'-UTR, a stretch of 64 adenosines (poly(A)-sequence), a stretch of 30 cytosines (poly(C)-sequence), and a histone stem loop.

Preparation of the Vaccine

The 'naked' mRNA R2564 was administered in Ringer's Lactate solution (RiLa). The co-formulation of naked mRNA R2564 with PB83 and 3-C12-OH was generated by mixing all components directly before administration.

Immunization

Balb/c mice (n=8 per group) were vaccinated intramuscularly (left M. tibialis) on day 0 and boosted on day 25, either with 10 μg HA-mRNA (R2564, SEQ ID NO: 17, 'naked' HA-mRNA) alone or with 10 μg HA-mRNA co-formulated with PB83 N/P 0.7, 0.4 3-C12-OH; see table 1 below. Therein, the indicated amount in μg refers to the mass of the nucleic acid molecule per se.

TABLE 1

Experimental setup

| Group | Treatment | RNA dose | Route (Volume) | Mice # |
|---|---|---|---|---|
| 1 | RiLa buffer | 10 μg | i.m. (25 μL) | 8 |
| 2 | Naked HA-mRNA | 10 μg | i.m. (25 μL) | 8 |
| 4 | R2564 PB83 N/P 0.7, 0.4 3-C12—OH | 10 μg | i.m. (25 μL) | 8 |

All animals received boost injections on day 25. Induction of functional humoral responses was analysed on day 40 by collecting blood samples and determining the serum hemagglutination inhibition (HI) antibody titer (see table 2 below), which is generally used as a surrogate marker of immune protection against influenza virus infection. A HI titer of 1:40 or greater is typically considered to confer protection. Ringer lactate-buffer (RiLa) treated mice served as negative controls.

TABLE 2

Vaccination schedule

| Day | Treatment | Sampling |
|---|---|---|
| d 0 | Prime | |
| d 25 | Boost | |
| d 40 | Termination | Blood + spleen collection |

Hemagglutination Inhibition Assay

For hemagglutination inhibition (HI) assay mouse sera were heat inactivated (56° C., 30 min), incubated with kaolin, and pre-adsorbed to chicken red blood cells (CRBC) (both Labor Dr. Merck & Kollegen, Ochsenhausen, Germany). For the HI assay, 50 µL of 2-fold dilutions of pre-treated sera were incubated for 45 minutes with 4 hemagglutination units (HAU) of inactivated A/California/5 7/2009 (NIBSC, Potters Bar, UK) and 50 µL 0.5% CRBC were added.

Figure 5:
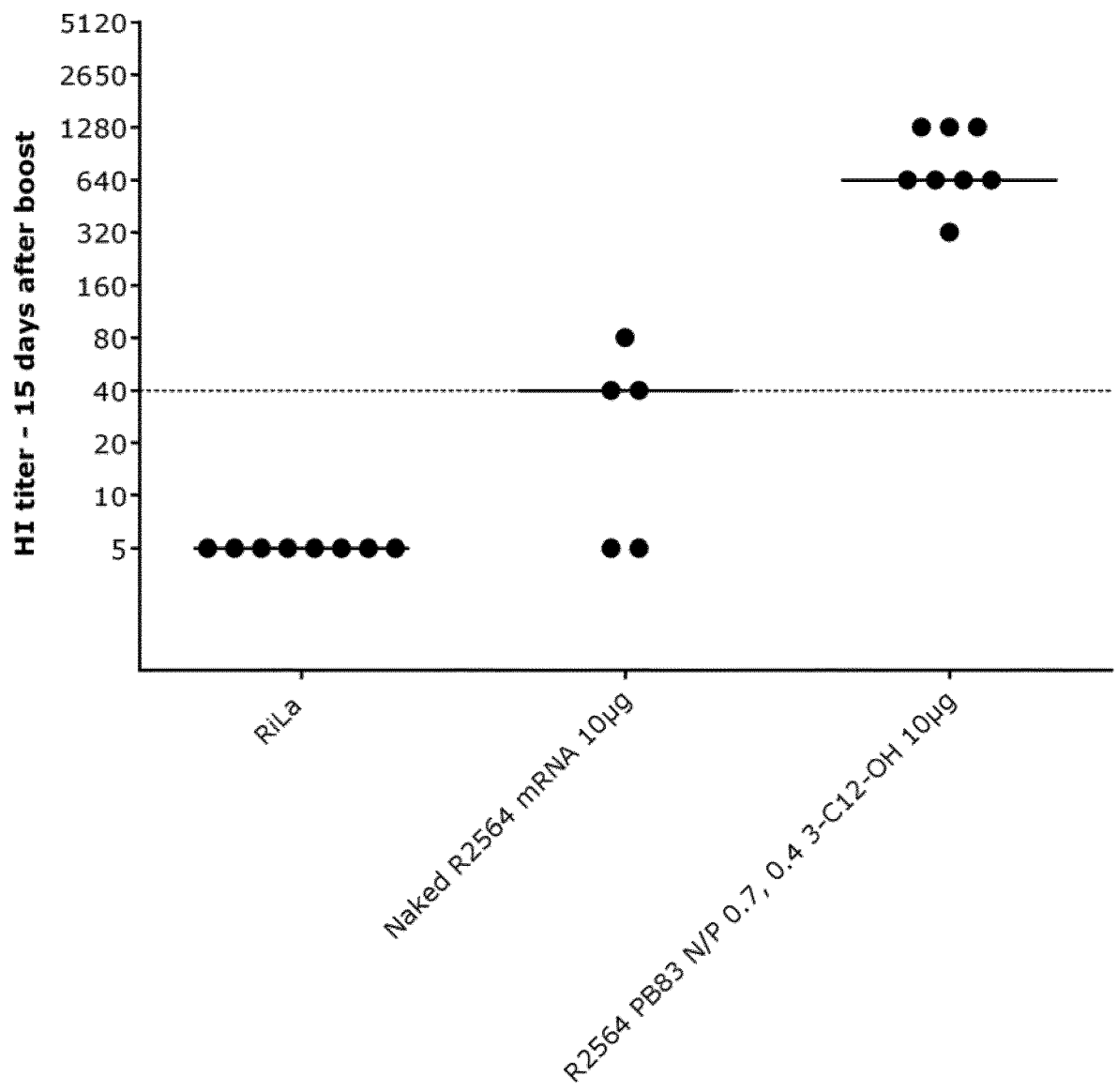
FIG. 5 shows the titers of antibodies against HA protein (hemagglutinin) as induced after intramuscular vaccination of Balb/c mice (n=8) with HA-mRNA (R2564, SEQ ID NO: 17) using an inventive polymer-lipidoid formulation of HA-mRNA or the 'naked' HA-mRNA alone. Each dot represents an individual animal and the horizontal lines represent median values. For further details, see Example 6.

Results:

As can be seen in FIG. 5, all mice vaccinated with the PB83 N/P 0.7, 0.4 3-C12-OH-formulation developed HI-titers ≥1:40. FIG. 5 further shows that the intramuscular vaccination with a formulation comprising HA-mRNA (R2564) and the polymer-lipidoid carrier based on PB83 and 3-C12-OH induces higher antibody titers against the HA protein compared to vaccination with the HA-mRNA (R2564) alone.

Example 7: Transfection Efficiency of Other Polymers in Combination with Different Lipids on A549 Cells This example describes the evaluation of the effect of polymers other than PB83 in combination with different lipids on transfection efficiency on A549 cells (human lung carcinoma cell line). For this, the polycationic block polymer Sunbright AS50-DT-A (NOF Corporation, Tokyo) was used for efficient delivery of mRNA. As a read-out for transfection efficiency, Gaussia princeps luciferase GpLuc mRNA was used as a cargo. Successful transfection with the cargo leads to the translation of the luciferase protein and to a secretion of luciferase protein into the cell culture supernatant.

Accordingly, A549 cells were seeded in 24-well-plates at a density of 75.000 cells per well in cell culture medium (Gibco (ThermoFisher) Ham's F-12K (Kaighn's) Medium, 10% Fetal Bovine Serum (FBS), 1% L-Glutamine, 1% Penicillin/Streptomycin). A549 cells were transfected in duplicates as described below with different carrier-lipid formulations and with mRNA encoding GpLuc (SEQ ID NO:12; R2851). As a negative control, mRNA encoding GpLuc without PB83 carrier was used. Luciferase expression was quantified after 24 h.#

TABLE 3

Transfection conditions

| # | polymer | lipid | mRNA | |
|---|---|---|---|---|
| 1 | 10 µl Sunbright [10 g/l] in 40 µl HEPES [10 mM] | w/o | 2.5 µl mRNA (1 µg/µl) 47.5 µl HEPES [10 mM] | up to 1 ml with media without serum 200 µl added per well |
| 2 | 8 µl Sunbright [10 g/l] in 42 µl NaCl [0.9%] | w/o | 2.5 µl mRNA (1 µg/µl) 47.5 µl NaCl [0.9%] | |
| 3 | 8 µl Sunbright [10 g/l] in 42 µl NaCl [0.9%] | 1 µl 3-C12—OH [100 µmol/ml] | 2.5 µl mRNA (1 µg/µl) 47.5 µl NaCl [0.9%] | |
| 4 | 10 µl Sunbright [10 g/l] in 40 µl HEPES [10 mM] | 1 µl DDAB [100 µmol/ml] | 2.5 µl mRNA (1 µg/µl) 47.5 µl HEPES [10 mM] | |

Figure 6:
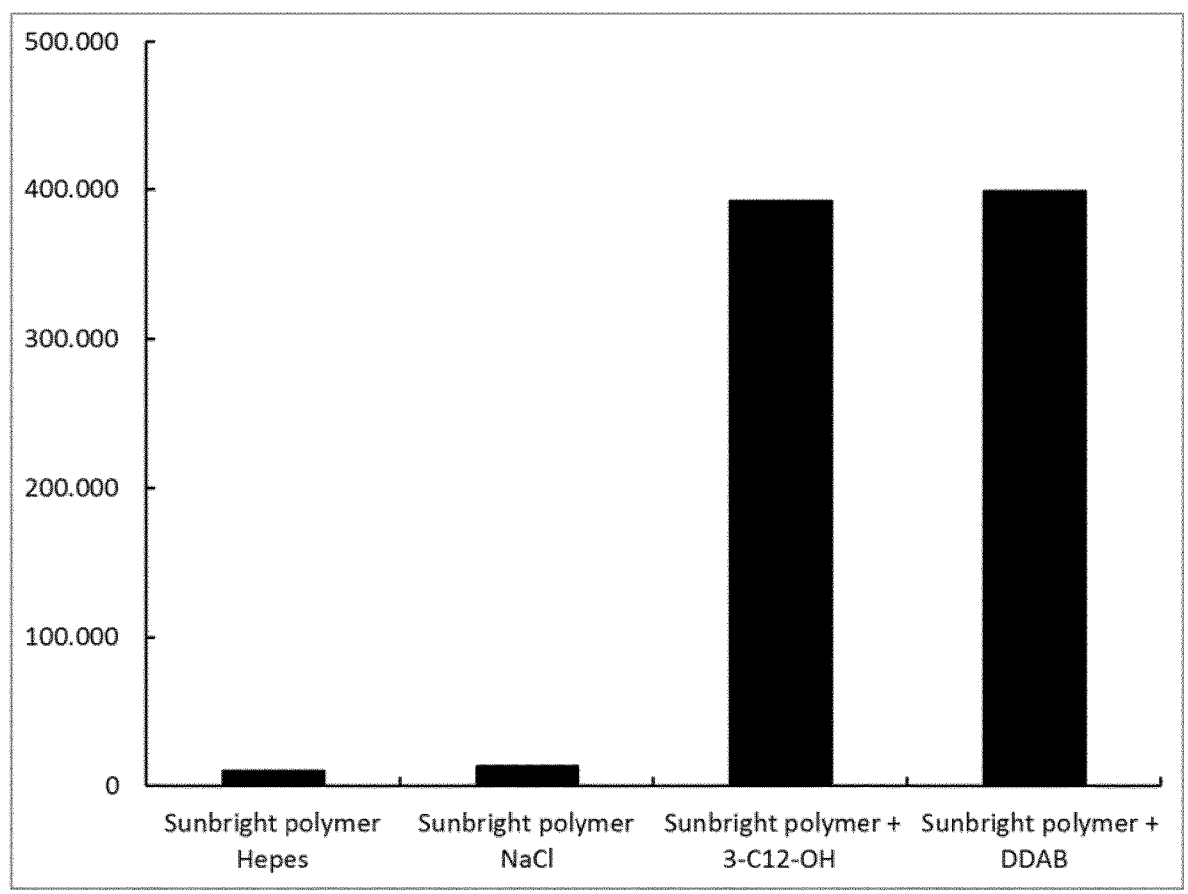
FIG. 6 shows GpLuc protein expression in A549 cells transfected with the mRNA construct R2851 using non-CVCM/PB83 polymers.

Results:

FIG. 6 shows that GpLuc protein was expressed in A549 cells transfected with the mRNA construct R2851 using non-PB83 polymers and that the tested formulations with added lipids were more efficient when compared to the Sunbright polymer control w/o added lipids. This shows that the combination of mRNA with very small amounts of lipid was able to increase the transfection efficiency when using cationic polymer systems.

Example 7: Transfection Efficiency of Other Polymers in Combination with Different Lipids on BHK Cells This example describes the evaluation of the effect of polymers other than PB83 in combination with different lipids on transfection efficiency on Baby Hamster Kidney (BHK) cells and Sol8 (Mus musculus skeletal muscle) cells. For this, the molecules

- GH5R4H5GC-S-S-CGH5R4H5G ('Inlay-Dimer'; S—S indicates that the units are covalently connected via Cysteine S—S bonds; Intavis Bioanalytical Instruments AG, Germany/Cologne);
- K(EEEKK)$_3$SGGGGH5R4H5GC-S-S-CGH5R4H5GGGGS(KKEEE)$_3$K ('(KKEEE)3K-Dimer'; S—S indicates that the units are covalently connected via Cysteine S—S bonds; Intavis Bioanalytical Instruments AG, Germany/Cologne);
- the polycationic linear polysaccharide Chitosan 95/50 ('Chitosan', CAS 9012-76-4; Intavis Bioanalytical Instruments AG, Germany/Cologne);
- (R$_{12}$C)—(CR$_{12}$C)—(R$_{12}$C) ('Trimer'; the R12C and CR12C units are covalently connected via Cysteine S—S bonds; Intavis Bioanalytical Instruments AG, Germany/Cologne);
- R$_{12}$C-PEG5000 ('R12C-PEG'); and
- (R$_{12}$CW)$_2$ (the two R12CW-units are covalently connected via Cysteine S—S bonds)

were used for delivery of mRNA. As a read-out for transfection efficiency, Gaussia princeps luciferase GpLuc mRNA was used as a cargo. Successful transfection with the cargo leads to the translation of the luciferase protein and to a secretion of luciferase protein into the cell culture supernatant.

For BHK cells, accordingly, cells were seeded in 96-well-plates at a density of 10.000 cells per well in cell culture medium (RPMI, 10% FCS, 1% L-Glutamine, 1% Penicillin/Streptomycin). BHK cells were transfected in duplicates as described below with different carrier-lipid formulations and with mRNA encoding GpLuc (SEQ ID NO:12; R2851). As a negative control, mRNA encoding GpLuc without PB83 carrier was used. Luciferase expression was quantified 24 h after transfection.

For Sol8 (differentiated) cells, accordingly, cells were seeded 7 days before transfection in 96-well-plates at a density of 10.000 cells per well in cell culture medium (DMEM, 1% Penicillin/Streptomycin, 1% L-Glutamine, 1% FCS). Medium was removed and DMEM containing 1% FCS was added to cells one day after seeding. Three days after seeding, medium of the cells was changed (DMEM, 1% FCS). On day 8, Sol8 cells were transfected in triplicates as described below with different carrier-lipid formulations and with mRNA encoding GpLuc (SEQ ID NO:12; R2851). As a negative control, mRNA encoding GpLuc without CVCM/PB83 carrier was used. Luciferase expression was quantified 24 h after transfection.

For HeLa cells, accordingly, cells were seeded in 96-well-plates at a density of 10.000 cells per well in cell culture medium (RPMI, 10% FCS, 1% L-Glutamine, 1% Penicillin/Streptomycin). HeLa cells were transfected in duplicates as described below with different carrier-lipid formulations and with 2 μg mRNA encoding PpLuc (SEQ ID NO: 19; R2244; see table below). As a negative control, mRNA encoding PpLuc without PB83 carrier was used. Luciferase expression was quantified 24 h after transfection.

TABLE 4

| | | | Transfection conditions | | |
|---|---|---|---|---|---|
| | | | | MC3 | 20% |
| CVCM type | water | $(R_{12}CW)_2$ (4 g/l) | 1:100 1 μmol/ml | 1:10 ml 10 μmol/ml | trehalose |
| CR12 0.8; 0.1 MC3 | 158.8 μl | 3.2 μl | 3 μl | | 75 μl |
| CR12 0.8; 0.3 MC3 | 152.8 μl | 3.2 μl | 9 μl | | 75 μl |
| CR12 0.8; 1.0 MC3 | 158.8 μl | 3.2 μl | | 3 μl | 75 μl |

Figure 7A:
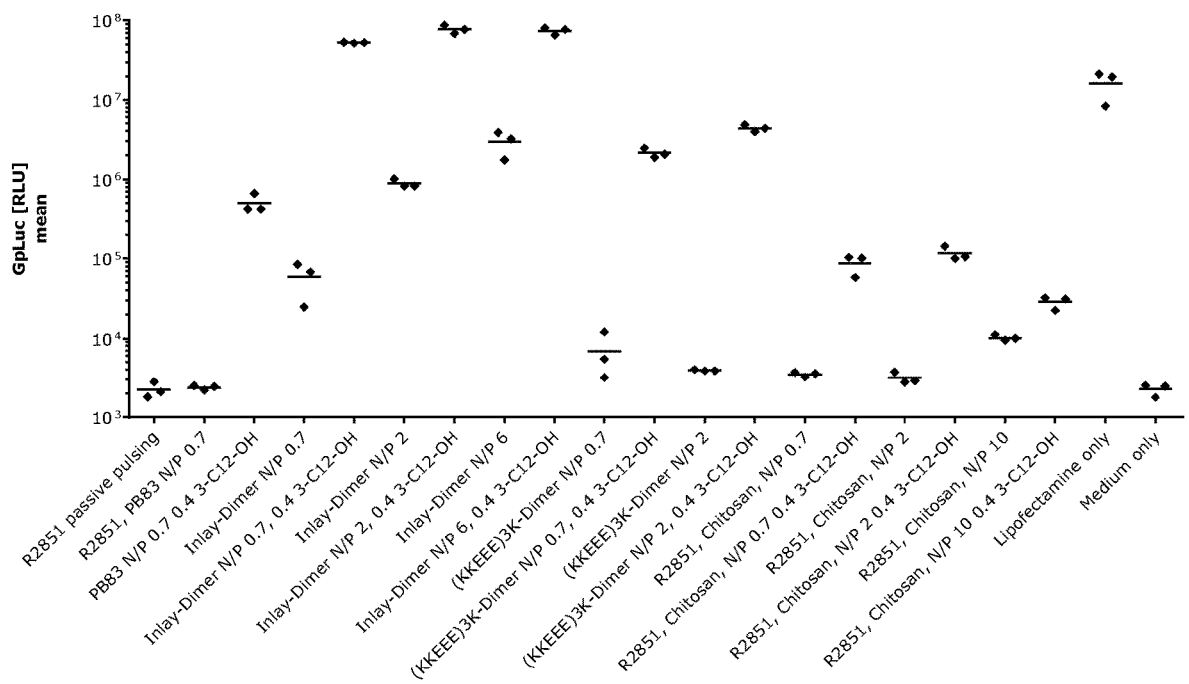
FIGS. 7A and 7B show that GpLuc protein expression in BHK and differentiated Sol8 cells transfected with the mRNA construct R2851 using non-CVCM/PB83 polymers.
Figure 7B:
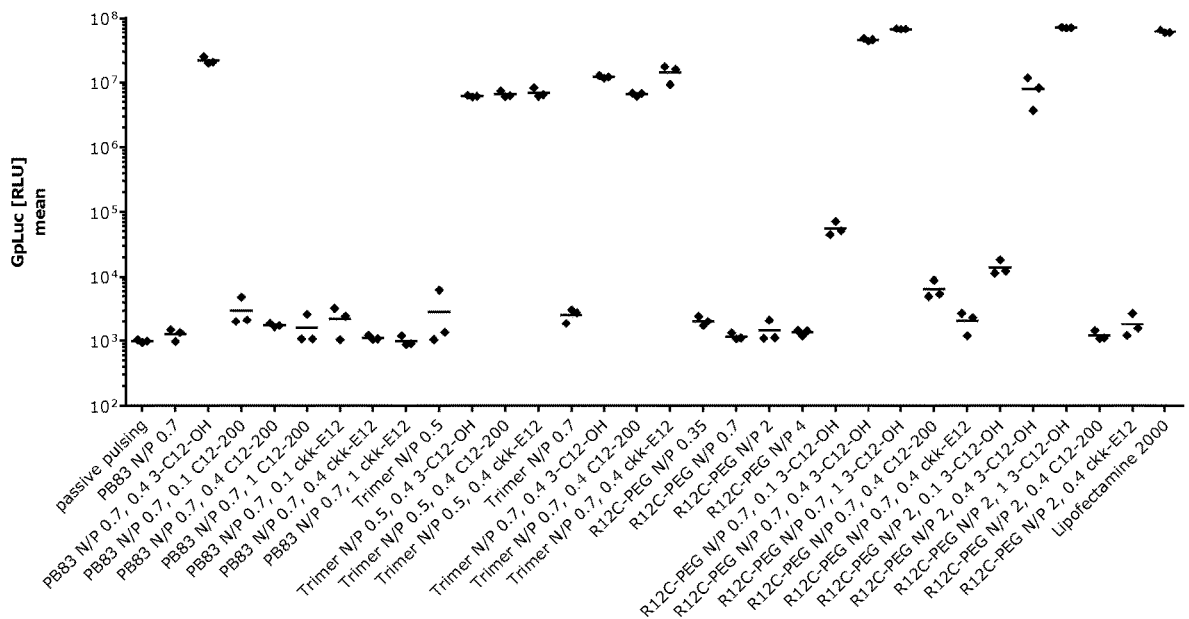
Figure 7C:
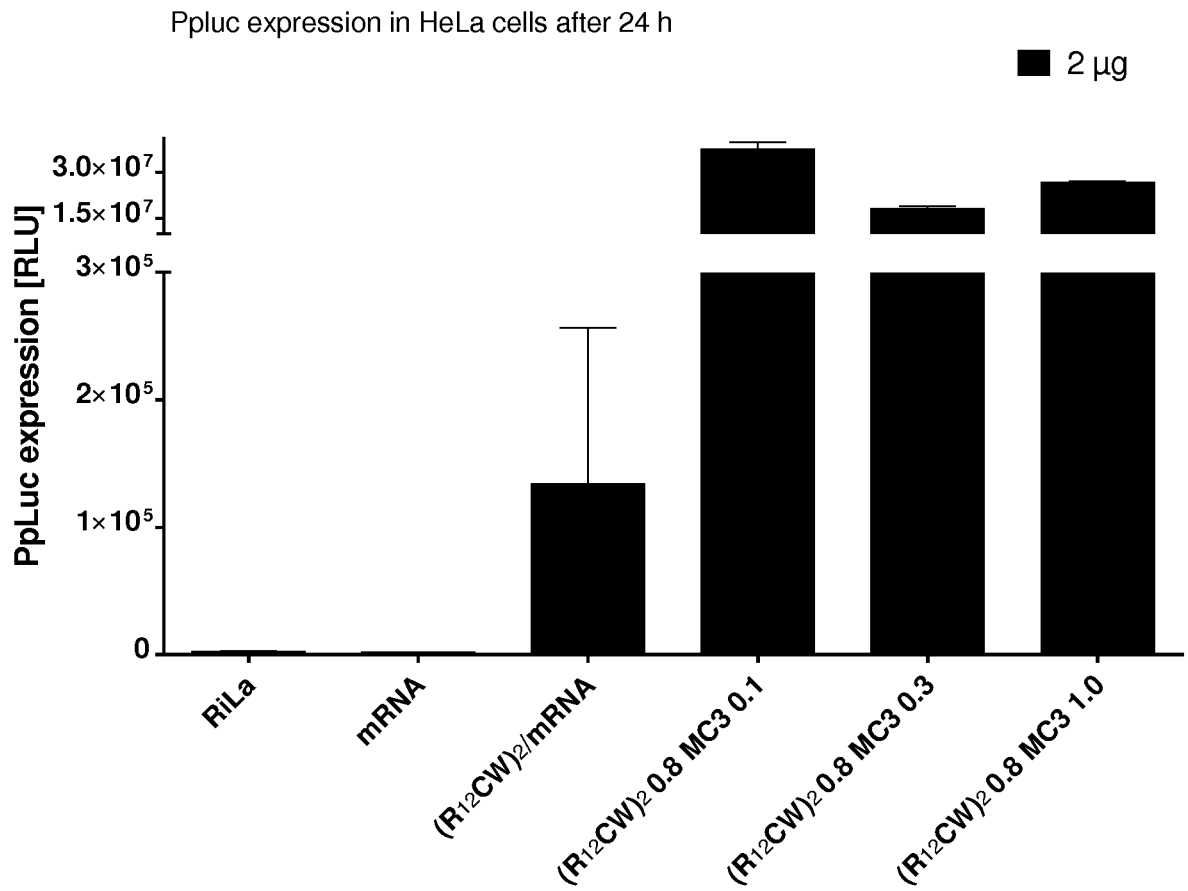
FIG. 7C shows PpLuc protein expression in HeLa cells transfected with the mRNA construct R2244 using non-CVCM/PB83 polymers.

Results:

FIGS. 7A and 7B show that GpLuc protein was expressed in BHK and differentiated Sol8 cells transfected with the mRNA construct R2851 using non-PB83 polymers and that the tested formulations with added lipids were more efficient when compared to the respective polymer control w/o added lipids. FIG. 7C shows that PpLuc protein was expressed in HeLa cells. This shows that the combination of mRNA with very small amounts of lipid was able to increase the transfection efficiency when using cationic polymer systems.

Example 8: Transfection Efficiency of Other Polymers in Combination with 3-C12-Amide Lipid This example describes the evaluation of the effect of different polymer-lipid formulations on transfection efficiency on HepG2 cells w/o FCS. As a read-out for transfection efficiency, Gaussia princeps luciferase GpLuc mRNA was used as a cargo. Successful transfection with the cargo leads to the translation of the luciferase protein and to a secretion of luciferase protein into the cell culture supernatant.

Accordingly, HepG2 cells were seeded in 24-well-plates at a density of 10.000 cells per well in cell culture medium (RPMI 1640 w/25 mM HEPES 500 ml, 10% FCS, 1% L-Glutamine, 1% Penicillin/Streptomycin; Lonza Group AG BE12-115F/6MB205; Basel/Switzerland). HepG2 cells were transfected in duplicates as described below with different carrier-lipid formulations and with mRNA encoding GpLuc (SEQ ID NO:12; R2851) with an N/P ratio of 0.7. As a negative control, mRNA encoding GpLuc without CVCM/PB83 carrier was used. Luciferase expression was quantified after 24 h.

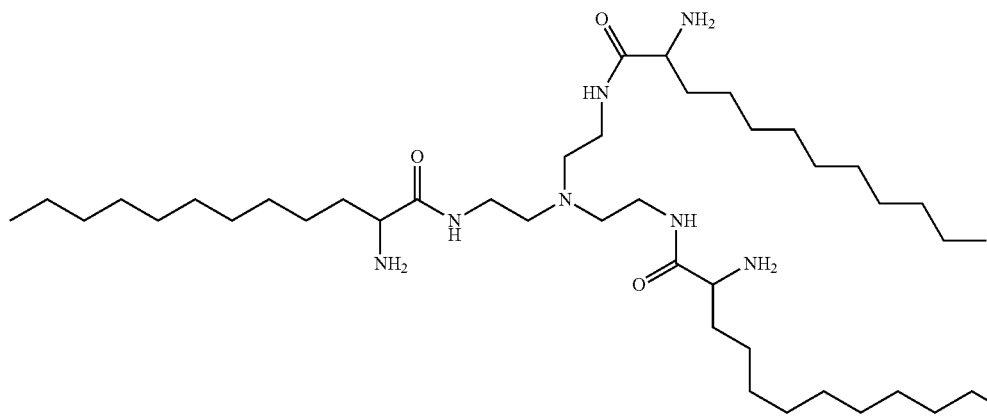

(formula X)

3-C12-amide

-continued

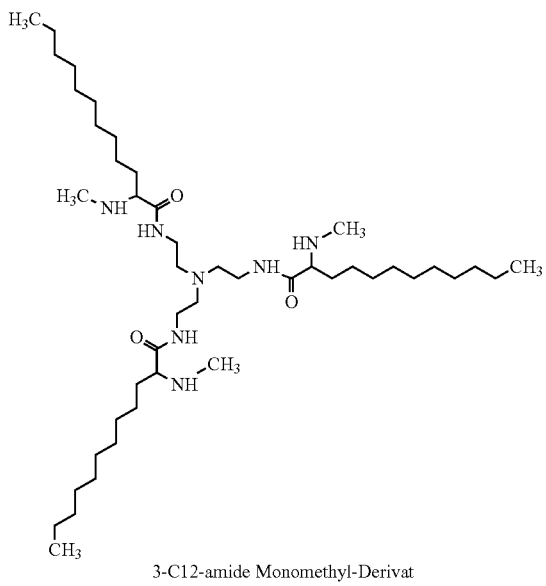

(formula Xa)

3-C12-amide Monomethyl-Derivat

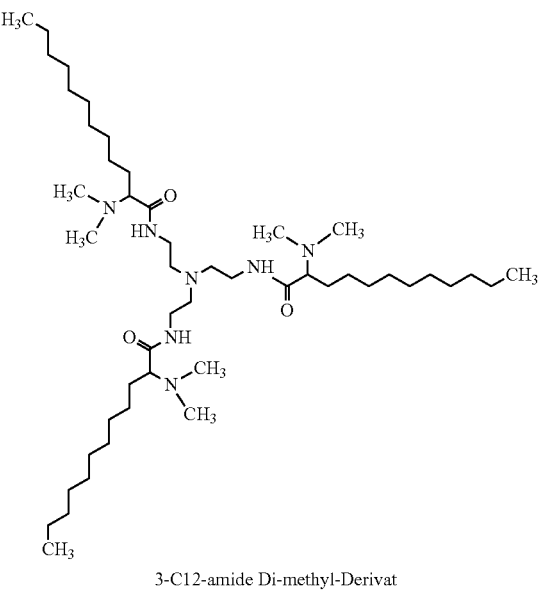

(formula Xb)

3-C12-amide Di-methyl-Derivat

TABLE 5

Transfection conditions:

| | Carrier | Lipid | N/P |
|---|---|---|---|
| Condition 1 | CVCM/PB83 | w/o | 0.7 |
| Condition 2 | CVCM/PB83 | 3-C12—OH | 0.7 |
| Condition 3 | CVCM/PB83 | 3-C12-amide | 0.7 |

Figure 8:
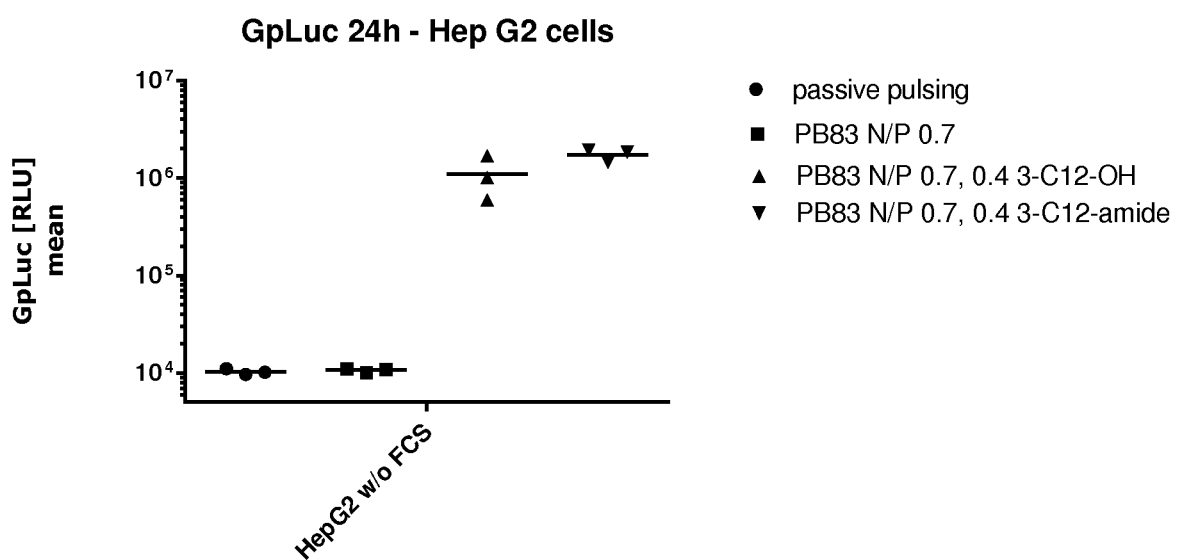
FIG. 8 shows GpLuc protein expression in Hep G2 cells transfected with the mRNA construct R2851.

Results:

FIG. 8 shows that GpLuc protein was expressed in Hep G2 cells transfected with the mRNA construct R2851 and that the tested formulations with added lipids were highly efficient when compared to the control w/o added lipids. This shows that the combination of mRNA with very small amounts of lipid was able to increase the transfection efficiency.

Example 9: Transfection Efficiency of Other Polymers in Combination with Different Lipids During Intravitreal Delivery This example describes the evaluation of the effect of different polymer-lipid formulations on transfection efficiency when performing ocular delivery. As a read-out for transfection efficiency, Photinus pyralis luciferase Ppluc mRNA was used as a cargo. Successful transfection with the cargo leads to the translation of the luciferase protein and to a secretion of luciferase protein into the cell culture supernatant.

mRNA complexes were prepared by mixing PpLuc mRNA (SEQ ID NO:19 R2244) and cationic polymer-lipid solutions at the same charge ratios. Formulations were prepared in Ringer's buffer according to the following scheme, leading to a final mRNA concentration of 2 µg/µl.

Formulation 1 (PpLuc mRNA R2244)
20 ml of mRNA (5 g/l)+25 ml water+5 ml of 10×RiLa resulting in 100 mg of mRNA in 50 ml equivalent to 2 mg/ml Formulation 2 (PpLuc mRNA R2244 in PB83 N/P 0.7, 0.4 3-C12-OH)
20 ml CVCM (PB83, 10 g/l)+0.4 ml 3-C12-OH (100 µmol/ml)+4.5 ml water+5 ml of 10×RiLa added to 20 ml of mRNA (R2244-luciferase; 5 g/l)
resulting in 100 mg of mRNA in 50 ml equivalent to 2 mg/ml 5 µl were injected into each eye (intravitreal). 4 eyes were treated per group. Animals treated with non-formulated mRNA prepared in Ringer's buffer served as controls. 24 hours after the treatment animals were sacrificed, their eyes removed and frozen. Subsequently, eye samples were analyzed for the levels of transfection. To that end the eyes were mechanically disrupted in a TissueLyser and lysed. Luciferase activity of each sample was assayed in a luminometer. The results of luciferase activity are expressed as relative light units (RLU).

Figure 9:
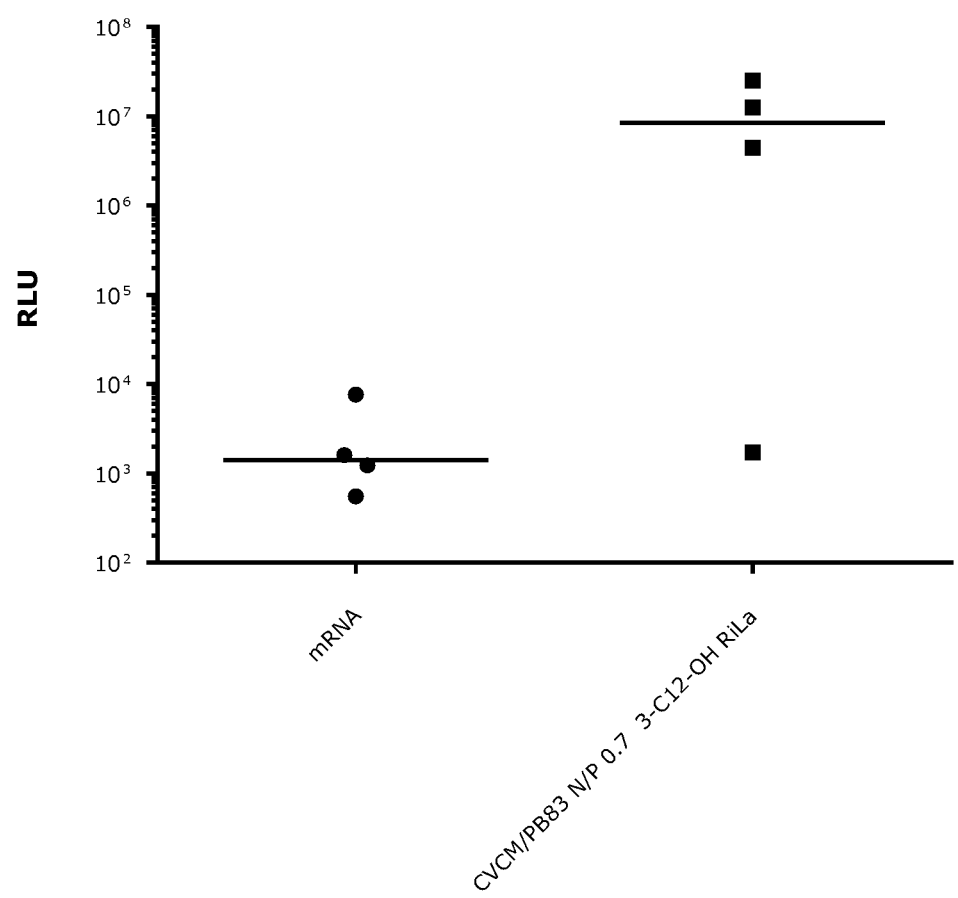
FIG. 9 shows PpLuc protein expression upon intravitreal injection.

Results:

FIG. 9 shows that PpLuc protein was expressed upon intravitreal injection and that the tested formulations with added lipids were highly efficient when compared to the control w/o added lipids. This shows that the combination of mRNA with very small amounts of lipid was able to increase the transfection efficiency intravitreally

Example 10: Transfection Efficiency of Different Polymers-Lipid Combinations on A549 Cells This example describes the evaluation of the effect of different polymer-lipid formulations on transfection efficiency on A549 cells (human lung carcinoma cell line). As a read-out for transfection efficiency, Gaussia princeps luciferase GpLuc mRNA was used as a cargo. Successful transfection with the cargo leads to the translation of the luciferase protein and to a secretion of luciferase protein into the cell culture supernatant.

Accordingly, A549 cells were seeded in 24-well-plates at a density of 75.000 cells per well in cell culture medium (Gibco (ThermoFisher) Ham's F-12K (Kaighn's) Medium, 10% Fetal Bovine Serum (FBS), 1% L-Glutamine, 1%

Penicillin/Streptomycin). A549 cells were transfected in duplicates as described below with different carrier-lipid formulations and with mRNA encoding GpLuc (SEQ ID NO:12; R2851). As a negative control, mRNA encoding GpLuc without CVCM/PB83 carrier was used. Luciferase expression was quantified after 24 h.

In this working example, the cationic lipid DDAB (dimethyldioctadecylammonium; CAS Number 3700-67-2; Avanti Polar Lipids, Alabaster, USA) was used:

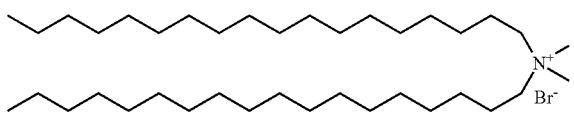 [SMILES: CCCCCCCCCCCCCCCCCC[N+](C)(C)CCCCCCCCCCCCCCCCCC ; [Br-]]

TABLE 6

Transfection conditions:

| | Step 1 (addition of CVCM/PB83 prepared in water) | Step 2 (addition of buffer or mRNA) | Step 3 (addition of buffer or mRNA) | Step 4 (fill up and distribution) |
|---|---|---|---|---|
| Condition 1 (w/o lipid) | 30 µl CVCM [1 µg/µl, diluted in water] | 20 µl RiLa | 2.5 µl mRNA (1 µg/µl) | up to 1 ml with media without serum |
| Condition 2 | 30 µl CVCM [1 µg/µl, diluted in water] + 1 µl DDAB (1 µmol/ml) | 20 µl RiLa | 2.5 µl mRNA (1 µg/µl) | 200 µl added per well |
| Condition 3 | 30 µl CVCM [1 µg/µl, diluted in water] + 1 µl DDAB (1 µmol/ml) | 2.5 µl mRNA (1 µg/µl) | 20 µl RiLa | |
| Condition 4 | 30 µl CVCM [1 µg/µl, diluted in water] + 1 µl DDAB (1 µmol/ml) | 10 µl RiLa | 2.5 µl mRNA (1 µg/µl) in 10 µl RiLa | |
| Condition 5 | 30 µl CVCM [1 µg/µl, diluted in water] + 1 µl 3-C12—OH (1:100) | 20 µl RiLa | 2.5 µl mRNA (1 µg/µl) | |

Figure 10:
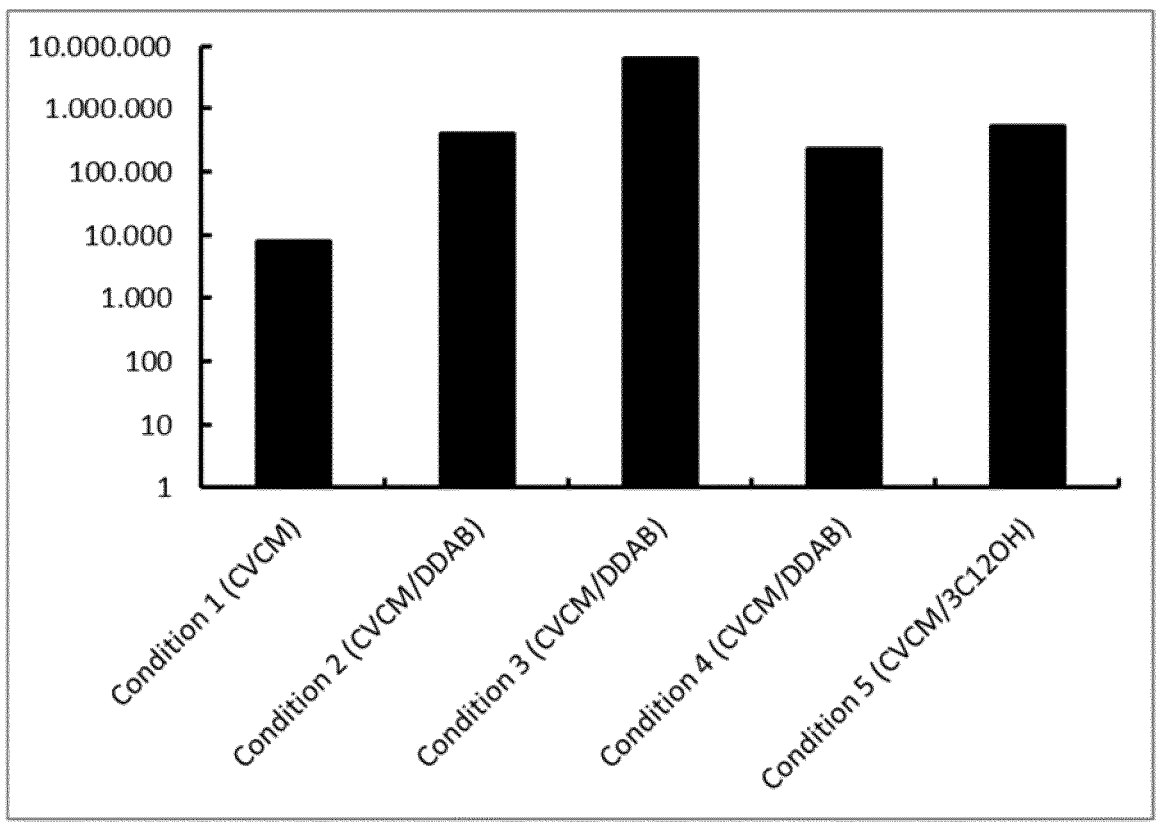
FIG. 10 shows GpLuc protein expression in A549 cells transfected with the mRNA construct R2851 formulated with different polymer/lipid compositions.

Results:

FIG. 10 shows that GpLuc protein was expressed in A549 cells transfected with the mRNA construct R2851 and that the tested formulations with added lipids were highly efficient when compared to the control w/o added lipids. This shows that the combination of mRNA with very small amounts of lipid was able to increase the transfection efficiency.

Example 11: Transfection Efficiency of Different Polymer-PEG-Lipid Combinations on A549 Cells This example describes the evaluation of the effect of different polymer-lipid formulations on transfection efficiency on A549 cells (human lung carcinoma cell line). As a read-out for transfection efficiency, Gaussia princeps luciferase GpLuc mRNA was used as a cargo. Successful transfection with the cargo leads to the translation of the luciferase protein and to a secretion of luciferase protein into the cell culture supernatant.

Accordingly, A549 cells were seeded in 24-well-plates at a density of 75.000 cells per well in cell culture medium (Gibco (ThermoFisher) Ham's F-12K (Kaighn's) Medium, 10% Fetal Bovine Serum (FBS), 1% L-Glutamine, 1% Penicillin/Streptomycin). A549 cells were transfected in duplicates as described below with different carrier-lipid formulations and with mRNA encoding GpLuc (SEQ ID NO:12; R2851). As a negative control, mRNA encoding GpLuc without CVCM/PB83 carrier was used. Luciferase expression was quantified after 24 h.

In this working example, $(R_{12}CW)_2$ was used as carrier polymer (two R12CW-units covalently bound via Cysteine S—S bonds) and pegylated 3-C12-OH lipid (ChiroBlock, Bitterfeld-Wolfen, Germany) was used:

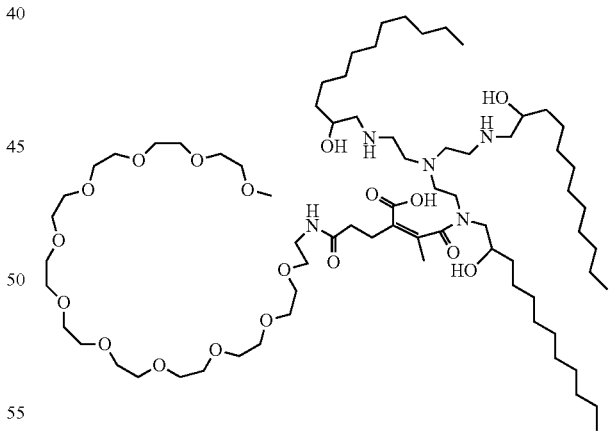

TABLE 7

| | Transfection conditions | | | |
|---|---|---|---|---|
| | Carrier | Lipid | mRNA | N/P |
| Condition 1 | 15 µl $(R_{12}CW)_2$ [0.25 g/l] | w/o | 2.5 µl Gpluc mRNA [5 g/l] | 0.7 | +20 µl RiLa filled up to 1 ml |

TABLE 7-continued

| | Transfection conditions | | | | |
|---|---|---|---|---|---|
| | Carrier | Lipid | mRNA | N/P | |
| Condition 2 | w/o | 5 µl pegylated 3-C12—OH [100 µmol/ml] | 2.5 µl Gpluc mRNA [5 g/l] | 0.7 | with media without serum 200 µl added per well |
| Condition 3 | 15 µl (R$_{12}$CW)$_2$ [0.25 g/l] | 5 µl pegylated 3-C12—OH [100 µmol/ml] | 2.5 µl Gpluc mRNA [5 g/l] | 0.7 | added per well |

In a second part, (R$_{12}$CW)$_2$ was used as carrier polymer (two R12CW-units covalently bound via Cysteine S—S bonds) and

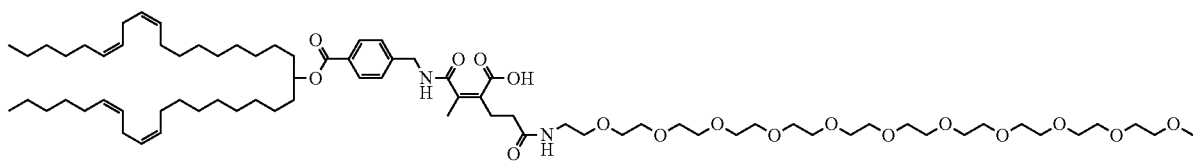 [SMILES: CCCCC/C=C\C/C=C\CCCCCCCCC(CCCCCCCC/C=C\C/C=C\CCCCC)OC(=O)c1ccc(CNC(=O)/C(C)=C(/CCC(=O)NCCOCCOCCOCCOCCOCCOCCOCCOCCOCCOCCOC)C(=O)O)cc1]

(ChiroBlock, Bitterfeld-Wolfen, Germany) was used:

TABLE 8

| | Transfection conditions | | | | |
|---|---|---|---|---|---|
| | Carrier | Lipid | mRNA | N/P | |
| Condition 4 | 45 µl (R$_{12}$CW)$_2$ [0.25 g/l] | w/o | 2.5 µl Gpluc mRNA [5 g/l] | 0.7 | +20 µl RiLa filled up to 1 ml |
| Condition 5 | w/o | 5 µl pegylated lipid [100 µmol/ml] | 2.5 µl Gpluc mRNA [5 g/l] | 0.7 | with media without serum 200 µl |
| Condition 6 | 45 µl (R$_{12}$CW)$_2$ [0.25 g/l] | 5 µl pegylated lipid [100 µmol/ml] | 2.5 µl Gpluc mRNA [5 g/l] | 0.7 | added per well |

Figure 11A:
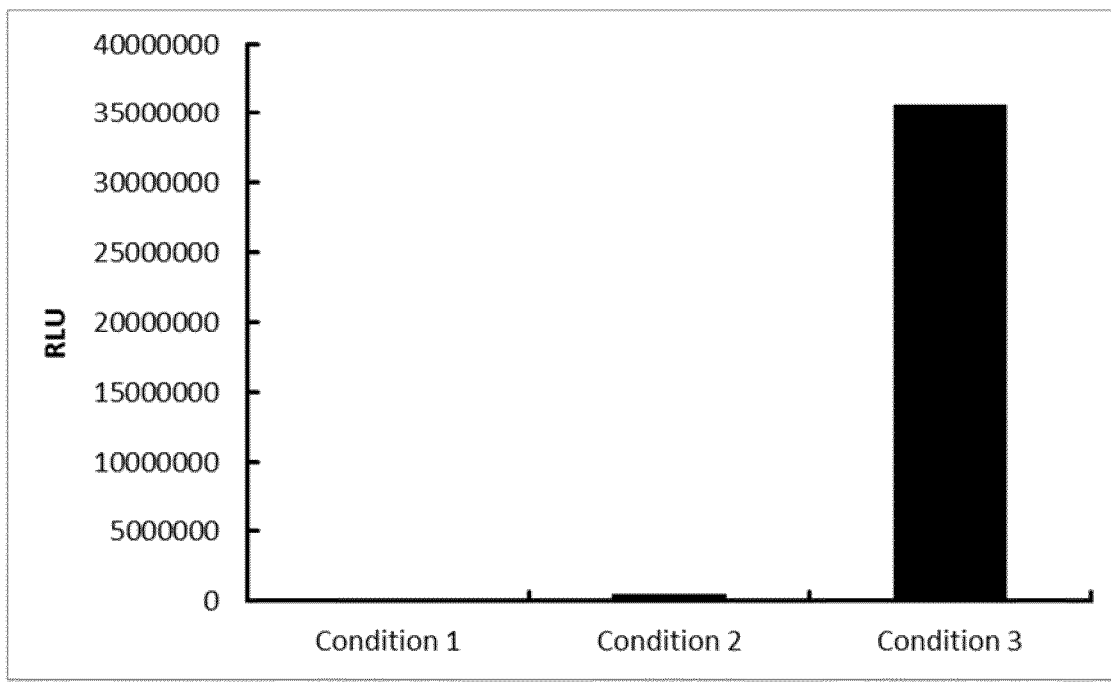
FIG. 11A and FIG. 11B show GpLuc protein expression in A549 cells transfected with the mRNA construct R2851 formulated with pegylated lipid.
Figure 11B:
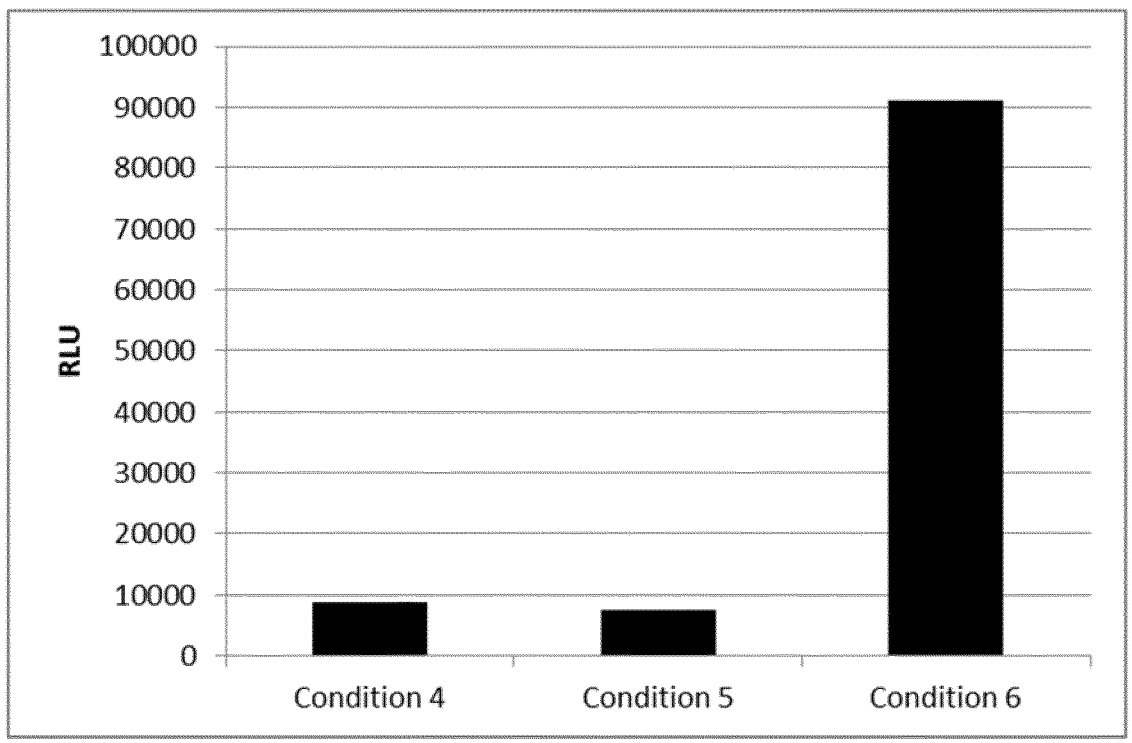

Results:

FIGS. 11A and 11B show that GpLuc protein was expressed in A549 cells transfected with the mRNA construct R2851 and that the tested formulations with added pegylated lipid were highly efficient when compared to the control w/o added lipids. This shows that the combination of mRNA with very small amounts of pegylated lipid was able to increase the transfection efficiency.

The invention claimed is:

1. A method of prophylaxis, treatment, and/or amelioration of a disease or disorder in a patient in need thereof comprising administering to the patient a safe and effective amount of a composition comprising a plurality of nanoparticles, wherein each nanoparticle of the plurality of nanoparticles comprises:
   (a) a cationic peptide or cationic polymer;
   (b) a cationic or permanent cationic lipidoid compound; and
   (c) a nucleic acid compound;
wherein the cationic or permanent cationic lipidoid compound comprises two or three moieties of formula IIa and/or formula IIb:

—N($R_1$)—$CH_2$—CH($R_5$)—$R_2$   (formula IIa)

—$N^+$($R_3$)($R_4$)—$CH_2$—CH($R_5$)—$R_2$   (formula IIb)

wherein independently for each individual moiety of formula IIa or formula IIb
   $R_1$ is selected from hydrogen or $C_1$-$C_4$-alkyl,
   $R_2$ is selected from linear or branched, saturated or unsaturated $C_6$-$C_{16}$ hydrocarbyl chain,
   $R_3$ and $R_4$ are selected from $C_1$-$C_4$-alkyl, and
   $R_5$ is selected from hydrogen or hydroxyl; and
wherein the cationic peptide or cationic polymer is a compound according to formula $L^1$-$P^1$-[P-]$_n$-$P^3$-$L^2$   (formula IV)

wherein
P is a cationic moiety having at least one —SH group capable of forming a disulfide linkage, or a disulfide-linked multimer thereof, wherein moiety P is selected from
   a polymer moiety having a molecular weight from about 0.5 kDa to about 30 kDa, or
   a peptide moiety composed of 3 to 100 amino acids, wherein at least 10% of the total number of amino acids of the peptide moiety represent basic amino acids selected from Arg, Lys, His and/or Orn;
$P^3$ is optional;
$P^1$ and $P^3$ are independently selected, each representing a linear or branched hydrophilic polymer chain selected from the group consisting of polyethylene glycol (PEG), poly-N-(2-hydroxypropyl)methacrylamide, poly-2-(methacryloyloxy)ethyl phosphorylcholines, poly(hydroxyalkyl L-asparagine), poly(2-(methacryloyloxy)ethyl phosphorylcholine), hydroxyethylstarch and poly(hydroxyalkyl L-glutamine), wherein the polymer chain exhibits a molecular weight from about 1 kDa to about 100 kDa, and wherein each of $P^1$ and $P^3$ is linked with a moiety P through a disulfide linkage;
$L^1$ and $L^2$ are optional ligands and independently selected from the group consisting of RGD, an RGD peptide, transferrin, folate, a signal peptide, a localization signal, a nuclear localization signal (NLS), an antibody, a cell penetrating peptide, a trans-activator of transcription (TAT), a ligand of a receptor, a cytokine, a hormone, a growth factor, a carbohydrate, a mannose, a galactose, an N-acetylgalactosamine, a synthetic ligand, an inhibitor of a receptor, an antagonist of a receptor, and a RGD peptidomimetic analogue;
n is an integer selected from 1 to about 50; and wherein, if n is greater than 1, each moiety P is linked with another moiety P through a disulfide linkage.

2. The method of claim 1, wherein the disease is selected from the group consisting of cancer diseases, tumour diseases, infectious diseases, genetic diseases, and autoimmune diseases.

3. The method of claim 2, wherein the disease is a viral, bacterial, or protozoological infectious disease.

4. The method of claim 1, wherein the composition is administered via ocular delivery.

5. The method of claim 4, wherein the ocular delivery is intravitreal, intracameral, subconjunctival, subretinal, subtenon, retrobulbar, topical, posterior juxtascleral administration or into the ciliary muscle.

6. The method of claim 5, wherein the ocular delivery is into the ciliary muscle.

7. The method of claim 5, wherein the plurality of nanoparticles comprises an mRNA encoding a protein such that the administration of the plurality of nanoparticles results in expression and/or activity of the protein encoded by the mRNA in the eye.

8. The method of claim 1, wherein moiety P is
   the peptide moiety composed of 7 to 30 amino acids, and wherein the at least one —SH group is provided by a Cys residue; or
   the polymer moiety selected from an optionally modified polyacrylate, chitosan, polyethylenimine, polyamine, polyaminoesters, polyamidoamine, or a copolymer thereof.

9. The method of claim 8, wherein the peptide moiety has two terminal ends, and wherein
   the Cys residue is located at, or in proximity to, one of the terminal ends; or
   the peptide moiety comprises at least two Cys residues, and wherein at least one of the Cys residues is located at, or in proximity to, each of the terminal ends.

10. The method of claim 1, wherein the weight ratio of the cationic peptide or cationic polymer to the nucleic acid compound is at least about 1, and wherein the ratio of the cationic or permanent cationic lipidoid compound to the nucleic acid compound is not higher than about 15 nmol of the cationic or permanent cationic lipidoid compound per μg of the nucleic acid compound.

11. The method of claim 1, wherein the weight ratio of the cationic or permanent cationic lipidoid compound to the cationic peptide or cationic polymer is not higher than about 1:50, and/or wherein the ratio of the cationic or permanent cationic lipidoid compound to the cationic peptide or cationic polymer is not higher than about 2 nmol of the cationic or permanent cationic lipidoid compound per μg of the cationic peptide or cationic polymer.

12. The method of claim 1, wherein the N/P ratio of the basic groups of the cationic peptide or cationic polymer to the phosphate groups of the nucleic acid compound from about 0.1 to about 20, or from about 0.2 to about 15, or from about 2 to about 15, or from about 2 to about 12, wherein the N/P ratio is defined as the mole ratio of the nitrogen atoms of the basic groups of the cationic peptide or cationic polymer to the phosphate groups of the nucleic acid compound.

13. The method of claim 1, wherein the plurality of nanoparticles comprises two or more different species of the cationic peptide and/or cationic polymer.

14. The method of claim 1, wherein the plurality of nanoparticles further comprises one or more compounds independently selected from targeting agents, cell penetrating agents, and stealth agents.

15. The method of claim 1, wherein the cationic or permanent cationic lipidoid compound is

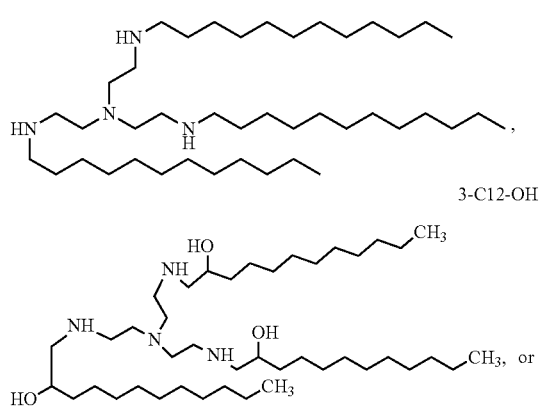

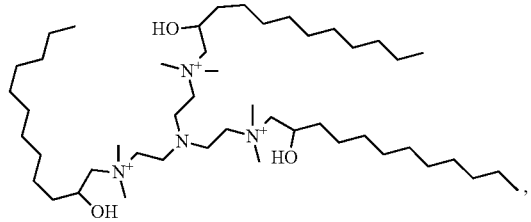

optionally further comprising a pharmaceutically acceptable anion.

16. The method of claim 1, wherein the nucleic acid compound is selected from the group consisting of chemically modified DNA, unmodified DNA, single stranded DNA, double stranded DNA, coding DNA, non-coding DNA, chemically modified RNA, unmodified RNA, single-stranded RNA, double-stranded RNA, coding RNA, and non-coding RNA.

17. The method of claim 16, wherein the nucleic acid compound comprises a plasmid, an oligodesoxynucleotide, genomic DNA, a DNA primer, a DNA probe, an immunostimulatory DNA, an aptamer, a messenger RNA (mRNA), an oligoribonucleotide, a viral RNA, a replicon RNA, a transfer RNA (tRNA), a ribosomal RNA (rRNA), an immunostimulatory RNA (isRNA), a microRNA, a small interfering RNA (siRNA), a small nuclear RNA (snRNA), a small-hairpin RNA (shRNA), a riboswitch, an RNA aptamer, an RNA decoy, an antisense RNA, a ribozyme, or a combination thereof.

18. The method of claim 16, wherein the nucleic acid compound comprises RNA.

19. The method of claim 18, wherein the nucleic acid compound comprises mRNA.

* * * * *

```
                          SEQUENCE LISTING

<160> NUMBER OF SEQ ID NOS: 19

<210> SEQ ID NO 1
<211> LENGTH: 60
<212> TYPE: RNA
<213> ORGANISM: Artificial Sequence
<220> FEATURE:
<223> OTHER INFORMATION: formula_V

<400> SEQUENCE: 1
uagcgaagcu cuuggaccua gguuuuuuuu uuuuuuuggg ugcguuccua gaaguacacg     60

<210> SEQ ID NO 2
<211> LENGTH: 120
<212> TYPE: RNA
<213> ORGANISM: Artificial Sequence
<220> FEATURE:
<223> OTHER INFORMATION: formula_V

<400> SEQUENCE: 2
```

```
uagcgaagcu cuuggaccua gguuuuuuuu uuuuuugggg ugcguuccua gaaguacacg    60
aucgcuucga gaaccuggau ccaaaaaaaa aaaaaaaccc acgcaaggau cuucaugugc   120
```

```
<210> SEQ ID NO 3
<211> LENGTH: 229
<212> TYPE: RNA
<213> ORGANISM: Artificial Sequence
<220> FEATURE:
<223> OTHER INFORMATION: formula_V

<400> SEQUENCE: 3
```

```
gggagaaagc ucaagcuugg agcaaugccc gcacauugag gaaaccgagu ugcauaucuc    60
agaguauugg cccccguagua gguuauucuu gacagacagu ggagcuuauu cacucccagg   120
auccgagucg cauacuacgg uacuggugac agaccuaggu cgucaguuga ccaguccgcc   180
acuagacgug aguccgucaa agcaguuaga uguuacacuc uauuagauc                229
```

```
<210> SEQ ID NO 4
<211> LENGTH: 547
<212> TYPE: RNA
<213> ORGANISM: Artificial Sequence
<220> FEATURE:
<223> OTHER INFORMATION: formula_V

<400> SEQUENCE: 4
```

```
gggagaaagc ucaagcuugg agcaaugccc gcacauugag gaaaccgagu ugcauaucuc    60
agaguauugg cccccguagua gguuauucuu gacagacagu ggagcuuauu cacucccagg   120
auccgagucg cauacuacgg uacuggugac agaccuaggu cgucaguuga ccaguccgcc   180
acuagacgug aguccgucaa agcaguuaga uguuacacuc uauuagaucu cggauuacag   240
cuggaaggag caggaguagu guucuugcuc uaaguaccga gugugcccaa uacccgauca   300
gcuuauuaac gaacggcucc uccucuuaga cugcagcgua agugcggaau cuggggauca   360
aauuacugac ugccuggauu acccucggac auauaaccuu guagcacgcu guugcuguau   420
aggugaccaa cgcccacucg aguagaccag cucucuuagu ccggacaaug auaggaggcg   480
cggucaaucu acuucuggcu aguuaagaau aggcugcacc gaccucuaua aguagcgugu   540
ccucuag                                                              547
```

```
<210> SEQ ID NO 5
<211> LENGTH: 1083
<212> TYPE: RNA
<213> ORGANISM: Artificial Sequence
<220> FEATURE:
<223> OTHER INFORMATION: formula_V

<400> SEQUENCE: 5
```

```
gggagaaagc ucaagcuugg agcaaugccc gcacauugag gaaaccgagu ugcauaucuc    60
agaguauugg cccccguagua gguuauucuu gacagacagu ggagcuuauu cacucccagg   120
auccgagucg cauacuacgg uacuggugac agaccuaggu cgucaguuga ccaguccgcc   180
acuagacgug aguccgucaa agcaguuaga uguuacacuc uauuagaucu cggauuacag   240
cuggaaggag caggaguagu guucuugcuc uaaguaccga gugugcccaa uacccgauca   300
gcuuauuaac gaacggcucc uccucuuaga cugcagcgua agugcggaau cuggggauca   360
aauuacugac ugccuggauu acccucggac auauaaccuu guagcacgcu guugcuguau   420
aggugaccaa cgcccacucg aguagaccag cucucuuagu ccggacaaug auaggaggcg   480
cggucaaucu acuucuggcu aguuaagaau aggcugcacc gaccucuaua aguagcgugu   540
```

```
ccucuagagc uacgcagguu cgcaauaaaa gcguugauua gugugcauag aacagaccuc      600
uuauucggug aaacgccaga augcuaaauu ccaauaacuc uucccaaaac gcguacggcc      660
gaagacgcgc gcuuaucuug uguacguucu cgcacaugga agaaucagcg ggcaugguggg     720 uagggcaaua ggggagcugg guagcagcga aaaagggccc cugcgcacgu agcuucgcug      780
uucgucugaa acaacccggc auccguugua gcgaucccgu aucaguguu auucuugugc       840 gcacuaagau ucaugguguua gucgacaaua acagcgucuu ggcagauucu ggucacgugc    900
ccuaugcccg ggcuugugcc ucucaggugc acagcgauac uuaaagccuu caaguacuc      960 gacguggguaa ccgauucgug acacuuccua agauuauucc acuguuuag ccccgcaccg    1020 ccgaccuaaa cugguccaau guauacgcau ucgcugagcg gaucgauaau aaaagcuuga    1080
auu                                                                  1083

<210> SEQ ID NO 6
<211> LENGTH: 229
<212> TYPE: RNA
<213> ORGANISM: Artificial Sequence
<220> FEATURE:
<223> OTHER INFORMATION: formula_V

<400> SEQUENCE: 6
gggagaaagc ucaagcuuau ccaaguaggc uggucaccug uacaacguag ccgguauuuu      60
uuuuuuuuuu uuuuuuuuga ccgucucaag guccaaguua gucugccuau aaaggugcgg     120
auccacagcu gaugaaagac uugugcggua cgguuaaucu ccccuuuuuu uuuuuuuuu     180 uuuuuaguaa augcgucuac ugaauccagc gaugaugcug gcccagauc                229

<210> SEQ ID NO 7
<211> LENGTH: 547
<212> TYPE: RNA
<213> ORGANISM: Artificial Sequence
<220> FEATURE:
<223> OTHER INFORMATION: formula_V

<400> SEQUENCE: 7
gggagaaagc ucaagcuuau ccaaguaggc uggucaccug uacaacguag ccgguauuuu      60
uuuuuuuuuu uuuuuuuuga ccgucucaag guccaaguua gucugccuau aaaggugcgg     120
auccacagcu gaugaaagac uugugcggua cgguuaaucu ccccuuuuuu uuuuuuuuu     180 uuuuuaguaa augcgucuac ugaauccagc gaugaugcug gcccagaucu cgaccacaa     240 gugcauauag uagucaucga gggucgccuu uuuuuuuuu uuuuuuuuu uggcccaguu      300 cugagacuuc gcuagagacu acaguuacag cugcaguagu aaccacugcg gcuauugcag    360
gaaaucccgu ucagguuuuu uuuuuuuuuu uuuuuccgc ucacuaugau uaagaaccag     420
gugggagugc acugcucucg aggucucacg agagcgcucg auacaguccu uggaagaauc    480 uuuuuuuuu uuuuuuuuu uugugcgacg aucacagaga acuucuauuc augcaggucu     540
gcucuag                                                             547

<210> SEQ ID NO 8
<211> LENGTH: 1083
<212> TYPE: RNA
<213> ORGANISM: Artificial Sequence
<220> FEATURE:
<223> OTHER INFORMATION: formula_V

<400> SEQUENCE: 8
```

```
gggagaaagc ucaagcuuau ccaaguaggc uggucaccug acaacguag ccgguauuuu    60 uuuuuuuuuu uuuuuuuuga ccgucucaag guccaaguua gucugccuau aaaggugcgg   120
auccacagcu gaugaaagac uugugcggua cgguuaaucu ccccuuuuuu uuuuuuuuu   180 uuuuuaguaa augcgucuac ugaauccagc gaugaugcug gcccagaucu ucgaccacaa   240
gugcauauag uagucaucga ggucgccuu uuuuuuuuuu uuuuuuuuuu uggcccaguu   300
cugagacuuc gcuagagacu acaguuacag cugcaguagu aaccacugcg gcuauugcag   360
gaaaucccgu ucagguuuuu uuuuuuuuuu uuuuuccgc ucacuaugau uaagaaccag   420 guggagugucu acugcucucg aggucucacg agagcgcucg auacaguccu uggaagaauc   480
uuuuuuuuuu uuuuuuuuuu uugugcgacg aucacagaga acuucuauuc augcaggucu   540
gcucuagaac gaacugaccu gacgccugaa cuuaugagcg ugcguauuu uuuuuuuuu   600 uuuuuuuuc cucccaacaa augucgauca auagcugggc uguggagac gcucagcaa   660 augccguggc uccauaggac guguagacuu cuauuuuuuu uuuuuuuuuu uuucccgggg   720
accacaaaua auauucuugc uugguugggc gcaagggccc cguaucaggu cauaaacggg   780
uacauguugc acaggcuccu uuuuuuuuuu uuuuuuuuuu uucgcugagu uauuccgguc   840
ucaaaagacg gcagacguca gucgacaaca cggucuaaag cagugcuaca aucugccgug   900
uucguguuuu uuuuuuuuuu uuuuuuguga accacacgg cgugcacugu aguucgcaau   960
ucauagggua ccggcucaga guuaugccuu gguugaaaac ugcccagcau acuuuuuuu  1020 uuuuuuuuuu uucauauucc caugcuaagc aagggaugcc gcgagucaug uuaagcuuga  1080
auu                                                               1083
```

<210> SEQ ID NO 9
<211> LENGTH: 59
<212> TYPE: RNA
<213> ORGANISM: Artificial Sequence
<220> FEATURE:
<223> OTHER INFORMATION: formula_VI

<400> SEQUENCE: 9

```
uagcgaagcu cuuggaccua ccuuuuuuuu uuuuuuccu gcguuccuag aaguacacg     59
```

<210> SEQ ID NO 10
<211> LENGTH: 120
<212> TYPE: RNA
<213> ORGANISM: Artificial Sequence
<220> FEATURE:
<223> OTHER INFORMATION: formula_VI

<400> SEQUENCE: 10

```
uagcgaagcu cuuggaccua ccuuuuuuuu uuuuuuccc ugcguuccua gaaguacacg    60
aucgcuucga gaaccuggau ggaaaaaaaa aaaaaaggg acgcaaggau cuucaugugc   120
```

<210> SEQ ID NO 11
<211> LENGTH: 185
<212> TYPE: PRT
<213> ORGANISM: Artificial Sequence
<220> FEATURE:
<223> OTHER INFORMATION: GpLuc amino acid sequence

<400> SEQUENCE: 11

Met Gly Val Lys Val Leu Phe Ala Leu Ile Cys Ile Ala Val Ala Glu
1               5                   10                  15

Ala Lys Pro Thr Glu Asn Asn Glu Asp Phe Asn Ile Val Ala Val Ala
            20                  25                  30

```
Ser Asn Phe Ala Thr Thr Asp Leu Asp Ala Asp Arg Gly Lys Leu Pro
        35                  40                  45
Gly Lys Lys Leu Pro Leu Glu Val Leu Lys Glu Met Glu Ala Asn Ala
 50                  55                  60
Arg Lys Ala Gly Cys Thr Arg Gly Cys Leu Ile Cys Leu Ser His Ile
 65                  70                  75                  80
Lys Cys Thr Pro Lys Met Lys Lys Phe Ile Pro Gly Arg Cys His Thr
                 85                  90                  95
Tyr Glu Gly Asp Lys Glu Ser Ala Gln Gly Ile Gly Glu Ala Ile
                100                 105                 110
Val Asp Ile Pro Glu Ile Pro Gly Phe Lys Asp Leu Glu Pro Met Glu
            115                 120                 125
Gln Phe Ile Ala Gln Val Asp Leu Cys Val Asp Cys Thr Thr Gly Cys
130                 135                 140
Leu Lys Gly Leu Ala Asn Val Gln Cys Ser Asp Leu Leu Lys Lys Trp
145                 150                 155                 160
Leu Pro Gln Arg Cys Ala Thr Phe Ala Ser Lys Ile Gln Gly Gln Val
                165                 170                 175
Asp Lys Ile Lys Gly Ala Gly Gly Asp
                180                 185
```

<210> SEQ ID NO 12
<211> LENGTH: 940
<212> TYPE: RNA
<213> ORGANISM: Artificial Sequence
<220> FEATURE:
<223> OTHER INFORMATION: GpLuc mRNA

<400> SEQUENCE: 12

| | | | | | |
|---|---|---|---|---|---|
| ggggcgcugc | cuacggaggu | ggcagccauc | uccuucucgg | caucaagcuu | accaugggcg | 60 |
| ugaagguccu | guucgcccuc | aucugcaucg | ccguggcgga | ggccaagccc | accgagaaca | 120 |
| acgaggacuu | caacaucgug | gccgucgcca | gcaacuucgc | caccacggac | cuggacgcgg | 180 |
| accgggggaa | gcugccgggc | aagaagcucc | cccuggaggu | gcugaaggag | auggaggcca | 240 |
| acgcccgcaa | ggccggggugc | acccggggcu | gccucaucug | ccugucccac | aucaagugca | 300 |
| ccccaagau | gaagaaguuc | auccccgggc | gcugccacac | cuacgagggc | gacaaggaga | 360 |
| gcgcgcaggg | cggaucggc | gaggccaucg | uggacauccc | ggagauccc | ggguucaagg | 420 |
| accuggagcc | cauggagcag | uucaucgccc | aggucgaccu | cugcguggac | ugcacgaccg | 480 |
| gcugccugaa | ggggcuggcc | aacgugcagu | gcuccgaccu | ccugaagaag | uggcugcccc | 540 |
| agcggugcgc | caccuucgcg | agcaagaucc | agggccaggu | cgacaagauc | aagggcgccg | 600 |
| ggggcgacug | aggacuagug | caucacauuu | aaaagcaucu | cagccuacca | ugagaauaag | 660 |
| agaaagaaaa | ugaagaucaa | uagcuuauuc | aucucuuuuu | cuuuuucguu | ggguguaaagc | 720 |
| caacacccug | ucuaaaaaac | auaaauuucu | uuaaucauuu | ugccucuuuu | cucugugcuu | 780 |
| caauuaauaa | aaauggaaa | gaaccuagau | cuaaaaaaaa | aaaaaaaaaa | aaaaaaaaa | 840 |
| aaaaaaaaa | aaaaaaaaa | aaaaaaaaa | aaaaaaugca | uccccccccc | cccccccccc | 900 |
| cccccccccc | ccaaaggcuc | uuuucagagc | caccagaauu | | | 940 |

<210> SEQ ID NO 13
<211> LENGTH: 42
<212> TYPE: DNA
<213> ORGANISM: Artificial Sequence
<220> FEATURE:

```
<223> OTHER INFORMATION: 5'-UTR of human ribosomal protein Large 32
      lacking the 5' terminal oligopyrimidine tract

<400> SEQUENCE: 13
ggcgctgcct acggaggtgg cagccatctc cttctcggca tc                        42

<210> SEQ ID NO 14
<211> LENGTH: 75
<212> TYPE: DNA
<213> ORGANISM: Artificial Sequence
<220> FEATURE:
<223> OTHER INFORMATION: 5'-UTR of ATP5A1 lacking the 5' terminal
      oligopyrimidine tract

<400> SEQUENCE: 14
gcggctcggc cattttgtcc cagtcagtcc ggaggctgcg gctgcagaag taccgcctgc     60
ggagtaactg caaag                                                     75

<210> SEQ ID NO 15
<211> LENGTH: 24
<212> TYPE: DNA
<213> ORGANISM: Artificial Sequence
<220> FEATURE:
<223> OTHER INFORMATION: histone stem-loop sequence

<400> SEQUENCE: 15
caaaggctct tttcagagcc acca                                            24

<210> SEQ ID NO 16
<211> LENGTH: 24
<212> TYPE: RNA
<213> ORGANISM: Artificial Sequence
<220> FEATURE:
<223> OTHER INFORMATION: histone stem-loop sequence

<400> SEQUENCE: 16
caaaggcucu uuucagagcc acca                                            24

<210> SEQ ID NO 17
<211> LENGTH: 2083
<212> TYPE: RNA
<213> ORGANISM: Artificial Sequence
<220> FEATURE:
<223> OTHER INFORMATION: HA-R2564 mRNA

<400> SEQUENCE: 17
ggggcgcugc cuacggaggu ggcagccauc uccuucucgg caucaagcuu accaugaagg     60
ccauccuggu gguccuccug uacaccuucg ccaccgcgaa cgccgacacg cugugcaucg    120
gcuaccacgc caacaacagc accgacaccu ggacaccgu gcucgagaag aacgucacgg     180
ugacccacuc cgugaaccug cuggaggaca agcacaacgg gaagcucugc aagcugcggg    240
gcgucgcccc gcugcaccuc gggaagugca acaucgccgg cuggauccug gggaacccgg    300
agugcgagag ccuguccacc gcgagcuccu ggagcuacau cguggagacc uccagcuccg    360
acaacggcac gugcuacccc ggcgacuuca ucgacuacga ggagcuccgc gagcagcuga    420
gcuccgugag cucuucgag cgguucgaga ucuuccccaa gaccagcucc uggcccaacc     480
acgacagcaa caaggggguc accgccgccu gcccgcacgc cggcgcgaag uccuucuaca    540
agaaccugau cuggcucgug aagaagggga cagcuacccc caagcugucc aagagcuaca    600
ucaacgacaa gggcaaggag gugcuggucc ucugggggau ccaccacccc agcaccuccg    660
ccgaccagca gagccuguac cagaacgccg acgccuacgu guucguggc uccagccgcu     720
```

```
acuccaagaa guucaagccc gagaucgcca uccggccgaa ggucccgcgac caggagggcc      780 ggaugaacua cuacuggacg cuggugagc ccggggacaa gaucaccuuc gaggcgaccg       840
gcaaccucgu ggucccccgc uacgccuucg ccauggagcg gaacgccggg agcggcauca      900
ucaucuccga caccccgug cacgacugca acacgaccug ccagaccccg aagggcgcca       960
ucaacaccag ccugcccuuc cagaacaucc accccaucac gaucgggaag ugccccaagu     1020
acgugaaguc caccaagcug cgccucgcga ccggccugcg gaacguccg agcauccagu      1080 cccgcgggcu guucggcgcc aucgccgggu caucgaggg cggcuggacc gggauggugg      1140 acggcugguua cggguaccac caccagaacg agcagggcag cgggucgcc gccgaccuca     1200 aguccacgca gaacgcgauc gacgagauca ccaacaaggu gaacagcguc aucgagaaga     1260
ugaacaccca guucaccgcc gugggcaagg aguucaacca ccuggagaag cggaucgaga     1320
accugaacaa gaaggucgac gacggcuucc ucgacaucug gacguacaac gccgagcugc     1380
uggugcuccu ggagaacgag cgcacccugg acuaccacga cuccaacgug aagaaccucu     1440
acgagaaggu ccggagccag cugaagaaca cgccaagga gaucgggaac ggcugcuucg     1500
aguucuacca caagugcgac aacaccgca uggaguccgu gaagaacggg accuacgacu     1560
accccaagua cagcgaggag gccaagcuga accgcgagga gaucgacggc gugaagcucg     1620
aguccacgcg gaucuaccag auccuggcga cuacagcac cgucgccagc ucccuggugc     1680
ucguggucag ccuggggggcc aucuccuucu ggaugugcag caacggcucc cugcagugcc     1740
gcaucugcau cugaccacua gugcaucaca uuuaaaagca cucagcccua ccaugagaau     1800
aagagaaaga aaaugaagau caauagcuua uucaucucuu uuucuuuuuc guugguguaa     1860
agccaacacc cugucuaaaa aacauaaauu ucuuuaauca uuuugccucu uuucucugug     1920
cuucaauuaa uaaaaauggg aaagaaccua gaucuaaaaa aaaaaaaaaa aaaaaaaaa     1980 aaaaaaaaaa aaaaaaaaaa aaaaaaaaaa aaaaaaaaau gcaucccccc ccccccccc     2040 ccccccccc ccccaaagg cucuuuucag agccaccaga auu                        2083
```

<210> SEQ ID NO 18
<211> LENGTH: 550
<212> TYPE: PRT
<213> ORGANISM: Artificial Sequence
<220> FEATURE:
<223> OTHER INFORMATION: Ppluc amino acid sequence

<400> SEQUENCE: 18

```
Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
                20                  25                  30

Tyr Ala Leu Val Pro Gly Thr Ile Ala Phe Thr Asp Ala His Ile Glu
            35                  40                  45

Val Asp Ile Thr Tyr Ala Glu Tyr Phe Glu Met Ser Val Arg Leu Ala
        50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Gly Ile Ser Gln Pro Thr Val Val Phe Val
```

-continued

```
            115                 120                 125
Ser Lys Lys Gly Leu Gln Lys Ile Leu Asn Val Gln Lys Lys Leu Pro
            130                 135                 140
Ile Ile Gln Lys Ile Ile Ile Met Asp Ser Lys Thr Asp Tyr Gln Gly
145                 150                 155                 160
Phe Gln Ser Met Tyr Thr Phe Val Thr Ser His Leu Pro Pro Gly Phe
                    165                 170                 175
Asn Glu Tyr Asp Phe Val Pro Glu Ser Phe Asp Arg Asp Lys Thr Ile
                180                 185                 190
Ala Leu Ile Met Asn Ser Ser Gly Ser Thr Gly Leu Pro Lys Gly Val
                    195                 200                 205
Ala Leu Pro His Arg Thr Ala Cys Val Arg Phe Ser His Ala Arg Asp
                210                 215                 220
Pro Ile Phe Gly Asn Gln Ile Ile Pro Asp Thr Ala Ile Leu Ser Val
225                 230                 235                 240
Val Pro Phe His His Gly Phe Gly Met Phe Thr Thr Leu Gly Tyr Leu
                    245                 250                 255
Ile Cys Gly Phe Arg Val Val Leu Met Tyr Arg Phe Glu Glu Glu Leu
                260                 265                 270
Phe Leu Arg Ser Leu Gln Asp Tyr Lys Ile Gln Ser Ala Leu Leu Val
                275                 280                 285
Pro Thr Leu Phe Ser Phe Phe Ala Lys Ser Thr Leu Ile Asp Lys Tyr
        290                 295                 300
Asp Leu Ser Asn Leu His Glu Ile Ala Ser Gly Gly Ala Pro Leu Ser
305                 310                 315                 320
Lys Glu Val Gly Glu Ala Val Ala Lys Arg Phe His Leu Pro Gly Ile
                    325                 330                 335
Arg Gln Gly Tyr Gly Leu Thr Glu Thr Thr Ser Ala Ile Leu Ile Thr
                340                 345                 350
Pro Glu Gly Asp Asp Lys Pro Gly Ala Val Gly Lys Val Val Pro Phe
                355                 360                 365
Phe Glu Ala Lys Val Val Asp Leu Asp Thr Gly Lys Thr Leu Gly Val
370                 375                 380
Asn Gln Arg Gly Glu Leu Cys Val Arg Gly Pro Met Ile Met Ser Gly
385                 390                 395                 400
Tyr Val Asn Asn Pro Glu Ala Thr Asn Ala Leu Ile Asp Lys Asp Gly
                405                 410                 415
Trp Leu His Ser Gly Asp Ile Ala Tyr Trp Asp Glu Asp Glu His Phe
                420                 425                 430
Phe Ile Val Asp Arg Leu Lys Ser Leu Ile Lys Tyr Lys Gly Tyr Gln
                435                 440                 445
Val Ala Pro Ala Glu Leu Glu Ser Ile Leu Leu Gln His Pro Asn Ile
            450                 455                 460
Phe Asp Ala Gly Val Ala Gly Leu Pro Asp Asp Asp Ala Gly Glu Leu
465                 470                 475                 480
Pro Ala Ala Val Val Val Leu Glu His Gly Lys Thr Met Thr Glu Lys
                    485                 490                 495
Glu Ile Val Asp Tyr Val Ala Ser Gln Val Thr Thr Ala Lys Lys Leu
                500                 505                 510
Arg Gly Gly Val Val Phe Val Asp Glu Val Pro Lys Gly Leu Thr Gly
            515                 520                 525
Lys Leu Asp Ala Arg Lys Ile Arg Glu Ile Leu Ile Lys Ala Lys Lys
            530                 535                 540
```

Gly Gly Lys Ile Ala Val
545             550

<210> SEQ ID NO 19
<211> LENGTH: 2035
<212> TYPE: RNA
<213> ORGANISM: Artificial Sequence
<220> FEATURE:
<223> OTHER INFORMATION: Ppluc mRNA

<400> SEQUENCE: 19

| | | | | | |
|---|---|---|---|---|---|
| ggggcgcugc | cuacggaggu | ggcagccauc | uccuucucgg | caucaagcuu | gaggauggag | 60 |
| gacgccaaga | acaucaagaa | gggcccggcg | cccuucuacc | cgcuggagga | cgggaccgcc | 120 |
| ggcgagcagc | uccacaaggc | caugaagcgg | uacgcccugg | ugccgggcac | gaucgccuuc | 180 |
| accgacgccc | acaucgaggu | cgacaucacc | uacgcggagu | acuucgagau | gagcgugcgc | 240 |
| cuggccgagg | ccaugaagcg | guacggccug | aacaccaacc | accggaucgu | ggugugcucg | 300 |
| gagaacagcc | ugcaguucuu | caugccggug | cuggcgccc | ucuucaucgg | cguggccguc | 360 |
| gccccggcga | acgacaucua | caacgagcgg | gagcugcuga | acagcauggg | gaucagccag | 420 |
| ccgaccgugg | uguucgugag | caagaagggc | cugcagaaga | uccugaacgu | gcagaagaag | 480 |
| cugcccauca | uccagaagau | caucaucaug | gacagcaaga | ccgacuacca | gggcuuccag | 540 |
| ucgauguaca | cguucgugac | cagccaccuc | ccgccgggcu | ucaacgagua | cgacuucguc | 600 |
| ccggagagcu | ucgaccggga | caagaccauc | gcccugauca | ugaacagcag | cggcagcacc | 660 |
| ggccugccga | aggggguggc | ccugccgcac | cggaccgccu | gcgugcgcuu | cucgcacgcc | 720 |
| cgggaccccca | ucuucggcaa | ccagaucauc | ccggacaccg | ccauccugag | cguggugccg | 780 |
| uuccaccacg | gcuucggcau | guucacgacc | cugggcuacc | ucaucugcgg | cuuccggguc | 840 |
| guccugaugu | accgguucga | ggaggagcug | uuccugcgga | gccugcagga | cuacaagauc | 900 |
| cagagcgcgc | ugcucgugcc | gacccuguuc | agcuucuucg | ccaagagcac | ccugaucgac | 960 |
| aaguacgacc | ugucgaaccu | gcacgagauc | gccagcgggg | gcgccccgcu | gagcaaggag | 1020 |
| gugggcgagg | ccguggccaa | gcgguuccac | cucccgggca | uccgccaggg | cuacggccug | 1080 |
| accgagacca | cgagcgcgau | ccugaucacc | cccgaggggg | acgacaagcc | gggcgccgug | 1140 |
| ggcaaggugg | ucccguucuu | cgaggccaag | guggugggacc | uggacaccgg | caagacccug | 1200 |
| ggcgugaacc | agcggggcga | gcugugcgug | cgggggccga | ugaucaugag | cggcuacgug | 1260 |
| aacaacccgg | aggccaccaa | cgcccucauc | gacaaggacg | gcuggcugca | cagcggcgac | 1320 |
| aucgccuacu | gggacgagga | cgagcacuuc | uucaucgucg | accggcugaa | gucgcugauc | 1380 |
| aaguacaagg | cuaccaggu | ggcgccggcc | gagcuggaga | gcauccugcu | ccagcacccc | 1440 |
| aacaucuucg | acgccggcgu | ggccgggcug | ccggacgacg | acgccggcga | gcugccggcc | 1500 |
| gcgguggugg | ugcuggagca | cggcaagacc | augacggaga | aggagaucgu | cgacuacgug | 1560 |
| gccagccagg | ugaccaccgc | caagaagcug | cggggcggcg | ugguguucgu | ggacgagguc | 1620 |
| ccgaagggcc | ugaccgggaa | gcucgacgcc | cggaagaucc | gcgagauccu | gaucaaggcc | 1680 |
| aagaagggcg | gcaagaucgc | cguguaagac | uagugcauca | cauuuaaaag | caucucagcc | 1740 |
| uaccaugaga | auaagagaaa | gaaaaugaag | aucaauagcu | auucaucuc | uuuucuuuu | 1800 |
| ucguuggugu | aaagccaaca | cccugucuaa | aaaacauaaa | uuucuuuaau | cauuuugccu | 1860 |

```
cuuuucucug ugcuucaauu aauaaaaaau ggaaagaacc uagaucuaaa aaaaaaaaaa    1920
aaaaaaaaaa aaaaaaaaaa aaaaaaaaaa aaaaaaaaaa aaaaaaaaaa augcaucccc    1980
cccccccccc cccccccccc ccccccaaa ggcucuuuuc agagccacca gaauu          2035
```